United States Patent
Wang et al.

(10) Patent No.: US 10,759,808 B2
(45) Date of Patent: Sep. 1, 2020

(54) MONOFUNCTIONAL INTERMEDIATES FOR LIGAND-DEPENDENT TARGET PROTEIN DEGRADATION

(71) Applicant: THE REGENTS OF THE UNIVERSITY OF MICHIGAN, Ann Arbor, MI (US)

(72) Inventors: Shaomeng Wang, Superior Township, MI (US); Yangbing Li, Ann Arbor, MI (US); Angelo Aguilar, Ann Arbor, MI (US); Bing Zhou, Ann Arbor, MI (US); Jiantao Hu, Ann Arbor, MI (US); Fuming Xu, Ypsilanti, MI (US); Chong Qin, Ann Arbor, MI (US); Yang Hu, Ann Arbor, MI (US); Weiguo Xiang, Ypsilanti, MI (US); Rohan Rej, Ann Arbor, MI (US); Jiuling Yang, Ann Arbor, MI (US); Xin Han, Ann Arbor, MI (US); Longchuan Bai, Ann Arbor, MI (US); Chao-Yie Yang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/091,544

(22) PCT Filed: Apr. 6, 2017

(86) PCT No.: PCT/US2017/026275
§ 371 (c)(1),
(2) Date: Oct. 5, 2018

(87) PCT Pub. No.: WO2017/176958
PCT Pub. Date: Oct. 12, 2017

(65) Prior Publication Data
US 2019/0119289 A1    Apr. 25, 2019

Related U.S. Application Data

(60) Provisional application No. 62/409,571, filed on Oct. 18, 2016, provisional application No. 62/409,592, filed on Oct. 18, 2016, provisional application No. 62/393,874, filed on Sep. 13, 2016, provisional application No. 62/393,888, filed on Sep. 13, 2016, provisional application No. 62/393,935, filed on Sep. 13, 2016, provisional application No. 62/321,499, filed on Apr. 12, 2016, provisional application No. 62/318,974, filed on Apr. 6, 2016.

(51) Int. Cl.
*C07D 401/04*   (2006.01)
*C07D 487/10*   (2006.01)
*C07D 401/14*   (2006.01)
*C07D 487/04*   (2006.01)
*C07D 495/14*   (2006.01)

(52) U.S. Cl.
CPC ......... *C07D 487/10* (2013.01); *C07D 401/04* (2013.01); *C07D 401/14* (2013.01); *C07D 487/04* (2013.01); *C07D 495/14* (2013.01)

(58) Field of Classification Search
CPC .................................................. C07D 401/04
USPC .......................................................... 546/200
See application file for complete search history.

(56) References Cited

U.S. PATENT DOCUMENTS

| 2003/0096841 A1 | 5/2003 | Robarge et al. |
| 2015/0291562 A1 | 10/2015 | Crew et al. |
| 2016/0058872 A1 | 3/2016 | Crew et al. |

FOREIGN PATENT DOCUMENTS

| WO | WO-02/059106 A1 | 8/2002 |
| WO | WO-2013/158644 A2 | 10/2013 |

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*

(Continued)

*Primary Examiner* — Patricia L Morris
(74) *Attorney, Agent, or Firm* — Marshall, Gerstein & Borun LLP

(57) ABSTRACT

The present disclosure provides compounds represented by Formula I: and the salts or solvates thereof, wherein X, L, Y, and B are as defined in the specification. Compounds having Formula I are immunomodulators and/or monofunctional synthetic intermediates that can be used to prepare small-molecule drug conjugates.

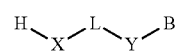

20 Claims, No Drawings

(56) References Cited

OTHER PUBLICATIONS

Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*
Ruchelman et al., "Isosteric analogs, etc.," Bioorganic & Medicinal Chemistry Lettersd 23 360-365. (Year: 2013).*
Lai, A. C., et al., "Modular PROTAC Design for the Degradation of Oncogenic BCR-ABL" (2016) *Angewandte Chemie International Edition*, vol. 55, No. 2, pp. 807-810.
International Search Report for Application No. PCT/US2017/026275, dated Sep. 8, 2017.
Stewart, S.G., et al., "New Thalidomide Analogues Derived Through Sonogashira or Suzuki Reactions and Their TNF Expression Inhibition Profiles," *Bioorganic & Medicinal Chemistry* (2010), vol. 18, No. 2, pp. 650-662.

\* cited by examiner

MONOFUNCTIONAL INTERMEDIATES FOR LIGAND-DEPENDENT TARGET PROTEIN DEGRADATION

BACKGROUND OF THE INVENTION

Field of the Invention

The present disclosure provides compounds that are medically useful, e.g., as immunomodulators for the treatment of cancer, and/or synthetically useful as monofunctional intermediates for the preparation of small-molecule drug conjugates. Coupling the monofunctional synthetic intermediates of this disclosure with an inhibitor of a target protein of interest, e.g., an oncogenic protein inhibitor, e.g., a BET bromodomain inhibitor or MDM2 inhibitor, provides a heterobifunctional small-molecule that simultaneously binds the target protein and a ubiquitin ligase, enabling ubiquitination and degradation of the target protein.

Background

Phthalimide-based drugs, e.g., thalidomide or lenalidomide, bind to protein-degradation machinery, e.g., cereblon (CRBN; part of an ubiquitin E3 ligase complex). This may promote the recruitment of two transcription factors (IKZF1 and IKZF3) that are essential to disease progression, resulting in drug-induced ubiquitylation and degradation by the proteasome. See, e.g., Ito et al., *Science* 327:1345-1350 (2010) and Winter et al., *Science* 348:1376-1381 (2015).

A high-affinity VHL ligand, see Bondeson et al., *Nat. Chem. Biol.* 11:611-617 (2015), may recruit a target protein to an E3 ubiquitin ligase, resulting in drug induced ubiquitination and degradation. See, e.g., van Hagen et al., *Nucleic Acids Research* 38: 1922-1931 (2010); Buckley et al., *J. Am. Chem. Soc.* 134:4465-4468 (2012); Buckley et al., *Angew, Chem. Int. Ed. Engl.* 51:11463-11467 (2012); Lipkowitz and Weissman, *Nat Rev Cancer* 11:629-643 (2011); and Zengerle et al., *ACS Chem. Biol.* 10:1770-1777 (2015).

There is an ongoing need for immunomodulatory drugs. There is also an ongoing need for monofunctional synthetic intermediates comprising a ligand for an E3 ubiquitin ligase protein, e.g., thalidomide, for use in preparing heterobifunctional protein degraders.

BRIEF SUMMARY OF THE INVENTION

In one aspect, the present disclosure provides compounds having any one of Formulae I-VI, VIa, or VIb below, and the salts or solvates thereof, collectively referred to as "Compounds of the Disclosure." Compounds of the Disclosure comprise a ligand for an E3 ubiquitin ligase protein and thus can be used as an immunomodulatory drug to treat cancer, e.g., multiple myeloma, and other diseases responsive to inducing, enhancing, or suppressing an immune response, e.g., Crohn's disease, sarcoidosis, graft-versus-host disease, and rheumatoid arthritis, in a subject in need thereof.

In another aspect, the present disclosure provides Compounds of the Disclosure as monofunctional synthetic intermediates that can be used to prepare heterobifunctional protein degraders.

In another aspect, the present disclosure provides methods of preparing heterobifunctional protein degraders having any one of Formulae VII-IX or XI-XXXII, below, and the pharmaceutically acceptable salts or solvates thereof. Heterobifunctional protein degraders comprise a target protein inhibitor, a linker, and a ligand for an E3 ubiquitin ligase protein.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Compounds of the Disclosure are immunomodulators and/or monofunctional synthetic intermediates that can be used to prepare heterobifunctional protein degraders.

In one embodiment, Compounds of the Disclosure are compounds represented by Formula I:

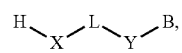

and the salts or solvates thereof, wherein:

X is selected from the group consisting of —C≡C—, —O—, —N(R$^{2a}$)—, —OC(=O)—,

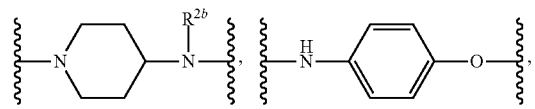

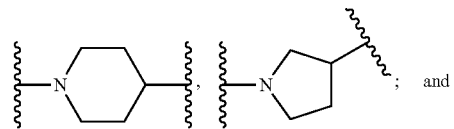

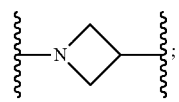

wherein the —N(R$^{2b}$)— of

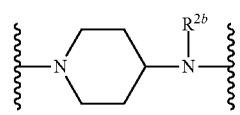

is attached to L;

the —O— of

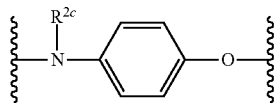

is attached to L;
the —C(=O)— of —OC(=O)— is attached to L; and the carbon atom of

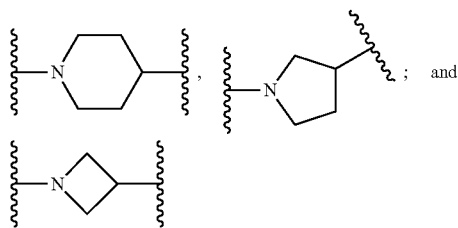

is attached to L;
L is selected from the group consisting of alkylenyl, heteroalkylenyl, -A-(CH$_2$)$_m$—W—(CH$_2$)$_n$—, and —(CH$_2$)$_r$—W—(CH$_2$)$_u$—O—(CH$_2$)$_v$—;
A is absent; or
A is heteroarylenyl;
W is selected from the group consisting of phenylenyl, heteroarylenyl, heterocyclenyl, and cycloalkylenyl;
m is 0, 1, 2, 3, 4, 5, 6, or 7;
n is 0, 1, 2, 3, 4, 5, 6, 7, or 8;
r is 0, 1, 2 or 3;
u is 0, 1, 2, or 3;
v is 1, 2, 3, or 4;
Y is selected from the group consisting of —C≡C—, —CH=CH—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or
Y is absent;
wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;
R$^{2a}$, R$^{2b}$, R$^{2c}$, R$^{2d}$, R$^{2e}$, and R$^{2f}$ are each independently selected from the group consisting of hydrogen and C$_{1-4}$ alkyl; and
B is a monovalent radical of a ligand for an E3 ubiquitin ligase protein.

In another embodiment, Compounds of the Disclosure are compounds represented by Formula I, and the salts or solvates thereof, wherein:
X is selected from the group consisting of —C≡C—, —O—, —N(R$^{2a}$)—,

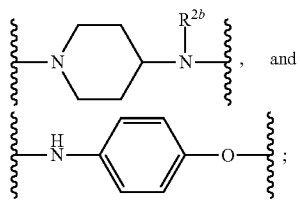

wherein the —N(R$^{2b}$)— of

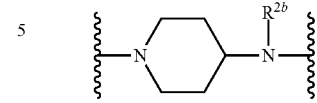

is attached to L and the —O— of

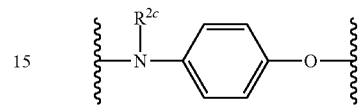

is attached to L.

In one embodiment, Compounds of the Disclosure are compounds represented by Formula I, and the salts or solvates thereof, wherein X is selected from the group consisting of —C≡C—, —O—, —N(R$^{2a}$)—,

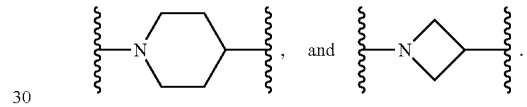

In one embodiment, Compounds of the Disclosure are compounds represented by Formula I, and the salts or solvates thereof, wherein X is —OC(=O)—, wherein the —C(=O)— of —OC(=O)— is attached to L.

In another embodiment, Compounds of the Disclosure are compounds having Formula I, and the salts or solvates thereof, wherein:
B is selected from the group consisting of:

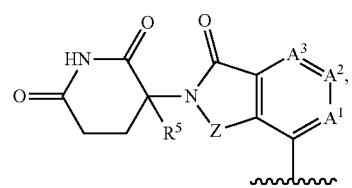

B-1a

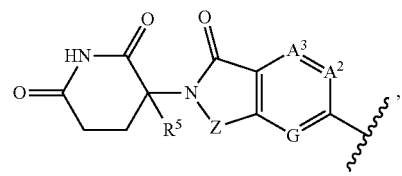

B-1b

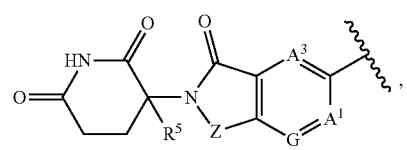

B-1c

-continued

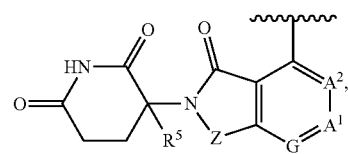
B-1d

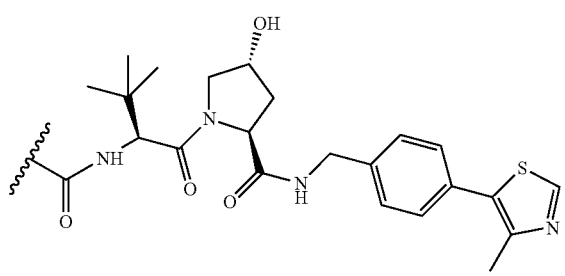
B-2

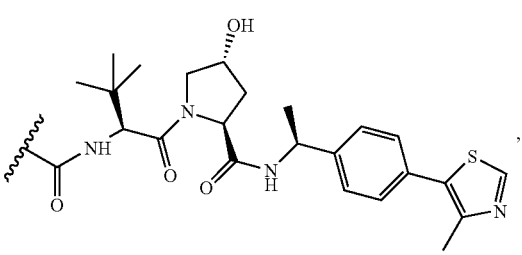
B-2a

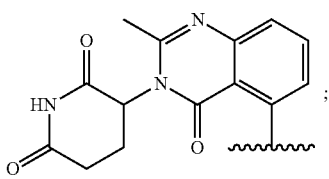
B-3

$A^1$ is selected from the group consisting of —C($R^{16a}$)= and —N=;
$A^2$ is selected from the group consisting of —C($R^{16b}$)= and —N=;
$A^3$ is selected from the group consisting of —C($R^{16c}$)= and —N=;
G is selected from the group consisting of —C($R^{16d}$)= and —N=;
Z is selected from the group consisting of —CH$_2$R and —C(=O)—;
$R^5$ is selected from the group consisting of hydrogen, methyl, and fluoro;
$R^{16a}$ is selected from the group consisting of hydrogen, halo, and $C_{1-4}$ alkyl;
$R^{16b}$ is selected from the group consisting of hydrogen, halo, and $C_{1-4}$ alkyl; and
$R^{16c}$ is selected from the group consisting of hydrogen, halo, and $C_{1-4}$ alkyl; and
$R^{16d}$ is selected from the group consisting of hydrogen, halo, and $C_{1-4}$ alkyl.

In another embodiment, Compounds of the Disclosure are compounds having Formula I, and the salts or solvates thereof, wherein B is B-1a, B-1b, B-1c, or B-1d, and $R^5$ is partially or entirely enriched with an isotope of hydrogen, e.g., $R^5$ is about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% deuterium.

In another embodiment, Compounds of the Disclosure are compounds having Formula I, and the salts or solvates thereof, wherein B is selected from the group consisting of:

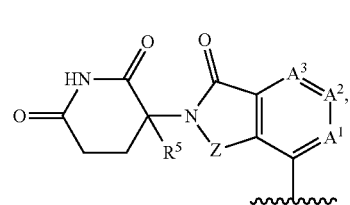
B-1a

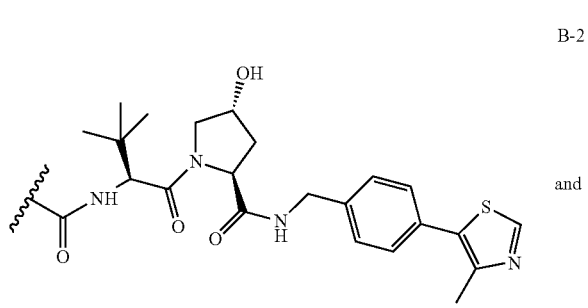
B-2

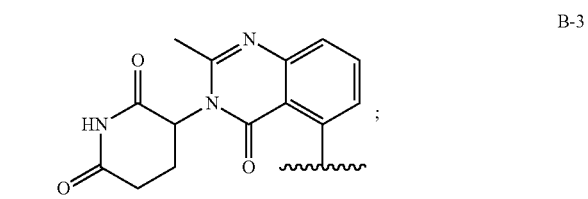
B-3

$A^1$ is selected from the group consisting of —C($R^{16a}$)= and —N=;
$A^2$ is selected from the group consisting of —C($R^{16b}$)= and —N=;
$A^3$ is selected from the group consisting of —C($R^{16c}$)= and —N=;
Z is selected from the group consisting of —CH$_2$ and —C(=O)—;
$R^5$ is selected from the group consisting of hydrogen, methyl, and fluoro;
$R^{16a}$ is selected from the group consisting of hydrogen, halo, and $C_{1-4}$ alkyl;
$R^{16b}$ is selected from the group consisting of hydrogen, halo, and $C_{1-4}$ alkyl; and
$R^{16c}$ is selected from the group consisting of hydrogen, halo, and $C_{1-4}$ alkyl.

In another embodiment, Compounds of the Disclosure are compounds having Formula I that are not any one of the compounds of Table 6, or any stereoisomer thereof.

TABLE 6
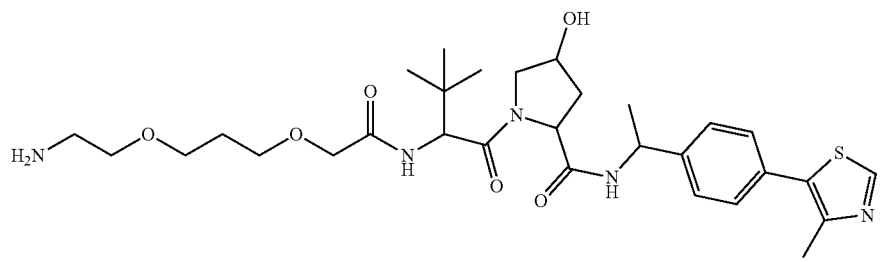 [SMILES: Cc1ncsc1-c1ccc(C(C)NC(=O)C2CC(O)CN2C(=O)C(NC(=O)COCCCOCCN)C(C)(C)C)cc1]
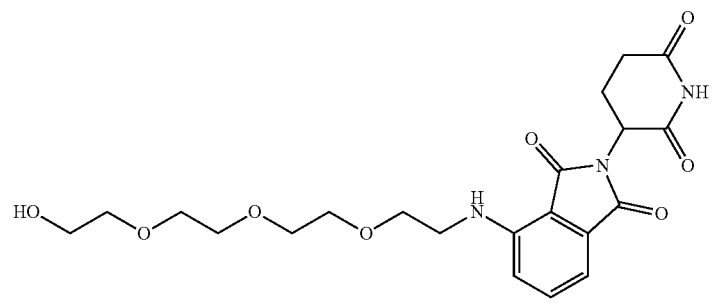 [SMILES: O=C1CCC(N2C(=O)c3cccc(NCCOCCOCCOCCO)c3C2=O)C(=O)N1]
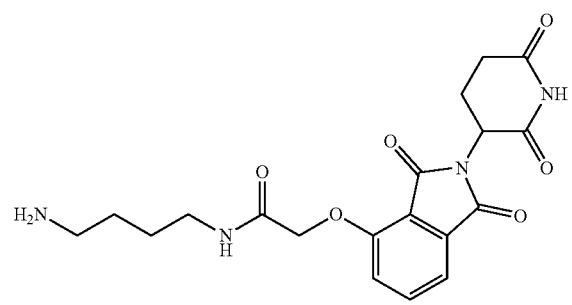 [SMILES: NCCCCNC(=O)COc1cccc2c1C(=O)N(C1CCC(=O)NC1=O)C2=O]
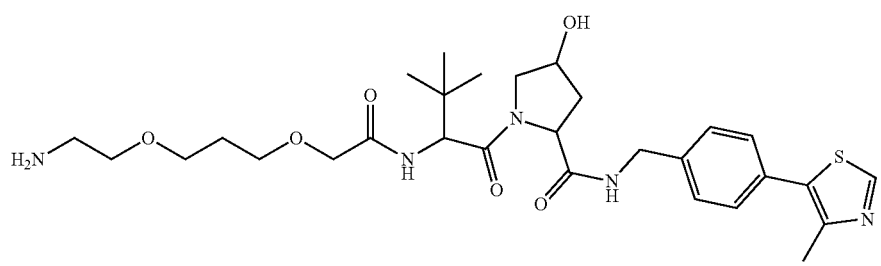 [SMILES: Cc1ncsc1-c1ccc(CNC(=O)C2CC(O)CN2C(=O)C(NC(=O)COCCCOCCN)C(C)(C)C)cc1]
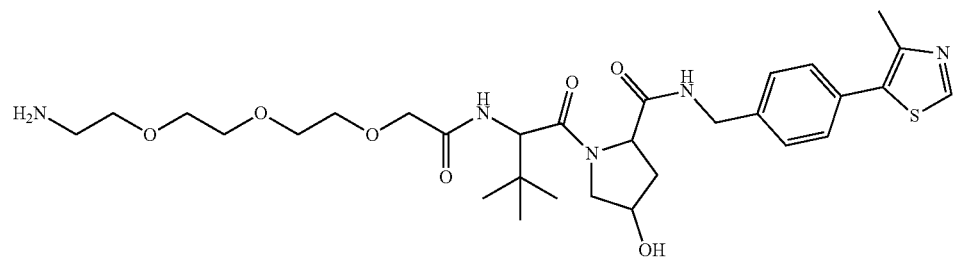 [SMILES: Cc1ncsc1-c1ccc(CNC(=O)C2CC(O)CN2C(=O)C(NC(=O)COCCOCCOCCN)C(C)(C)C)cc1]

TABLE 6-continued

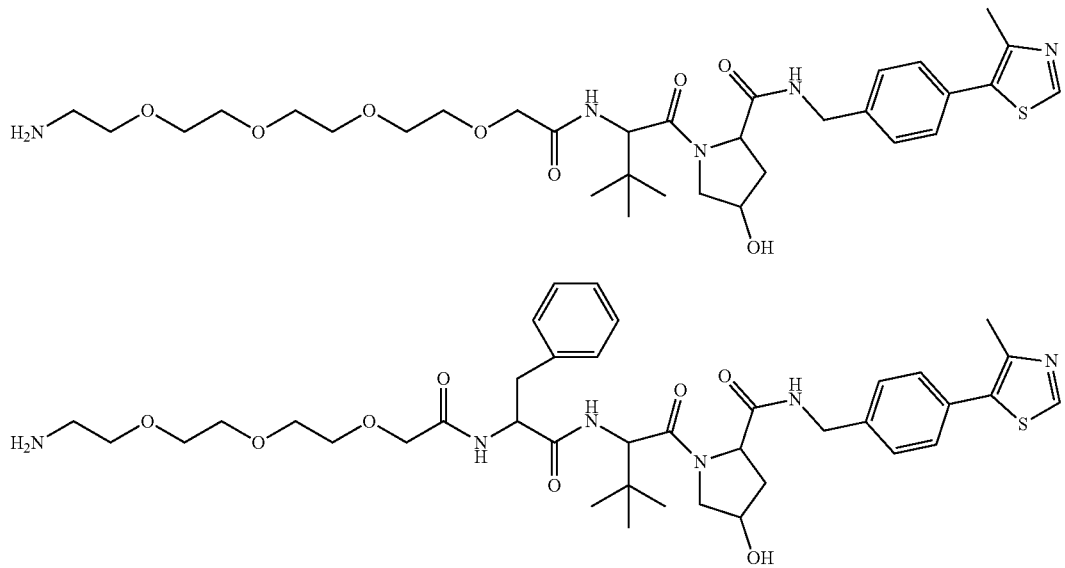

In another embodiment, Compounds of the Disclosure are compounds having Formula I, and the salts or solvates thereof, wherein X is —C≡C—.

In another embodiment, Compounds of the Disclosure are compounds having Formula I, and the salts or solvates thereof, wherein X is —N(H)—.

In another embodiment, Compounds of the Disclosure are compounds having Formula I, and the salts or solvates thereof, wherein X is —OC(=O)—.

In another embodiment, Compounds of the Disclosure are compounds having Formula I, and the salts or solvates thereof, wherein X is

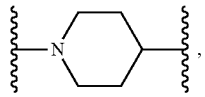

and the carbon atom of

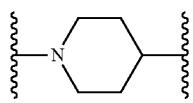

is attached to L.

In another embodiment, Compounds of the Disclosure are compounds having Formula I, and the salts or solvates thereof, wherein L is $C_{1-12}$ alkylenyl.

In another embodiment, Compounds of the Disclosure are compounds having Formula I, and the salts or solvates thereof, wherein L is selected from the group consisting of —CH$_2$—, —CH$_2$CH$_2$—, —CH$_2$CH$_2$CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, and —CH$_2$(CH$_2$)$_6$CH$_2$—.

In another embodiment, Compounds of the Disclosure are compounds having Formula I, and the salts or solvates thereof, wherein L is 3- to 12-membered heteroalkylenyl.

In another embodiment, Compounds of the Disclosure are compounds having Formula I, and the salts or solvates thereof, wherein:

L is —(CH$_2$)$_o$O—(CH$_2$CH$_2$O)$_p$—(CH$_2$)$_q$—;

o is 1, 2, or 3;

p is 0, 1, 2, 3, 4, or 5; and q is 1, 2, or 3.

In another embodiment, Compounds of the Disclosure are compounds having Formula I, and the salts or solvates thereof, wherein L is selected from the group consisting of

—CH$_2$OCH$_2$CH$_2$—

—CH$_2$CH$_2$OCH$_2$CH$_2$—,

—CH$_2$O(CH$_2$CH$_2$O)CH$_2$CH$_2$—

—CH$_2$O(CH$_2$CH$_2$O)$_2$CH$_2$CH$_2$—,

—CH$_2$O(CH$_2$CH$_2$O)$_3$CH$_2$CH$_2$—,

—CH$_2$CH$_2$O(CH$_2$CH$_2$O)$_6$CH$_2$CH$_2$—,

—CH$_2$CH$_2$O(CH$_2$CH$_2$O)$_6$CH$_2$CH$_2$—,

—CH$_2$CH$_2$CH$_2$OCH$_2$CH$_2$OCH$_2$CH$_2$CH$_2$—,

—CH$_2$CH$_2$CH$_2$O(CH$_2$CH$_2$O)$_2$CH$_2$CH$_2$CH$_2$—, and

—CH$_2$CH$_2$CH$_2$O(CH$_2$)$_4$OCH$_2$CH$_2$CH$_2$—.

In another embodiment, Compounds of the Disclosure are compounds having Formula I, and the salts or solvates thereof, wherein L is -A-(CH$_2$)$_m$—W—(CH$_2$)$_n$— and A is absent.

In another embodiment, Compounds of the Disclosure are compounds having Formula I, and the salts or solvates thereof, wherein L is -A-(CH$_2$)$_m$—W—(CH$_2$)$_n$—, A is absent, and W is phenylenyl. In another embodiment, m is 0.

In another embodiment, Compounds of the Disclosure are compounds having Formula I, and the salts or solvates thereof, wherein L is selected from the group consisting of:

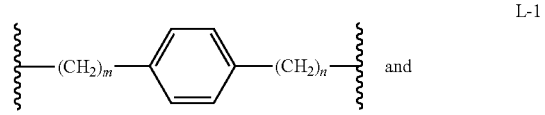

L-1 and

-continued

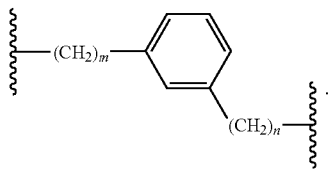
L-2

In another embodiment, Compounds of the Disclosure are compounds having Formula I, and the salts or solvates thereof, wherein L is -A-(CH$_2$)$_m$—W—(CH$_2$)$_n$—, A is absent, and W is 5-membered heteroarylenyl. In another embodiment, m is 0.

In another embodiment, Compounds of the Disclosure are compounds having Formula I, and the salts or solvates thereof, wherein:

L is selected from the group consisting of:

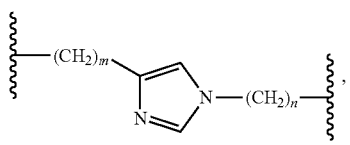
L-3

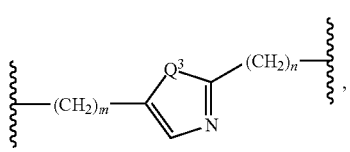
L-4

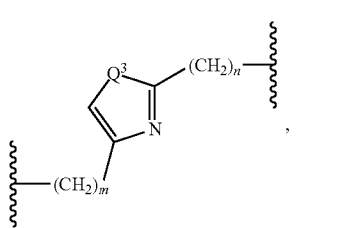
L-5

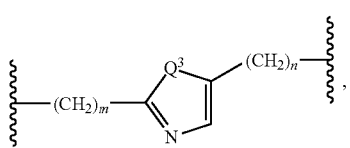
L-6

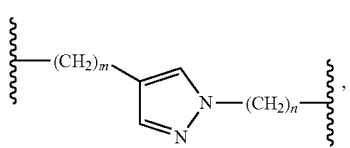
L-7

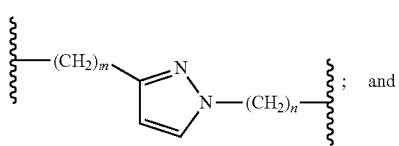
L-8

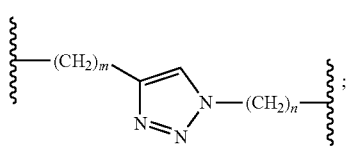
L-9

Q$^3$ is selected from the group consisting of —O—, —S—, and —N(R$^6$)—; and

R$^6$ is selected from the group consisting of hydrogen and C$_{1-4}$ alkyl.

In another embodiment, Compounds of the Disclosure are compounds having Formula I, and the salts or solvates thereof, wherein L is -A-(CH$_2$)$_m$—W—(CH$_2$)$_n$—, A is absent, and W is 6-membered heteroarylenyl. In another embodiment, m is 0.

In another embodiment, Compounds of the Disclosure are compounds having Formula I, and the salts or solvates thereof, wherein L is selected from the group consisting of:

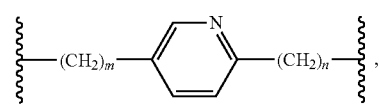
L-10

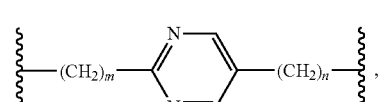
L-11

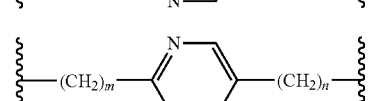
L-12 and

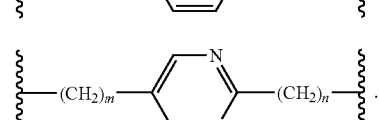
L-13

In another embodiment, Compounds of the Disclosure are compounds having Formula I, and the salts or solvates thereof, wherein L is -A-(CH$_2$)$_m$—W—(CH$_2$)$_n$—, A is absent, and W is heterocyclenyl. In another embodiment, m is 0.

In another embodiment, Compounds of the Disclosure are compounds having Formula I, and the salts or solvates thereof, wherein L is selected from the group consisting of:

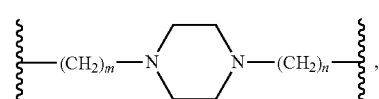
L-14

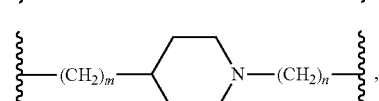
L-15

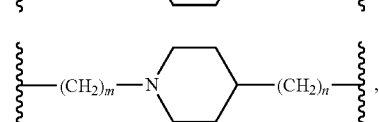
L-16

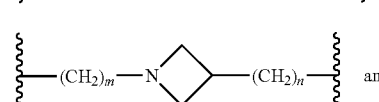
L-17 and

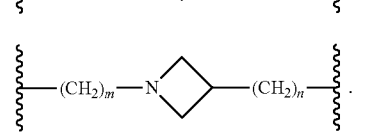
L-18

In another embodiment, Compounds of the Disclosure are compounds having Formula I, and the salts or solvates thereof, wherein L is -A-$(CH_2)_m$—W—$(CH_2)_n$—, A is absent, and W is cycloalkylenyl. In another embodiment, m is 0.

In another embodiment, Compounds of the Disclosure are compounds having Formula I, and the salts or solvates thereof, wherein L is selected from the group consisting of:

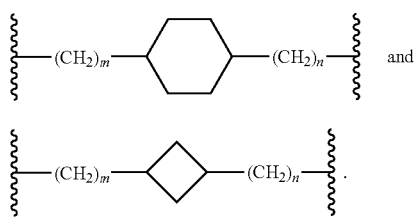

L-19 and

L-20

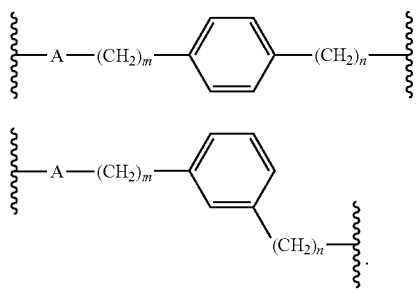

In another embodiment, Compounds of the Disclosure are compounds having Formula I, and the salts or solvates thereof, wherein:

L is -A-$(CH_2)_m$—W—$(CH_2)_n$—; and

A is selected from the group consisting of 5-membered heteroarylenyl and 6-membered heteroarylenyl.

In another embodiment, Compounds of the Disclosure are compounds having Formula I, and the salts or solvates thereof, wherein L is -A-$(CH_2)_m$—W—$(CH_2)_n$— and W is phenylenyl.

In another embodiment, Compounds of the Disclosure are compounds having Formula I, and the salts or solvates thereof, wherein L is selected from the group consisting of:

L-21 and

L-22

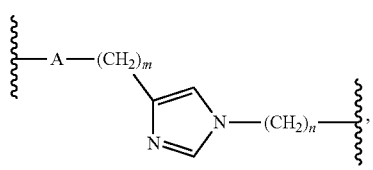

In another embodiment, Compounds of the Disclosure are compounds having Formula I, and the salts or solvates thereof, wherein L is -A-$(CH_2)_m$—W—$(CH_2)_n$— and W is 5-membered heteroarylenyl.

In another embodiment, Compounds of the Disclosure are compounds having Formula I, and the salts or solvates thereof, wherein L is selected from the group consisting of:

L-23

L-24

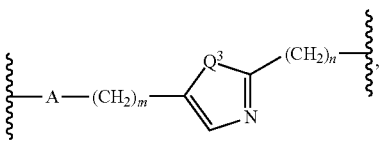

L-25

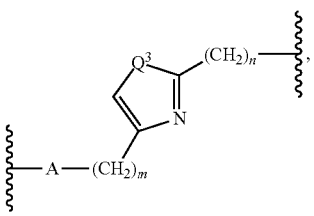

L-26

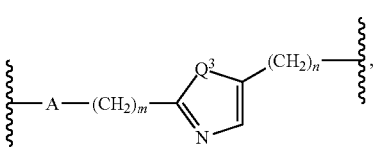

L-27

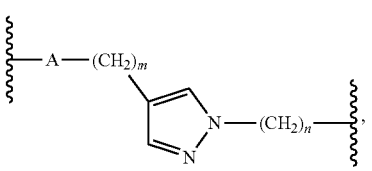

L-28

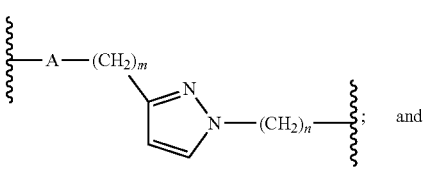

and

L-29

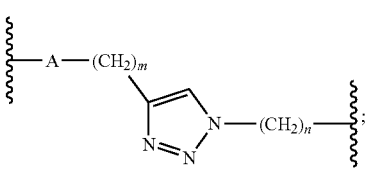

$Q^3$ is selected from the group consisting of —O—, —S—, and —N($R^6$)—; and $R^6$ is selected from the group consisting of hydrogen and $C_{1-4}$ alkyl.

In another embodiment, Compounds of the Disclosure are compounds having Formula I, and the salts or solvates thereof, wherein L is -A-$(CH_2)_m$—W—$(CH_2)_n$— and W is 6-membered heteroarylenyl.

In another embodiment, Compounds of the Disclosure are compounds having Formula I, and the salts or solvates thereof, wherein L is selected from the group consisting of:

L-30

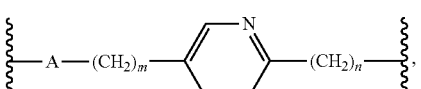

L-31

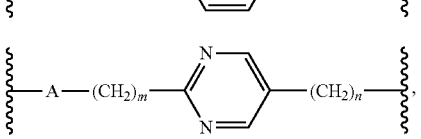

-continued

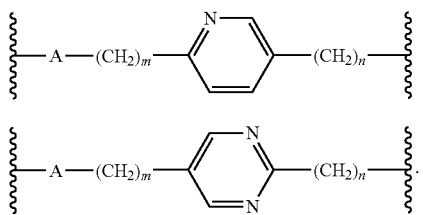

L-32

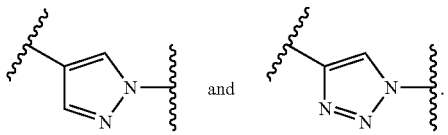 [SMILES: *c1cnn(*)c1 ; *c1cn(*)nn1]

L-33

In another embodiment, Compounds of the Disclosure are compounds having Formula I, and the salts or solvates thereof, wherein L is -A-(CH$_2$)$_m$—W—(CH$_2$)$_n$— and W is heterocyclenyl.

In another embodiment, Compounds of the Disclosure are compounds having Formula I, and the salts or solvates thereof, wherein L is selected from the group consisting of:

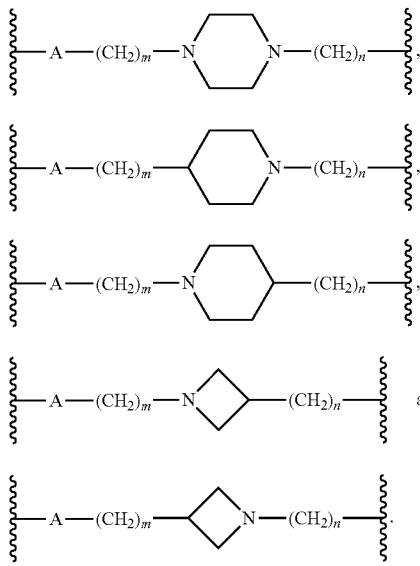

L-34

L-35

L-36

L-37 and

L-38

In another embodiment, Compounds of the Disclosure are compounds having Formula I, and the salts or solvates thereof, wherein L is -A-(CH$_2$)$_m$—W—(CH$_2$)$_n$— and W is cycloalkylenyl.

In another embodiment, Compounds of the Disclosure are compounds having Formula I, and the salts or solvates thereof, wherein L is selected from the group consisting of:

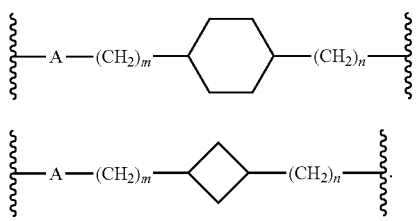

L-39 and

L-40

In another embodiment, Compounds of the Disclosure are compounds having Formula I, and the salts or solvates thereof, wherein L is -A-(CH$_2$)$_m$—W—(CH$_2$)$_n$— and A is a 5-membered heteroarylenyl. In another embodiment, A is a 5-membered heteroarylenyl selected from the group consisting of:

and

In another embodiment, Compounds of the Disclosure are compounds having Formula I, and the salts or solvates thereof, wherein L is -A-(CH$_2$)$_m$—W—(CH$_2$)$_n$— and A is a 6-membered heteroarylenyl. In another embodiment, A is:

In another embodiment, Compounds of the Disclosure are compounds having Formula I, and the salts or solvates thereof, wherein:
L is —(CH$_2$)$_r$—W—(CH$_2$)$_u$—O—(CH$_2$)$_v$—;
r is 0, 1, or 2;
u is 1, 2, or 3; and
v is 1, 2, or 3.

In another embodiment, Compounds of the Disclosure are compounds having Formula I, and the salts or solvates thereof, wherein L is —(CH$_2$)$_r$—W—(CH$_2$)$_u$—O—(CH$_2$)$_v$— and W is selected from the group consisting of phenylenyl and heteroarylenyl. In another embodiment, W is 5-membered heteroarylenyl. In another embodiment, W is 6-membered heteroarylenyl.

In another embodiment, Compounds of the Disclosure are compounds having Formula I, and the salts or solvates thereof, wherein Y is selected from the group consisting of —C≡C—, —CH=CH—, —CH$_2$—, —O—, and —N(R$^{2c}$)—. In another embodiment, Y is —C≡C—. In another embodiment, Y is —CH$_2$—. In another embodiment, Y is —O—. In another embodiment, Y is —N(H)—. In another embodiment, Y is —CH=CH—.

In another embodiment, Compounds of the Disclosure are compounds having Formula I, and the salts or solvates thereof, wherein B is B-1a.

In another embodiment, Compounds of the Disclosure are compounds having Formula I, and the salts or solvates thereof, wherein:
B is B-1a;
A$^1$ is selected from the group consisting of —C(R$^{16a}$)= and —N=; and
R$^{16a}$ is selected from the group consisting of hydrogen and halo.

In another embodiment, Compounds of the Disclosure are compounds having Formula I, and the salts or solvates thereof, wherein:
B is B-1a;
A$^2$ is selected from the group consisting of —C(R$^{16b}$)= and —N=; and
R$^{16b}$ is selected from the group consisting of hydrogen and halo.

In another embodiment, Compounds of the Disclosure are compounds having Formula I, and the salts or solvates thereof, wherein:

B is B-1a;

A³ is selected from the group consisting of —C(R¹⁶ᶜ)═ and —N═; and

R¹⁶ᶜ is selected from the group consisting of hydrogen and halo.

In another embodiment, Compounds of the Disclosure are compounds having Formula I, and the salts or solvates thereof, wherein B is B-1a and Z is —CH₂—.

In another embodiment, Compounds of the Disclosure are compounds having Formula I, and the salts or solvates thereof, wherein B is B-1a and Z is —C(═O)—.

In another embodiment, Compounds of the Disclosure are compounds having Formula I, and the salts or solvates thereof, wherein B is B-1a and R⁵ is hydrogen.

In another embodiment, Compounds of the Disclosure are compounds having Formula I, and the salts or solvates thereof, wherein B is B-2.

In another embodiment, Compounds of the Disclosure are compounds having Formula I, and the salts or solvates thereof, wherein B-3.

In another embodiment, Compounds of the Disclosure are compounds having Formula I, and the salts or solvates thereof, wherein B is:

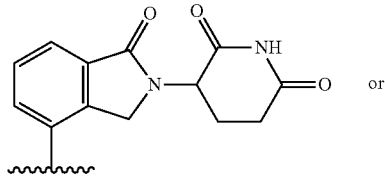

or

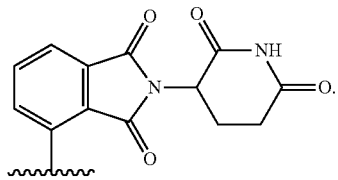

In another embodiment, Compounds of the Disclosure are compounds having Formula I, and the salts or solvates thereof, wherein embodiment, B is:

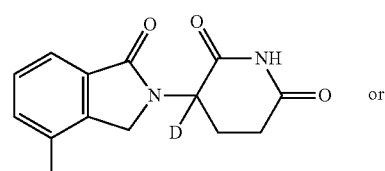

or

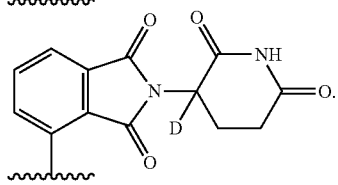

In another embodiment, Compounds of the Disclosure are compounds represented by Formula I, and the salts or solvates thereof, wherein:

B is selected from the group consisting of:

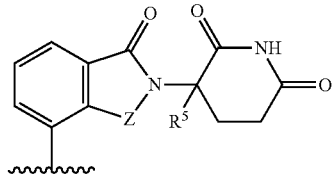

B-1

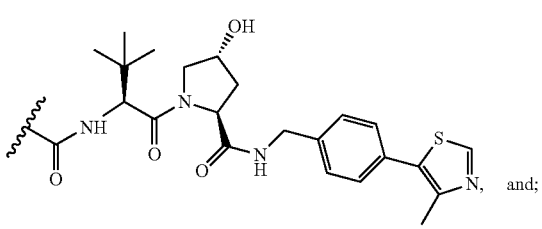

B-2

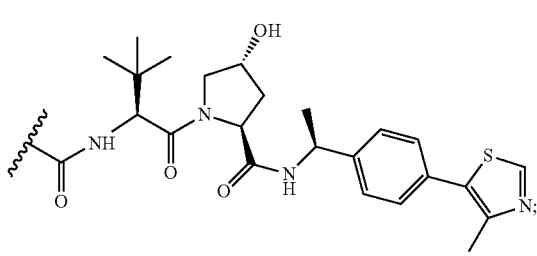

B-2a

X is selected from the group consisting of —N(R²ᵃ)—,

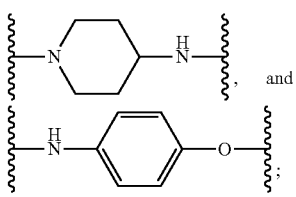

and or

X is absent;

wherein the —N(H)— of

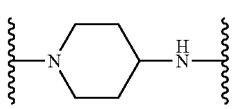

is attached to L and the —O— of

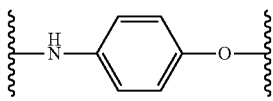

is attached to L;

L is selected from the group consisting of alkylenyl, heteroalkylenyl, and —(CH₂)ₘ—W—(CH₂)ₙ—;

W is selected from the group consisting of optionally substituted phenylenyl, optionally substituted 5-membered heteroarylenyl, and optionally substituted 6-membered heteroarylenyl;

m is 0, 1, 2, 3, 4, 5, 6, or 7;

n is 0, 1, 2, 3, 4, 5, 6, 7, or 8;

Y is selected from the group consisting of —C≡C—, —CH═CH—, —O—, —N($R^{2c}$)—, —C(═O)N($R^{2d}$)—, —N($R^{2e}$)C(═O)CH$_2$O—, and —N($R^{2e}$)C(═O)CH$_2$N($R^{2f}$)—; or Y is absent;

wherein the carboxamide nitrogen atom of —N($R^{2e}$)C(═O)CH$_2$O— and —N($R^{2e}$)C(═O)CH$_2$N($R^{2f}$)—, and the carbon atom of —C(═O)N($R^{2d}$)— is attached to L;

$R^{2c}$, $R^{2d}$, $R^{2e}$, and $R^{2f}$ are each independently selected from the group consisting of hydrogen and $C_{1-4}$ alkyl;

Z is selected from the group consisting of —CH$_2$— and —C(═O)—; and $R^5$ is selected from the group consisting of hydrogen, methyl, and fluoro, with the proviso that Y is absent when B is B-2.

In another embodiment, Compounds of the Disclosure are compounds represented by Formula I, and the salts or solvates thereof, wherein B is B-2a In another embodiment, Compounds of the Disclosure are compounds represented by Formula II:

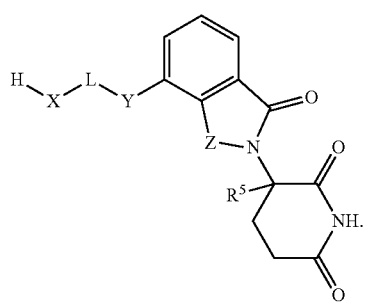

II and the pharmaceutically acceptable salts or solvates thereof, wherein X, L, Y, Z, and $R^5$ are as defined in connection with Formula I. In another embodiment, $R^5$ is hydrogen. In another embodiment, Z is —CH$_2$—. In another embodiment, Z is —C(═O)—. In another embodiment, Y is selected from the group consisting of —C≡C—, —O—, —N(H)—, —C(═O)N(H)—, —N(H)C(═O)CH$_2$O—, and —N(H)C(═O)CH$_2$N(H)—. In another embodiment, Y is selected from the group consisting of —C≡C—, —CH═CH—, —O—, and —N(H)—. In another embodiment, Y is absent. In another embodiment, Y is —C≡C—.

In another embodiment, Compounds of the Disclosure are compounds represented by Formula III:

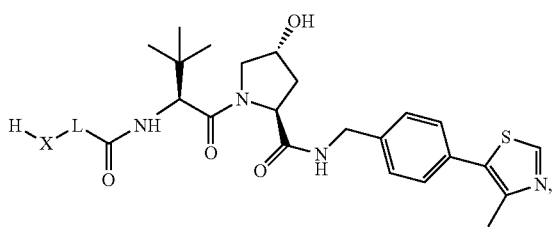

III and the pharmaceutically acceptable salts or solvates thereof, wherein X and L are as defined in connection with Formula I.

In another embodiment, Compounds of the Disclosure are compounds represented by Formula IIIa:

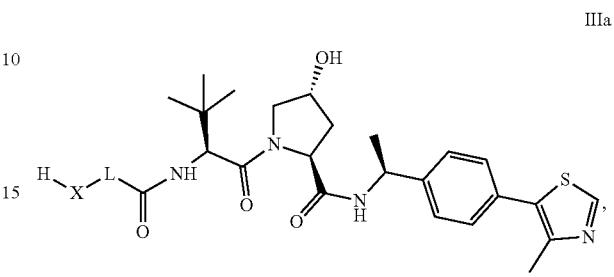

IIIa and the pharmaceutically acceptable salts or solvates thereof, wherein X and L are as defined in connection with Formula I.

In another embodiment, Compounds of the Disclosure are compounds represented by Formula IV:

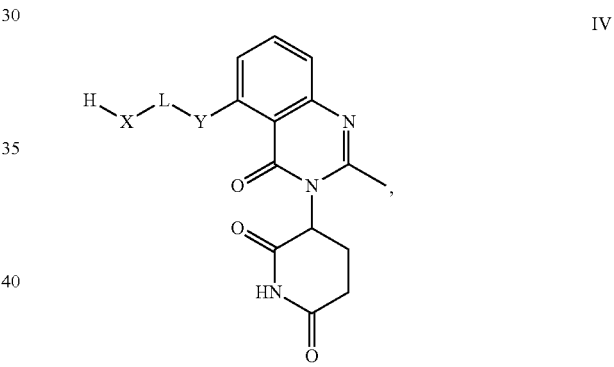

IV and the pharmaceutically acceptable salts or solvates thereof, wherein X, L, and Y are as defined in connection with Formula I. In another embodiment, Y is selected from the group consisting of —C≡C—, —CH═CH—, —O—, —N(H)—, —C(═O)N(H)—, —N(H)C(═O)CH$_2$O—, and —N(H)C(═O)CH$_2$N(H)—. In another embodiment, Y is selected from the group consisting of —C≡C—, —O—, and —N(H)—. In another embodiment, Y is absent. In another embodiment, Y is —C≡C—.

In another embodiment, Compounds of the Disclosure are compounds represented by Formula V:

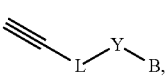

V and the salts or solvates thereof, wherein:
B is selected from the group consisting of:

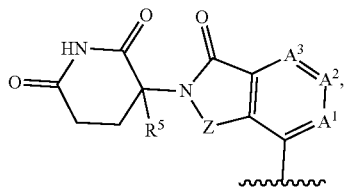

B-1a

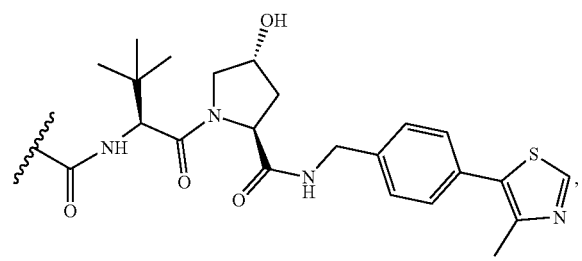

B-2

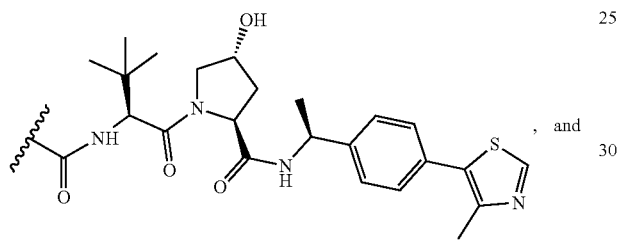

B-2a

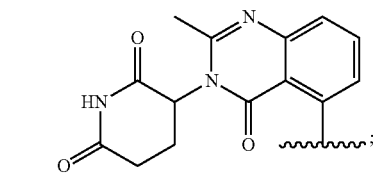

B-3

L is selected from the group consisting of alkylenyl, heteroalkylenyl, -A-$(CH_2)_m$—W—$(CH_2)_n$— and —$(CH_2)_m$—W—$(CH_2)_u$—O—$(CH_2)_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

Y is selected from the group consisting of —C≡C—, —CH=CH—, —$CH_2$—, —O—, —N($R^{2c}$)—, —C(=O)N($R^{2d}$)—, —N($R^{2e}$)C(=O)$CH_2$O—, and —N($R^{2e}$)C(=O)$CH_2$N($R^{2f}$)—; or Y is absent;

wherein the carboxamide nitrogen atom of —N($R^{2e}$)C(=O)$CH_2$O— and —N($R^{2e}$)C(=O)$CH_2$N($R^{2f}$)—, and the carbon atom of —C(=O)N($R^{2d}$)— is attached to L;

$R^{2c}$, $R^{2d}$, $R^{2e}$, and $R^{2f}$ are each independently selected from the group consisting of hydrogen and $C_{1-4}$ alkyl;

Z is selected from the group consisting of —$CH_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl.

In another embodiment, Compounds of the Disclosure are compounds represented by Formula VI:

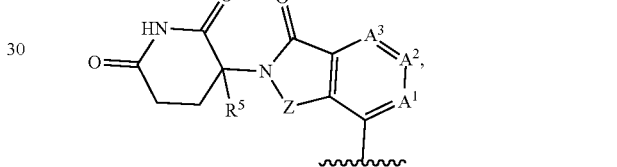

VI and the salts or solvates thereof, wherein:
B is selected from the group consisting of:

B-1a

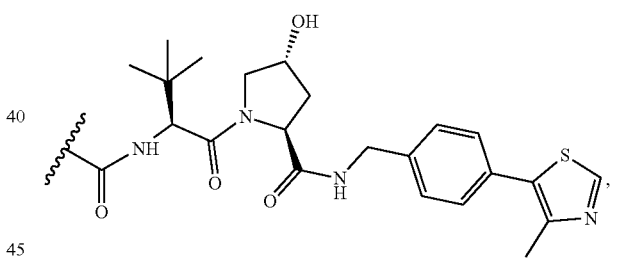

B-2

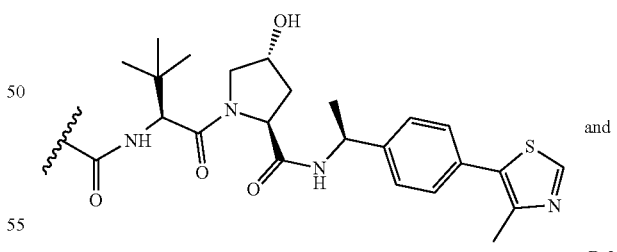

B-2a

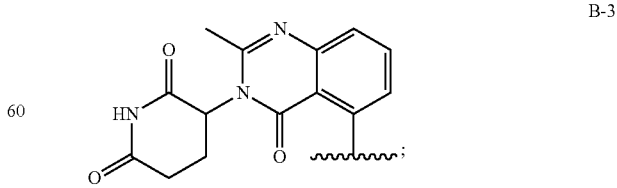

and

B-3

L is selected from the group consisting of alkylenyl, heteroalkylenyl, -A-$(CH_2)_m$—W—$(CH_2)_n$— and —$(CH_2)_m$—W—$(CH_2)_u$—O—$(CH_2)_v$—;

A is selected from the group consisting of 5-membered heteroarylenyl and 6-membered heteroarylenyl; or A is absent:

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

Y is selected from the group consisting of —C≡C—, —CH=CH—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or Y is absent;

wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;

R$^{2c}$, R$^{2d}$, R$^{2e}$, and R$^{2f}$ are each independently selected from the group consisting of hydrogen and C$_{1-4}$ alkyl;

Z is selected from the group consisting of —CH$_2$ and —C(=O)—;

R$^5$ is selected from the group consisting of hydrogen, methyl, and fluoro;

A$^1$ is selected from the group consisting of —C(R$^{16a}$)= and —N=;

A$^2$ is selected from the group consisting of —C(R$^{16b}$)= and —N=;

A$^3$ is selected from the group consisting of —C(R$^{16c}$)= and —N=;

R$^{16a}$ is selected from the group consisting of hydrogen, halo, and C$_{1-4}$ alkyl;

R$^{16b}$ is selected from the group consisting of hydrogen, halo, and C$_{1-4}$ alkyl; and R$^{16c}$ is selected from the group consisting of hydrogen, halo, and C$_{1-4}$ alkyl.

In another embodiment, Compounds of the Disclosure are compounds represented by Formula VIa:

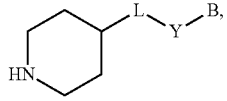

VIa and the salts or solvates thereof, wherein:

B is selected from the group consisting of:

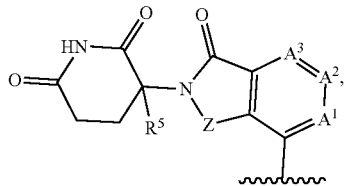

B-1a

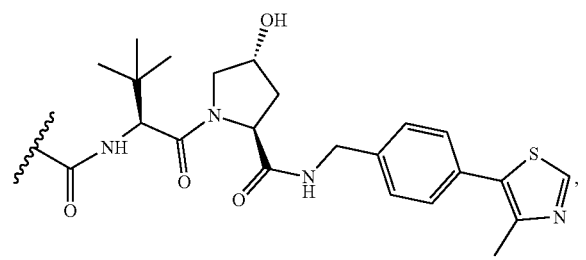

B-2

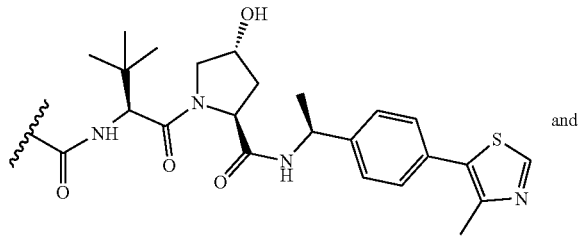

B-2a

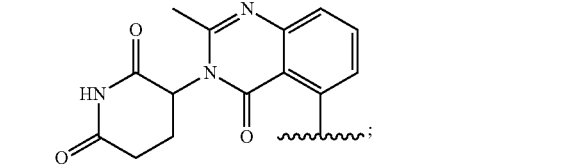

B-3

L is selected from the group consisting of alkylenyl, heteroalkylenyl, -A-(CH$_2$)$_m$—W—(CH$_2$)$_n$— and —(CH$_2$)$_m$—W—(CH$_2$)$_u$—O—(CH$_2$)$_v$—; or L is absent;

A is selected from the group consisting of 5-membered heteroarylenyl and 6-membered heteroarylenyl; or A is absent:

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

Y is selected from the group consisting of —C≡C—, —CH=CH—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;

R$^{2c}$, R$^{2d}$, R$^{2e}$, and R$^{2f}$ are each independently selected from the group consisting of hydrogen and C$_{1-4}$ alkyl;

Z is selected from the group consisting of —CH$_2$ and —C(=O)—;

R$^5$ is selected from the group consisting of hydrogen, methyl, and fluoro;

A$^1$ is selected from the group consisting of —C(R$^{16a}$)= and —N=;

A$^2$ is selected from the group consisting of —C(R$^{16b}$)= and —N=;

A$^3$ is selected from the group consisting of —C(R$^{16c}$)= and —N=;

R$^{16a}$ is selected from the group consisting of hydrogen, halo, and C$_{1-4}$ alkyl;

R$^{16b}$ is selected from the group consisting of hydrogen, halo, and C$_{1-4}$ alkyl; and R$^{16c}$ is selected from the group consisting of hydrogen, halo, and C$_{1-4}$ alkyl.

In another embodiment, Compounds of the Disclosure are compounds represented by Formula VIb:

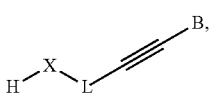

VIb and the salts or solvates thereof, wherein:

X is selected from the group consisting of —C≡C—, —O—, and —N(R$^{2a}$)—:

R$^{2a}$ is selected from the group consisting of hydrogen and C$_{1-4}$ alkyl;

B is selected from the group consisting of:

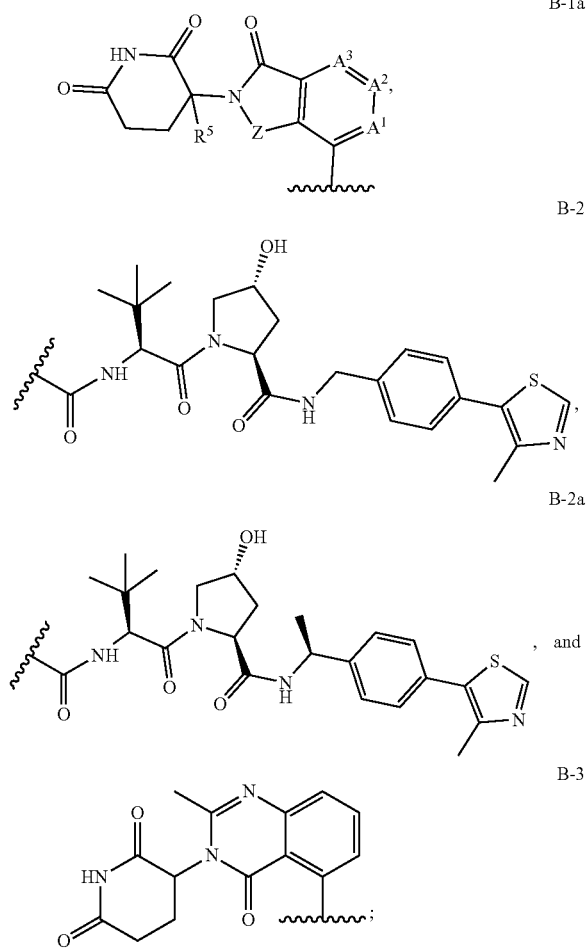

L is selected from the group consisting of alkylenyl, heteroalkylenyl, -A-(CH$_2$)$_m$—W—(CH$_2$)$_n$— and —(CH$_2$)$_m$—W—(CH$_2$)$_u$—O—(CH$_2$)$_v$—;

A is selected from the group consisting of 5-membered heteroarylenyl and 6-membered heteroarylenyl; or A is absent:

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;
n is 0, 1, 2, 3, 4, 5, 6, 7, or 8;
u is 0, 1, 2, or 3;
v is 1, 2, 3, or 4;

Z is selected from the group consisting of —CH$_2$ and —C(=O)—;

R$^5$ is selected from the group consisting of hydrogen, methyl, and fluoro;

A$^1$ is selected from the group consisting of —C(R$^{16a}$)═ and —N═;

A$^2$ is selected from the group consisting of —C(R$^{16b}$)═ and —N═;

A$^3$ is selected from the group consisting of —C(R$^{16c}$)═ and —N═;

R$^{16a}$ is selected from the group consisting of hydrogen, halo, and C$_{1-4}$ alkyl;

R$^{16b}$ is selected from the group consisting of hydrogen, halo, and C$_{1-4}$ alkyl; and R$^{16c}$ is selected from the group consisting of hydrogen, halo, and C$_{1-4}$ alkyl.

In another embodiment, Compounds of the Disclosure are compounds represented by any one of Formulae I-IV, and the pharmaceutically acceptable salts or solvates thereof, wherein X is selected from the group consisting of —N(H)—,

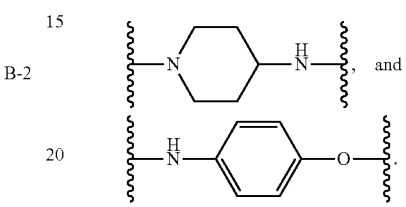

In another embodiment, Compounds of the Disclosure are compounds represented by any one of Formulae I-VI, VIa, or VIb, and the pharmaceutically acceptable salts or solvates thereof, wherein L is C$_{1-12}$ alkylenyl. In another embodiment, L is selected from the group consisting of —CH$_2$—, —CH$_2$CH$_2$—, —CH$_2$CH$_2$CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, and —CH$_2$(CH$_2$)$_6$CH$_2$—.

In another embodiment, Compounds of the Disclosure are compounds represented by any one of Formulae I-VI, VIa, or VIb, and the pharmaceutically acceptable salts or solvates thereof, wherein L is 3- to 20-membered heteroalkylenyl. In another embodiment, L is selected from the group consisting of —(CH$_2$)$_o$O—(CH$_2$CH$_2$O)$_p$—(CH$_2$)$_q$— and —(CH$_2$)$_r$O—(CH$_2$)$_s$—O(CH$_2$)$_t$—; wherein o is 2 or 3; p is 0, 1, 2, 3, 4, 5, 6, or 7; q is 2 or 3; r is 2, 3, or 4; s is 3, 4, or 5; and t is 2 or 3. In another embodiment, L is selected from the group consisting of
—CH$_2$CH$_2$OCH$_2$CH$_2$—,
—CH$_2$CH$_2$O(CH$_2$CH$_2$O)$_2$CH$_2$CH$_2$—,
—CH$_2$CH$_2$O(CH$_2$CH$_2$O)$_3$CH$_2$CH$_2$—,
—CH$_2$CH$_2$O(CH$_2$CH$_2$O)$_4$CH$_2$CH$_2$—,
—CH$_2$CH$_2$O(CH$_2$CH$_2$O)$_6$CH$_2$CH$_2$—,
—CH$_2$CH$_2$O(CH$_2$CH$_2$O)$_6$CH$_2$CH$_2$—,
—CH$_2$CH$_2$CH$_2$OCH$_2$CH$_2$OCH$_2$CH$_2$CH$_2$—,
—CH$_2$CH$_2$CH$_2$O(CH$_2$CH$_2$O)$_2$CH$_2$CH$_2$CH$_2$—, and
—CH$_2$CH$_2$CH$_2$O(CH$_2$)$_4$OCH$_2$CH$_2$CH$_2$—.

In another embodiment, Compounds of the Disclosure are compounds represented by any one of Formulae I-VI, VIa, or VIb, and the pharmaceutically acceptable salts or solvates thereof, wherein L is —(CH$_2$)$_m$—W—(CH$_2$)$_n$—. In another embodiment, W is phenylenyl. In another embodiment, W is 5-membered heteroarylenyl. In another embodiment, W is 6-membered heteroarylenyl.

In another embodiment, Compounds of the Disclosure are compounds represented by any one of Formulae I-VI, VIa, or VIb, and the pharmaceutically acceptable salts or solvates thereof, wherein L is selected from the group consisting of.

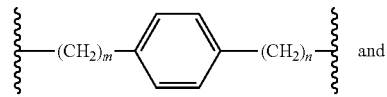

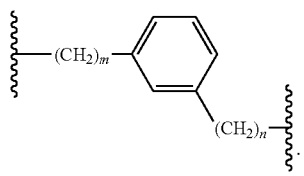

L-2

In another embodiment, Compounds of the Disclosure are compounds represented by any one of Formulae I-VI, VIa, or VIb, and the pharmaceutically acceptable salts or solvates thereof, wherein L is selected from the group consisting of:

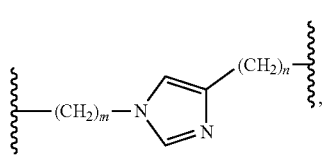

L-3

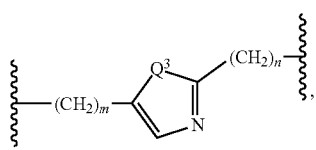

L-4

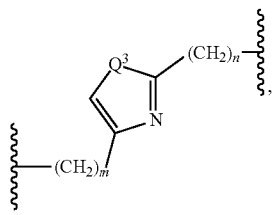

L-5

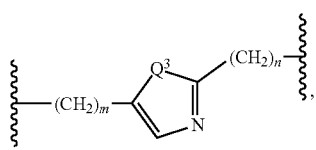

L-6

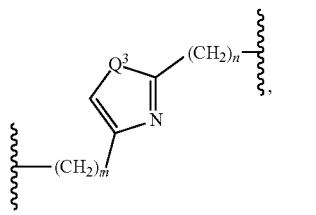

L-7 and $Q^3$ is selected from the group consisting of —O—, —S—, and —N($R^6$)—; and $R^6$ is selected from the group consisting of hydrogen and $C_{1-4}$ alkyl.

In another embodiment, Compounds of the Disclosure are compounds represented by any one of Formulae I-VI, VIa, or VIb, and the pharmaceutically acceptable salts or solvates thereof, wherein L is selected from the group consisting of:

L-10

L-11

In another embodiment, Compounds of the Disclosure are any one or more of the compounds of Table 1, and salts and solvates thereof.

TABLE 1

| Cpd. No. | Structure | Name |
|---|---|---|
| 1 | 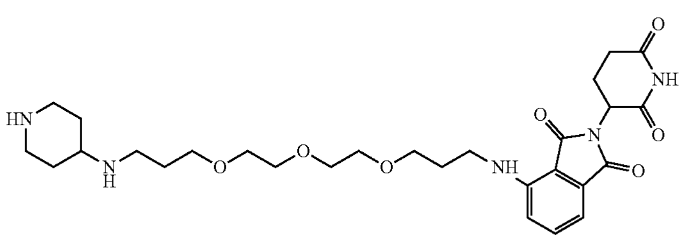 [SMILES: O=C1CCC(N2C(=O)c3cccc(NCCCOCCOCCOCCCNC4CCNCC4)c3C2=O)C(=O)N1] | 2-(2,6-dioxopiperidin-3-yl)-4-((3-(2-(2-(3-(piperidin-4-ylamino)propoxy)ethoxy)ethoxy)propyl)amino)isoindoline-1,3-dione |
| 2 | 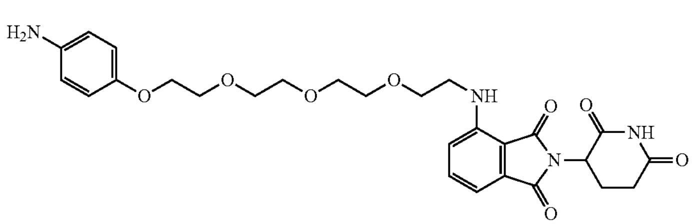 [SMILES: Nc1ccc(OCCOCCOCCOCCNc2cccc3c2C(=O)N(C2CCC(=O)NC2=O)C3=O)cc1] | 4-((2-(2-(2-(2-(4-aminophenoxy)ethoxy)ethoxy)ethoxy)ethyl)amino)-2-(2,6-dioxopiperidin-3-yl)isoindoline-1,3-dione |

TABLE 1-continued

| Cpd. No. | Structure | Name |
|---|---|---|
| 3 | 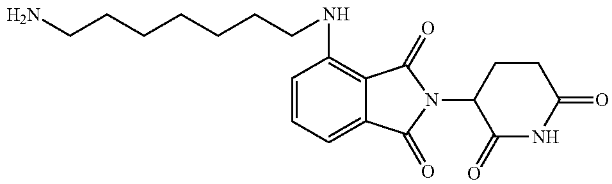 [SMILES: NCCCCCCCNc1cccc2c1C(=O)N(C1CCC(=O)NC1=O)C2=O] | 4-((7-aminoheptyl)amino)-2-(2,6-dioxopiperidin-3-yl)isoindoline-1,3-dione |
| 4 | 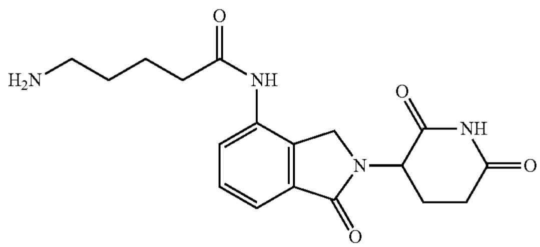 [SMILES: NCCCCC(=O)Nc1cccc2c1CN(C1CCC(=O)NC1=O)C2=O] | 5-amino-N-(2-(2,6-dioxopiperidin-3-yl)-1-oxoisoindolin-4-yl)pentanamide |
| 5 | 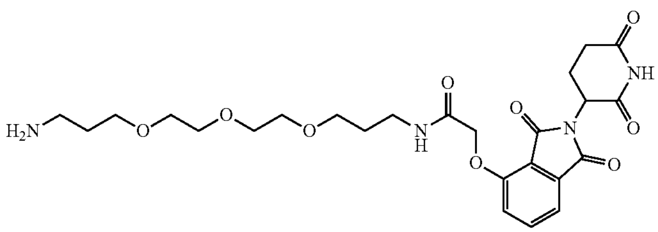 [SMILES: NCCCOCCOCCOCCCNC(=O)COc1cccc2c1C(=O)N(C1CCC(=O)NC1=O)C2=O] | N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide |
| 6 | 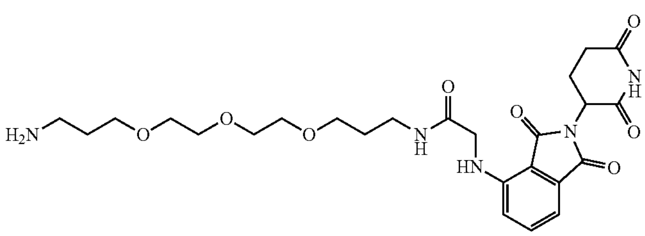 [SMILES: NCCCOCCOCCOCCCNC(=O)CNc1cccc2c1C(=O)N(C1CCC(=O)NC1=O)C2=O] | N-(3-(2-(2-(3-aminopropoxy)ethoxy)ethoxy)propyl)-2-((2-(2,6-dioxopiperidin-3-yl)-1,3-dioxoisoindolin-4-yl)amino)acetamide |
| 7 | 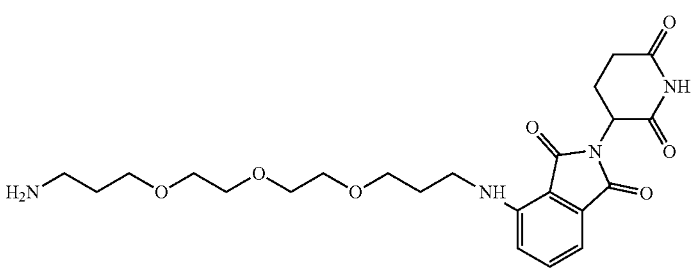 [SMILES: NCCCOCCOCCOCCCNc1cccc2c1C(=O)N(C1CCC(=O)NC1=O)C2=O] | 4-((3-(2-(2-(3-aminopropoxy)ethoxy)ethoxy)propyl)amino)-2-(2,6-dioxopiperidin-3-yl)isoindoline-1,3-dione |
| 8 | 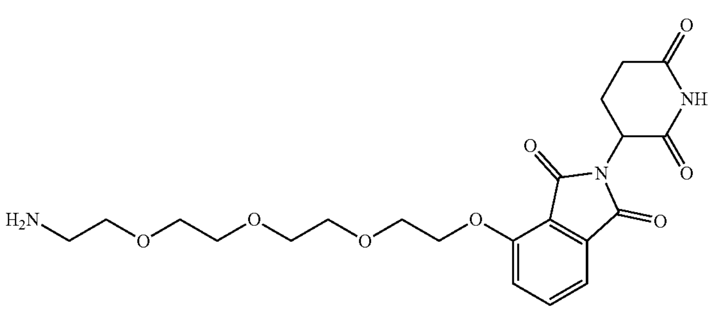 [SMILES: NCCOCCOCCOCCOc1cccc2c1C(=O)N(C1CCC(=O)NC1=O)C2=O] | 4-(2-(2-(2-(2-aminoethoxy)ethoxy)ethoxy)ethoxy)-2-(2,6-dioxopiperidin-3-yl)isoindoline-1,3-dione |

| Cpd. No. | Structure | Name |
|---|---|---|
| 9 | 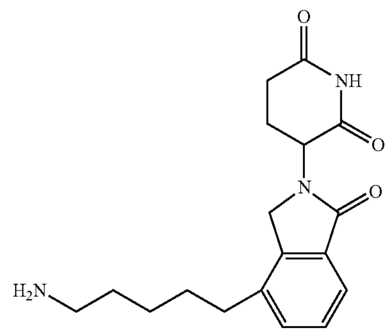 [SMILES: NCCCCCc1cccc2c1CN(C1CCC(=O)NC1=O)C2=O] | 3-(4-(5-aminopentyl)-1-oxoisoindolin-2-yl)piperidine-2,6-dione |
| 10 | 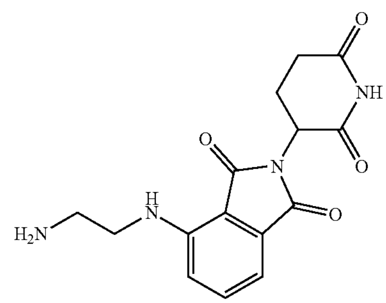 [SMILES: NCCNc1cccc2c1C(=O)N(C1CCC(=O)NC1=O)C2=O] | 3-(4-(5-aminopentyl)-1-oxoisoindolin-2-yl)piperidine-2,6-dione |
| 11 | 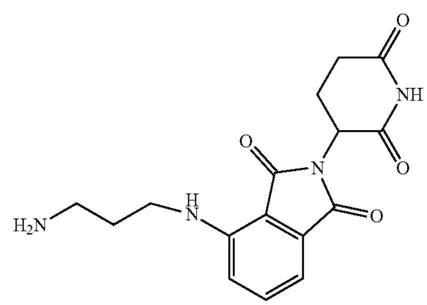 [SMILES: NCCCNc1cccc2c1C(=O)N(C1CCC(=O)NC1=O)C2=O] | 4-((3-aminopropyl)amino)-2-(2,6-dioxopiperidin-3-yl)isoindoline-1,3-dione |
| 12 | 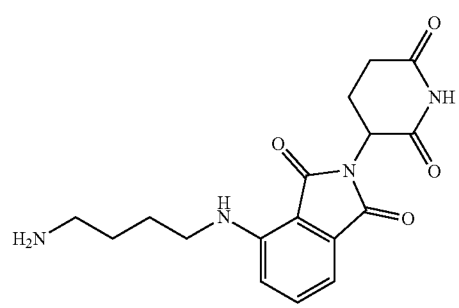 [SMILES: NCCCCNc1cccc2c1C(=O)N(C1CCC(=O)NC1=O)C2=O] | 4-((4-aminobutyl)amino)-2-(2,6-dioxopiperidin-3-yl)isoindoline-1,3-dione |
| 13 | 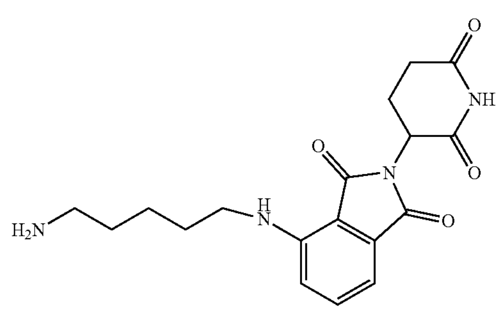 [SMILES: NCCCCCNc1cccc2c1C(=O)N(C1CCC(=O)NC1=O)C2=O] | 4-((5-aminopentyl)amino)-2-(2,6-dioxopiperidin-3-yl)isoindoline-1,3-dione |

TABLE 1-continued

| Cpd. No. | Structure | Name |
|---|---|---|
| 14 | 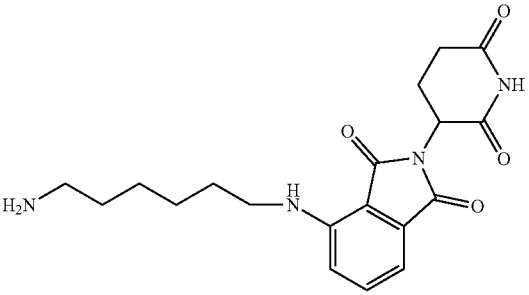 [SMILES: NCCCCCCNc1cccc2c1C(=O)N(C1CCC(=O)NC1=O)C2=O] | 4-((6-aminohexyl)amino)-2-(2,6-dioxopiperidin-3-yl)isoindoline-1,3-dione |
| 15 | 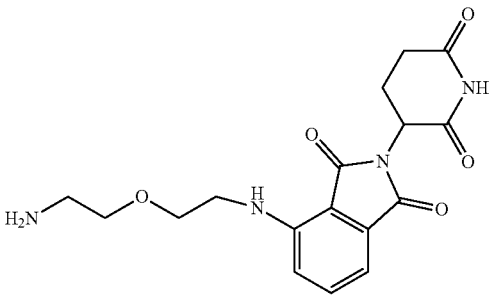 [SMILES: NCCOCCNc1cccc2c1C(=O)N(C1CCC(=O)NC1=O)C2=O] | 4-((2-(2-aminoethoxy)ethyl)amino)-2-(2,6-dioxopiperidin-3-yl)isoindoline-1,3-dione |
| 16 | 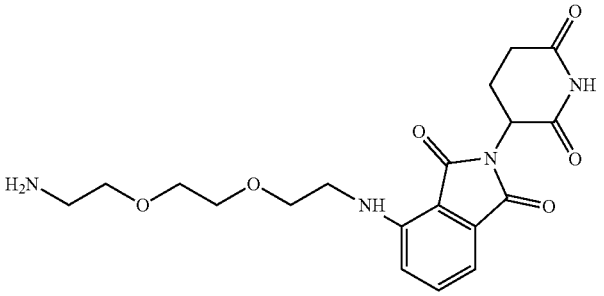 [SMILES: NCCOCCOCCNc1cccc2c1C(=O)N(C1CCC(=O)NC1=O)C2=O] | 4-((2-(2-(2-aminoethoxy)ethoxy)ethyl)amino)-2-(2,6-dioxopiperidin-3-yl)isoindoline-1,3-dione |
| 17 | 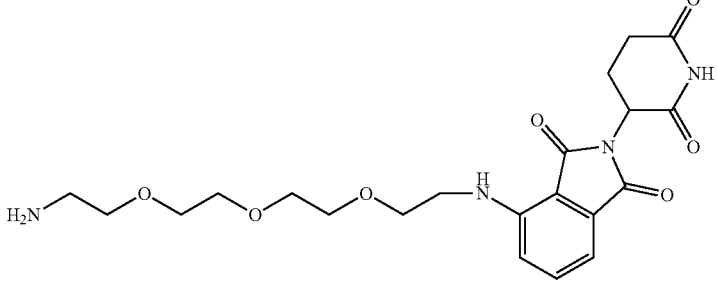 | 4-((2-(2-(2-(2-aminoethoxy)ethoxy)ethoxy)ethyl)amino)-2-(2,6-dioxopiperidin-3-yl)isoindoline-1,3-dione |
| 18 | 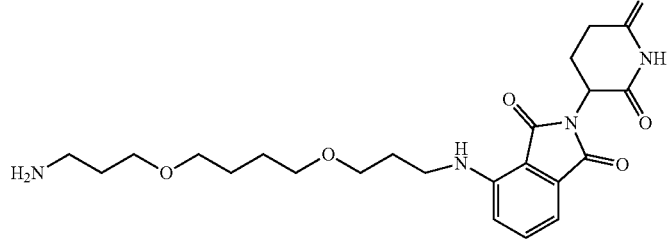 | 4-((3-(4-(3-aminopropoxy)butoxy)propyl)amino)-2-(2,6-dioxopiperidin-3-yl)isoindoline-1,3-dione |

TABLE 1-continued

| Cpd. No. | Structure | Name |
|---|---|---|
| 19 | 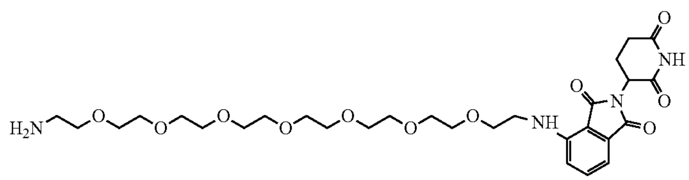 [SMILES: NCCOCCOCCOCCOCCOCCOCCOCCNc1cccc2c1C(=O)N(C1CCC(=O)NC1=O)C2=O] | 4-((23-amino-3,6,9,12,15,18,21-heptaoxatricosyl)amino)-2-(2,6-dioxopiperidin-3-yl)isoindoline-1,3-dione |
| 20 | 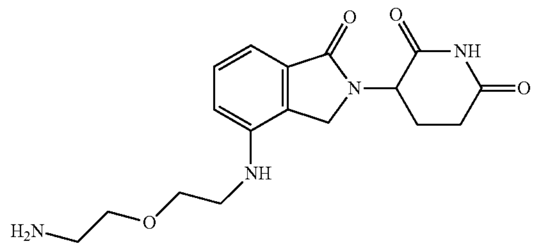 [SMILES: NCCOCCNc1cccc2c1CN(C1CCC(=O)NC1=O)C2=O] | 3-(4-((2-(2-aminoethoxy)ethyl)amino)-1-oxoisoindolin-2-yl)piperidine-2,6-dione |
| 21 | 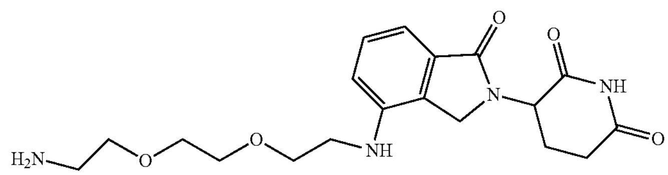 [SMILES: NCCOCCOCCNc1cccc2c1CN(C1CCC(=O)NC1=O)C2=O] | 3-(4-((2-(2-(2-aminoethoxy)ethoxy)ethyl)amino)-1-oxoisoindolin-2-yl)piperidine-2,6-dione |
| 22 | 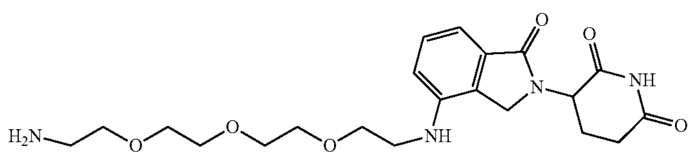 [SMILES: NCCOCCOCCOCCNc1cccc2c1CN(C1CCC(=O)NC1=O)C2=O] | 3-(4-((2-(2-(2-(2-aminoethoxy)ethoxy)ethoxy)ethyl)amino)-1-oxoisoindolin-2-yl)piperidine-2,6-dione |
| 23 | 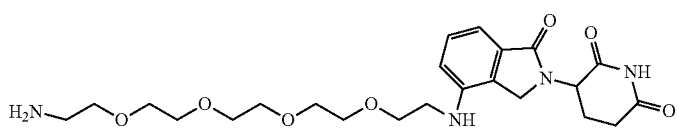 [SMILES: NCCOCCOCCOCCOCCNc1cccc2c1CN(C1CCC(=O)NC1=O)C2=O] | 3-(4-((14-amino-3,6,9,12-tetraoxatetradecyl)amino)-1-oxoisoindolin-2-yl)piperidine-2,6-dione |
| 24 | 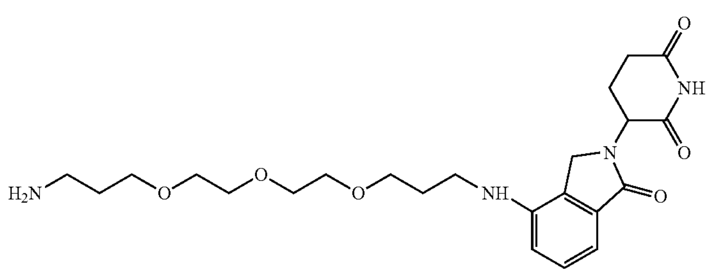 [SMILES: NCCCOCCOCCOCCCNc1cccc2c1CN(C1CCC(=O)NC1=O)C2=O] | 3-(4-((3-(2-(2-(3-aminopropoxy)ethoxy)ethoxy)propyl)amino)-1-oxoisoindolin-2-yl)piperidine-2,6-dione |
| 25 | 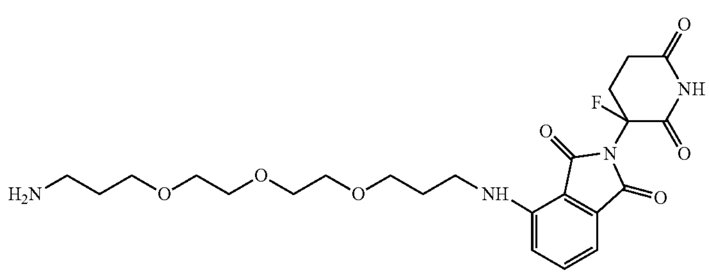 [SMILES: NCCCOCCOCCOCCCNc1cccc2c1C(=O)N(C1(F)CCC(=O)NC1=O)C2=O] | 4-((3-(2-(2-(3-aminopropoxy)ethoxy)ethoxy)propyl)amino)-2-(3-fluoro-2,6-dioxopiperidin-3-yl)isoindoline-1,3-dione |

TABLE 1-continued

| Cpd. No. | Structure | Name |
|---|---|---|
| 26 | 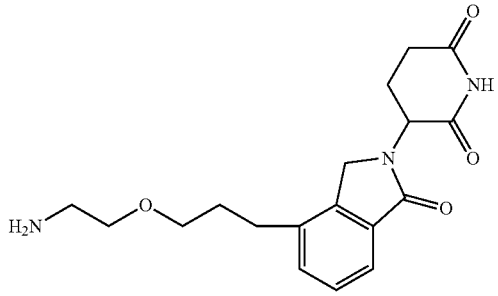 [SMILES: NCCOCCCc1cccc2c1CN(C1CCC(=O)NC1=O)C2=O] | 3-(4-(3-(2-aminoethoxy)propyl)-1-oxoisoindolin-2-yl)piperidine-2,6-dione |
| 27 | 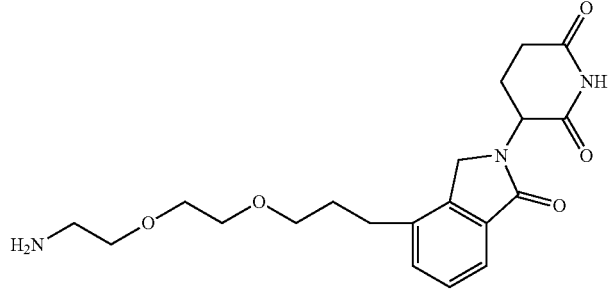 [SMILES: NCCOCCOCCCc1cccc2c1CN(C1CCC(=O)NC1=O)C2=O] | 3-(4-(3-(2-(2-aminoethoxy)ethoxy)propyl)-1-oxoisoindolin-2-yl)piperidine-2,6-dione |
| 28 | 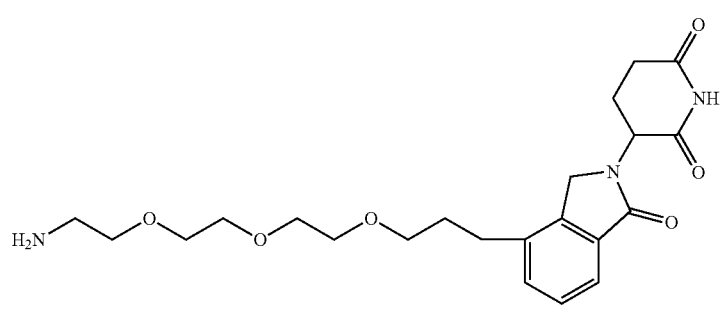 [SMILES: NCCOCCOCCOCCCc1cccc2c1CN(C1CCC(=O)NC1=O)C2=O] | 3-(4-(3-(2-(2-(2-aminoethoxy)ethoxy)ethoxy)propyl)-1-oxoisoindolin-2-yl)piperidine-2,6-dione |
| 29 | 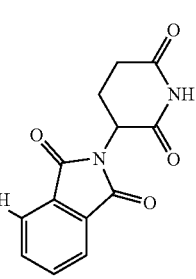 | 4-((4-(2-(2-(2-aminoethoxy)ethoxy)ethoxy)butyl)amino)-2-(2,6-dioxopiperidin-3-yl)isoindoline-1,3-dione |
| 30 | 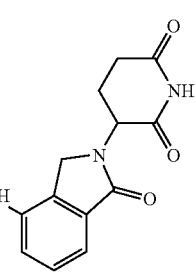 | 3-(4-((4-(2-(2-(2-aminoethoxy)ethoxy)ethoxy)butyl)amino)-1-oxoisoindolin-2-yl)piperidine-2,6-dione |

TABLE 1-continued

| Cpd. No. | Structure | Name |
|---|---|---|
| 31 | 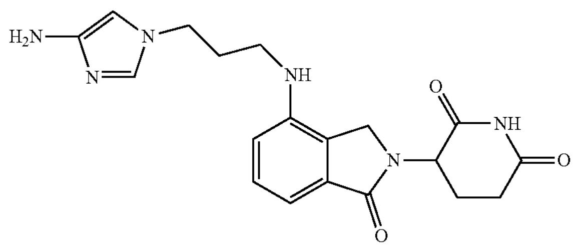 [SMILES: Nc1cn(CCCNc2cccc3c2CN(C2CCC(=O)NC2=O)C3=O)cn1] | 3-(4-((3-(4-amino-1H-imidazol-1-yl)propyl)amino)-1-oxoisoindolin-2-yl)piperidine-2,6-dione |
| 32 | 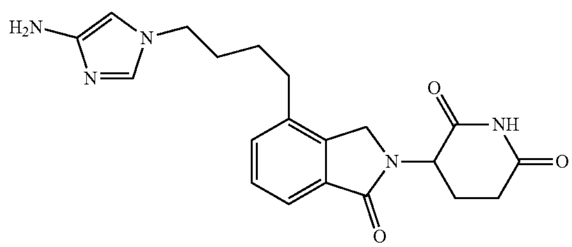 [SMILES: Nc1cn(CCCCc2cccc3c2CN(C2CCC(=O)NC2=O)C3=O)cn1] | 3-(4-(4-(4-amino-1H-imidazol-1-yl)butyl)-1-oxoisoindolin-2-yl)piperidine-2,6-dione |
| 33 | 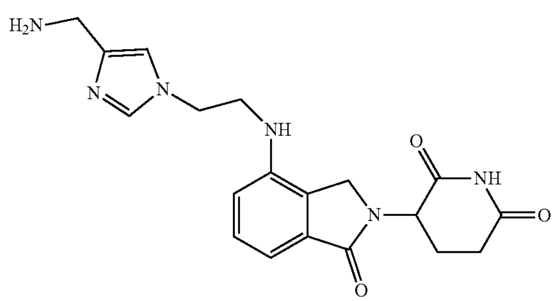 [SMILES: NCc1cn(CCNc2cccc3c2CN(C2CCC(=O)NC2=O)C3=O)cn1] | 3-(4-((2-(4-(aminomethyl)-1H-imidazol-1-yl)ethyl)amino)-1-oxoisoindolin-2-yl)piperidine-2,6-dione |
| 34 | 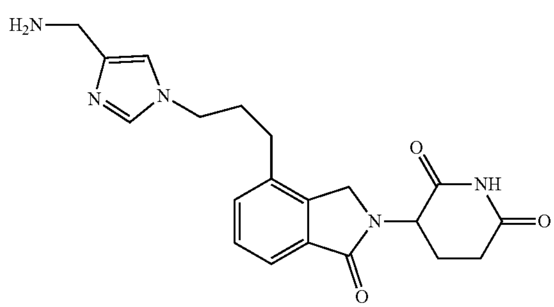 [SMILES: NCc1cn(CCCc2cccc3c2CN(C2CCC(=O)NC2=O)C3=O)cn1] | 3-(4-(3-(4-(aminomethyl)-1H-imidazol-1-yl)propyl)-1-oxoisoindolin-2-yl)piperidine-2,6-dione |
| 35 | 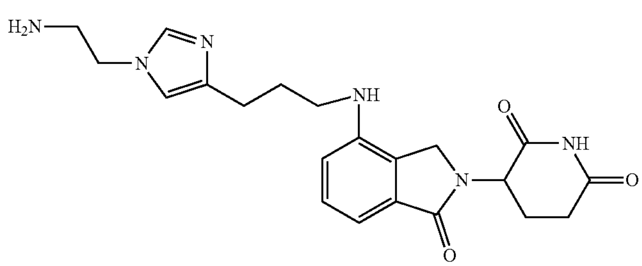 [SMILES: NCCn1cnc(CCCNc2cccc3c2CN(C2CCC(=O)NC2=O)C3=O)c1] | 3-(4-((3-(1-(2-aminoethyl)-1H-imidazol-4-yl)propyl)amino)-1-oxoisoindolin-2-yl)piperidine-2,6-dione |

TABLE 1-continued

| Cpd. No. | Structure | Name |
|---|---|---|
| 36 | 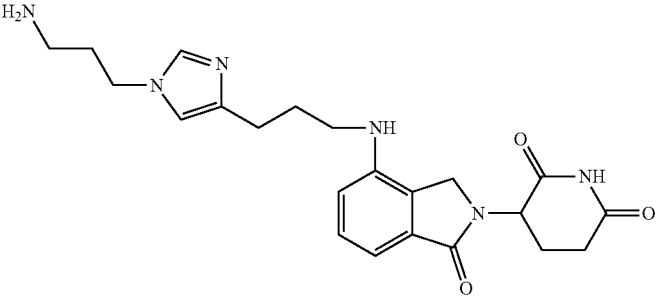 [SMILES: NCCCn1cnc(CCCNc2cccc3c2CN(C2CCC(=O)NC2=O)C3=O)c1] | 3-(4-((3-(1-(3-aininopropyl)-1H-imidazol-4-yl)propyl)amino)-1-oxoisoindolin-2-yl)piperidine-2,6-dione |
| 37 | 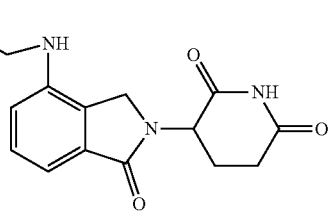 | 3-(4-((3-(4-(3-aminopropyl)-1H-imidazol-1-yl)propyl)amino)-1-oxoisoindolin-2-yl)piperidine-2,6-dione |
| 38 | 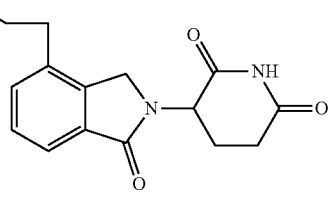 | 3-(4-(4-(4-(3-aminopropyl)-1H-imidazol-1-yl)butyl)-1-oxoisoindolin-2-yl)piperidine-2,6-dione |
| 39 | 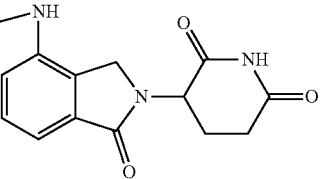 | 3-(4-((3-(5-(2-aminoethyl)-1H-imidazol-2-yl)propyl)amino)-1-oxoisoindolin-2-yl)piperidine-2,6-dione |
| 40 | 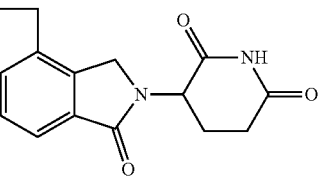 | 3-(4-(4-(5-(2-aminoethyl)-1H-imidazol-2-yl)butyl)-1-oxoisoindolin-2-yl)piperidine-2,6-dione |

TABLE 1-continued

| Cpd. No. | Structure | Name |
|---|---|---|
| 41 | 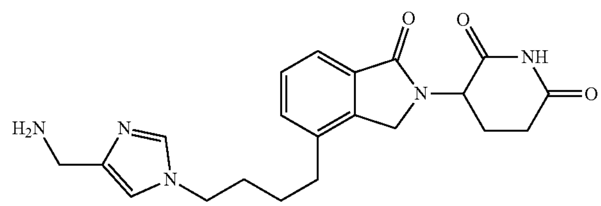 [SMILES: NCc1cn(CCCCc2cccc3c2CN(C2CCC(=O)NC2=O)C3=O)cn1] | 3-(4-(4-(4-aminomethyl)-1H-imidazol-1-yl)butyl)-1-oxoisoindolin-2-yl)piperidine-2,6-dione |
| 42 | 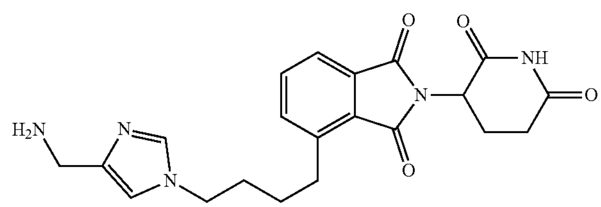 [SMILES: NCc1cn(CCCCc2cccc3c2C(=O)N(C2CCC(=O)NC2=O)C3=O)cn1] | 4-(4-(4-aminomethyl)-1H-imidazol-1-yl)butyl)-2-(2,6-dioxopiperidin-3-yl)isoindoline-1,3-dione |
| 43 | 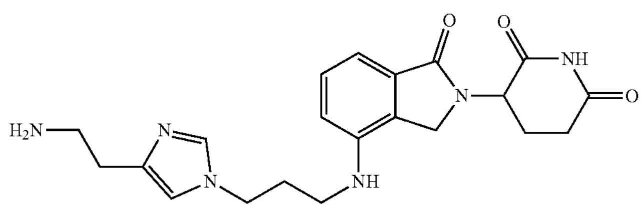 | 3-(4-((3-(4-(2-aminoethyl)-1H-imidazol-1-yl)propyl)amino)-1-oxoisoindolin-2-yl)piperidine-2,6-dione |
| 44 | 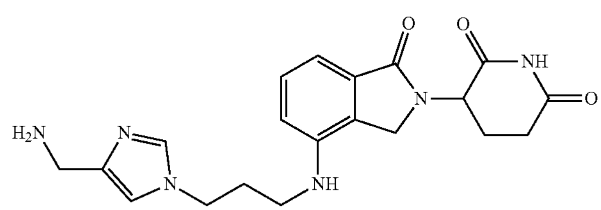 [SMILES: NCc1cn(CCCNc2cccc3c2CN(C2CCC(=O)NC2=O)C3=O)cn1] | 3-(4-((3-(4-(aminomethyl)-1H-imidazol-1-yl)propyl)amino)-1-oxoisoindolin-2-yl)piperidine-2,6-dione |
| 45 | 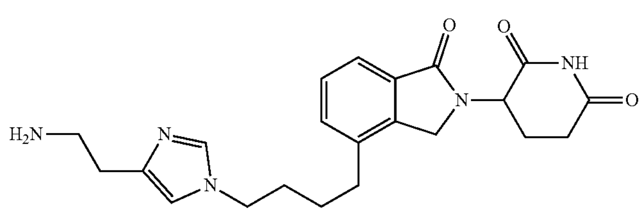 [SMILES: NCCc1cn(CCCCc2cccc3c2CN(C2CCC(=O)NC2=O)C3=O)cn1] | 3-(4-(4-(4-(2-aminoethyl)-1H-imidazol-1-yl)butyl)-1-oxoisoindolin-2-yl)piperidine-2,6-dione |
| 46 | 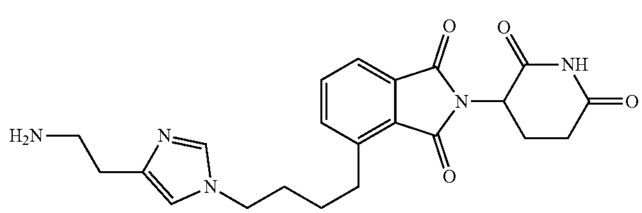 [SMILES: NCCc1cn(CCCCc2cccc3c2C(=O)N(C2CCC(=O)NC2=O)C3=O)cn1] | 4-(4-(4-(2-aminoethyl)-1H-imidazol-1-yl)butyl)-2-(2,6-dioxopiperidin-3-yl)isoindoline-1,3-dione |
| 47 | 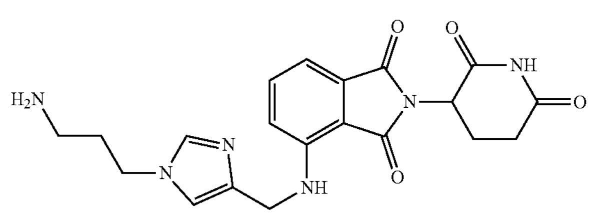 [SMILES: NCCCn1cnc(CNc2cccc3c2C(=O)N(C2CCC(=O)NC2=O)C3=O)c1] | 3-(4-(((1-(3-aminopropyl)-1H-imidazol-4-yl)methyl)amino)-1-oxoisoindolin-2-yl)piperidine-2,6-dione |

TABLE 1-continued

| Cpd. No. | Structure | Name |
|---|---|---|
| 48 | 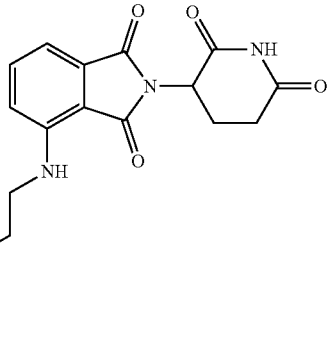 | 3-(4-((2-(4-(3-aminopropyl)-1H-imidazol-2-yl)ethyl)amino)-1-oxoisoindolin-2-yl)piperidine-2,6-dione |
| 49 | 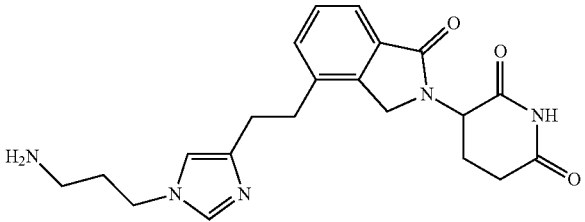 [SMILES: NCCCn1cnc(CCc2cccc3c2CN(C2CCC(=O)NC2=O)C3=O)c1] | 3-(4-(2-(1-(3-aminopropyl)-1H-imidazol-4-yl)ethyl)-1-oxoisoindolin-2-yl)piperidine-2,6-dione |
| 50 | 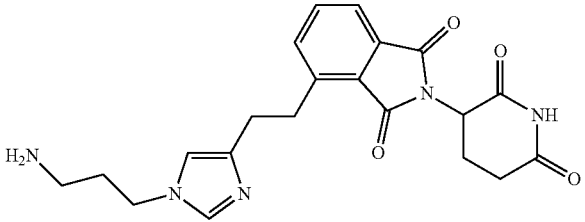 [SMILES: NCCCn1cnc(CCc2cccc3c2C(=O)N(C2CCC(=O)NC2=O)C3=O)c1] | 4-(2-(1-(3-aminopropyl)-1H-imidazol-4-yl)ethyl)-2-(2,6-dioxopiperidin-3-yl)isoindoline-1,3-dione |
| 51 | 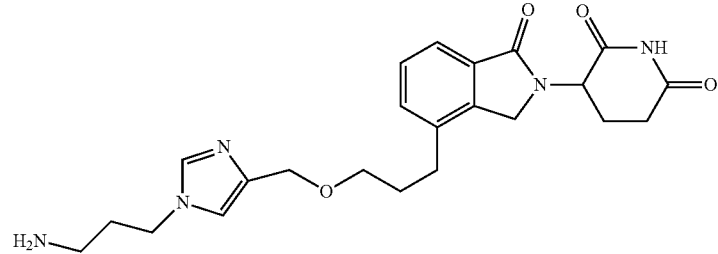 [SMILES: NCCCn1cnc(COCCCc2cccc3c2CN(C2CCC(=O)NC2=O)C3=O)c1] | 3-(4-(3-((1-(3-aminopropyl)-1H-imidazol-4-yl)methoxy)propyl)-1-oxoisoindolin-2-yl)piperidine-2,6-dione |
| 52 | 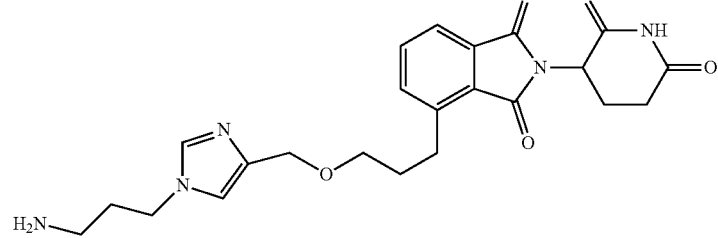 | 4-(3-((1-(3-aminopropy1)-1H-imidazol-4-yl)methoxy)propyl)-2-(2,6-dioxopiperidin-3-yl)isoindoline-1,3-dione |

TABLE 1-continued
| Cpd. No. | Structure | Name |
|---|---|---|
| 53 | 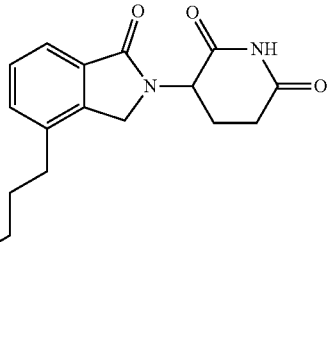 | 3-(4-(3-(4-(3-aminopropyl)-1H-imidazol-2-yl)propyl)-1-oxoisoindolin-2-yl)piperidine-2,6-dione |
| 54 | 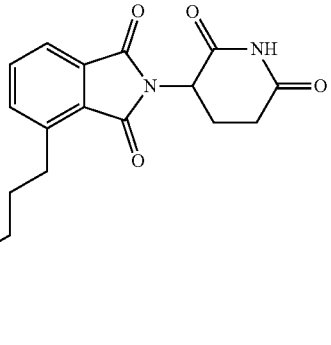 | 4-(3-(4-(3-aminopropyl)-1H-imidazol-2-yl)propyl)-2-(2,6-dioxopiperidin-3-yl)isoindoline-1,3-dione |
| 55 | 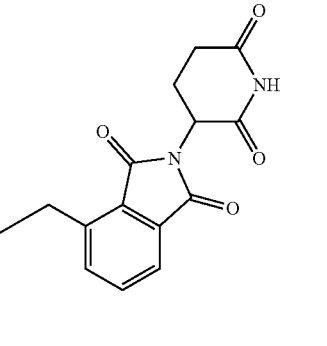 | 4-(5-aminopentyl)-2-(2,6-dioxopiperidin-3-yl)isoindoline-1,3-dione |
| 56 | 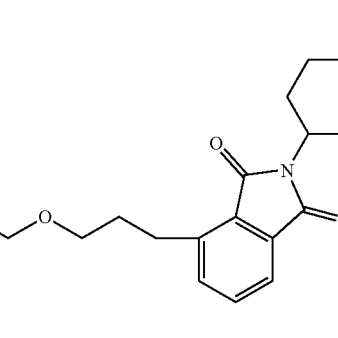 | 4-(3-(2-(2-(2-aminoethoxy)ethoxy)ethoxy)propyl)-2-(2,6-dioxopiperidin-3-yl)isoindoline-1,3-dione |

TABLE 1-continued

| Cpd. No. | Structure | Name |
|---|---|---|
| 57 | 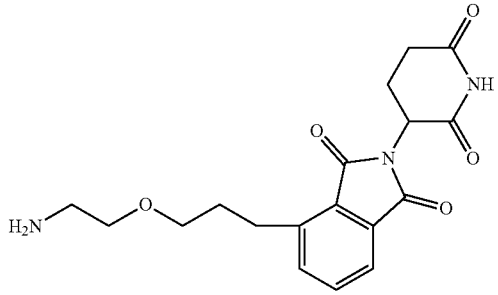 [SMILES: NCCOCCCc1cccc2c1C(=O)N(C1CCC(=O)NC1=O)C2=O] | 4-(3-(2-aminoethoxy)propyl)-2-(2,6-dioxopiperidin-3-yl)isoindoline-1,3-dione |
| 58 | 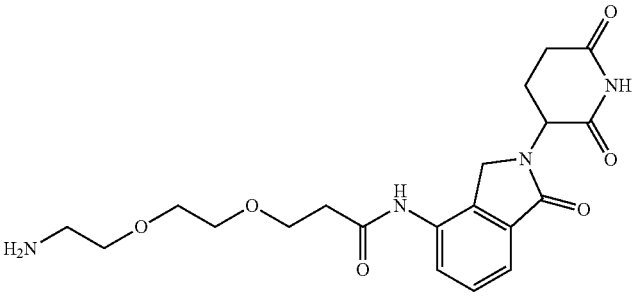 [SMILES: NCCOCCOCCC(=O)Nc1cccc2c1CN(C1CCC(=O)NC1=O)C2=O] | 3-(2-(2-aminoethoxy)ethoxy)-N-(2-(2,6-dioxopiperidin-3-yl)-1-oxoisoindolin-4-yl)propanamide |
| 59 | 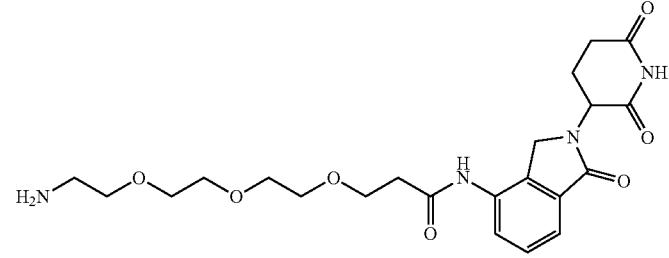 [SMILES: NCCOCCOCCOCCC(=O)Nc1cccc2c1CN(C1CCC(=O)NC1=O)C2=O] | 3-(2-(2-(2-aminoethoxy)ethoxy)ethoxy)-N-(2-(2,6-dioxopiperidin-3-yl)-1-oxoisoindolin-4-yl)propanamide |
| 60 | 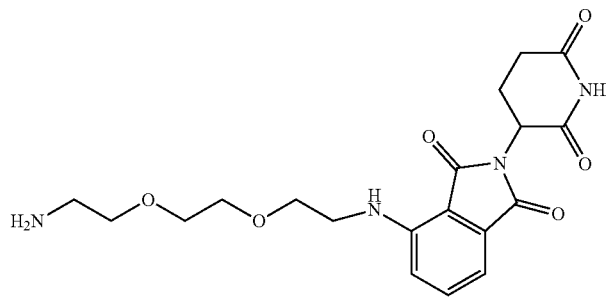 [SMILES: NCCOCCOCCNc1cccc2c1C(=O)N(C1CCC(=O)NC1=O)C2=O] | 4-((2-(2-(2-aminoethoxy)ethoxy)ethyl)amino)-2-(2,6-dioxopiperidin-3-yl)isoindoline-1,3-dione |
| 61 | 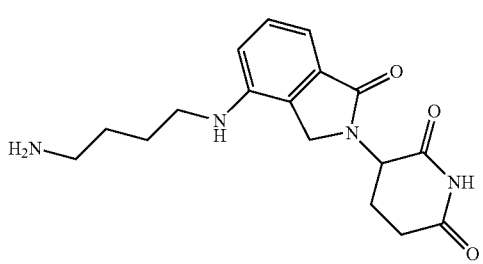 [SMILES: NCCCCNc1cccc2c1CN(C1CCC(=O)NC1=O)C2=O] | 3-(4-((4-aminobutyl)amino)-1-oxoisoindolin-2-yl)piperidine-2,6-dione |

TABLE 1-continued

| Cpd. No. | Structure | Name |
|---|---|---|
| 62 | 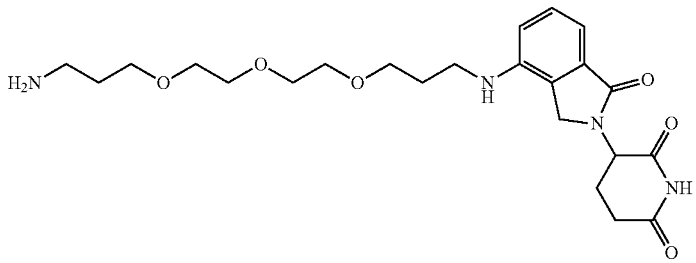 [SMILES: NCCCOCCOCCOCCCNc1cccc2c1CN(C1CCC(=O)NC1=O)C2=O] | 3-(4-((3-(2-(2-(3-aminopropoxy)ethoxy)ethoxy)propyl)amino)-1-oxoisoindolin-2-yl)piperidine-2,6-dione |
| 63 | 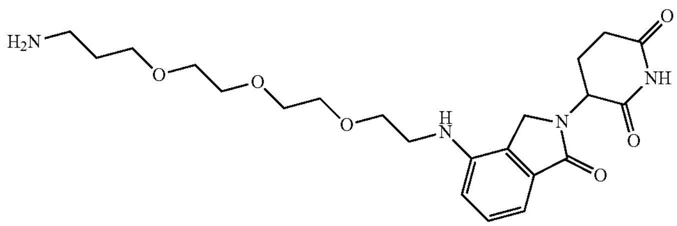 [SMILES: NCCCOCCOCCOCCNc1cccc2c1CN(C1CCC(=O)NC1=O)C2=O] | 3-(4-((2-(2-(2-(3-aminopropoxy)ethoxy)ethoxy)ethyl)amino)-1-oxoisoindolin-2-yl)piperidine-2,6-dione |
| 64 | 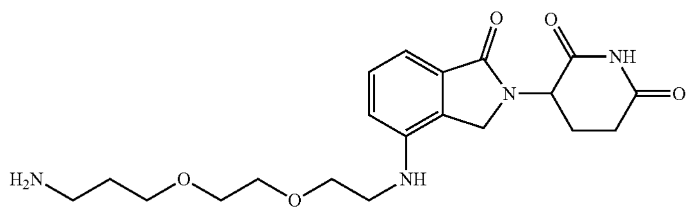 [SMILES: NCCCOCCOCCNc1cccc2c1CN(C1CCC(=O)NC1=O)C2=O] | 3-(4-((2-(2-(3-aminopropoxy)ethoxy)ethyl)amino)-1-oxoisoindolin-2-yl)piperidine-2,6-dione |
| 65 | 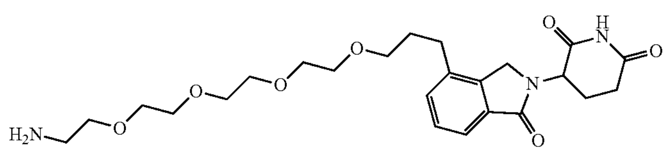 [SMILES: NCCOCCOCCOCCOCCCc1cccc2c1CN(C1CCC(=O)NC1=O)C2=O] | 3-(4-(1-amino-3,6,9,12-tetraoxapentadecan-15-yl)-1-oxoisoindolin-2-yl)piperidine-2,6-dione |
| 66 | 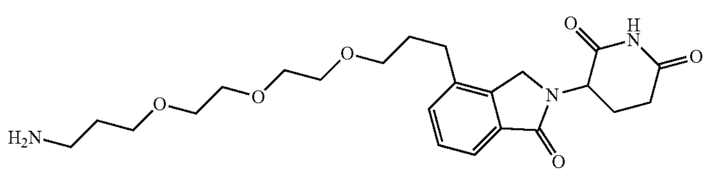 [SMILES: NCCCOCCOCCOCCCc1cccc2c1CN(C1CCC(=O)NC1=O)C2=O] | 3-(4-(3-(2-(2-(3-aminopropoxy)ethoxy)ethoxy)propyl)-1-oxoisoindolin-2-yl)piperidine-2,6-dione |
| 67 | 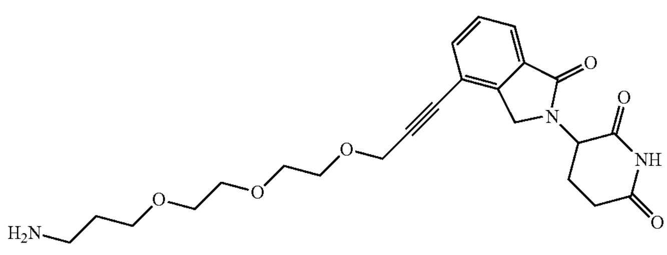 [SMILES: NCCCOCCOCCOCC#Cc1cccc2c1CN(C1CCC(=O)NC1=O)C2=O] | 3-(4-(3-(2-(2-(3-aminopropoxy)ethoxy)ethoxy)prop-1-yn-1-yl)-1-oxoisoindolin-2-yl)piperidine-2,6-dione |
| 68 | 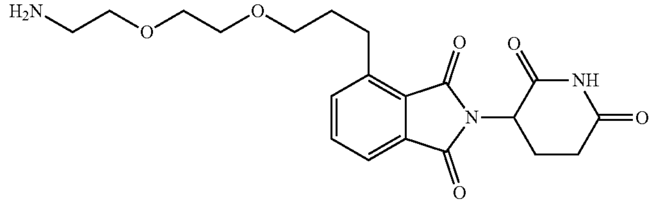 | 4-(3-(2-(2-aminoethoxy)ethoxy)propyl)-2-(2,6-dioxopiperidin-3-yl)isoindoline-1,3-dione |

TABLE 1-continued

| Cpd. No. | Structure | Name |
|---|---|---|
| 69 | 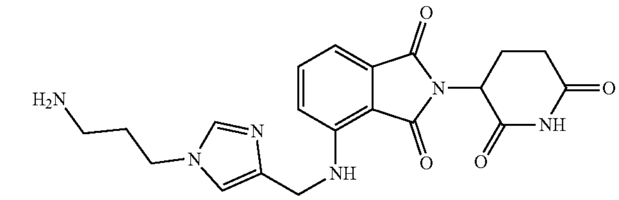 [SMILES: NCCCn1cnc(CNc2cccc3c2C(=O)N(C2CCC(=O)NC2=O)C3=O)c1] | 4-(((1-(3-aminopropyl)-1H-imidazol-4-yl)methyl)amino)-2-(2,6-dioxopiperidin-3-yl)isoindoline-1,3-dione |
| 70 | 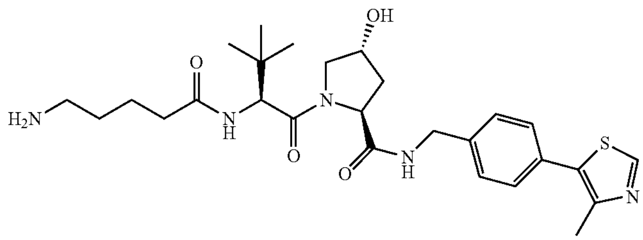 [SMILES: Cc1ncsc1-c1ccc(CNC(=O)[C@@H]2C[C@@H](O)CN2C(=O)[C@@H](NC(=O)CCCCN)C(C)(C)C)cc1] | (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide |
| 71 | 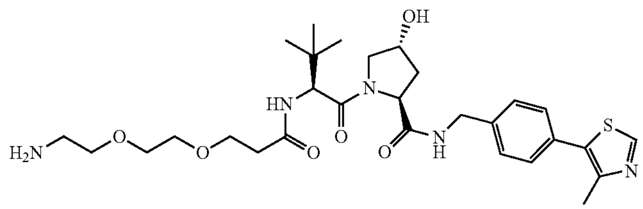 [SMILES: Cc1ncsc1-c1ccc(CNC(=O)[C@@H]2C[C@@H](O)CN2C(=O)[C@@H](NC(=O)CCOCCOCCN)C(C)(C)C)cc1] | (2S,4R)-1-((S)-2-(3-(2-(2-aminoethoxy)ethoxy)propanamido)-3,3-dimethylbutanoyl)-4-hydroxy-N-(4-(4-methylthiazol-5-yl)benzyl)pyrrolidine-2-carboxamide |
| 73 | 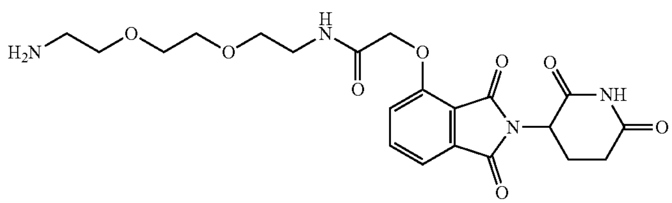 | N-(2-(2-(2-aminoethoxy)ethoxy)ethyl)-2-((2-(2,6-dioxopiperidin-3-yl)-1,3-dioxoisoindolin-4-yl)oxy)acetamide |

In another embodiment, Compounds of the Disclosure are any one or more of the compounds of Table 2, and salts and solvates thereof.

TABLE 2

| Cpd. No. | Structure | Name |
|---|---|---|
| 75 | 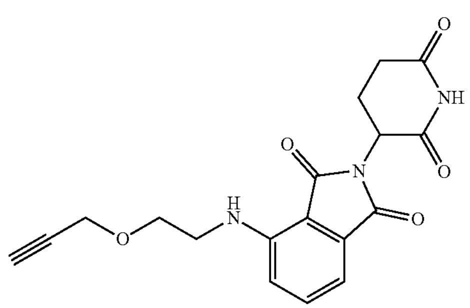 [SMILES: C#CCOCCNc1cccc2c1C(=O)N(C1CCC(=O)NC1=O)C2=O] | 2-(2,6-dioxopiperidin-3-yl)-4-((2-(prop-2-yn-1-yloxy)ethyl)amino)isoindoline-1,3-dione |

TABLE 2-continued

| Cpd. No. | Structure | Name |
|---|---|---|
| 76 | 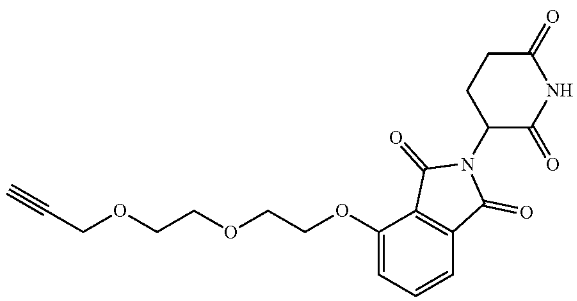 [SMILES: C#CCOCCOCCOc1cccc2c1C(=O)N(C1CCC(=O)NC1=O)C2=O] | 2-(2,6-dioxopiperidin-3-yl)-4-(2-(2-(prop-2-yn-1-yloxy)ethoxy)ethoxy)isoindoline-1,3-dione |
| 77 | 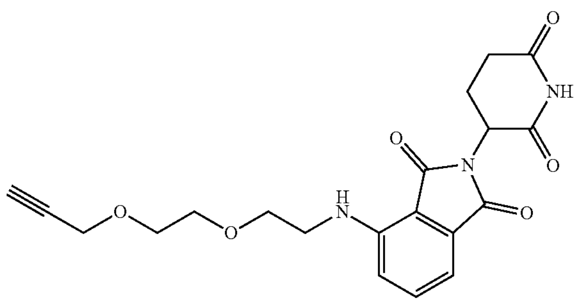 [SMILES: C#CCOCCOCCNc1cccc2c1C(=O)N(C1CCC(=O)NC1=O)C2=O] | 2-(2,6-dioxopiperidin-3-yl)-4-((2-(2-(prop-2-yn-1-yloxy)ethoxy)ethyl)amino)isoindoline-1,3-dione |
| 78 | 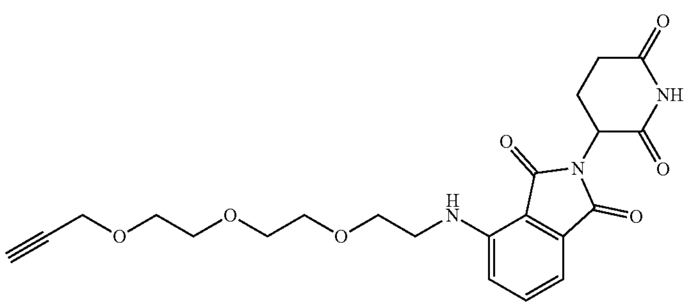 [SMILES: C#CCOCCOCCOCCNc1cccc2c1C(=O)N(C1CCC(=O)NC1=O)C2=O] | 2-(2,6-dioxopiperidin-3-yl)-4-((2-(2-(2-(prop-2-yn-1-yloxy)ethoxy)ethoxy)ethyl)amino)isoindoline-1,3-dione |
| 79 | 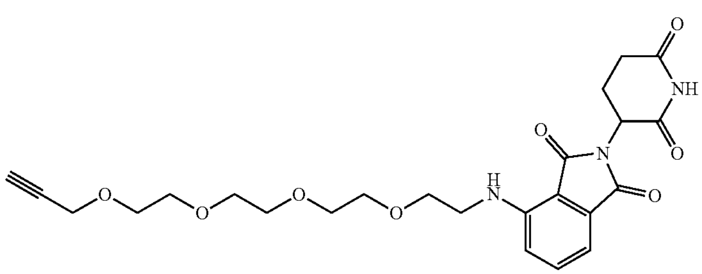 [SMILES: C#CCOCCOCCOCCOCCNc1cccc2c1C(=O)N(C1CCC(=O)NC1=O)C2=O] | 4-((3,6,9,12-tetraoxapentadec-14-yn-1-yl)amino)-2-(2,6-dioxopiperidin-3-yl)isoindoline-1,3-dione |
| 80 | 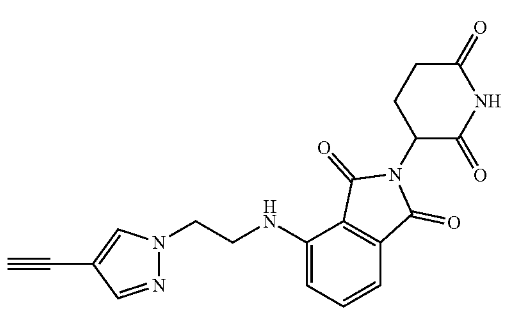 [SMILES: C#Cc1cnn(CCNc2cccc3c2C(=O)N(C2CCC(=O)NC2=O)C3=O)c1] | 2-(2,6-dioxopiperidin-3-yl)-4-((2-(4-ethynyl-1H-pyrazol-1-yl)ethyl)amino)isoindoline-1,3-dione |

TABLE 2-continued

| Cpd. No. | Structure | Name |
|---|---|---|
| 81 | 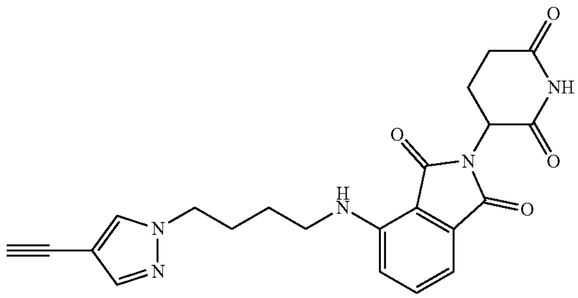 [SMILES: C#Cc1cnn(CCCCNc2cccc3c2C(=O)N(C2CCC(=O)NC2=O)C3=O)c1] | 2-(2,6-dioxopiperidin-3-yl)-4-((4-(4-ethynyl-1H-pyrazol-1-yl)butyl)amino)isoindoline-1,3-dione |
| 82 | 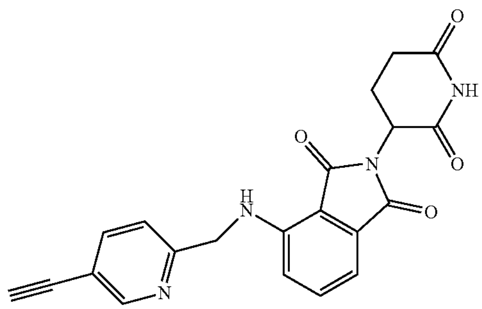 [SMILES: C#Cc1ccc(CNc2cccc3c2C(=O)N(C2CCC(=O)NC2=O)C3=O)nc1] | 2-(2,6-dioxopiperidin-3-yl)-4-(((5-ethynylpyridin-2-yl)methyl)amino)isoindoline-1,3-dione |
| 83 | 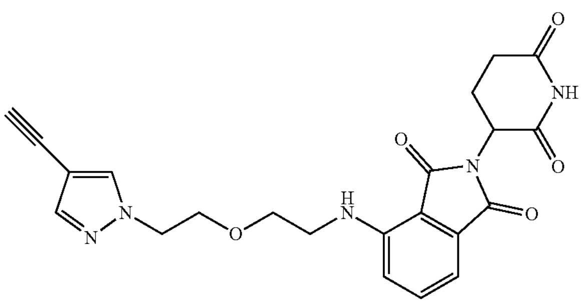 [SMILES: C#Cc1cnn(CCOCCNc2cccc3c2C(=O)N(C2CCC(=O)NC2=O)C3=O)c1] | 2-(2,6-dioxopiperidin-3-yl)-4-((2-(2-(4-ethynyl-1H-pyrazol-1-yl)ethoxy)ethyl)amino)isoindoline-1,3-dione |
| 84 | 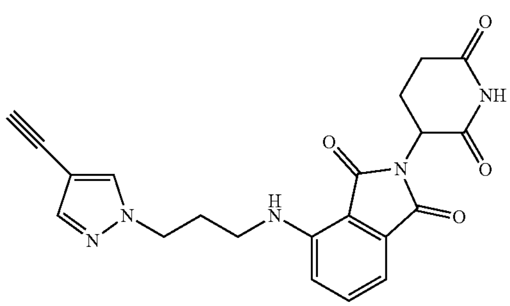 [SMILES: C#Cc1cnn(CCCNc2cccc3c2C(=O)N(C2CCC(=O)NC2=O)C3=O)c1] | 2-(2,6-dioxopiperidin-3-yl)-4-((3-(4-ethynyl-1H-pyrazol-1-yl)propyl)amino)isoindoline-1,3-dione |
| 85 | 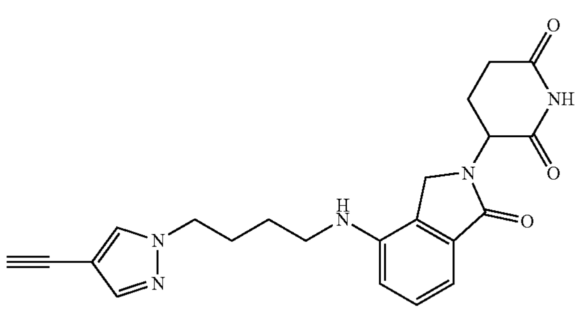 [SMILES: C#Cc1cnn(CCCCNc2cccc3c2CN(C2CCC(=O)NC2=O)C3=O)c1] | 3-(4-((4-(4-ethynyl-1H-pyrazol-1-yl)butyl)amino)-1-oxoisoindolin-2-yl)piperidine-2,6-dione |

TABLE 2-continued

| Cpd. No. | Structure | Name |
|---|---|---|
| 86 | 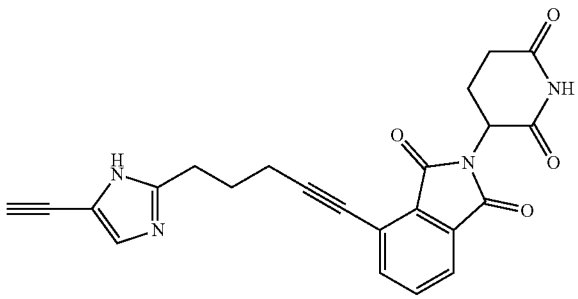 [SMILES: C#Cc1cnc(CCCC#Cc2cccc3c2C(=O)N(C2CCC(=O)NC2=O)C3=O)[nH]1] | 2-(2,6-dioxopiperidin-3-yl)-4-(5-(5-ethynyl-1H-imidazol-2-yl)pent-1-yn-1-yl)isoindoline-1,3-dione |
| 87 | 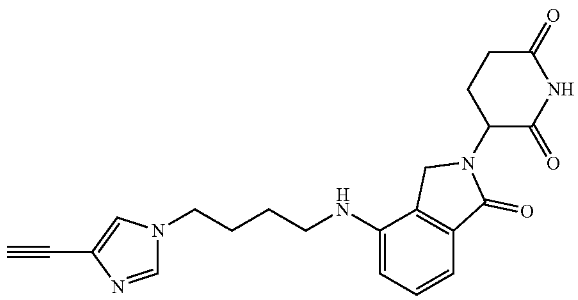 [SMILES: C#Cc1cn(CCCCNc2cccc3c2CN(C2CCC(=O)NC2=O)C3=O)cn1] | 3-(4-((4-(4-ethynyl-1H-imidazol-1-yl)butyl)amino)-1-oxoisoindolin-2-yl)piperidine-2,6-dione |
| 88 | 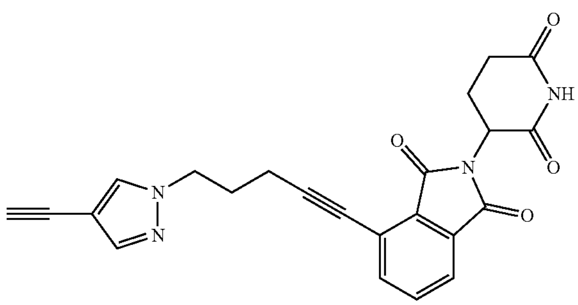 [SMILES: C#Cc1cnn(CCCC#Cc2cccc3c2C(=O)N(C2CCC(=O)NC2=O)C3=O)c1] | 2-(2,6-dioxopiperidin-3-yl)-4-(5-(4-ethynyl-1H-pyrazol-1-yl)pent-1-yn-1-yl)isoindoline-1,3-dione |
| 89 | 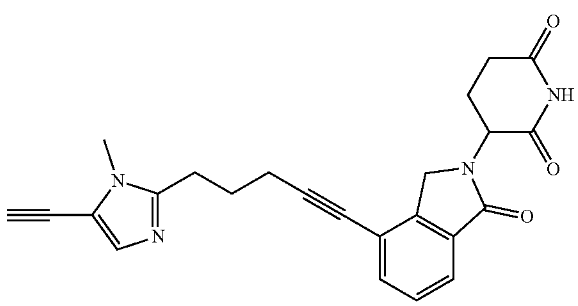 [SMILES: C#Cc1cnc(CCCC#Cc2cccc3c2CN(C2CCC(=O)NC2=O)C3=O)n1C] | 3-(4-(5-(5-ethynyl-1-methyl-1H-imidazol-2-yl)pent-1-yn-1-yl)-1-oxoisoindolin-2-yl)piperidine-2,6-dione |
| 90 | 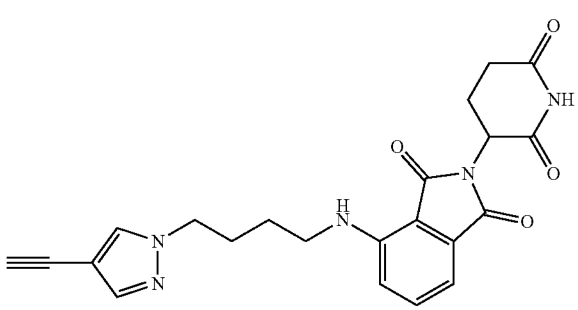 [SMILES: C#Cc1cnn(CCCCNc2cccc3c2C(=O)N(C2CCC(=O)NC2=O)C3=O)c1] | 2-(2,6-dioxopiperidin-3-yl)-4-((4-(4-ethynyl-1H-pyrazol-1-yl)butyl)amino)isoindoline-1,3-dione |

TABLE 2-continued
| Cpd. No. | Structure | Name |
|---|---|---|
| 91 | 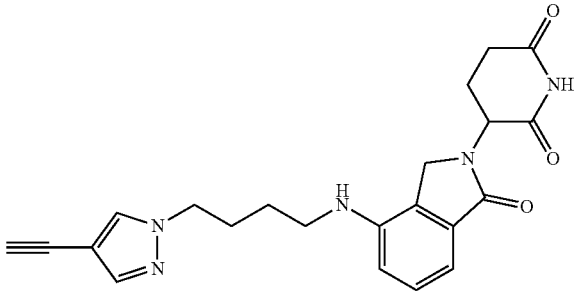 [SMILES: C#Cc1cnn(CCCCNc2cccc3c2CN(C2CCC(=O)NC2=O)C3=O)c1] | 3-(4-((4-(4-ethynyl-1H-pyrazol-1-yl)butyl)amino)-1-oxoisoindolin-2-yl)piperidine-2,6-dione |
| 92 | 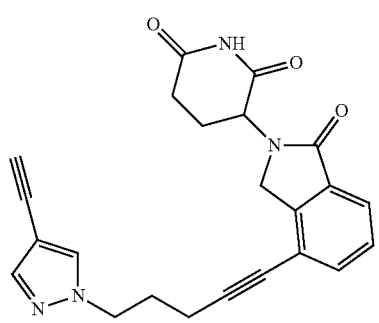 [SMILES: C#Cc1cnn(CCCC#Cc2cccc3c2CN(C2CCC(=O)NC2=O)C3=O)c1] | 3-(4-(5-(4-ethynyl-1H-pyrazol-1-yl)pent-1-yn-1-yl)-1-oxoisoindolin-2-yl)piperidine-2,6-dione |
| 93 | 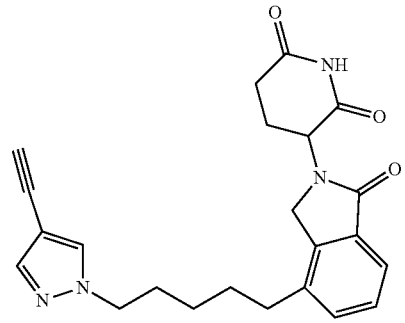 [SMILES: C#Cc1cnn(CCCCCc2cccc3c2CN(C2CCC(=O)NC2=O)C3=O)c1] | 3-(4-(5-(4-ethynyl-1H-pyrazol-1-yl)pentyl)-1-oxoisoindolin-2-yl)piperidine-2,6-dione |
| 94 | 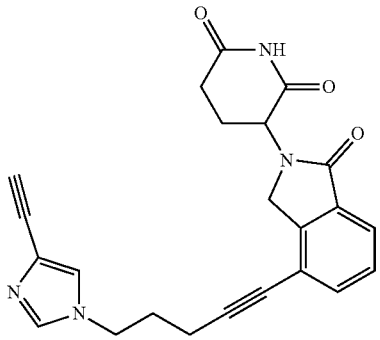 [SMILES: C#Cc1cn(CCCC#Cc2cccc3c2CN(C2CCC(=O)NC2=O)C3=O)cn1] | 3-(4-(5-(4-ethynyl-1H-imidazol-1-yl)pent-1-yn-1-yl)-1-oxoisoindolin-2-yl)piperidine-2,6-dione |

TABLE 2-continued

| Cpd. No. | Structure | Name |
|---|---|---|
| 95 | 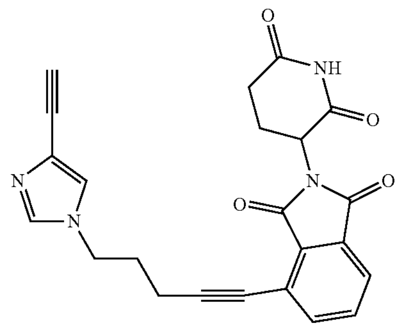 [SMILES: C#Cc1cn(CCCC#Cc2cccc3c2C(=O)N(C2CCC(=O)NC2=O)C3=O)cn1] | 2-(2,6-dioxopiperidin-3-yl)-4-(5-(4-ethynyl-1H-imidazol-1-yl)pent-1-yn-1-yl)isoindoline-1,3-dione |
| 96 | 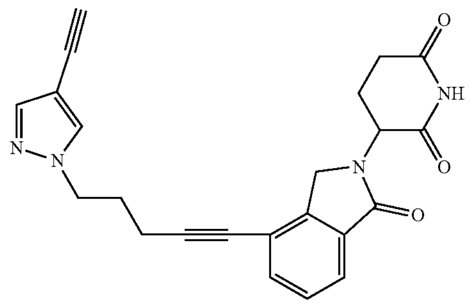 [SMILES: C#Cc1cnn(CCCC#Cc2cccc3c2CN(C2CCC(=O)NC2=O)C3=O)c1] | 2-(2,6-dioxopiperidin-3-yl)-4-(5-(4-ethynyl-1H-imidazol-1-yl)pent-1-yn-1-yl)isoindoline-1,3-dione |
| 97 | 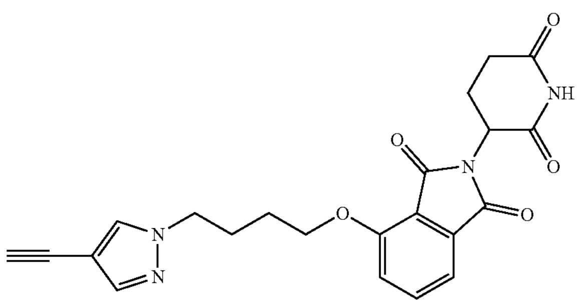 [SMILES: C#Cc1cnn(CCCCOc2cccc3c2C(=O)N(C2CCC(=O)NC2=O)C3=O)c1] | 2-(2,6-dioxopiperidin-3-yl)-4-(4-(4-ethynyl-1H-pyrazol-1-yl)butoxy)isoindoline-1,3-dione |
| 98 | 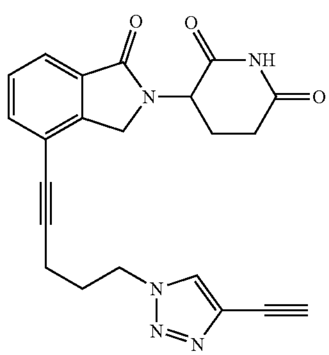 [SMILES: C#Cc1cn(CCCC#Cc2cccc3c2CN(C2CCC(=O)NC2=O)C3=O)nn1] | 3-(4-(5-(4-ethynyl-1H-1,2,3-triazol-1-yl)pent-1-yn-1-yl)-1-oxoisoindolin-2-yl)piperidine-2,6-dione |
| 99 | 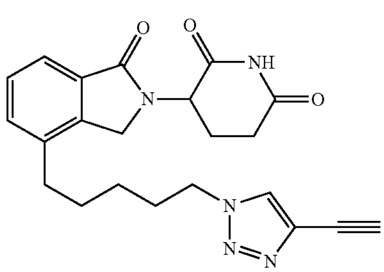 [SMILES: C#Cc1cn(CCCCCc2cccc3c2CN(C2CCC(=O)NC2=O)C3=O)nn1] | 3-(4-(5-(4-ethynyl-1H-1,2,3-triazol-1-yl)pentyl)-1-oxoisoindolin-2-yl)piperidine-2,6-dione |

TABLE 2-continued

| Cpd. No. | Structure | Name |
|---|---|---|
| 100 | 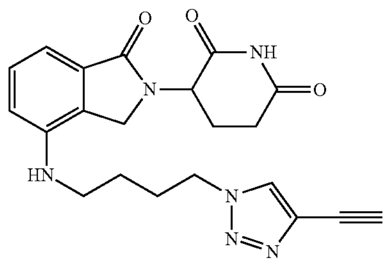 [SMILES: C#Cc1cn(CCCCNc2cccc3c2CN(C2CCC(=O)NC2=O)C3=O)nn1] | 3-(4-((4-(4-ethynyl-1H-1,2,3-triazol-1-yl)butyl)amino)-1-oxoisoindolin-2-yl)piperidine-2,6-dione |
| 101 | 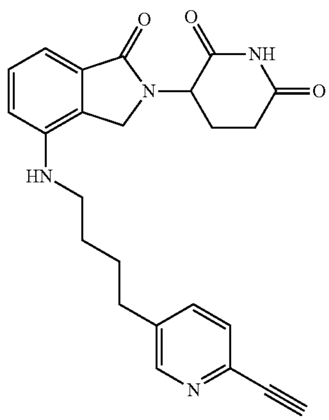 [SMILES: C#Cc1ccc(CCCCNc2cccc3c2CN(C2CCC(=O)NC2=O)C3=O)cn1] | 3-(4-((4-(6-ethynylpyridin-3-yl)butyl)amino)-1-oxoisoindolin-2-yl)piperidine-2,6-dione |
| 102 | 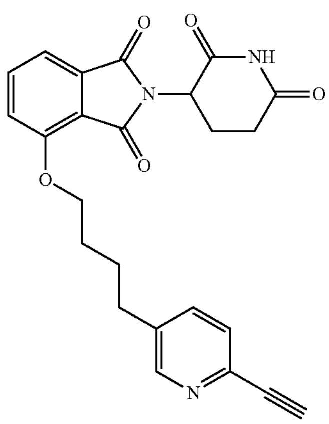 [SMILES: C#Cc1ccc(CCCCOc2cccc3c2C(=O)N(C2CCC(=O)NC2=O)C3=O)cn1] | 2-(2,6-dioxopiperidin-3-yl)-4-(4-(6-ethynylpyridin-3-yl)butoxy)isoindoline-1,3-dione |
| 103 | 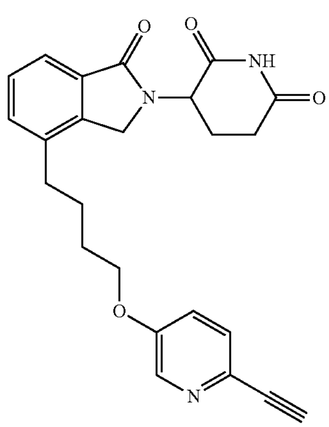 [SMILES: C#Cc1ccc(OCCCCc2cccc3c2CN(C2CCC(=O)NC2=O)C3=O)cn1] | 3-(4-(4-((6-ethynylpyridin-3-yl)oxy)butyl)-1-oxoisoindolin-2-yl)piperidine-2,6-dione |

TABLE 2-continued

| Cpd. No. | Structure | Name |
|---|---|---|
| 104 | 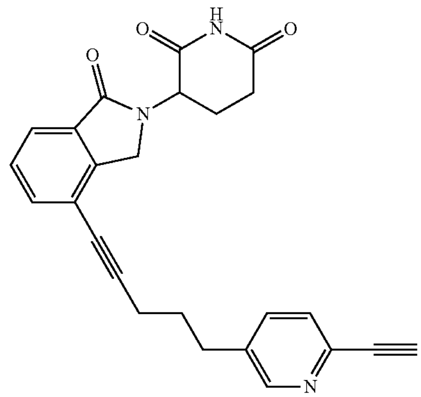 [SMILES: C#Cc1ccc(CCCC#Cc2cccc3c2CN(C2CCC(=O)NC2=O)C3=O)cn1] | 3-(4-(5-(6-ethynylpyridin-3-yl)pent-1-yn-1-yl)-1-oxoisoindolin-2-yl)piperidine-2,6-dione |
| 105 | 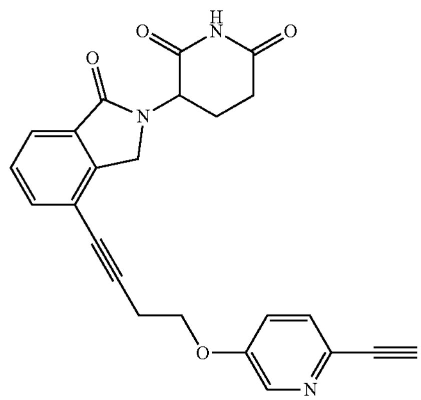 [SMILES: C#Cc1ccc(OCCC#Cc2cccc3c2CN(C2CCC(=O)NC2=O)C3=O)cn1] | 3-(4-(4-((6-ethynylpyridin-3-yl)oxy)but-1-yn-1-yl)-1-oxoisoindolin-2-yl)piperidine-2,6-dione |
| 106 | 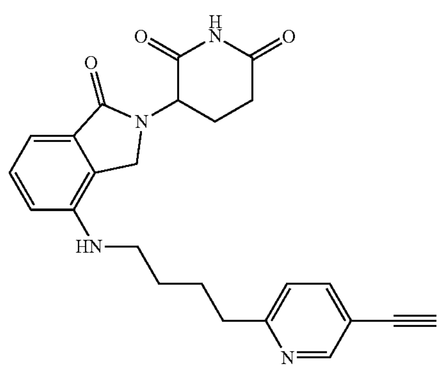 [SMILES: C#Cc1ccc(CCCCNc2cccc3c2CN(C2CCC(=O)NC2=O)C3=O)nc1] | 3-(4-((4-(5-ethynylpyridin-2-yl)butyl)amino)-1-oxoisoindolin-2-yl)piperidine-2,6-dione |
| 107 | 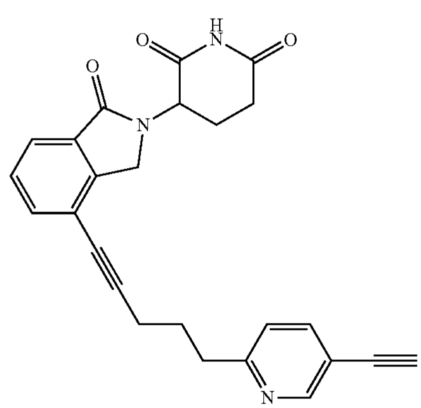 [SMILES: C#Cc1ccc(CCCC#Cc2cccc3c2CN(C2CCC(=O)NC2=O)C3=O)nc1] | 3-(4-(5-(5-ethynylpyridin-2-yl)pent-1-yn-1-yl)-1-oxoisoindolin-2-yl)piperidine-2,6-dione |

TABLE 2-continued

| Cpd. No. | Structure | Name |
|---|---|---|
| 108 | 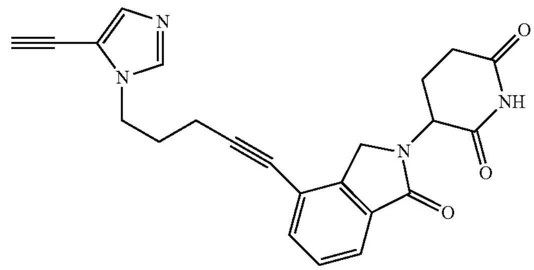 [SMILES: C#Cc1cncn1CCCC#Cc1cccc2c1CN(C1CCC(=O)NC1=O)C2=O] | 3-(4-(5-(5-ethynyl-1H-imidazol-1-yl)pent-1-yn-1-yl)-1-oxoisoindolin-2-yl)piperidine-2,6-dione |
| 109 | 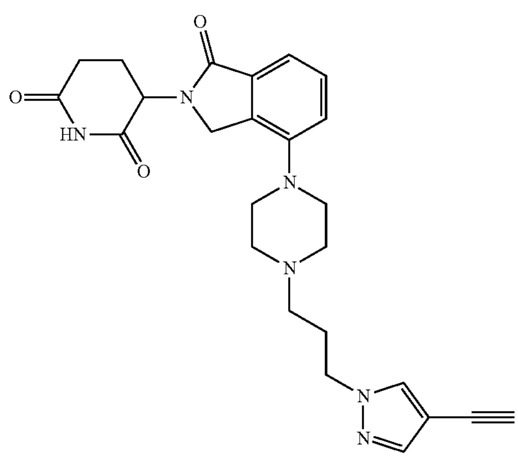 [SMILES: C#Cc1cnn(CCCN2CCN(c3cccc4c3CN(C3CCC(=O)NC3=O)C4=O)CC2)c1] | 3-(4-(4-(3-(4-ethynyl-1H-pyrazol-1-yl)propyl)piperazin-1-yl)-1-oxoisoindolin-2-yl)piperidine-2,6-dione |
| 110 | 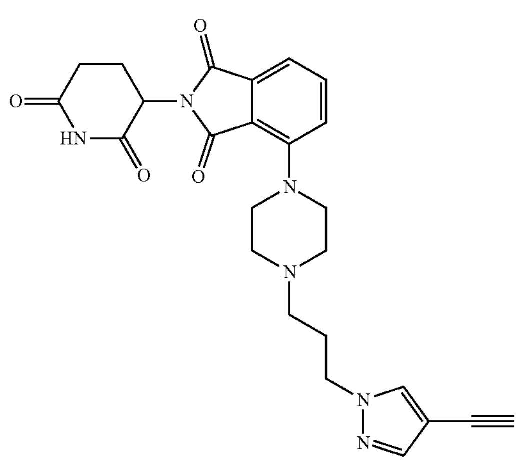 [SMILES: C#Cc1cnn(CCCN2CCN(c3cccc4c3C(=O)N(C3CCC(=O)NC3=O)C4=O)CC2)c1] | 2-(2,6-dioxopiperidin-3-yl)-4-(4-(3-(4-ethynyl-1H-pyrazol-1-yl)propyl)piperazin-1-yl)isoindoline-1,3-dione |

TABLE 2-continued

| Cpd. No. | Structure | Name |
|---|---|---|
| 111 | 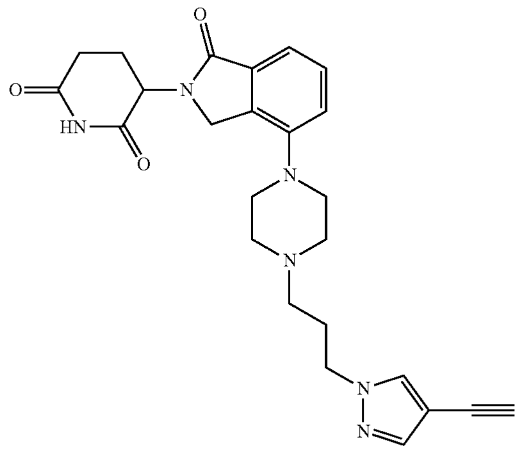 [SMILES: C#Cc1cnn(CCCN2CCN(c3cccc4c3CN(C3CCC(=O)NC3=O)C4=O)CC2)c1] | 3-(4-(4-(3-(4-ethynyl-1H-pyrazol-1-yl)propyl)piperazin-1-yl)-1-oxoisoindolin-2-yl)piperidine-2,6-dione |
| 112 | 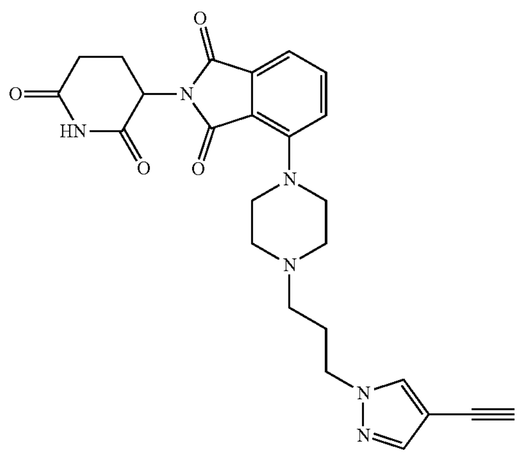 [SMILES: C#Cc1cnn(CCCN2CCN(c3cccc4c3C(=O)N(C3CCC(=O)NC3=O)C4=O)CC2)c1] | 2-(2,6-dioxopiperidin-3-yl)-4-(4-(3-(4-ethynyl-1H-pyrazol-1-yl)propyl)piperazin-1-yl)isoindoline-1,3-dione |
| 113 | 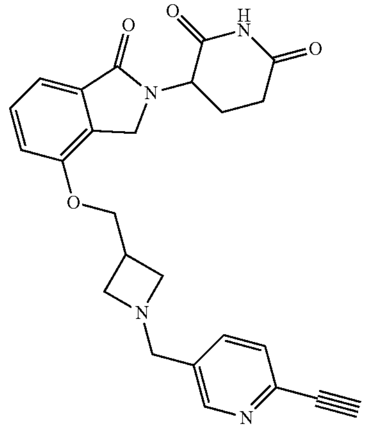 [SMILES: CCc1ccc(CN2CC(COc3cccc4c3CN(C3CCC(=O)NC3=O)C4=O)C2)cn1] | 3-(4-((1-((6-ethynylpyridin-3-yl)methyl)azetidin-3-yl)methoxy)-1-oxoisoindolin-2-yl)piperidine-2,6-dione |

TABLE 2-continued

| Cpd. No. | Structure | Name |
|---|---|---|
| 114 | 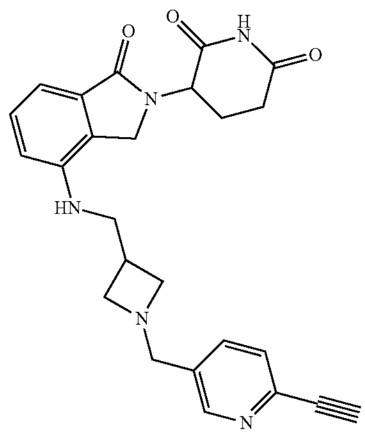 [SMILES: CCc1ccc(CN2CC(CNc3cccc4c3CN(C3CCC(=O)NC3=O)C4=O)C2)cn1] | 3-(4-(((1-((6-ethynylpyridin-3-yl)methyl)azetidin-3-yl)methyl)amino)-1-oxoisoindolin-2-yl)piperidine-2,6-dione |
| 115 | 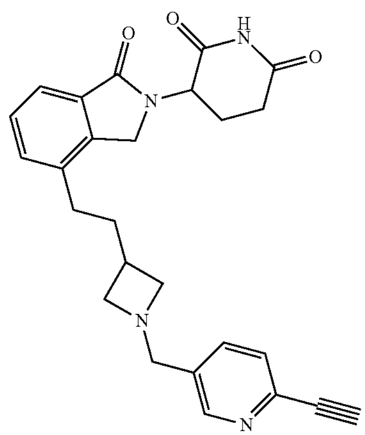 [SMILES: CCc1ccc(CN2CC(CCc3cccc4c3CN(C3CCC(=O)NC3=O)C4=O)C2)cn1] | 3-(4-(2-(1-((6-ethynylpyridin-3-yl)methyl)azetidin-3-yl)ethyl)-1-oxoisoindolin-2-yl)piperidine-2,6-dione |
| 116 | 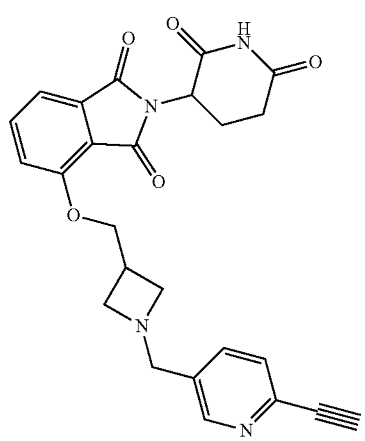 [SMILES: CCc1ccc(CN2CC(COc3cccc4c3C(=O)N(C3CCC(=O)NC3=O)C4=O)C2)cn1] | 2-(2,6-dioxopiperidin-3-yl)-4-((1-((6-ethynylpyridin-3-yl)methyl)azetidin-3-yl)methoxy)isoindoline-1,3-dione |

TABLE 2-continued

| Cpd. No. | Structure | Name |
|---|---|---|
| 117 | | 2-(2,6-dioxopiperidin-3-yl)-4-(((1-((6-ethynylpyridin-3-yl)methyl)azetidin-3-yl)methyl)amino)isoindoline-1,3-dione |
| 117 | | 2-(2,6-dioxopiperidin-3-yl)-4-(2-(1-((6-ethynylpyridin-3-yl)methyl)azetidin-3-yl)ethyl)isoindoline-1,3-dione |
| 119 | 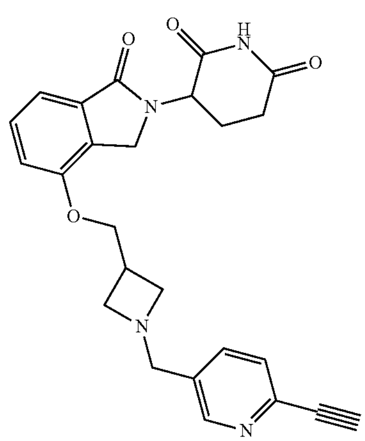 [SMILES: CCc1ccc(CN2CC(COc3cccc4c3CN(C3CCC(=O)NC3=O)C4=O)C2)cn1] | 3-(4-((1-((6-ethynylpyridin-3-yl)methyl)azetidin-3-yl)methoxy)-1-oxoisoindolin-2-yl)piperidine-2,6-dione |

TABLE 2-continued

| Cpd. No. | Structure | Name |
|---|---|---|
| 120 | 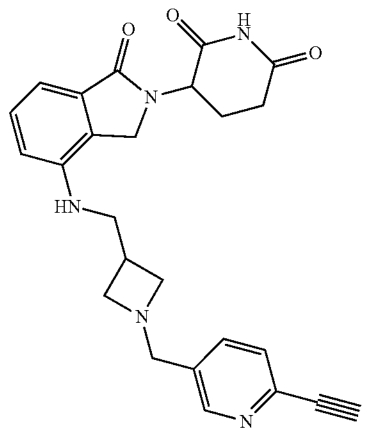 [SMILES: CCc1ccc(CN2CC(CNc3cccc4c3CN(C3CCC(=O)NC3=O)C4=O)C2)cn1] | 3-(4-(((1-((6-ethynylpyridin-3-yl)methyl)azetidin-3-yl)methyl)amino)-1-oxoisoindolin-2-yl)piperidine-2,6-dione |
| 121 | 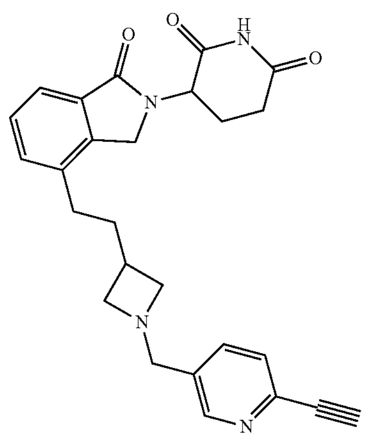 | 3-(4-(2-(1-((6-ethynylpyridin-3-yl)methyl)azetidin-3-yl)ethyl)-1-oxoisoindolin-2-yl)piperidine-2,6-dione |
| 122 | 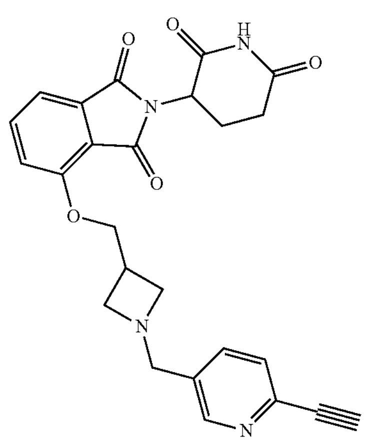 [SMILES: CCc1ccc(CN2CC(COc3cccc4c3C(=O)N(C3CCC(=O)NC3=O)C4=O)C2)cn1] | 2-(2,6-dioxopiperidin-3-yl)-4-((1-((6-ethynylpyridin-3-yl)methyl)azetidin-3-yl)methoxy)isoindoline-1,3-dione |

TABLE 2-continued

| Cpd. No. | Structure | Name |
|---|---|---|
| 123 | 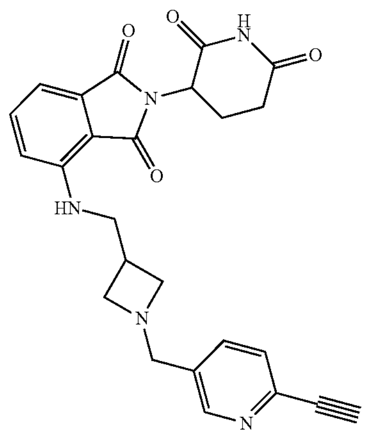 [SMILES: CCc1ccc(CN2CC(CNc3cccc4c3C(=O)N(C3CCC(=O)NC3=O)C4=O)C2)cn1] | 2-(2,6-dioxopiperidin-3-yl)-4-(((1-((6-ethynylpyridin-3-yl)methyl)azetidin-3-yl)methoxy)amino)isoindoline-1,3-dione |
| 124 | 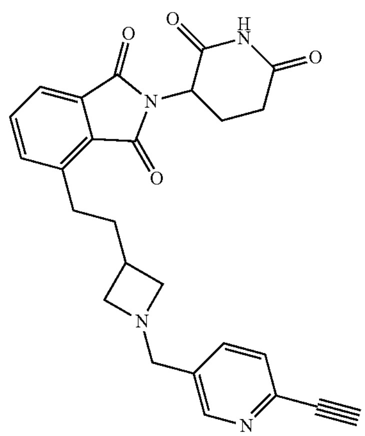 [SMILES: CCc1ccc(CN2CC(CCc3cccc4c3C(=O)N(C3CCC(=O)NC3=O)C4=O)C2)cn1] | 2-(2,6-dioxopiperidin-3-yl)-4-(2-(1-((6-ethynylpyridin-3-yl)methyl)azetidin-3-yl)ethyl)isoindoline-1,3-dione |
| 125 | 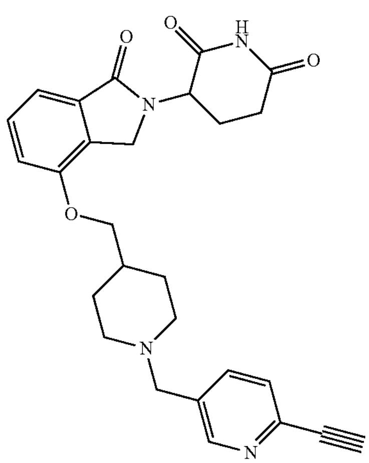 [SMILES: CCc1ccc(CN2CCC(COc3cccc4c3CN(C3CCC(=O)NC3=O)C4=O)CC2)cn1] | 3-(4-((1-((6-ethynylpyridin-3-yl)methyl)piperidin-4-yl)methoxy)-1-oxoisoindolin-2-yl)piperidine-2,6-dione |

TABLE 2-continued

| Cpd. No. | Structure | Name |
|---|---|---|
| 126 | 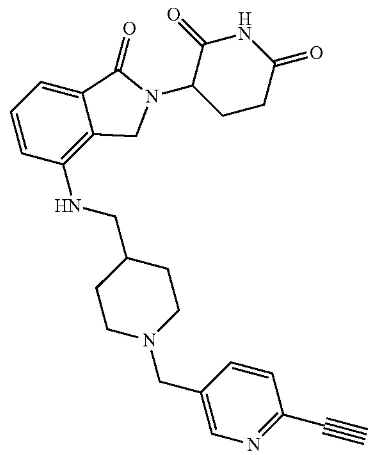 [SMILES: CCc1ccc(CN2CCC(CNc3cccc4c3CN(C3CCC(=O)NC3=O)C4=O)CC2)cn1] | 3-(4-(((1-((6-ethynylpyridin-3-yl)methyl)piperidin-4-yl)methyl)amino)-1-oxoisoindolin-2-yl)piperidine-2,6-dione |
| 127 | 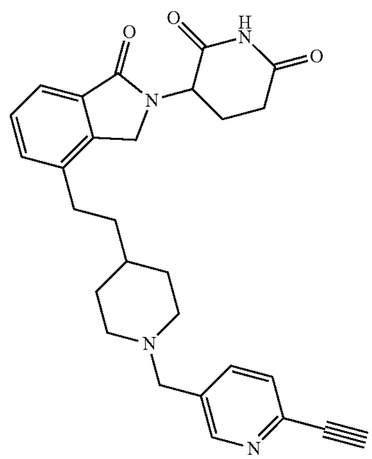 [SMILES: CCc1ccc(CN2CCC(CCc3cccc4c3CN(C3CCC(=O)NC3=O)C4=O)CC2)cn1] | 3-(4-(2-(1-((6-ethynylpyridin-3-yl)methyl)piperidin-4-yl)ethyl)-1-oxoisoindolin-2-yl)piperidine-2,6-dione |
| 128 | 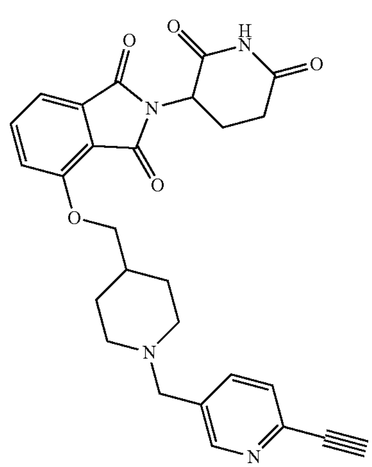 | 2-(2,6-dioxopiperidin-3-yl)-4-((1-((6-ethynylpyridin-3-yl)methyl)piperidin-4-yl)methoxy)isoindoline-1,3-dione |

TABLE 2-continued

| Cpd. No. | Structure | Name |
|---|---|---|
| 129 | 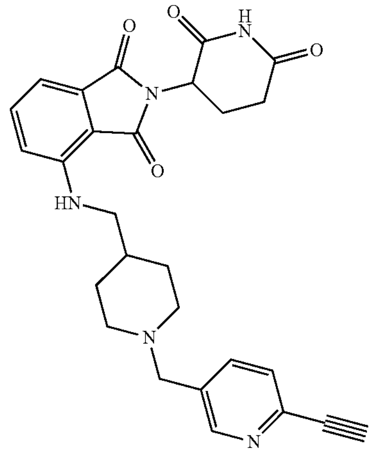 [SMILES: CCc1ccc(CN2CCC(CNc3cccc4c3C(=O)N(C3CCC(=O)NC3=O)C4=O)CC2)cn1] | 2-(2,6-dioxopiperidin-3-yl)-4-(((1-((6-ethynylpyridin-3-yl)methyl)piperidin-4-yl)methyl)amino)isoindoline-1,3-dione |
| 130 | 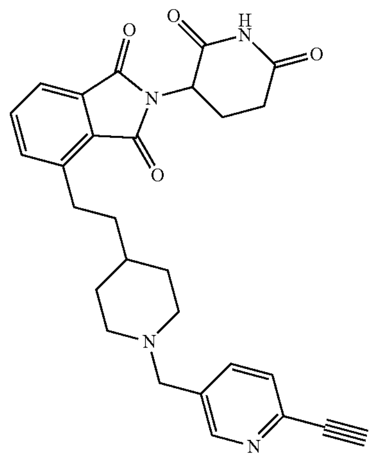 | 2-(2,6-dioxopiperidin-3-yl)-4-(2-(1-((6-ethynylpyridin-3-yl)methyl)piperidin-4-yl)ethyl)isoindoline-1,3-dione |
| 131 | 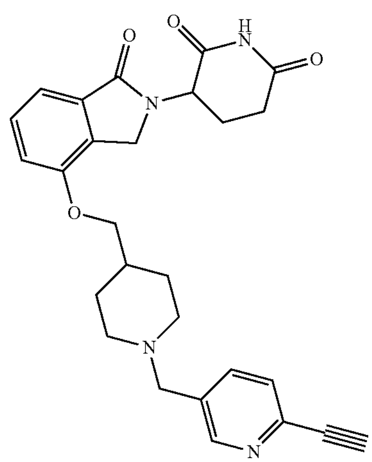 | 3-(4-((1-((6-ethynylpyridin-3-yl)methyl)piperidin-4-yl)methoxy)-1-oxoisoindolin-2-yl)piperidine-2,6-dione |

TABLE 2-continued

| Cpd. No. | Structure | Name |
|---|---|---|
| 132 | 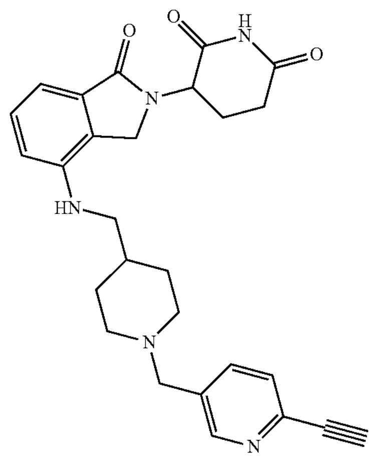 [SMILES: CCc1ccc(CN2CCC(CNc3cccc4c3CN(C3CCC(=O)NC3=O)C4=O)CC2)cn1] | 3-(4-(((1-((6-ethynylpyridin-3-yl)methyl)piperidin-4-yl)methyl)amino)-1-oxoisoindolin-2-yl)piperidine-2,6-dione |
| 133 | 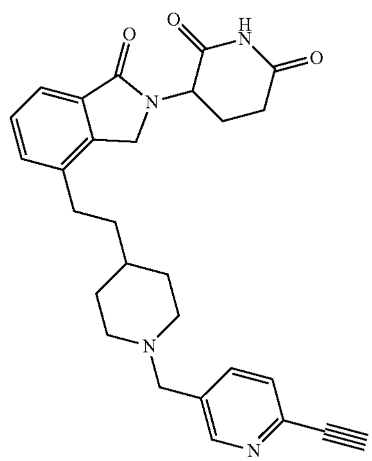 [SMILES: CCc1ccc(CN2CCC(CCc3cccc4c3CN(C3CCC(=O)NC3=O)C4=O)CC2)cn1] | 3-(4-(2-(1-((6-ethynylpyridin-3-yl)methyl)piperidin-4-yl)ethyl)-1-oxoisoindolin-2-yl)piperidine-2,6-dione |
| 134 | 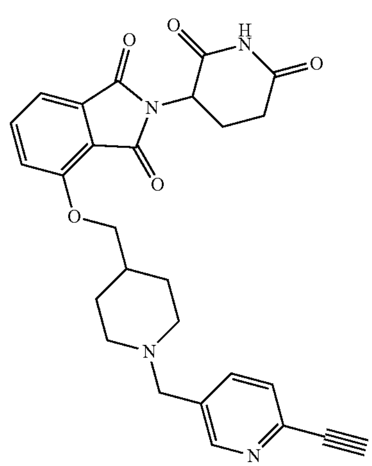 [SMILES: CCc1ccc(CN2CCC(COc3cccc4c3C(=O)N(C3CCC(=O)NC3=O)C4=O)CC2)cn1] | 2-(2,6-dioxopiperidin-3-yl)-4-((1-((6-ethynylpyridin-3-yl)methyl)piperidin-4-yl)methoxy)isoindoline-1,3-dione |

TABLE 2-continued

| Cpd. No. | Structure | Name |
|---|---|---|
| 135 | 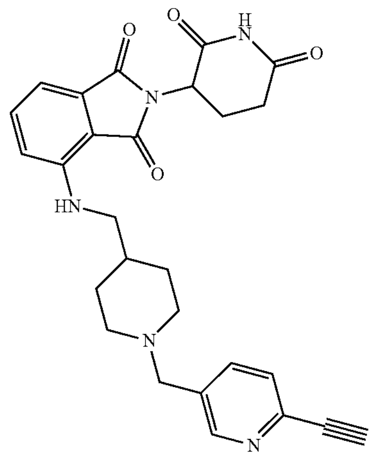 [SMILES: CCc1ccc(CN2CCC(CNc3cccc4c3C(=O)N(C3CCC(=O)NC3=O)C4=O)CC2)cn1] | 2-(2,6-dioxopiperidin-3-yl)-4-(((1-((6-ethynylpyridin-3-yl)methyl)piperidin-4-yl)methyl)amino)isoindoline-1,3-dione |
| 136 | 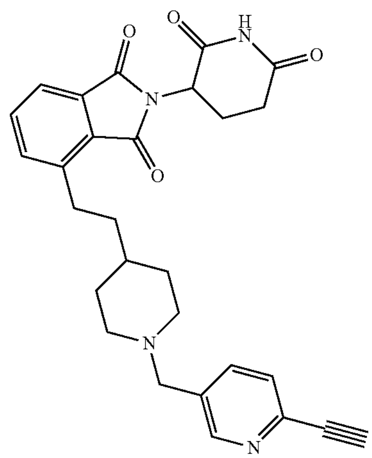 [SMILES: CCc1ccc(CN2CCC(CCc3cccc4c3C(=O)N(C3CCC(=O)NC3=O)C4=O)CC2)cn1] | 2-(2,6-dioxopiperidin-3-yl)-4-(2-(1-((6-ethynylpyridin-3-yl)methyl)piperidin-4-yl)ethyl)isoindoline-1,3-dione |
| 137 | 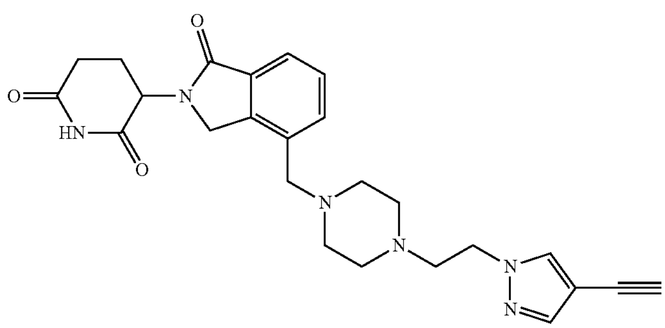 [SMILES: C#Cc1cnn(CCN2CCN(Cc3cccc4c3CN(C3CCC(=O)NC3=O)C4=O)CC2)c1] | 3-(4-((4-(2-(4-ethynyl-1H-pyrazol-1-yl)ethyl)piperazin-1-yl)methyl)-1-oxoisoindolin-2-yl)piperidine-2,6-dione |
| 138 | 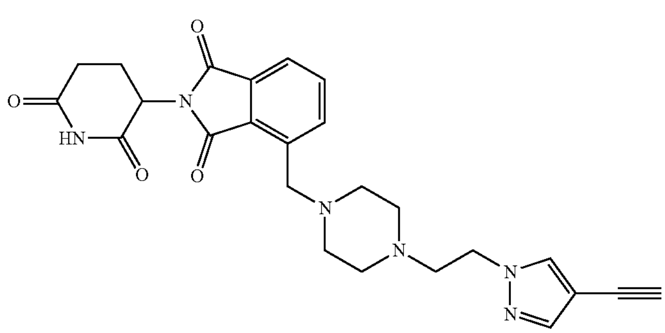 [SMILES: C#Cc1cnn(CCN2CCN(Cc3cccc4c3C(=O)N(C3CCC(=O)NC3=O)C4=O)CC2)c1] | 2-(2,6-dioxopiperidin-3-yl)-4-((4-(2-(4-ethynyl-1H-pyrazol-1-yl)ethyl)piperazin-1-yl)methyl)isoindoline-1,3-dione |

TABLE 2-continued

| Cpd. No. | Structure | Name |
|---|---|---|
| 139 | 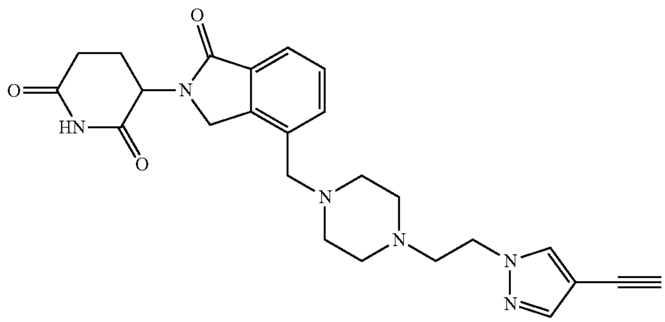 [SMILES: C#Cc1cnn(CCN2CCN(Cc3cccc4c3CN(C3CCC(=O)NC3=O)C4=O)CC2)c1] | 3-(4-((4-(2-(4-ethynyl-1H-pyrazol-1-yl)ethyl)piperazin-1-yl)methyl)-1-oxoisoindolin-2-yl)piperidine-2,6-dione |
| 140 | 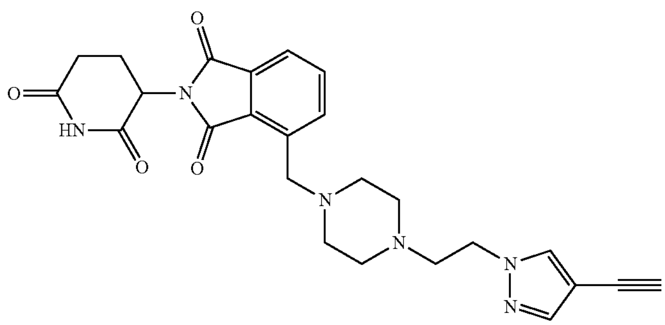 [SMILES: C#Cc1cnn(CCN2CCN(Cc3cccc4c3C(=O)N(C3CCC(=O)NC3=O)C4=O)CC2)c1] | 2-(2,6-dioxopiperidin-3-yl)-4-((4-(2-(4-ethynyl-1H-pyrazol-1-yl)ethyl)piperazin-1-yl)methyl)isoindoline-1,3-dione |
| 141 | 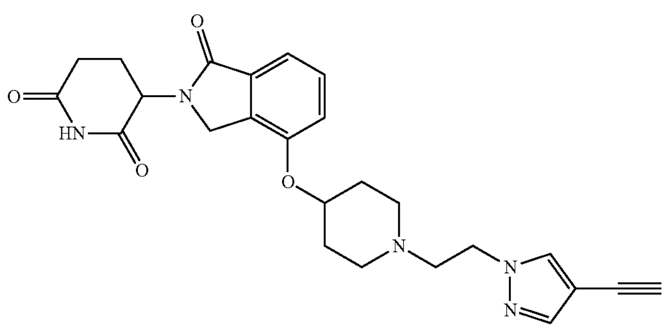 [SMILES: C#Cc1cnn(CCN2CCC(Oc3cccc4c3CN(C3CCC(=O)NC3=O)C4=O)CC2)c1] | 3-(4-((1-(2-(4-ethynyl-1H-pyrazol-1-yl)ethyl)piperidin-4-yl)oxy)-1-oxoisoindolin-2-yl)piperidine-2,6-dione |
| 142 | 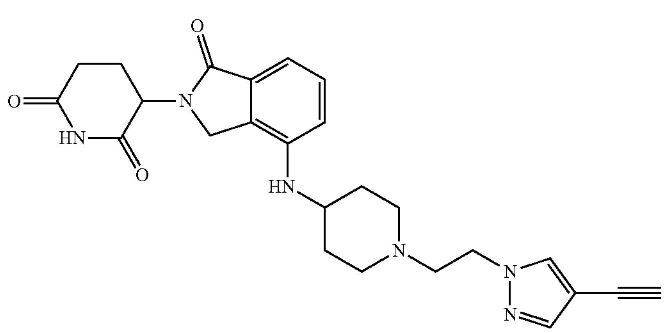 [SMILES: C#Cc1cnn(CCN2CCC(Nc3cccc4c3CN(C3CCC(=O)NC3=O)C4=O)CC2)c1] | 3-(4-((1-(2-(4-ethynyl-1H-pyrazol-1-yl)ethyl)piperidin-4-yl)amino)-1-oxoisoindolin-2-yl)piperidine-2,6-dione |

TABLE 2-continued

| Cpd. No. | Structure | Name |
|---|---|---|
| 143 | 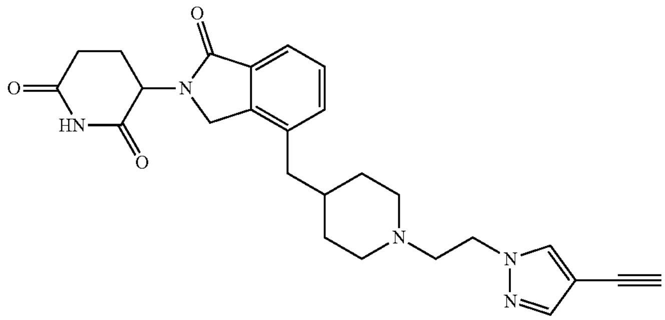 [SMILES: C#Cc1cnn(CCN2CCC(Cc3cccc4c3CN(C3CCC(=O)NC3=O)C4=O)CC2)c1] | 3-(4-((1-(2-(4-ethynyl-1H-pyrazol-1-yl)ethyl)piperidin-4-yl)methyl)-1-oxoisoindolin-2-yl)piperidine-2,6-dione |
| 144 | 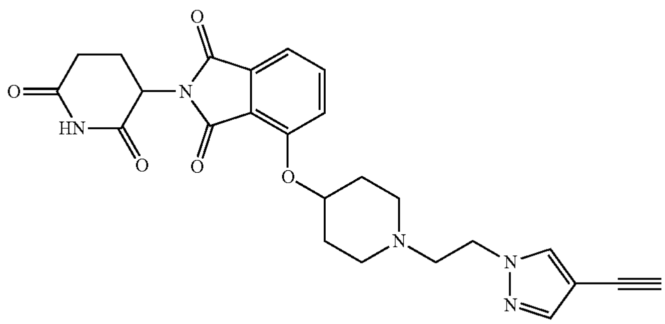 [SMILES: C#Cc1cnn(CCN2CCC(Oc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperazin-4-yl)oxy)isoindoline-1,3-dione |
| 145 | 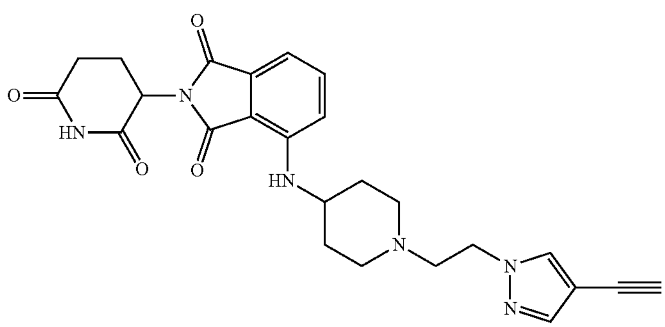 [SMILES: C#Cc1cnn(CCN2CCC(Nc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperazin-4-yl)amino)isoindoline-1,3-dione |
| 146 | 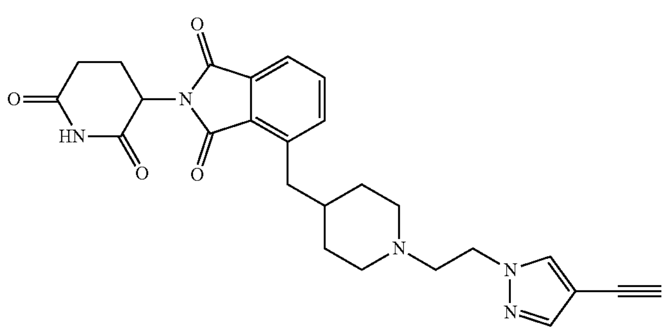 [SMILES: C#Cc1cnn(CCN2CCC(Cc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperazin-4-yl)methyl)isoindoline-1,3-dione |

TABLE 2-continued

| Cpd. No. | Structure | Name |
|---|---|---|
| 147 | 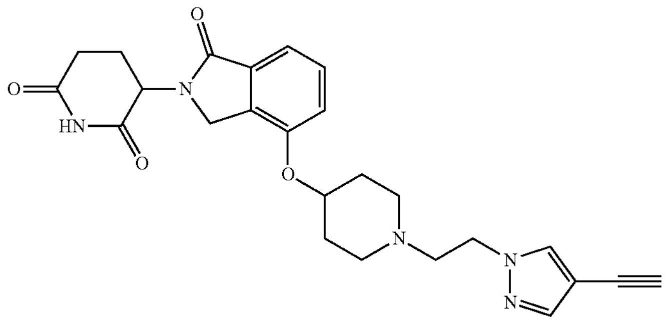 [SMILES: C#Cc1cnn(CCN2CCC(Oc3cccc4c3CN(C3CCC(=O)NC3=O)C4=O)CC2)c1] | 3-(4-((1-(2-(4-ethynyl-1H-pyrazol-1-yl)ethyl)piperidin-4-yl)oxy)-1-oxoisoindolin-2-yl)piperidine-2,6-dione |
| 148 | 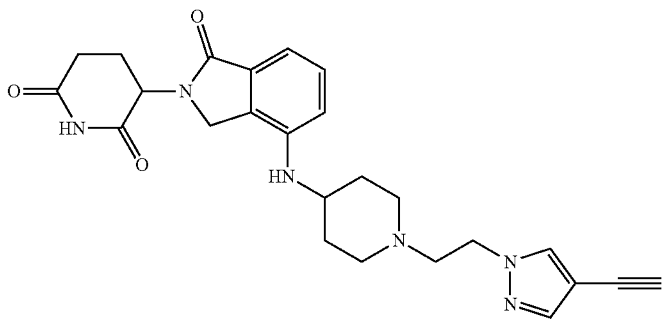 [SMILES: C#Cc1cnn(CCN2CCC(Nc3cccc4c3CN(C3CCC(=O)NC3=O)C4=O)CC2)c1] | 3-(4-((1-(2-(4-ethynyl-1H-pyrazol-1-yl)ethyl)piperidin-4-yl)amino)-1-oxoisoindolin-2-yl)piperidine-2,6-dione |
| 149 | 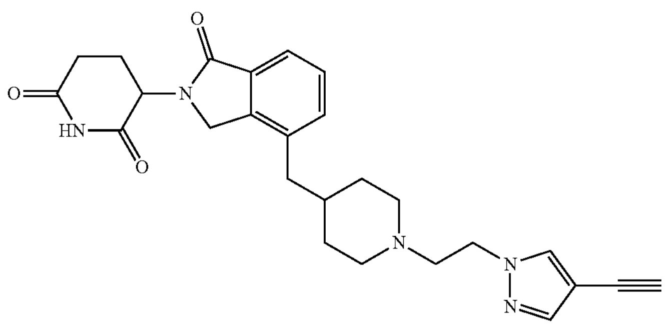 [SMILES: C#Cc1cnn(CCN2CCC(Cc3cccc4c3CN(C3CCC(=O)NC3=O)C4=O)CC2)c1] | 3-(4-((1-(2-(4-ethynyl-1H-pyrazol-1-yl)ethyl)piperidin-4-yl)methyl)-1-oxoisoindolin-2-yl)piperidine-2,6-dione |
| 150 | 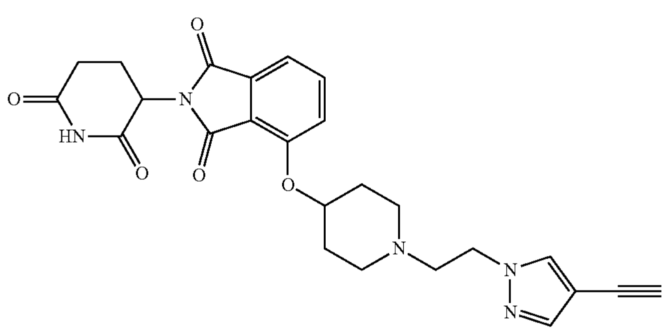 [SMILES: C#Cc1cnn(CCN2CCC(Oc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperazin-4-yl)oxy)isoindoline-1,3-dione |

TABLE 2-continued

| Cpd. No. | Structure | Name |
|---|---|---|
| 151 | 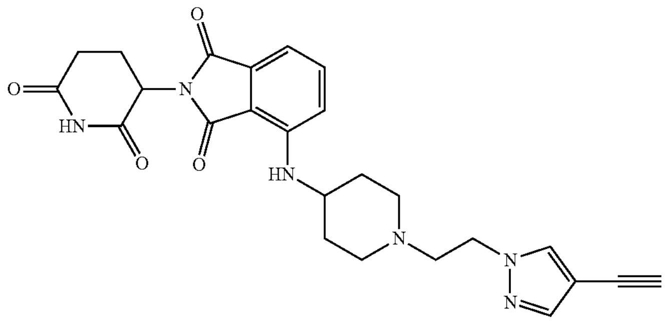 [SMILES: C#Cc1cnn(CCN2CCC(Nc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperazin-4-yl)amino)isoindoline-1,3-dione |
| 152 | 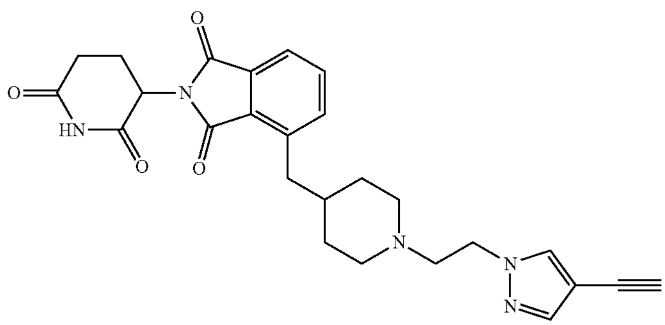 [SMILES: C#Cc1cnn(CCN2CCC(Cc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperazin-4-yl)methyl)isoindoline-1,3-dione |
| 153 | 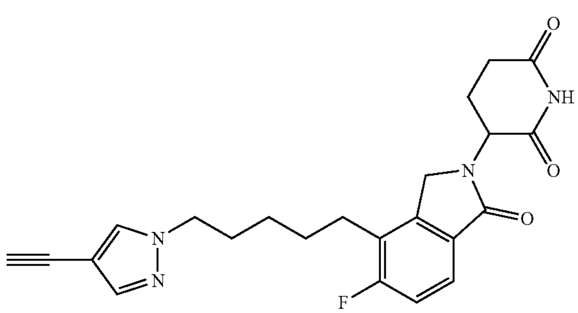 [SMILES: C#Cc1cnn(CCCCCc2c(F)ccc3c2CN(C2CCC(=O)NC2=O)C3=O)c1] | 3-(4-(5-(4-ethynyl-1H-pyrazol-1-yl)pentyl)-5-fluoro-1-oxoisoindolin-2-yl)piperidine-2,6-dione |
| 154 | 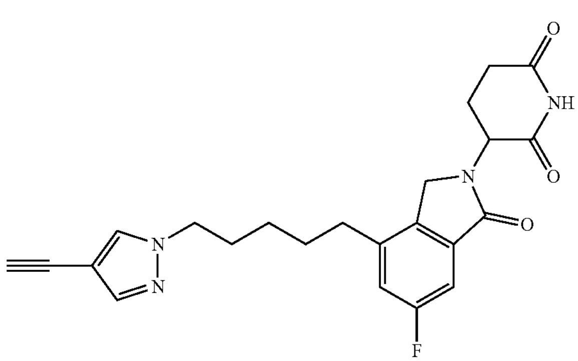 [SMILES: C#Cc1cnn(CCCCCc2cc(F)cc3c2CN(C2CCC(=O)NC2=O)C3=O)c1] | 3-(4-(5-(4-ethynyl-1H-pyrazol-1-yl)pentyl)-6-fluoro-1-oxoisoindolin-2-yl)piperidine-2,6-dione |

TABLE 2-continued

| Cpd. No. | Structure | Name |
|---|---|---|
| 155 | 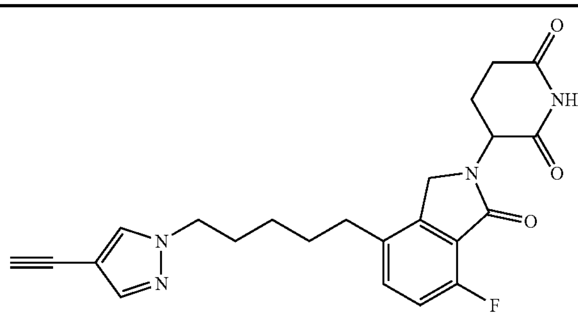 | 3-(4-(5-(4-ethynyl-1H-pyrazol-1-yl)pentyl)-7-fluoro-1-oxoisoindolin-2-yl)piperidine-2,6-dione |
| 156 | 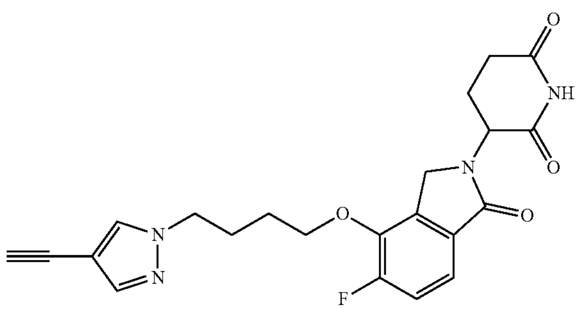 [SMILES: C#Cc1cnn(CCCCOc2c(F)ccc3c2CN(C2CCC(=O)NC2=O)C3=O)c1] | 3-(4-(4-(4-ethynyl-1H-pyrazol-1-yl)butoxy)-5-fluoro-1-oxoisoindolin-2-yl)piperidine-2,6-dione |
| 157 | 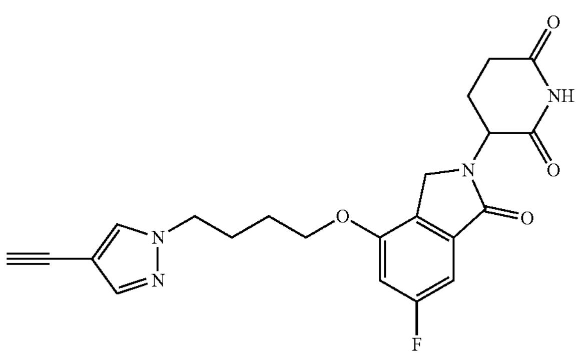 [SMILES: C#Cc1cnn(CCCCOc2cc(F)cc3c2CN(C2CCC(=O)NC2=O)C3=O)c1] | 3-(4-(4-(4-ethynyl-1H-pyrazol-1-yl)butoxy)-6-fluoro-1-oxoisoindolin-2-yl)piperidine-2,6-dione |
| 158 | 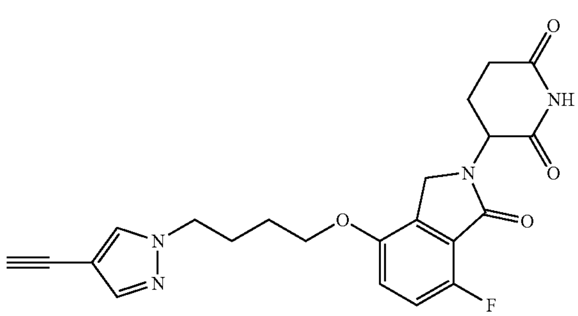 [SMILES: C#Cc1cnn(CCCCOc2ccc(F)c3c2CN(C2CCC(=O)NC2=O)C3=O)c1] | 3-(4-(4-(4-ethynyl-1H-pyrazol-1-yl)butoxy)-7-fluoro-1-oxoisoindolin-2-yl)piperidine-2,6-dione |
| 159 | 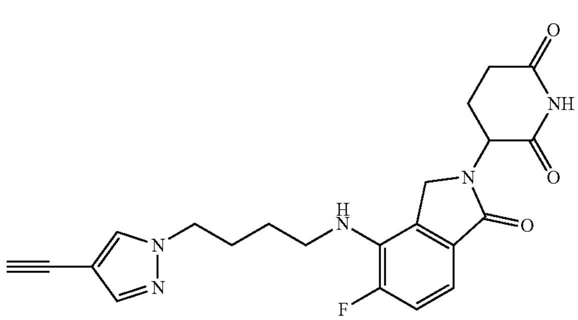 [SMILES: C#Cc1cnn(CCCCNc2c(F)ccc3c2CN(C2CCC(=O)NC2=O)C3=O)c1] | 3-(4-((4-(4-ethynyl-1H-pyrazol-1-yl)butyl)amino)-5-fluoro-1-oxoisoindolin-2-yl)piperidine-2,6-dione |

TABLE 2-continued

| Cpd. No. | Structure | Name |
|---|---|---|
| 160 | 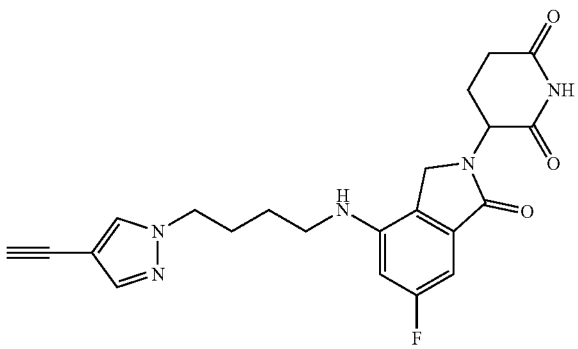 [SMILES: C#Cc1cnn(CCCCNc2cc(F)cc3c2CN(C2CCC(=O)NC2=O)C3=O)c1] | 3-(4-((4-(4-ethynyl-1H-pyrazol-1-yl)butyl)amino)-6-fluoro-1-oxoisoindolin-2-yl)piperidine-2,6-dione |
| 161 | 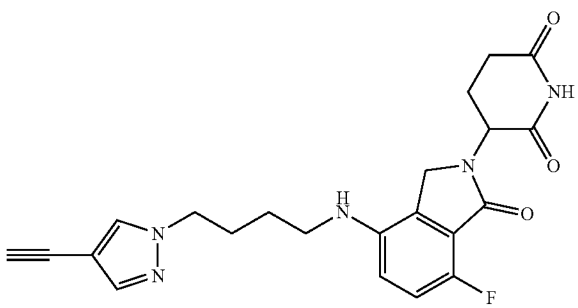 [SMILES: C#Cc1cnn(CCCCNc2ccc(F)c3c2CN(C2CCC(=O)NC2=O)C3=O)c1] | 3-(4-((4-(4-ethynyl-1H-pyrazol-1-yl)butyl)amino)-7-fluoro-1-oxoisoindolin-2-yl)piperidine-2,6-dione |
| 162 | 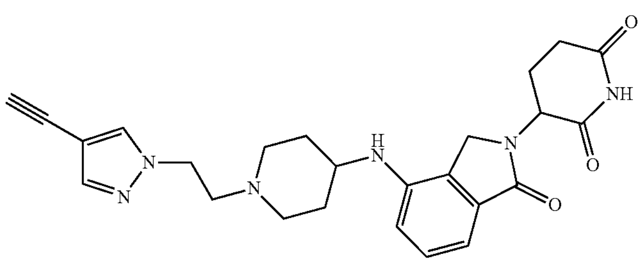 [SMILES: C#Cc1cnn(CCN2CCC(Nc3cccc4c3CN(C3CCC(=O)NC3=O)C4=O)CC2)c1] | 3-(4-((1-(2-(4-ethynyl-1H-pyrazol-1-yl)ethyl)piperidin-4-yl)amino)-1-oxoisoindolin-2-yl)piperidine-2,6-dione |
| 163 | 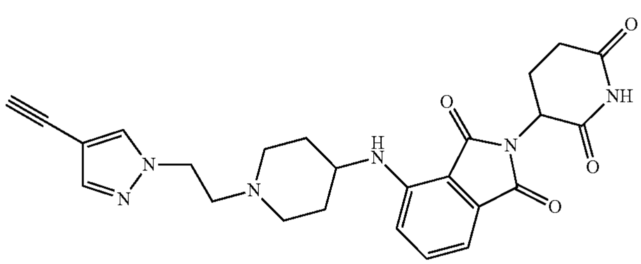 [SMILES: C#Cc1cnn(CCN2CCC(Nc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperidin-4-yl)amino)isoindoline-1,3-dione |
| 164 | 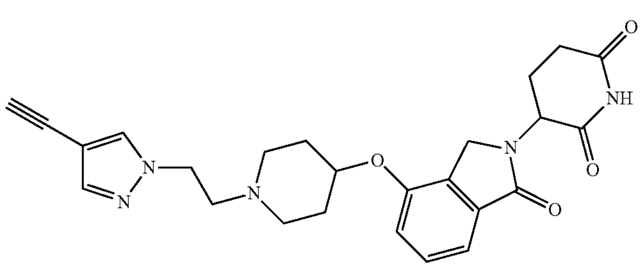 [SMILES: C#Cc1cnn(CCN2CCC(Oc3cccc4c3CN(C3CCC(=O)NC3=O)C4=O)CC2)c1] | 3-(4-((1-(2-(4-ethynyl-1H-pyrazol-1-yl)ethyl)piperidin-4-yl)oxy)-1-oxoisoindolin-2-yl)piperidine-2,6-dione |

TABLE 2-continued

| Cpd. No. | Structure | Name |
|---|---|---|
| 165 | 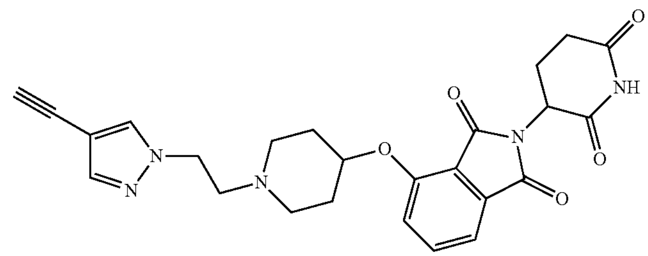 [SMILES: C#Cc1cnn(CCN2CCC(Oc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperidin-4-yl)oxy)isoindoline-1,3-dione |
| 166 | 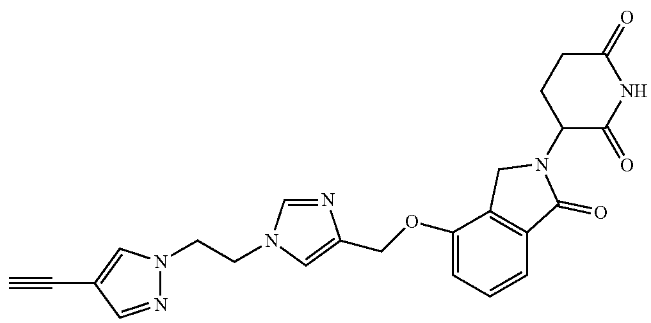 [SMILES: C#Cc1cnn(CCn2cnc(COc3cccc4c3CN(C3CCC(=O)NC3=O)C4=O)c2)c1] | 3-(4-((1-(2-(4-ethynyl-1H-pyrazol-1-yl)ethyl)-1H-imidazol-4-yl)methoxy)-1-oxoisoindolin-2-yl)piperidine-2,6-dione |
| 167 | 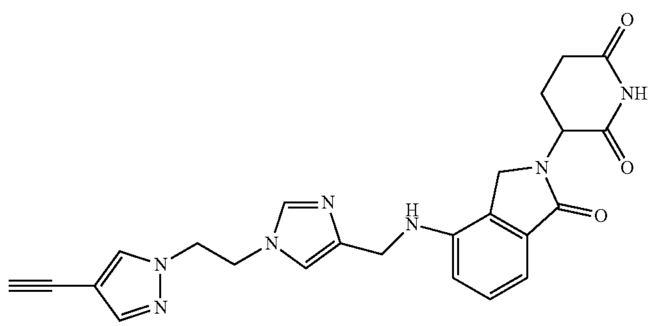 [SMILES: C#Cc1cnn(CCn2cnc(CNc3cccc4c3CN(C3CCC(=O)NC3=O)C4=O)c2)c1] | 3-(4-(((1-(2-(4-ethynyl-1H-pyrazol-1-yl)ethyl)-1H-imidazol-4-yl)methyl)amino)-1-oxoisoindolin-2-yl)piperidine-2,6-dione |
| 168 | 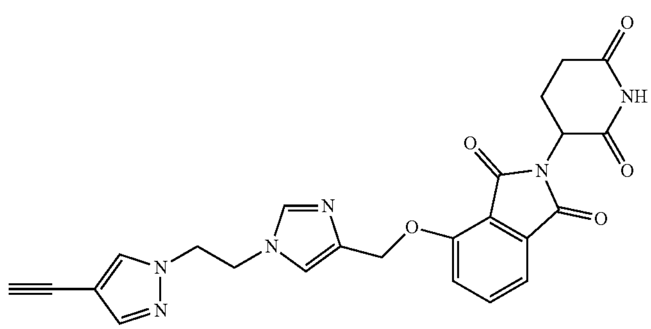 [SMILES: C#Cc1cnn(CCn2cnc(COc3cccc4c3C(=O)N(C3CCC(=O)NC3=O)C4=O)c2)c1] | 2-(2,6-dioxopiperidin-3-yl)-4-((1-(2-(4-ethynyl-1H-pyrazol-1-yl)ethyl)-1H-imidazol-4-yl)methoxy)isoindoline-1,3-dione |
| 169 | 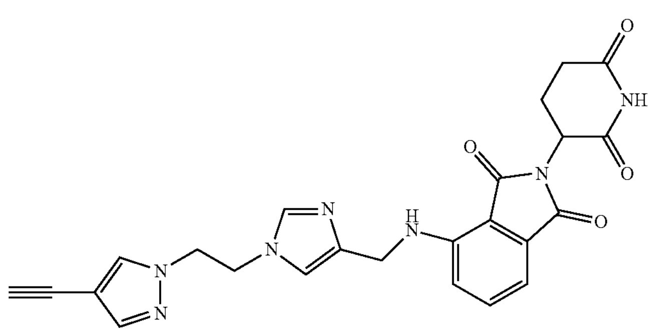 [SMILES: C#Cc1cnn(CCn2cnc(CNc3cccc4c3C(=O)N(C3CCC(=O)NC3=O)C4=O)c2)c1] | 2-(2,6-dioxopiperidin-3-yl)-4-(((1-(2-(4-ethynyl-1H-pyrazol-1-yl)ethyl)-1H-imidazol-4-yl)methyl)amino)isoindoline-1,3-dione |

TABLE 2-continued

| Cpd. No. | Structure | Name |
|---|---|---|
| 170 | 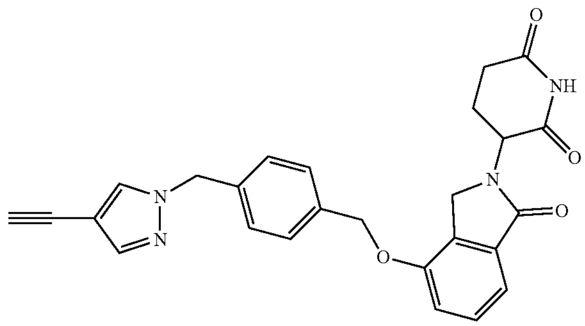 [SMILES: C#Cc1cnn(Cc2ccc(COc3cccc4c3CN(C3CCC(=O)NC3=O)C4=O)cc2)c1] | 3-(4-((4-((4-ethynyl-1H-pyrazol-1-yl)methyl)benzyl)oxy)-1-oxoisoindolin-2-yl)piperidine-2,6-dione |
| 171 | 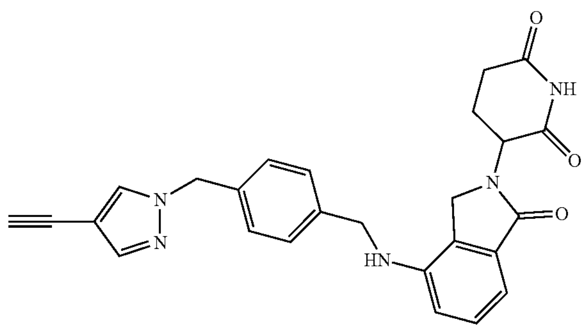 [SMILES: C#Cc1cnn(Cc2ccc(CNc3cccc4c3CN(C3CCC(=O)NC3=O)C4=O)cc2)c1] | 3-(4-((4-((4-ethynyl-1H-pyrazol-1-yl)methyl)benzyl)amino)-1-oxoisoindolin-2-yl)piperidine-2,6-dione |
| 172 | 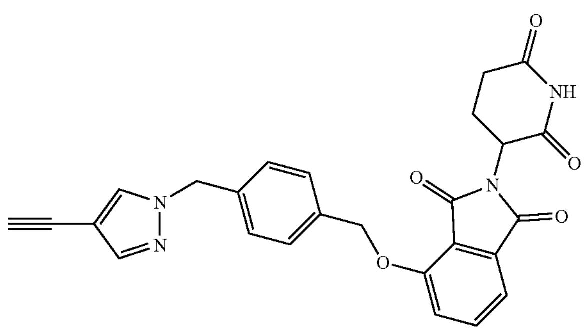 [SMILES: C#Cc1cnn(Cc2ccc(COc3cccc4c3C(=O)N(C3CCC(=O)NC3=O)C4=O)cc2)c1] | 2-(2,6-dioxopiperidin-3-yl)-4-((4-((4-ethynyl-1H-pyrazol-1-yl)methyl)benzyl)oxy)isoindoline-1,3-dione |
| 173 | 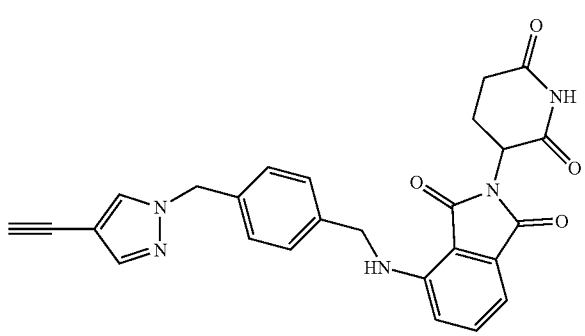 [SMILES: C#Cc1cnn(Cc2ccc(CNc3cccc4c3C(=O)N(C3CCC(=O)NC3=O)C4=O)cc2)c1] | 2-(2,6-dioxopiperidin-3-yl)-4-((4-((4-ethynyl-1H-pyrazol-1-yl)methyl)benzyl)amino)isoindoline-1,3-dione |

In another embodiment, Compounds of the Disclosure are any one or more of the compounds of Table 3, and salts and solvates thereof.

TABLE 3

| Cpd. No. | Structure | Name |
|---|---|---|
| 174 | 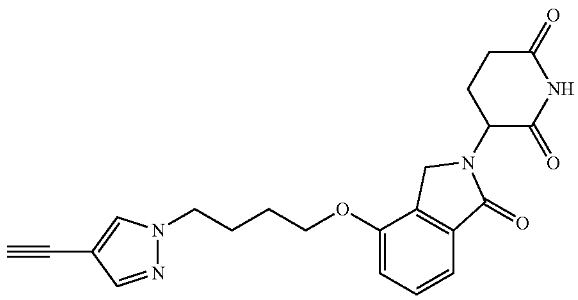 [SMILES: C#Cc1cnn(CCCCOc2cccc3c2CN(C2CCC(=O)NC2=O)C3=O)c1] | 3-(4-(4-(4-ethynyl-1H-pyrazol-1-yl)butoxy)-1-oxoisoindolin-2-yl)piperidine-2,6-dione |
| 175 | 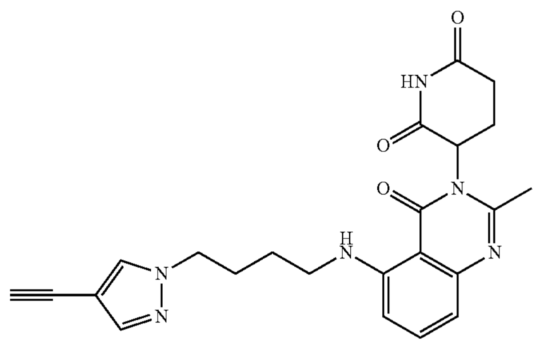 [SMILES: C#Cc1cnn(CCCCNc2cccc3nc(C)n(C4CCC(=O)NC4=O)c(=O)c23)c1] | 3-(5-((4-(4-ethynyl-1H-pyrazol-1-yl)butyl)amino)-2-methyl-4-oxoquinazolin-3(4H)-yl)piperidine-2,6-dione |
| 176 | 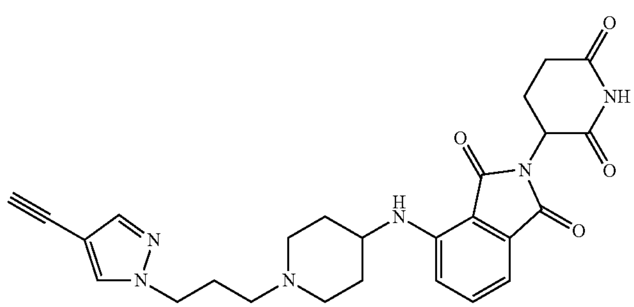 [SMILES: C#Cc1cnn(CCCN2CCC(Nc3cccc4c3C(=O)N(C3CCC(=O)NC3=O)C4=O)CC2)c1] | 2-(2,6-dioxopiperidin-3-yl)-4-((1-(3-(4-ethynyl-1H-pyrazol-1-yl)propyl)piperidin-4-yl)amino)isoindoline-1,3-dione |
| 177 | 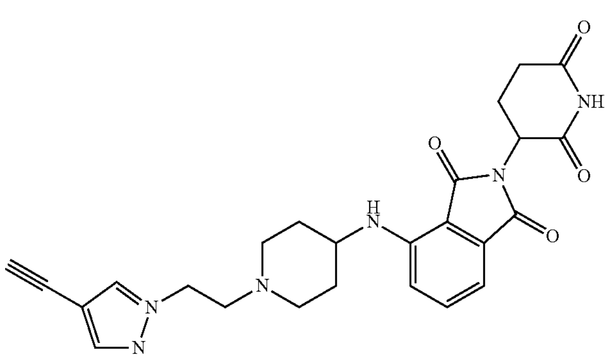 | 2-(2,6-dioxopiperidin-3-yl)-4-((1-(2-(4-ethynyl-1H-pyrazol-1-yl)ethyl)piperidin-4-yl)amino)isoindoline-1,3-dione |

TABLE 3-continued

| Cpd. No. | Structure | Name |
|---|---|---|
| 178 | 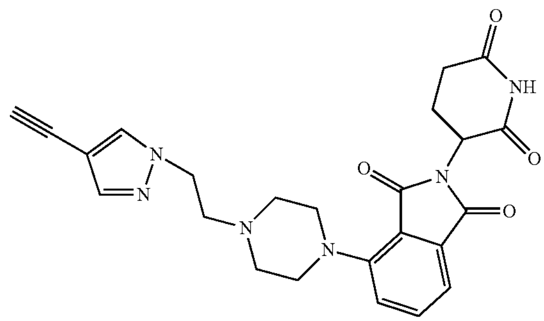 [SMILES: C#Cc1cnn(CCN2CCN(c3cccc4c3C(=O)N(C3CCC(=O)NC3=O)C4=O)CC2)c1] | 2-(2,6-dioxopiperidin-3-yl)-4-(4-(2-(4-ethynyl-1H-pyrazol-1-yl)ethyl)piperazin-1-yl)isoindoline-1,3-dione |
| 179 | 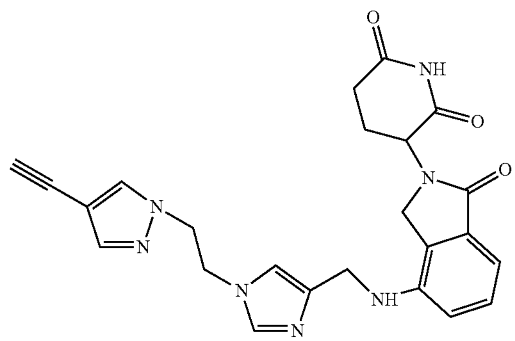 [SMILES: C#Cc1cnn(CCn2cnc(CNc3cccc4c3CN(C3CCC(=O)NC3=O)C4=O)c2)c1] | 3-(4-(((1-(2-(4-ethynyl-1H-pyrazol-1-yl)ethyl)-1H-imidazol-4-yl)methyl)amino)-1-oxoisoindolin-2-yl)piperidine-2,6-dione |
| 180 | 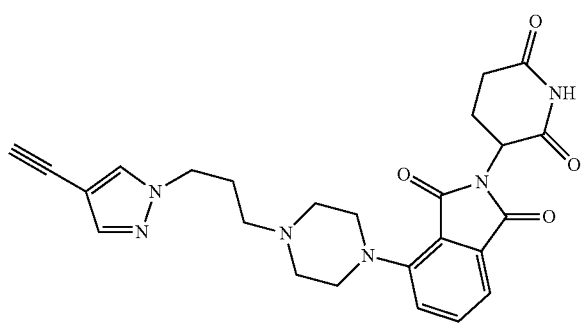 [SMILES: C#Cc1cnn(CCCN2CCN(c3cccc4c3C(=O)N(C3CCC(=O)NC3=O)C4=O)CC2)c1] | 2-(2,6-dioxopiperidin-3-yl)-4-(4-(3-(4-ethynyl-1H-pyrazol-1-yl)propyl)piperazin-1-yl)isoindoline-1,3-dione |
| 181 | 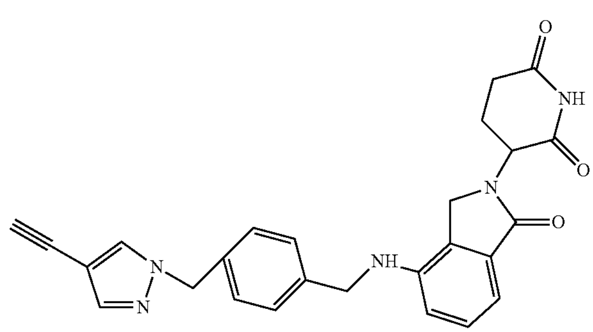 [SMILES: C#Cc1cnn(Cc2ccc(CNc3cccc4c3CN(C3CCC(=O)NC3=O)C4=O)cc2)c1] | 3-(4-((4-((4-ethynyl-1H-pyrazol-1-yl)methyl)benzyl)amino)-1-oxoisoindolin-2-yl)piperidine-2,6-dione |

TABLE 3-continued

| Cpd. No. | Structure | Name |
|---|---|---|
| 182 | 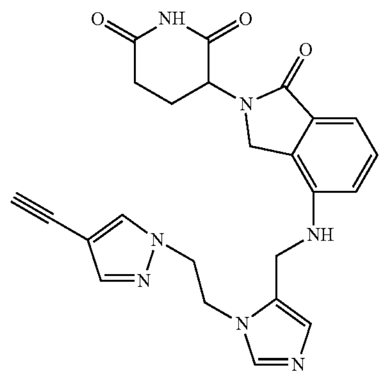 [SMILES: C#Cc1cnn(CCn2cncc2CNc2cccc3c2CN(C2CCC(=O)NC2=O)C3=O)c1] | 3-(4-(((1-(2-(4-ethynyl-1H-pyrazol-1-yl)ethyl)-1H-imidazol-5-yl)methyl)amino)-1-oxoisoindolin-2-yl)piperidine-2,6-dione |
| 183 | 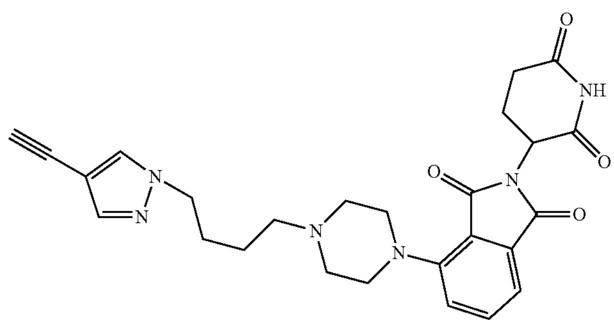 [SMILES: C#Cc1cnn(CCCCN2CCN(c3cccc4c3C(=O)N(C3CCC(=O)NC3=O)C4=O)CC2)c1] | 2-(2,6-dioxopiperidin-3-yl)-4-(4-(4-(4-ethynyl-1H-pyrazol-1-yl)butyl)piperazin-1-yl)isoindoline-1,3-dione |
| 184 | 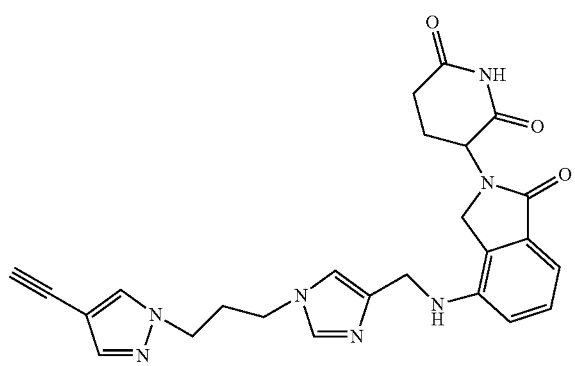 [SMILES: C#Cc1cnn(CCCn2cnc(CNc3cccc4c3CN(C3CCC(=O)NC3=O)C4=O)c2)c1] | 3-(4-(((1-(3-(4-ethynyl-1H-pyrazol-1-yl)propyl)-1H-imidazol-4-yl)methyl)amino)-1-oxoisoindolin-2-yl)piperidine-2,6-dione |
| 185 | 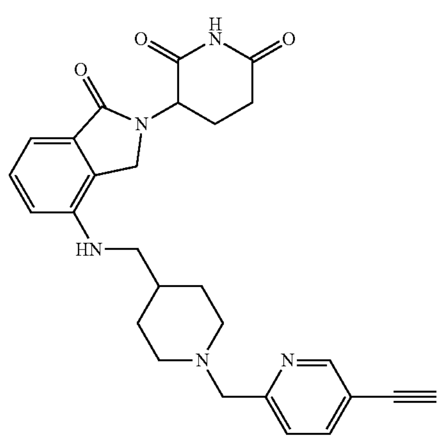 [SMILES: C#Cc1ccc(CN2CCC(CNc3cccc4c3CN(C3CCC(=O)NC3=O)C4=O)CC2)nc1] | 3-(4-(((1-((5-ethynylpyridin-2-yl)methyl)piperidin-4-yl)methyl)amino)-1-oxoisoindolin-2-yl)piperidine-2,6-dione |

TABLE 3-continued

| Cpd. No. | Structure | Name |
| --- | --- | --- |
| 186 | 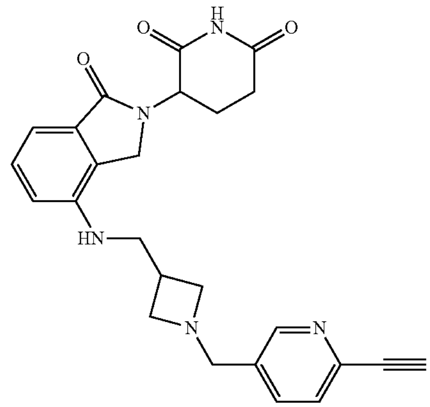 [SMILES: C#Cc1ccc(CN2CC(CNc3cccc4c3CN(C3CCC(=O)NC3=O)C4=O)C2)cn1] | 3-(4-(((1-((6-ethynylpyridin-3-yl)methyl)azetidin-3-yl)methyl)amino)-1-oxoisoindolin-2-yl)piperidine-2,6-dione |
| 187 | 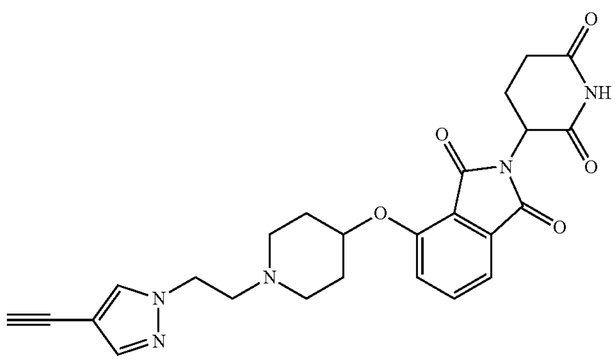 [SMILES: C#Cc1cnn(CCN2CCC(Oc3cccc4c3C(=O)N(C3CCC(=O)NC3=O)C4=O)CC2)c1] | 2-(2,6-dioxopiperidin-3-yl)-4-((1-(2-(4-ethynyl-1H-pyrazol-1-yl)ethyl)piperidin-4-yl)oxy)isoindoline-1,3-dione |
| 188 | 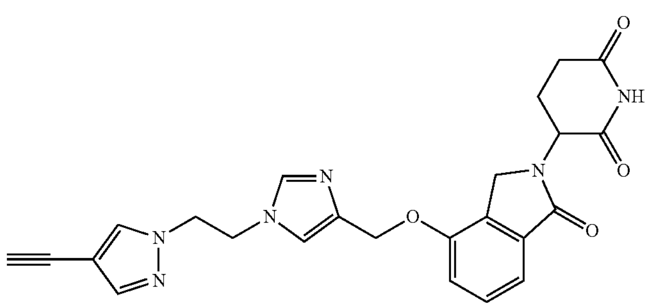 [SMILES: C#Cc1cnn(CCn2cnc(COc3cccc4c3CN(C3CCC(=O)NC3=O)C4=O)c2)c1] | 3-(4-((1-(2-(4-ethynyl-1H-pyrazol-1-yl)ethyl)-1H-imidazol-4-yl)methoxy)-1-oxoisoindolin-2-yl)piperidine-2,6-dione |
| 189 | 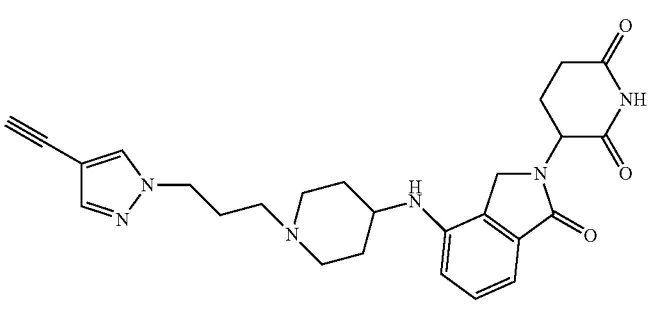 [SMILES: C#Cc1cnn(CCCN2CCC(Nc3cccc4c3CN(C3CCC(=O)NC3=O)C4=O)CC2)c1] | 3-(4-((1-(3-(4-ethynyl-1H-pyrazol-1-yl)propyl)piperidin-4-yl)amino)-1-oxoisoindolin-2-yl)piperidine-2,6-dione |

TABLE 3-continued

| Cpd. No. | Structure | Name |
|---|---|---|
| 190 | 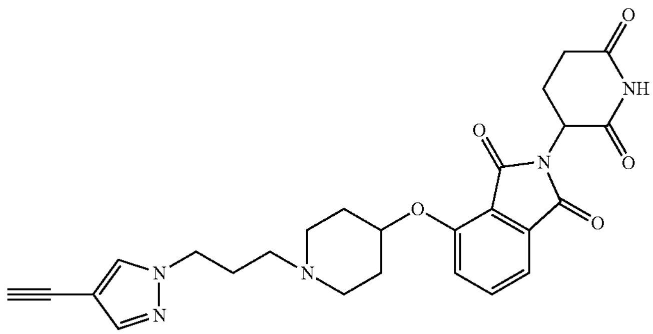 [SMILES: C#Cc1cnn(CCCN2CCC(Oc3cccc4c3C(=O)N(C3CCC(=O)NC3=O)C4=O)CC2)c1] | 2-(2,6-dioxopiperidin-3-yl)-4-((1-(3-(4-ethynyl-1H-pyrazol-1-yl)propyl)piperidin-4-yl)oxy)isoindoline-1,3-dione |
| 191 | 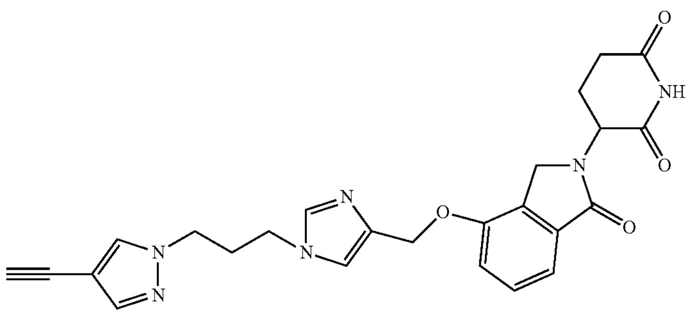 [SMILES: C#Cc1cnn(CCCn2cnc(COc3cccc4c3CN(C3CCC(=O)NC3=O)C4=O)c2)c1] | 3-(4-((1-(3-(4-ethynyl-1H-pyrazol-1-yl)propyl)-1H-imidazol-4-yl)methoxy)-1-oxoisoindolin-2-yl)piperidine-2,6-dione |
| 192 | 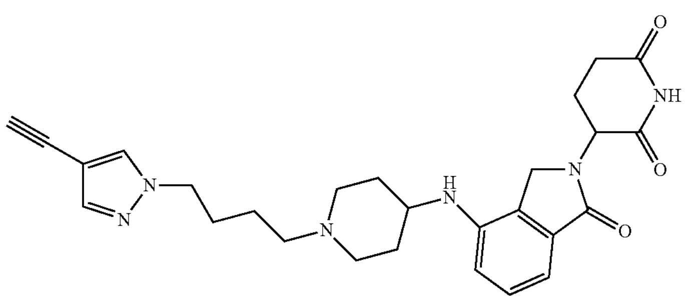 [SMILES: C#Cc1cnn(CCCCN2CCC(Nc3cccc4c3CN(C3CCC(=O)NC3=O)C4=O)CC2)c1] | 3-(4-((1-(4-(4-ethynyl-1H-pyrazol-1-yl)butyl)piperidin-4-yl)amino)-1-oxoisoindolin-2-yl)piperidine-2,6-dione |
| 193 | 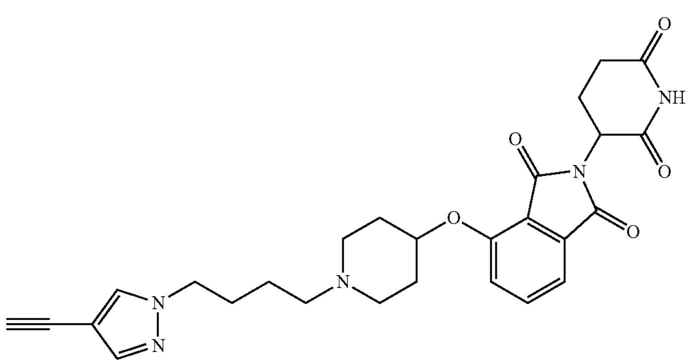 [SMILES: C#Cc1cnn(CCCCN2CCC(Oc3cccc4c3C(=O)N(C3CCC(=O)NC3=O)C4=O)CC2)c1] | 2-(2,6-dioxopiperidin-3-yl)-4-((1-(4-(4-ethynyl-1H-pyrazol-1-yl)butyl)piperidin-4-yl)oxy)isoindoline-1,3-dione |

TABLE 3-continued

| Cpd. No. | Structure | Name |
|---|---|---|
| 194 | 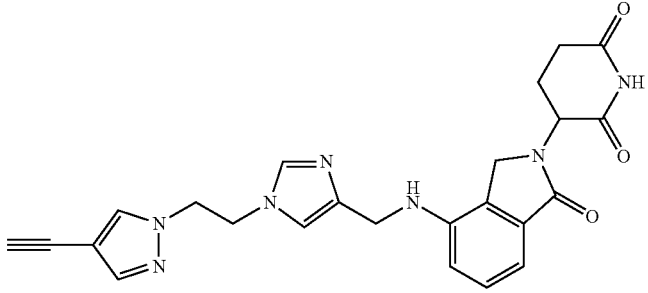 | 3-(4-(((1-(2-(4-ethynyl-1H-pyrazol-1-yl)ethyl)-1H-imidazol-4-yl)methyl)amino)-1-oxoisoindolin-2-yl)piperidine-2,6-dione |
| 195 | 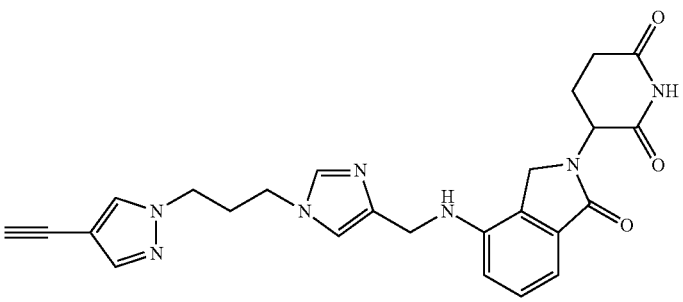 [SMILES: C#Cc1cnn(CCCn2cnc(CNc3cccc4c3CN(C3CCC(=O)NC3=O)C4=O)c2)c1] | 3-(4-(((1-(3-(4-ethynyl-1H-pyrazol-1-yl)propyl)-1H-imidazol-4-yl)methyl)amino)-1-oxoisoindolin-2-yl)piperidine-2,6-dione |
| 196 | 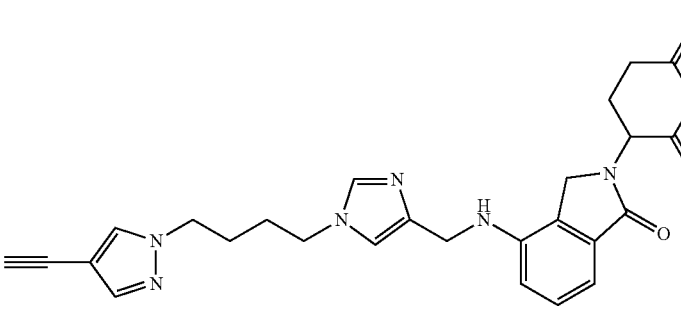 | 3-(4-(((1-(4-(4-ethynyl-1H-pyrazol-1-yl)butyl)-1H-imidazol-4-yl)methyl)amino)-1-oxoisoindolin-2-yl)piperidine-2,6-dione |
| 197 | 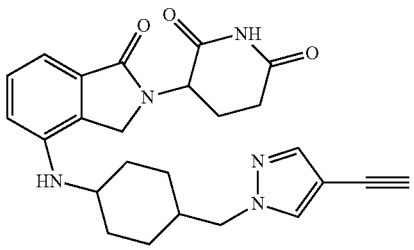 [SMILES: C#Cc1cnn(CC2CCC(Nc3cccc4c3CN(C3CCC(=O)NC3=O)C4=O)CC2)c1] | 3-(4-((4-((4-ethynyl-1H-pyrazol-1-yl)methyl)cyclohexyl)amino)-1-oxoisoindolin-2-yl)piperidine-2,6-dione |
| 198 | 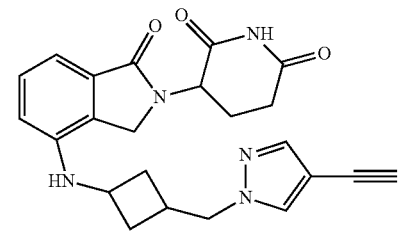 [SMILES: C#Cc1cnn(CC2CC(Nc3cccc4c3CN(C3CCC(=O)NC3=O)C4=O)C2)c1] | 3-(4-((3-((4-ethynyl-1H-pyrazol-1-yl)methyl)cyclobutyl)amino)-1-oxoisoindolin-2-yl)piperidine-2,6-dione |

TABLE 3-continued

| Cpd. No. | Structure | Name |
|---|---|---|
| 199 | 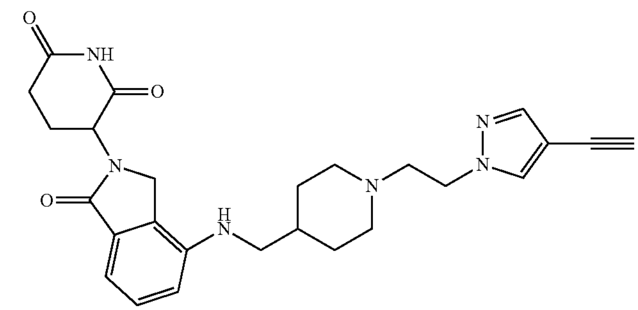 [SMILES: C#Cc1cnn(CCN2CCC(CNc3cccc4c3CN(C3CCC(=O)NC3=O)C4=O)CC2)c1] | 3-(4-(((1-(2-(4-ethynyl-1H-pyrazol-1-yl)ethyl)piperidin-4-yl)methyl)amino)-1-oxoisoindolin-2-yl)piperidine-2,6-dione |
| 200 | 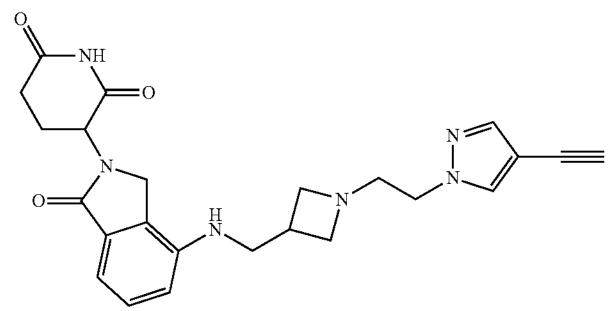 [SMILES: C#Cc1cnn(CCN2CC(CNc3cccc4c3CN(C3CCC(=O)NC3=O)C4=O)C2)c1] | 3-(4-(((1-(2-(4-ethynyl-1H-pyrazol-1-yl)ethyl)azetidin-3-yl)methyl)amino)-1-oxoisoindolin-2-yl)piperidine-2,6-dione |
| 201 | 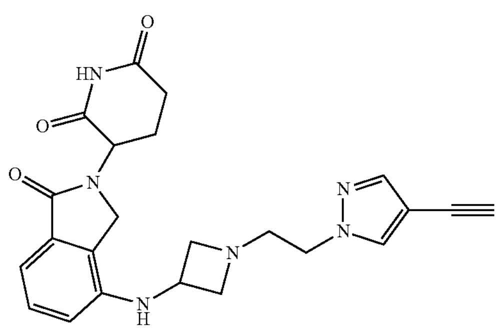 [SMILES: C#Cc1cnn(CCN2CC(Nc3cccc4c3CN(C3CCC(=O)NC3=O)C4=O)C2)c1] | 3-(4-((1-(2-(4-ethynyl-1H-pyrazol-1-yl)ethyl)azetidin-3-yl)amino)-1-oxoisoindolin-2-yl)piperidine-2,6-dione |
| 202 | 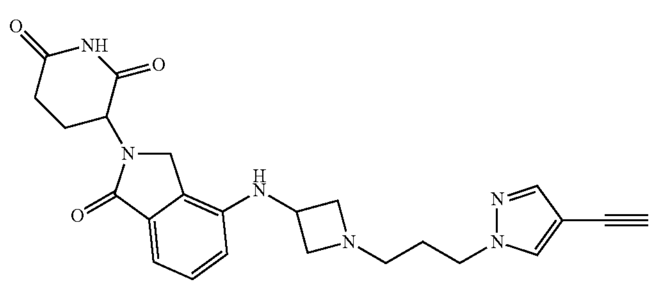 [SMILES: C#Cc1cnn(CCCN2CC(Nc3cccc4c3CN(C3CCC(=O)NC3=O)C4=O)C2)c1] | 3-(4-((1-(3-(4-ethynyl-1H-pyrazol-1-yl)propyl)azetidin-3-yl)amino)-1-oxoisoindolin-2-yl)piperidine-2,6-dione |

TABLE 3-continued

| Cpd. No. | Structure | Name |
|---|---|---|
| 203 | 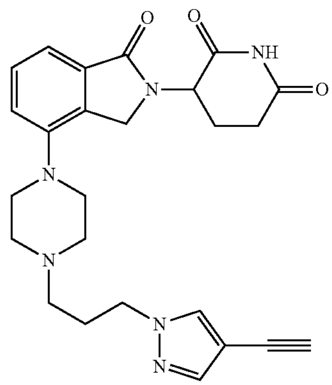 [SMILES: C#Cc1cnn(CCCN2CCN(c3cccc4c3CN(C3CCC(=O)NC3=O)C4=O)CC2)c1] | 3-(4-(4-(3-(4-ethynyl-1H-pyrazol-1-yl)propyl)piperazin-yl)-1-oxoisoindolin-2-yl)piperidine-2,6-dione |

In another embodiment, Compounds of the Disclosure are any one or more of the compounds of Table 4, and salts and solvates thereof.

TABLE 4

| Cpd. No. | Structure | Name |
|---|---|---|
| 204 | 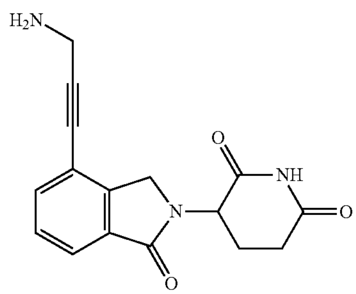 [SMILES: NCC#Cc1cccc2c1CN(C1CCC(=O)NC1=O)C2=O] | 3-(4-(3-aminoprop-1-yn-1-yl)-1-oxoisoindolin-2-yl)piperidine-2,6-dione |
| 205 | 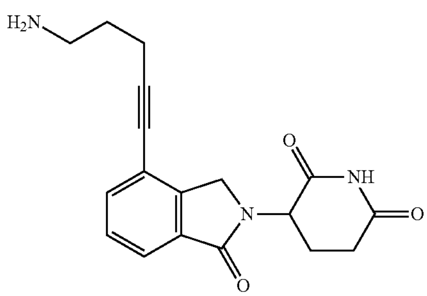 [SMILES: NCCCC#Cc1cccc2c1CN(C1CCC(=O)NC1=O)C2=O] | 3-(4-(5-aminopent-1-yn-1-yl)-1-oxoisoindolin-2-yl)piperidine-2,6-dione |
| 206 | 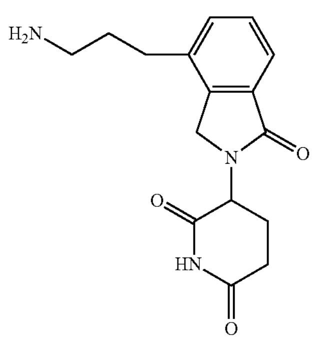 [SMILES: NCCCc1cccc2c1CN(C1CCC(=O)NC1=O)C2=O] | 3-(4-(3-aminopropyl)-1-oxoisoindolin-2-yl)piperidine-2,6-dione |

TABLE 4-continued

| Cpd. No. | Structure | Name |
|---|---|---|
| 207 | 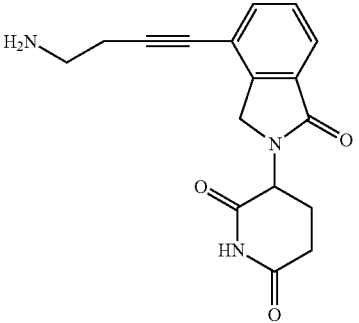 [SMILES: NCCC#Cc1cccc2c1CN(C1CCC(=O)NC1=O)C2=O] | 3-(4-(4-aminobut-1-yn-1-yl)-1-oxoisoindolin-2-yl)piperidine-2,6-dione |
| 208 | 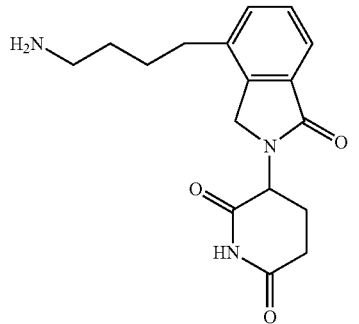 [SMILES: NCCCCc1cccc2c1CN(C1CCC(=O)NC1=O)C2=O] | 3-(4-(4-aminobutyl)-1-oxoisoindolin-2-yl)piperidine-2,6-dione |
| 209 | 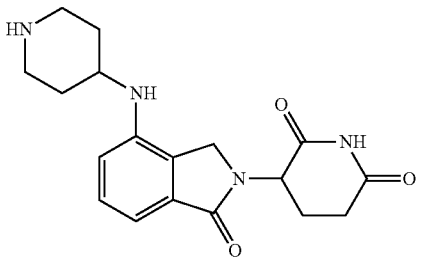 [SMILES: O=C1CCC(N2Cc3c(NC4CCNCC4)cccc3C2=O)C(=O)N1] | 3-(1-oxo-4-(piperidin-4-ylamino)isoindolin-2-yl)piperidine-2,6-dione |
| 210 | 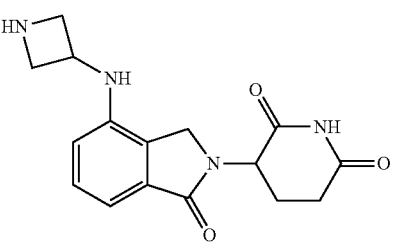 [SMILES: O=C1CCC(N2Cc3c(NC4CNC4)cccc3C2=O)C(=O)N1] | 3-(4-(azetidin-3-ylamino)-1-oxoisoindolin-2-yl)piperidine-2,6-dione |
| 211 | 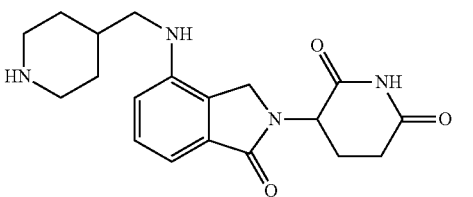 [SMILES: O=C1CCC(N2Cc3c(NCC4CCNCC4)cccc3C2=O)C(=O)N1] | 3-(1-oxo-4-((piperidin-4-ylmethyl)amino)isoindolin-2-yl)piperidine-2,6-dione |
| 212 | 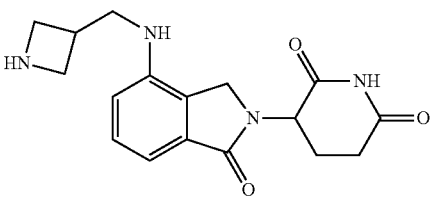 [SMILES: O=C1CCC(N2Cc3c(NCC4CNC4)cccc3C2=O)C(=O)N1] | 3-(4-((azetidin-3-ylmethyl)amino)-1-oxoisoindolin-2-yl)piperidine-2,6-dione |

TABLE 4-continued

| Cpd. No. | Structure | Name |
|---|---|---|
| 213 | 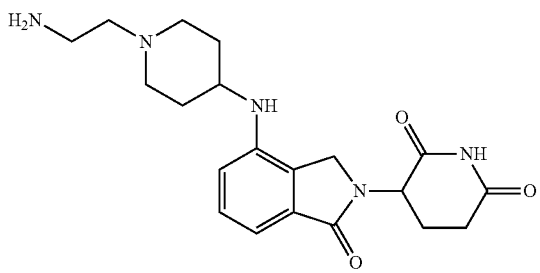 [SMILES: NCCN1CCC(Nc2cccc3c2CN(C2CCC(=O)NC2=O)C3=O)CC1] | 3-(4-((1-(2-aminoethyl)piperidin-4-yl)amino)-1-oxoisoindolin-2-yl)piperidine-2,6-dione |
| 214 | 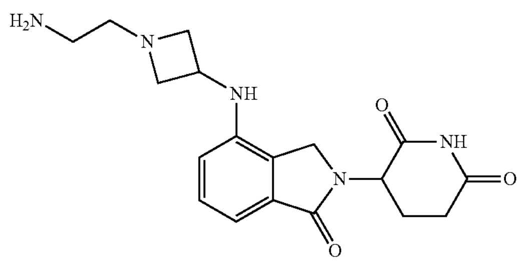 [SMILES: NCCN1CC(Nc2cccc3c2CN(C2CCC(=O)NC2=O)C3=O)C1] | 3-(4-((1-(2-aminoethyl)azetidin-3-yl)amino)-1-oxoisoindolin-2-yl)piperidine-2,6-dione |
| 215 | 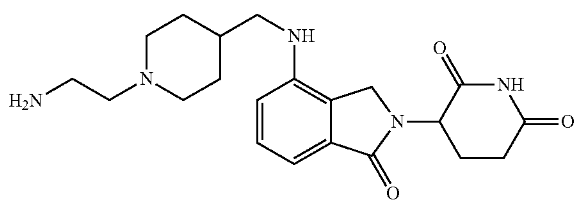 [SMILES: NCCN1CCC(CNc2cccc3c2CN(C2CCC(=O)NC2=O)C3=O)CC1] | 3-(4-(((1-(2-aminoethyl)piperidin-4-yl)methyl)amino)-1-oxoisoindolin-2-yl)piperidine-2,6-dione |
| 216 | 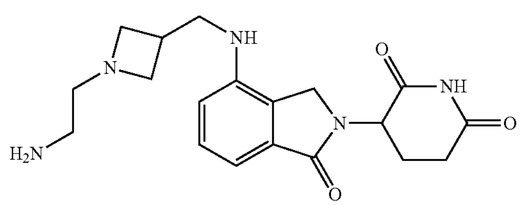 [SMILES: NCCN1CC(CNc2cccc3c2CN(C2CCC(=O)NC2=O)C3=O)C1] | 3-(4-(((1-(2-aminoethyl)azetidin-3-yl)methyl)amino)-1-oxoisoindolin-2-yl)piperidine-2,6-dione |
| 217 | 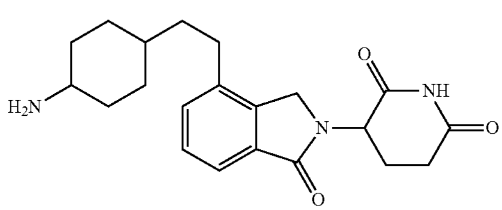 [SMILES: NC1CCC(CCc2cccc3c2CN(C2CCC(=O)NC2=O)C3=O)CC1] | 3-(4-(2-(4-aminocyclohexyl)ethyl)-1-oxoisoindolin-2-yl)piperidine-2,6-dione |
| 218 | 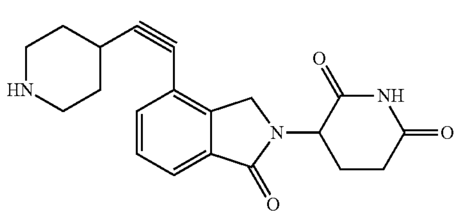 [SMILES: O=C1CCC(N2Cc3c(C#CC4CCNCC4)cccc3C2=O)C(=O)N1] | 3-(1-oxo-4-(piperidin-4-ylethynyl)isoindolin-2-yl)piperidine-2,6-dione |
| 219 | 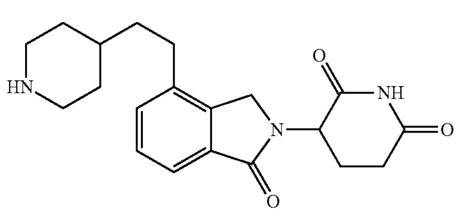 [SMILES: O=C1CCC(N2Cc3c(CCC4CCNCC4)cccc3C2=O)C(=O)N1] | 3-(1-oxo-4-(2-(piperidin-4-yl)ethyl)isoindolin-2-yl)piperidine-2,6-dione |

TABLE 4-continued

| Cpd. No. | Structure | Name |
|---|---|---|
| 220 | 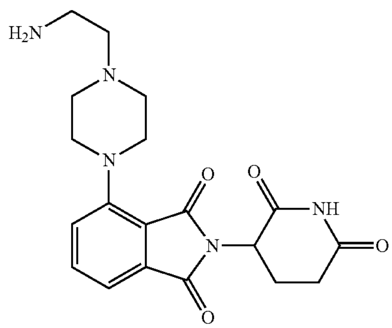 [SMILES: NCCN1CCN(c2cccc3c2C(=O)N(C2CCC(=O)NC2=O)C3=O)CC1] | 4-(4-(2-aminoethyl)piperazin-1-yl)-2-(2,6-dioxopiperidin-3-yl)isoindoline-1,3-dione |

In another embodiment, Compounds of the Disclosure are any one or more of the compounds of Table 5, and salts and solvates thereof.

TABLE 5

| Cpd. No. | Structure | Name |
|---|---|---|
| 221 | 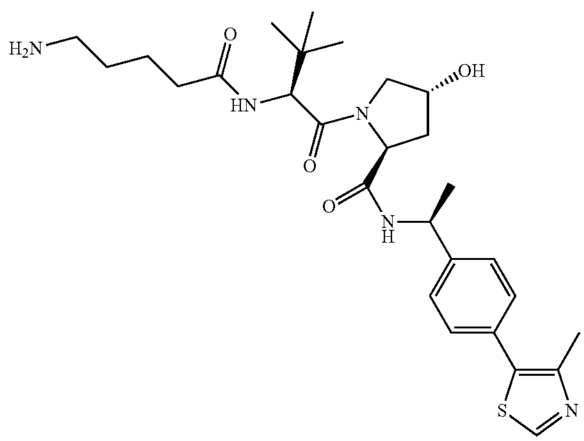 [SMILES: Cc1ncsc1-c1ccc([C@H](C)NC(=O)[C@@H]2C[C@@H](O)CN2C(=O)[C@@H](NC(=O)CCCCN)C(C)(C)C)cc1] | (2S,4R)-1-((S)-2-(5-aminopentanamido)-3,3-dimethylbutanoyl)-4-hydroxy-N-((S)-1-(4-(4-methylthiazol-5-yl)phenyl)ethyl)pyrrolidine-2-carboxamide |
| 222 | 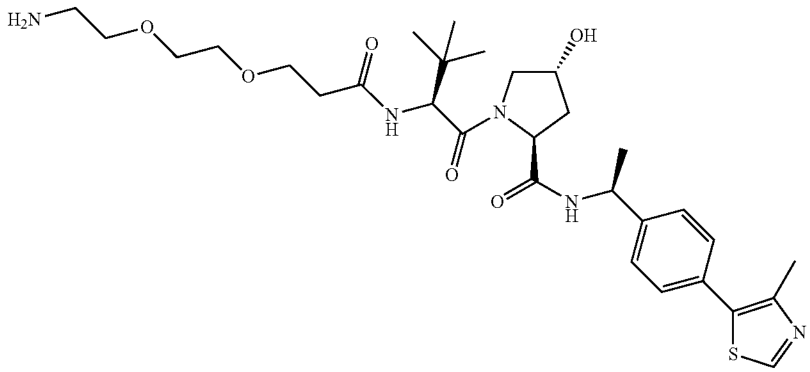 [SMILES: Cc1ncsc1-c1ccc([C@H](C)NC(=O)[C@@H]2C[C@@H](O)CN2C(=O)[C@@H](NC(=O)CCOCCOCCN)C(C)(C)C)cc1] | (2S,4R)-1-((S)-2-(3-(2-(2-aminoethoxy)ethoxy)propanamido)-3,3-dimethylbutanoyl)-4-hydroxy-N-((S)-1-(4-(4-methylthiazol-5-yl)phenyl)ethyl)pyrrolidine-2-carboxamide |

TABLE 5-continued

| Cpd. No. | Structure | Name |
|---|---|---|
| 223 | 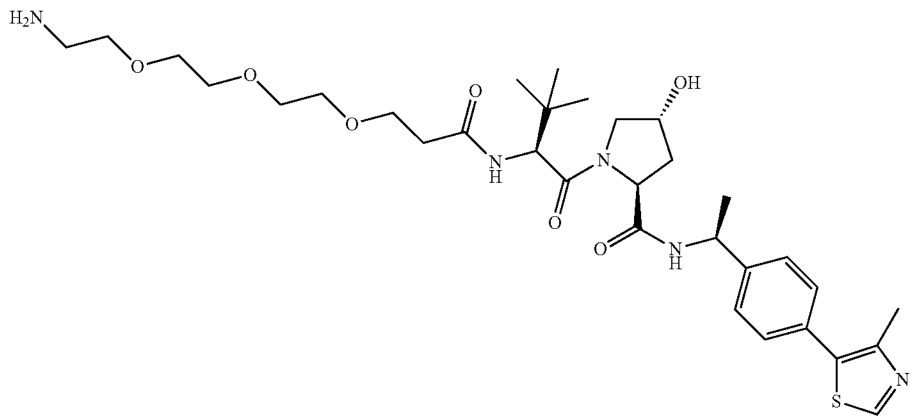 [SMILES: Cc1ncsc1-c1ccc([C@H](C)NC(=O)[C@@H]2C[C@@H](O)CN2C(=O)[C@@H](NC(=O)CCOCCOCCOCCN)C(C)(C)C)cc1] | (2S,4R)-1-((S)-1-amino-14-(tert-butyl)-12-oxo-3,6,9-trioxa-13-azapentadecan-15-oyl)-4-hydroxy-N-((S)-1-(4-(4-methylthiazol-5-yl)phenyl)ethyl)pyrrolidine-2-carboxamide |
| 224 | 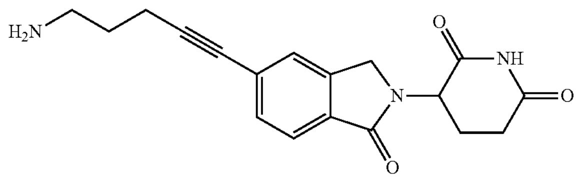 [SMILES: NCCCC#Cc1ccc2c(c1)CN(C1CCC(=O)NC1=O)C2=O] | 3-(5-(5-aminopent-1-yn-1-yl)-1-oxoisoindolin-2-yl)piperidine-2,6-dione |
| 225 | 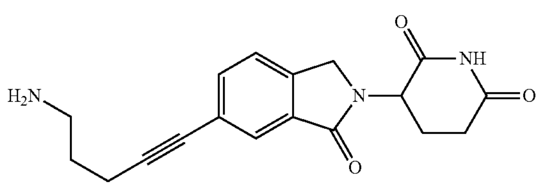 [SMILES: NCCCC#Cc1ccc2c(c1)C(=O)N(C1CCC(=O)NC1=O)C2] | 3-(6-(5-aminopent-1-yn-1-yl)-1-oxoisoindolin-2-yl)piperidine-2,6-dione |
| 226 | 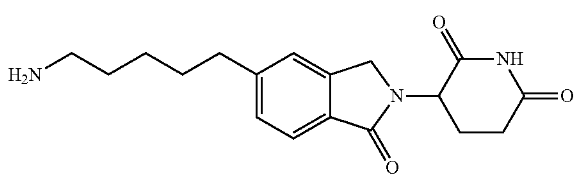 [SMILES: NCCCCCc1ccc2c(c1)CN(C1CCC(=O)NC1=O)C2=O] | 3-(5-(5-aminopentyl)-1-oxoisoindolin-2-yl)piperidine-2,6-dione |
| 227 | 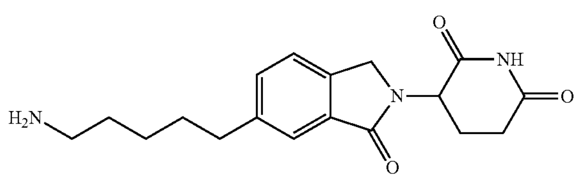 [SMILES: NCCCCCc1ccc2c(c1)C(=O)N(C1CCC(=O)NC1=O)C2] | 3-(6-(5-aminopentyl)-1-oxoisoindolin-2-yl)piperidine-2,6-dione |
| 228 | 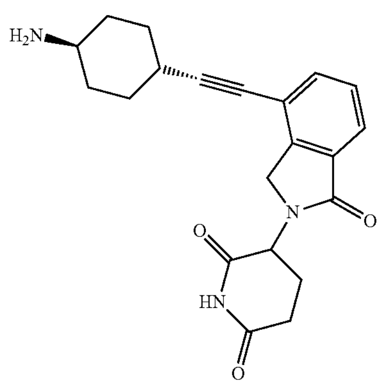 | 3-(4-(((1r,4r)-4-aminocyclohexyl)ethynyl)-1-oxoisoindolin-2-yl)piperidine-2,6-dione |

TABLE 5-continued

| Cpd. No. | Structure | Name |
|---|---|---|
| 229 | 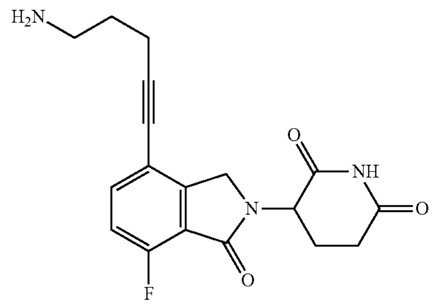 [SMILES: NCCCC#Cc1ccc(F)c2c1CN(C1CCC(=O)NC1=O)C2=O] | 3-(4-(5-aminopent-1-yn-1-yl)-7-fluoro-1-oxoisoindolin-2-yl)piperidine-2,6-dione |
| 230 | 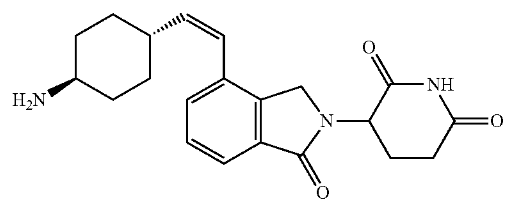 [SMILES: N[C@H]1CC[C@H](/C=C\c2cccc3c2CN(C2CCC(=O)NC2=O)C3=O)CC1] | 3-(4-((Z)-2-((1r,4r)-4-aminocyclohexyl)vinyl)-1-oxoisoindolin-2-yl)piperidine-2,6-dione |
| 231 | 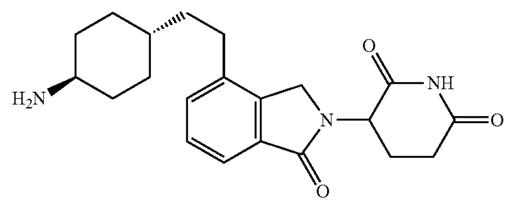 [SMILES: N[C@H]1CC[C@H](CCc2cccc3c2CN(C2CCC(=O)NC2=O)C3=O)CC1] | 3-(4-(2-((1r,4s)-4-aminocyclohexyl)ethyl)-1-oxoisoindolin-2-yl)piperidine-2,6-dione |
| 232 | 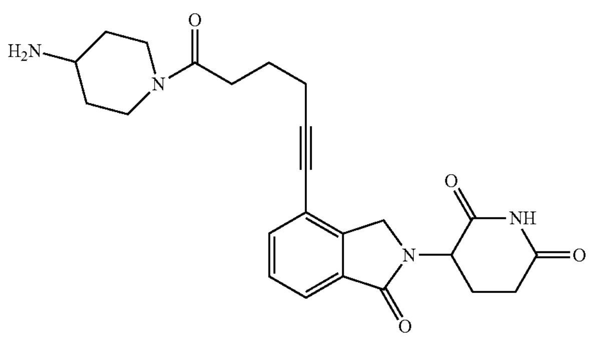 [SMILES: NC1CCN(C(=O)CCCC#Cc2cccc3c2CN(C2CCC(=O)NC2=O)C3=O)CC1] | 3-(4-(6-(4-aminopiperidin-1-yl)-6-oxohex-1-yn-1-yl)-1-oxoisoindolin-2-yl)piperidine-2,6-dione |
| 233 | 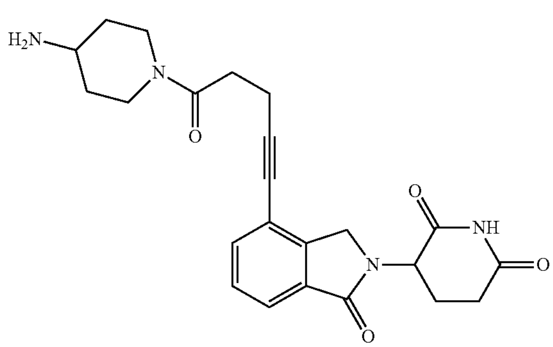 [SMILES: NC1CCN(C(=O)CCC#Cc2cccc3c2CN(C2CCC(=O)NC2=O)C3=O)CC1] | 3-(4-(5-(4-aminopiperidin-1-yl)-5-oxopent-1-yn-1-yl)-1-oxoisoindolin-2-yl)piperidine-2,6-dione |

TABLE 5-continued

| Cpd. No. | Structure | Name |
|---|---|---|
| 234 | 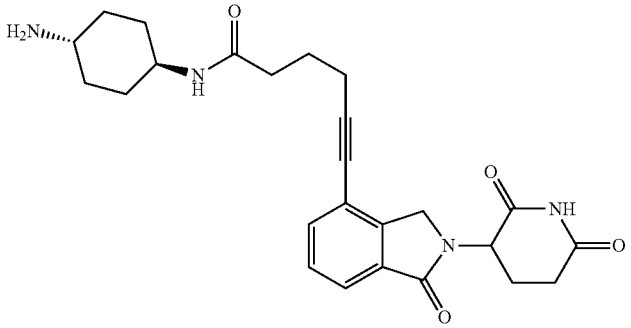 [SMILES: N[C@H]1CC[C@H](NC(=O)CCCC#Cc2cccc3c2CN(C2CCC(=O)NC2=O)C3=O)CC1] | N-((1r,4r)-4-aminocyclohexyl)-6-(2-(2,6-dioxopiperidin-3-yl)-1-oxoisoindolin-4-yl)hex-5-ynamide |
| 235 | 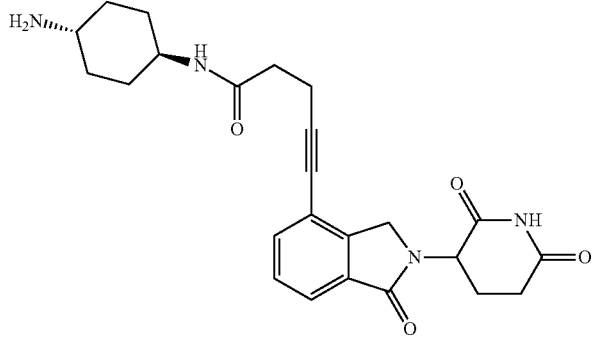 [SMILES: N[C@H]1CC[C@H](NC(=O)CCC#Cc2cccc3c2CN(C2CCC(=O)NC2=O)C3=O)CC1] | N-((1r,4r)-4-aminocyclohexyl)-5-(2-(2,6-dioxopiperidin-3-yl)-1-oxoisoindolin-4-yl)pent-4-ynamide |
| 236 | 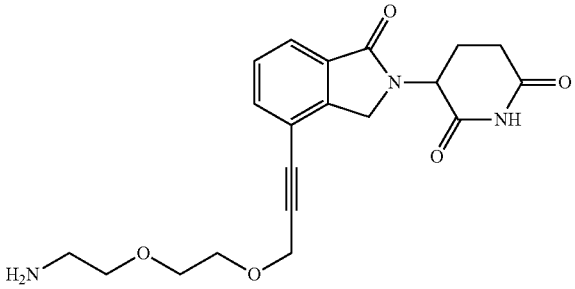 [SMILES: NCCOCCOCC#Cc1cccc2c1CN(C1CCC(=O)NC1=O)C2=O] | 3-(4-(3-(2-(2-aminoethoxy)ethoxy)prop-1-yn-1-yl)-1-oxoisoindolin-2-yl)piperidine-2,6-dione |
| 237 | 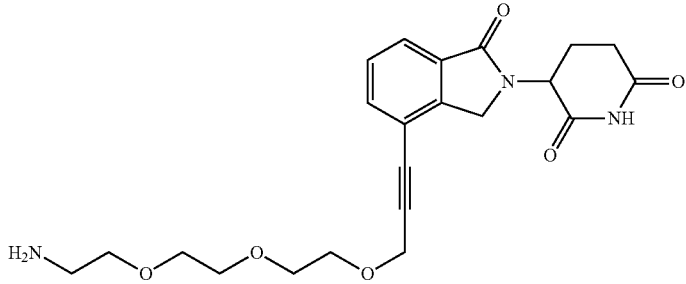 [SMILES: NCCOCCOCCOCC#Cc1cccc2c1CN(C1CCC(=O)NC1=O)C2=O] | 3-(4-(3-(2-(2-(2-aminoethoxy)ethoxy)ethoxy)prop-1-yn-1-yl)-1-oxoisoindolin-2-yl)piperidine-2,6-dione |
| 238 | 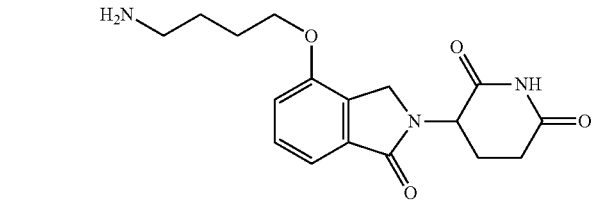 [SMILES: NCCCCOc1cccc2c1CN(C1CCC(=O)NC1=O)C2=O] | 3-(4-(4-aminobutoxy)-1-oxoisoindolin-2-yl)piperidine-2,6-dione |

TABLE 5-continued

| Cpd. No. | Structure | Name |
|---|---|---|
| 239 | 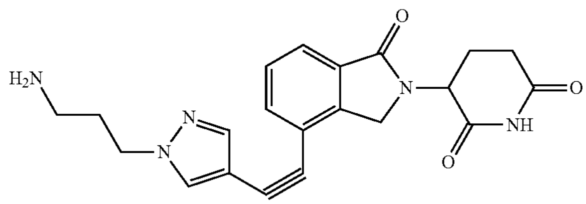 [SMILES: NCCCn1cc(C#Cc2cccc3c2CN(C2CCC(=O)NC2=O)C3=O)cn1] | 3-(4-((1-(3-aminopropyl)-1H-pyrazol-4-yl)ethynyl)-1-oxoisoindolin-2-yl)piperidine-2,6-dione |
| 240 | 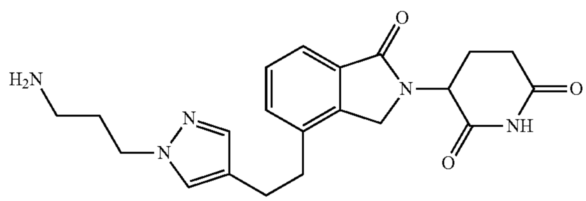 [SMILES: NCCCn1cc(CCc2cccc3c2CN(C2CCC(=O)NC2=O)C3=O)cn1] | 3-(4-(2-(1-(3-aminopropyl)-1H-pyrazol-4-yl)ethyl)-1-oxoisoindolin-2-yl)piperidine-2,6-dione |
| 241 | 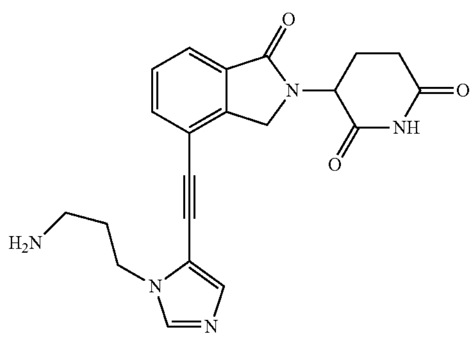 [SMILES: NCCCn1cncc1C#Cc1cccc2c1CN(C1CCC(=O)NC1=O)C2=O] | 3-(4-((1-(3-aminopropyl)-1H-imidazol-5-yl)ethynyl)-1-oxoisoindolin-2-yl)piperidine-2,6-dione |
| 242 | 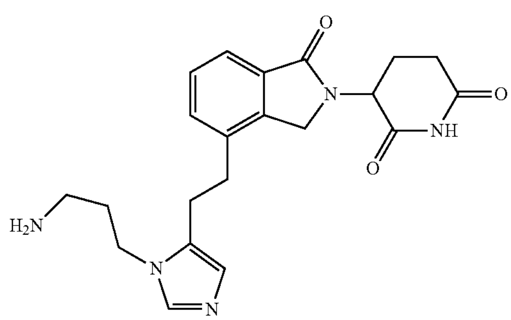 [SMILES: NCCCn1cncc1CCc1cccc2c1CN(C1CCC(=O)NC1=O)C2=O] | 3-(4-(2-(1-(3-aminopropyl)-1H-imidazol-5-yl)ethyl)-1-oxoisoindolin-2-yl)piperidine-2,6-dione |
| 243 | 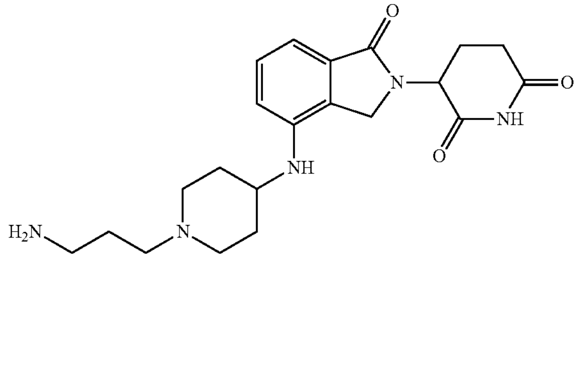 [SMILES: NCCCN1CCC(Nc2cccc3c2CN(C2CCC(=O)NC2=O)C3=O)CC1] | 3-(4-((1-(3-aminopropyl)piperidin-4-yl)amino)-1-oxoisoindolin-2-yl)piperidine-2,6-dione |

TABLE 5-continued

| Cpd. No. | Structure | Name |
|---|---|---|
| 244 | 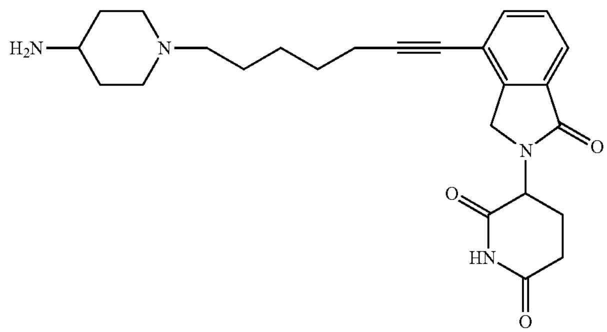 [SMILES: NC1CCN(CCCCCC#Cc2cccc3c2CN(C2CCC(=O)NC2=O)C3=O)CC1] | 3-(4-(7-(4-aminopiperidin-1-yl)hept-1-yn-1-yl)-1-oxoisoindolin-2-yl)piperidine-2,6-dione |
| 245 | 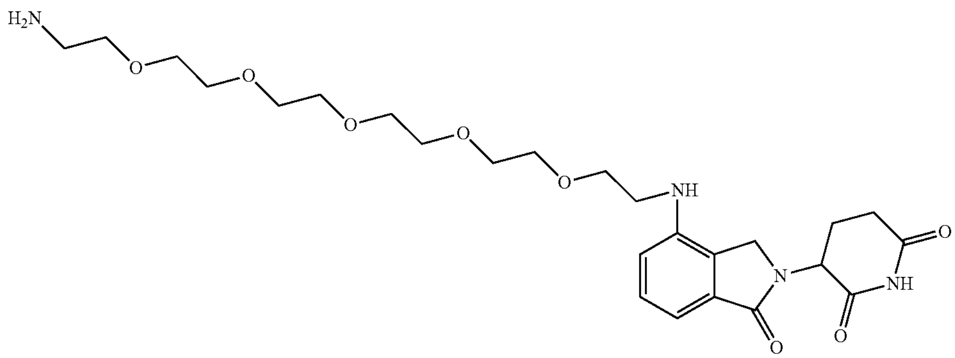 [SMILES: NCCOCCOCCOCCOCCOCCNc1cccc2c1CN(C1CCC(=O)NC1=O)C2=O] | 3-(4-((17-amino-3,6,9,12,15-pentaoxa-heptadecyl)amino)-1-oxoisoindolin-2-yl)piperidine-2,6-dione |
| 246 | 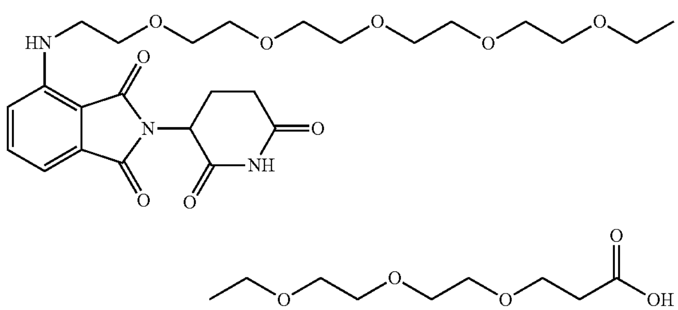 | 1-((2-(2,6-dioxopiperidin-3-yl)-1,3-dioxoisoindolin-4-yl)amino)-3,6,9,12,15,18,21,24-octaoxa-heptacosan-27-oic acid |
| 247 | 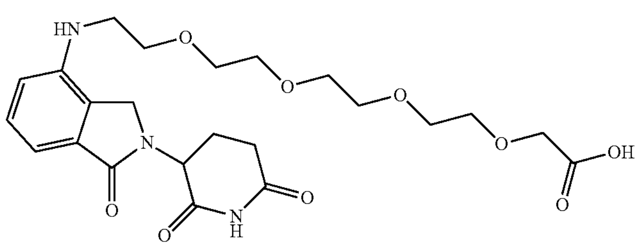 [SMILES: O=C(O)COCCOCCOCCOCCNc1cccc2c1CN(C1CCC(=O)NC1=O)C2=O] | 14-((2-(2,6-dioxopiperidin-3-yl)-1-oxoisoindolin-4-yl)amino)-3,6,9,12-tetraoxatetra-decanoic acid |
| 248 | 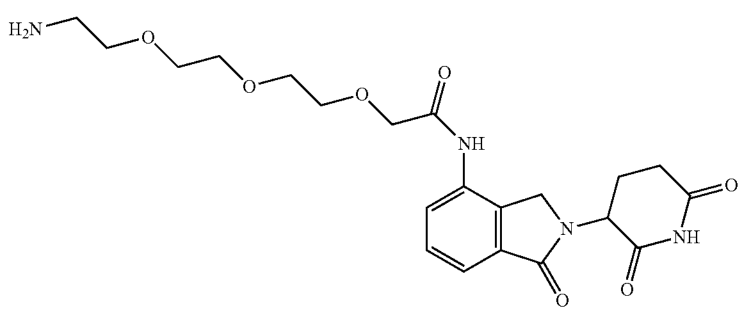 [SMILES: NCCOCCOCCOCC(=O)Nc1cccc2c1CN(C1CCC(=O)NC1=O)C2=O] | 2-(2-(2-(2-aminoethoxy)ethoxy)ethoxy)-N-(2-(2,6-dioxopiperidin-3-yl)-1-oxoisoindolin-4-yl)acetamide |

TABLE 5-continued

| Cpd. No. | Structure | Name |
|---|---|---|
| 249 | 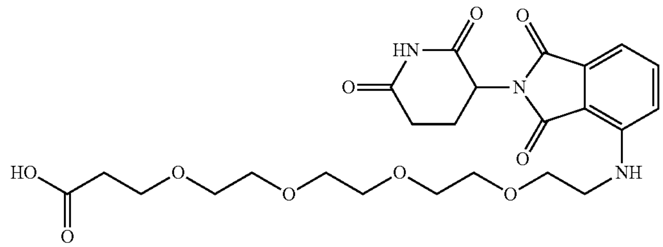 [SMILES: O=C(O)CCOCCOCCOCCOCCNc1cccc2c1C(=O)N(C1CCC(=O)NC1=O)C2=O] | 1-((2-(2,6-dioxopiperidin-3-yl)-1,3-dioxoisoindolin-4-yl)amino)-3,6,9,12-tetraoxapentadecan-15-oic acid |
| 250 | 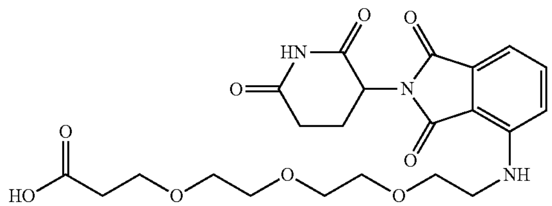 [SMILES: O=C(O)CCOCCOCCOCCNc1cccc2c1C(=O)N(C1CCC(=O)NC1=O)C2=O] | 3-(2-(2-(2-((2-(2,6-dioxopiperidin-3-yl)-1,3-dioxoisoindolin-4-yl)amino)ethoxy)ethoxy)ethoxy)propanoic acid |
| 251 | 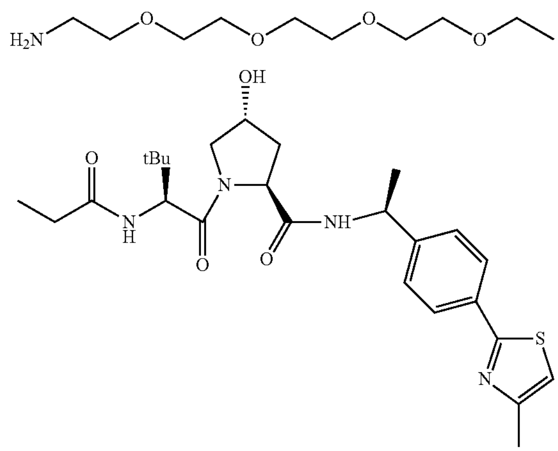 | (2S,4R)-1-((S)-1-amino-17-(tert-butyl)-15-oxo-3,6,9,12-tetraoxa-16-azaoctadecan-18-oyl)-4-hydroxy-N-((S)-1-(4-(4-methylthiazol-2-yl)phenyl)ethyl)pyrrolidine-2-carboxamide |
| 252 | 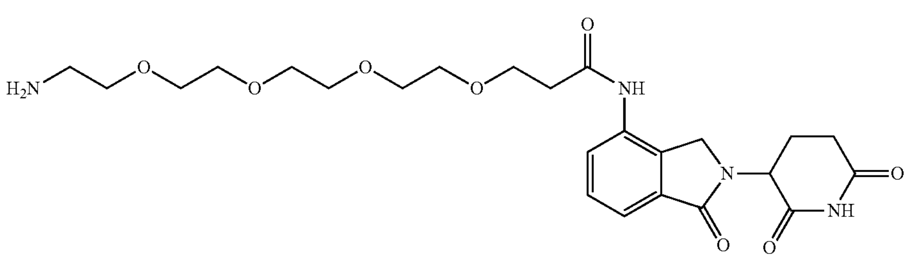 [SMILES: NCCOCCOCCOCCOCCC(=O)Nc1cccc2c1CN(C1CCC(=O)NC1=O)C2=O] | 1-amino-N-(2-(2,6-dioxopiperidin-3-yl)-1-oxoisoindolin-4-yl)-3,6,9,12-tetraoxapentadecan-15-amide |

In another embodiment, the disclosure provides a method of preparing a compound having Formula IX:

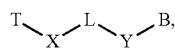  IX and the pharmaceutically acceptable salts or solvates thereof, wherein T is a monovalent radical of a target protein inhibitor, and X, L, Y, and B are as defined in connection with Formula I.

In another embodiment, the disclosure provides a method of preparing a compound having Formula IX:

and the pharmaceutically acceptable salts or solvates thereof, wherein T is a monovalent radical of a target protein inhibitor, and X, L, Y, and B are as defined in connection with Formula I, the method comprising condensing a compound having Formula I, with compound having Formula X:

T-X³X wherein:

T is a monovalent radical of a target protein inhibitor;

X³ is selected from the group consisting of —C(═O)OH and -LG; and

LG is a leaving group, e.g., –Cl, —Br, —I, —OTs, —OMs.

In another embodiment, the disclosure provides a method of preparing a compound having Formula IX, and the pharmaceutically acceptable salts or solvates thereof, comprising:

(1) condensing a compound having Formula I:

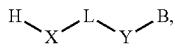

I wherein:
B is selected from the group consisting of:

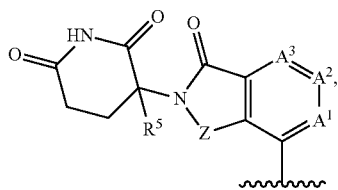

B-1a

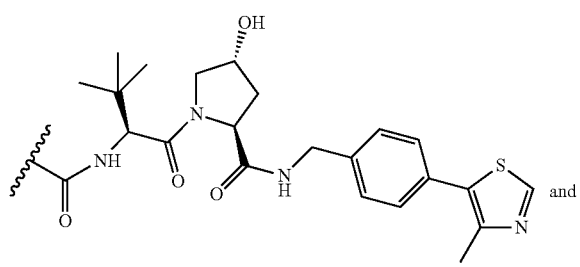

B-2 and

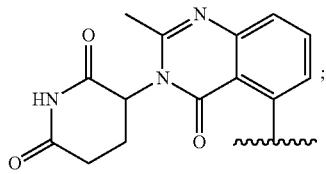

B-3

X is selected from the group consisting of —C≡C—, —O—, —N(R$^{2a}$)—,

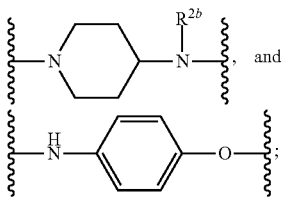

and

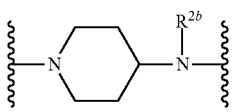

wherein the —N(R$^{2b}$)— of

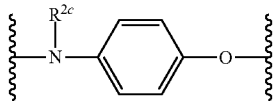

is attached to L and the —O— of is attached to L

L is selected from the group consisting of alkylenyl, heteroalkylenyl, -A-(CH$_2$)$_m$—W—(CH$_2$)$_n$—, and —(CH$_2$)$_r$—W—(CH$_2$)$_u$—O—(CH$_2$)$_v$—;
  A is absent; or
  A is heteroarylenyl;
  W is selected from the group consisting of phenylenyl, heteroarylenyl, heterocyclenyl, and cycloalkylenyl;
  m is 0, 1, 2, 3, 4, 5, 6, or 7;
  n is 0, 1, 2, 3, 4, 5, 6, 7, or 8;
  r is 0, 1, 2 or 3;
  u is 0, 1, 2, or 3;
  v is 1, 2, 3, or 4;
  Y is selected from the group consisting of —C≡C—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or
  Y is absent;
  wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;
  R$^{2a}$, R$^{2b}$, R$^{2c}$, R$^{2d}$, R$^{2e}$, and R$^{2f}$ are each independently selected from the group consisting of hydrogen and C$_{1-4}$ alkyl;
  B is selected from the group consisting of:

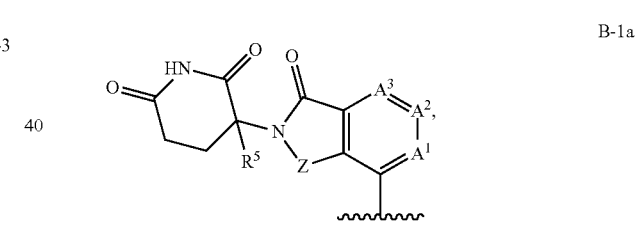

B-1a

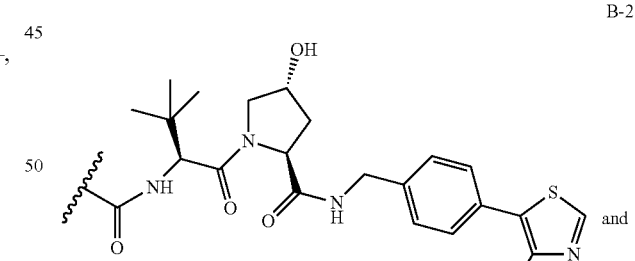

B-2 and

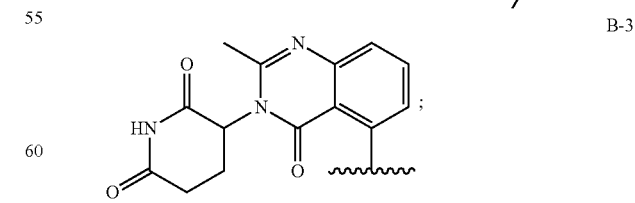

B-3

A$^1$ is selected from the group consisting of —C(R$^{16a}$)= and —N=;
A$^2$ is selected from the group consisting of —C(R$^{16b}$)= and —N=;

$A^3$ is selected from the group consisting of —C($R^{16c}$)═ and —N═;

Z is selected from the group consisting of —CH₂ and —C(═O)—;

$R^5$ is selected from the group consisting of hydrogen, methyl, and fluoro;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, with compound having Formula X:

T-X³X wherein:

T is a monovalent radical of a target protein inhibitor;

$X^3$ is selected from the group consisting of —C(═O)OH and -LG; and

LG is a leaving group, e.g., –Cl, —Br, —I, —OTs, —OMs, (2) isolating the compound having Formula IX.

In another embodiment, the disclosure provides a method of preparing a compound having Formula IX, and the pharmaceutically acceptable salts or solvates thereof, wherein the compound having Formula I are not any one of the compounds of Table 6, or any stereoisomer thereof.

In another embodiment, the disclosure provides a method of preparing a compound having Formula IX, and the salts or solvates thereof, wherein X is —C≡C—.

In another embodiment, the disclosure provides a method of preparing a compound having Formula IX, and the salts or solvates thereof, wherein X is —N(H)—.

In another embodiment, the disclosure provides a method of preparing a compound having Formula IX, and the salts or solvates thereof, wherein X is

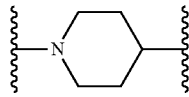

and the carbon atom of

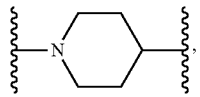

is attached to L.

In another embodiment, the disclosure provides a method of preparing a compound having Formula IX, and the salts or solvates thereof, wherein L is $C_{1-12}$ alkylenyl.

In another embodiment, the disclosure provides a method of preparing a compound having Formula IX, and the salts or solvates thereof, wherein L is selected from the group consisting of —CH₂—, —CH₂CH₂—, —CH₂CH₂CH₂—, —CH₂(CH₂)₂CH₂—, —CH₂(CH₂)₃CH₂—, —CH₂(CH₂)₄CH₂—, —CH₂(CH₂)₅CH₂—, and —CH₂(CH₂)₆CH₂—.

In another embodiment, the disclosure provides a method of preparing a compound having Formula IX, and the salts or solvates thereof, wherein L is 3- to 12-membered heteroalkylenyl.

In another embodiment, the disclosure provides a method of preparing a compound having Formula IX, and the salts or solvates thereof, wherein:

L is —(CH₂)ₒO—(CH₂CH₂O)ₚ—(CH₂)_q—;

o is 1, 2, or 3;

p is 0, 1, 2, 3, 4, or 5; and q is 1, 2, or 3.

In another embodiment, the disclosure provides a method of preparing a compound having Formula IX, and the salts or solvates thereof, wherein L is selected from the group consisting of —CH₂OOCH₂CH₂—
—CH₂CH₂OCH₂CH₂—,
—CH₂O(CH₂CH₂O)CH₂CH₂—
—CH₂O(CH₂CH₂O)₂CH₂CH₂—,
—CH₂O(CH₂CH₂O)₃CH₂CH₂—,
—CH₂CH₂O(CH₂CH₂O)₆CH₂CH₂—,
—CH₂CH₂O(CH₂CH₂O)₆CH₂CH₂—,
—CH₂CH₂CH₂OCH₂CH₂OCH₂CH₂CH₂—,
—CH₂CH₂CH₂O(CH₂CH₂O)₂CH₂CH₂CH₂—, and
—CH₂CH₂CH₂O(CH₂)₄OCH₂CH₂CH₂—.

In another embodiment, the disclosure provides a method of preparing a compound having Formula IX, and the salts or solvates thereof, wherein L is -A-(CH₂)_m—W—(CH₂)_n— and A is absent.

In another embodiment, the disclosure provides a method of preparing a compound having Formula IX, and the salts or solvates thereof, wherein L is -A-(CH₂)_m—W—(CH₂)_n—, A is absent, and W is phenylenyl.

In another embodiment, the disclosure provides a method of preparing a compound having Formula IX, and the salts or solvates thereof, wherein L is selected from the group consisting of:

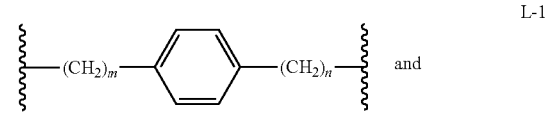

L-1

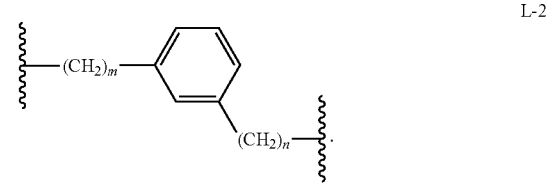

L-2

In another embodiment, the disclosure provides a method of preparing a compound having Formula IX, and the salts or solvates thereof, wherein L is -A-(CH₂)_m—W—(CH₂)_n—, A is absent, and W is 5-membered heteroarylenyl.

In another embodiment, the disclosure provides a method of preparing a compound having Formula IX, and the salts or solvates thereof, wherein:

L is selected from the group consisting of:

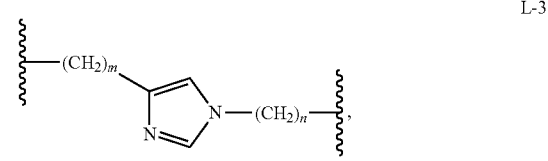

L-3

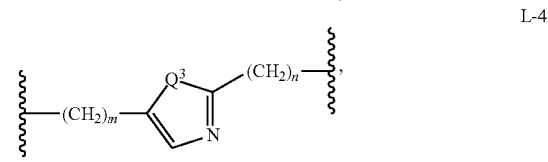

L-4

-continued

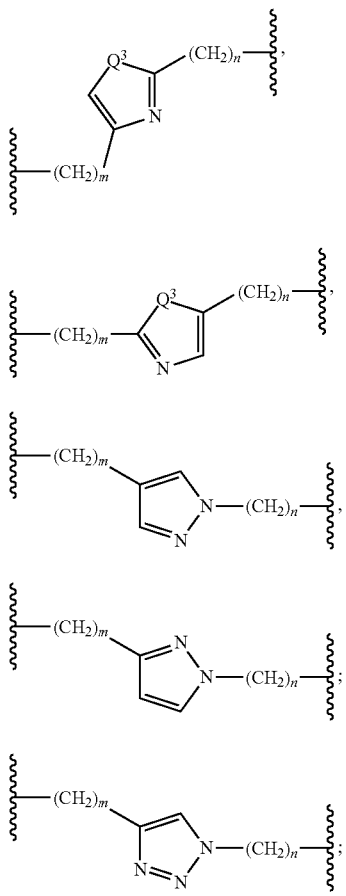

L-5

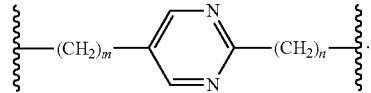

In another embodiment, the disclosure provides a method of preparing a compound having Formula IX, and the salts or solvates thereof, wherein L is -A-$(CH_2)_m$—W—$(CH_2)_n$—, A is absent, and W is heterocyclenyl.

In another embodiment, the disclosure provides a method of preparing a compound having Formula IX, and the salts or solvates thereof, wherein L is selected from the group consisting of:

L-14

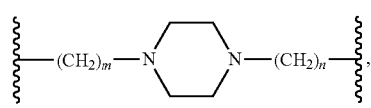

L-15

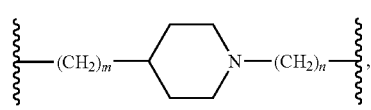

L-16

L-17

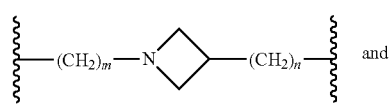 and

L-18

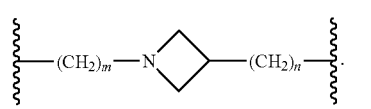

In another embodiment, the disclosure provides a method of preparing a compound having Formula IX, and the salts or solvates thereof, wherein L is -A-$(CH_2)_m$—W—$(CH_2)_n$—, A is absent, and W is cycloalkylenyl.

In another embodiment, the disclosure provides a method of preparing a compound having Formula IX, and the salts or solvates thereof, wherein L is selected from the group consisting of:

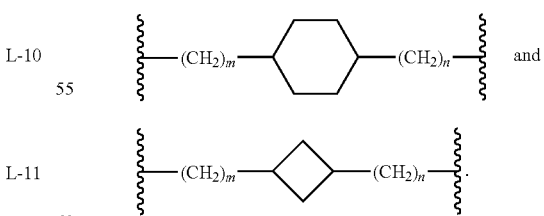

In another embodiment, the disclosure provides a method of preparing a compound having Formula IX, and the salts or solvates thereof, wherein:

L is -A-$(CH_2)_m$—W—$(CH_2)_n$—; and

A is selected from the group consisting of 5-membered heteroarylenyl and 6-membered heteroarylenyl.

$Q^3$ is selected from the group consisting of —O—, —S—, and —N($R^6$)—; and $R^6$ is selected from the group consisting of hydrogen and $C_{1-4}$ alkyl.

In another embodiment, the disclosure provides a method of preparing a compound having Formula IX, and the salts or solvates thereof, wherein L is -A-$(CH_2)_m$—W—$(CH_2)_n$—, A is absent, and W is 6-membered heteroarylenyl.

In another embodiment, the disclosure provides a method of preparing a compound having Formula IX, and the salts or solvates thereof, wherein L is selected from the group consisting of:

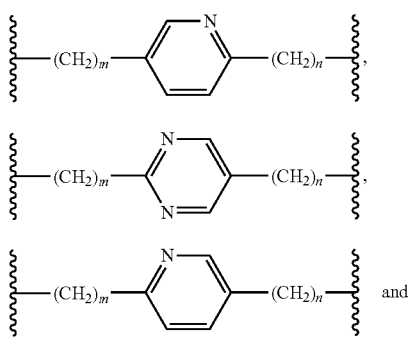

In another embodiment, the disclosure provides a method of preparing a compound having Formula IX, and the salts or solvates thereof, wherein L is -A-$(CH_2)_m$—W—$(CH_2)_n$— and W is phenylenyl.

In another embodiment, the disclosure provides a method of preparing a compound having Formula XX, and the salts or solvates thereof, wherein L is selected from the group consisting of:

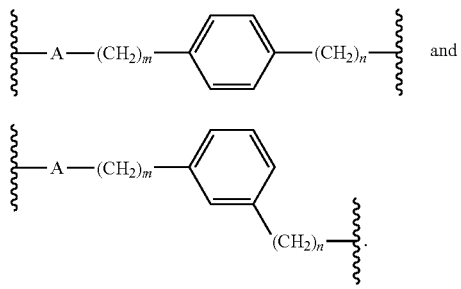

L-21

L-22

In another embodiment, the disclosure provides a method of preparing a compound having Formula IX, and the salts or solvates thereof, wherein L is -A-$(CH_2)_m$—W—$(CH_2)_n$— and W is 5-membered heteroarylenyl.

In another embodiment, the disclosure provides a method of preparing a compound having Formula IX, and the salts or solvates thereof, wherein L is selected from the group consisting of:

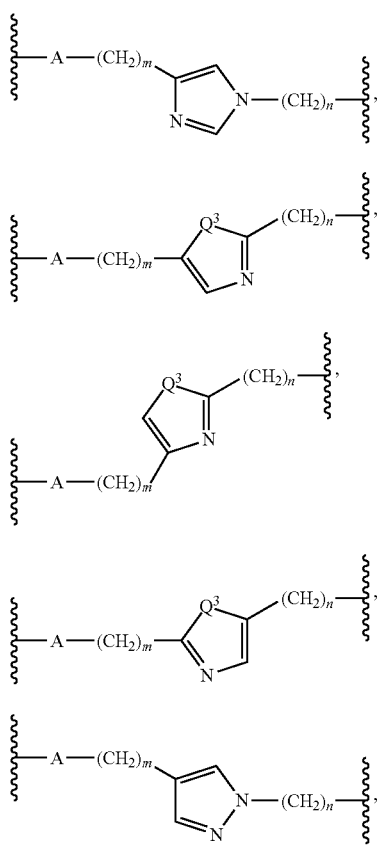

L-23

L-24

L-25

L-26

L-27

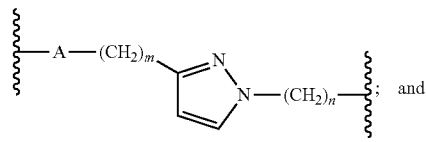

L-28

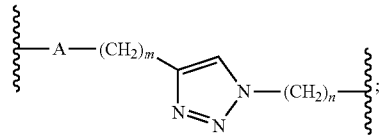

L-29

$Q^3$ is selected from the group consisting of —O—, —S—, and —N($R^6$)—; and $R^6$ is selected from the group consisting of hydrogen and $C_{1-4}$ alkyl.

In another embodiment, the disclosure provides a method of preparing a compound having Formula IX, and the salts or solvates thereof, wherein L is -A-$(CH_2)_m$—W—$(CH_2)_n$— and W is 6-membered heteroarylenyl.

In another embodiment, the disclosure provides a method of preparing a compound having Formula IX, and the salts or solvates thereof, wherein L is selected from the group consisting of:

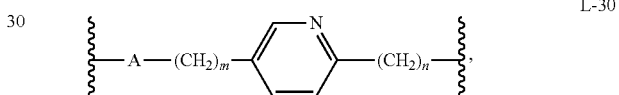

L-30

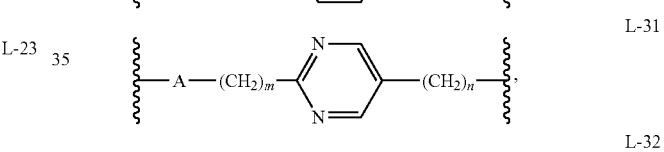

L-31

L-32

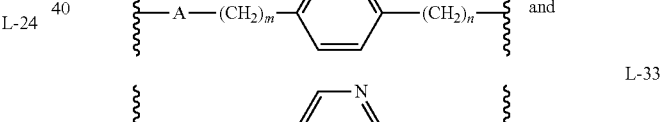

L-33

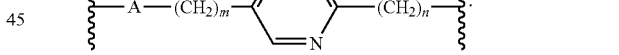

In another embodiment, the disclosure provides a method of preparing a compound having Formula IX, and the salts or solvates thereof, wherein L is -A-$(CH_2)_m$—W—$(CH_2)_n$— and W is heterocyclenyl.

In another embodiment, the disclosure provides a method of preparing a compound having Formula IX, and the salts or solvates thereof, wherein L is selected from the group consisting of:

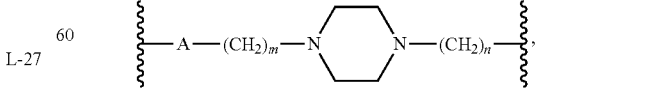

L-34

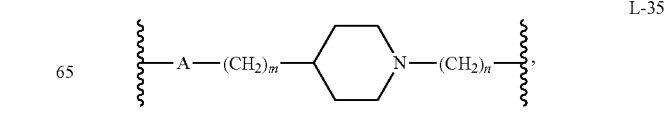

L-35

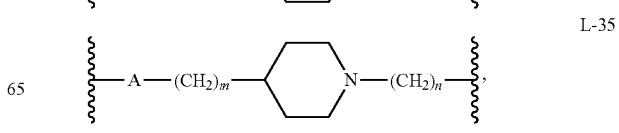

-continued

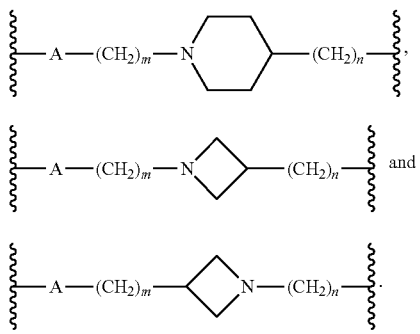

L-36

L-37

L-38

In another embodiment, the disclosure provides a method of preparing a compound having Formula IX, and the salts or solvates thereof, wherein L is -A-$(CH_2)_m$—W—$(CH_2)_n$— and W is cycloalkylenyl.

In another embodiment, the disclosure provides a method of preparing a compound having Formula IX, and the salts or solvates thereof, wherein L is selected from the group consisting of:

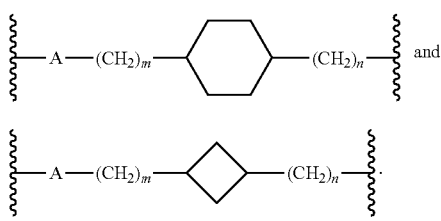

L-39

L-40

In another embodiment, the disclosure provides a method of preparing a compound having Formula IX, and the salts or solvates thereof, wherein L is -A-$(CH_2)_m$—W—$(CH_2)_n$— and A is a 5-membered heteroarylenyl. In another embodiment, A is a 5-membered heteroarylenyl selected from the group consisting of:

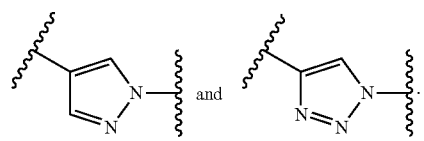 [SMILES: *c1cnn(*)c1 ; "and" ; *c1cn(*)nn1]

In another embodiment, the disclosure provides a method of preparing a compound having Formula IX, and the salts or solvates thereof, wherein L is -A-$(CH_2)_m$—W—$(CH_2)_n$— and A is a 6-membered heteroarylenyl. In another embodiment, A is:

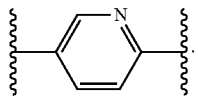

In another embodiment, the disclosure provides a method of preparing a compound having Formula IX, and the salts or solvates thereof, wherein:

L is —$(CH_2)_r$—W—$(CH_2)_u$—O—$(CH_2)_v$—;
r is 0, 1, or 2;
u is 1, 2, or 3; and
v is 1, 2, or 3.

In another embodiment, the disclosure provides a method of preparing a compound having Formula IX, and the salts or solvates thereof, wherein L is —$(CH_2)_r$—W—$(CH_2)_u$—O—$(CH_2)_v$— and W is selected from the group consisting of phenylenyl and heteroarylenyl. In another embodiment, W is 5-membered heteroarylenyl. In another embodiment, W is 6-membered heteroarylenyl.

In another embodiment, the disclosure provides a method of preparing a compound having Formula IX, and the salts or solvates thereof, wherein Y is selected from the group consisting of —C≡C—, —$CH_2$—, —O—, and —N($R^{2c}$)—. In another embodiment, Y is —C≡C—. In another embodiment, Y is —$CH_2$—. In another embodiment, Y is —O—. In another embodiment, Y is —N(H)—.

In another embodiment, the disclosure provides a method of preparing a compound having Formula IX, and the salts or solvates thereof, wherein B is B-1a.

In another embodiment, the disclosure provides a method of preparing a compound having Formula IX, and the salts or solvates thereof, wherein:
B is B-1a;
$A^1$ is selected from the group consisting of —C($R^{16a}$)═ and —N═; and
$R^{16a}$ is selected from the group consisting of hydrogen and halo.

In another embodiment, the disclosure provides a method of preparing a compound having Formula IX, and the salts or solvates thereof, wherein:
B is B-1a;
$A^2$ is selected from the group consisting of —C($R^{16b}$)═ and —N═; and
$R^{16b}$ is selected from the group consisting of hydrogen and halo.

In another embodiment, the disclosure provides a method of preparing a compound having Formula IX, and the salts or solvates thereof, wherein:
B is B-1a;
$A^3$ is selected from the group consisting of —C($R^{16c}$)═ and —N═; and
$R^{16c}$ is selected from the group consisting of hydrogen and halo.

In another embodiment, the disclosure provides a method of preparing a compound having Formula IX, and the salts or solvates thereof, wherein B is B-1a and Z is —$CH_2$—.

In another embodiment, the disclosure provides a method of preparing a compound having Formula IX, and the salts or solvates thereof, wherein B is B-1a and Z is —C(═O)—.

In another embodiment, the disclosure provides a method of preparing a compound having Formula IX, and the salts or solvates thereof, wherein B is B-1a and $R^5$ is hydrogen.

In another embodiment, the disclosure provides a method of preparing a compound having Formula IX, and the salts or solvates thereof, wherein B is B-2.

In another embodiment, the disclosure provides a method of preparing a compound having Formula IX, and the salts or solvates thereof, wherein B-3.

In another embodiment, the disclosure provides a method of preparing a compound having Formula IX, and the salts or solvates thereof, wherein T is a monovalent radical of an oncogenic protein inhibitor.

In another embodiment, the disclosure provides a method of preparing a compound having Formula IX, and the salts or solvates thereof, wherein T is a monovalent radical of a MDM2 protein inhibitor.

In another embodiment, the disclosure provides a method of preparing a compound having Formula IX, and the salts or solvates thereof, wherein T is a monovalent radical of a BET bromodomain protein inhibitor.

In another embodiment, the disclosure provides methods of making a compound having Formula VII:

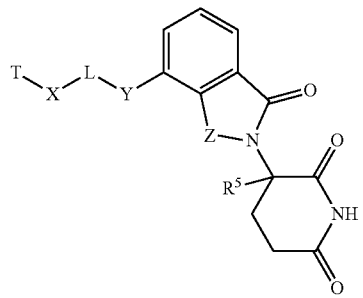

VII or a pharmaceutically acceptable salt or solvate thereof, wherein:

T is selected from the group consisting of:

T-1
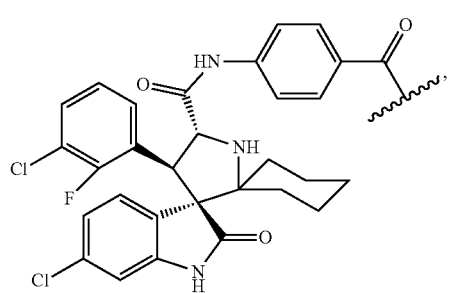

T-2
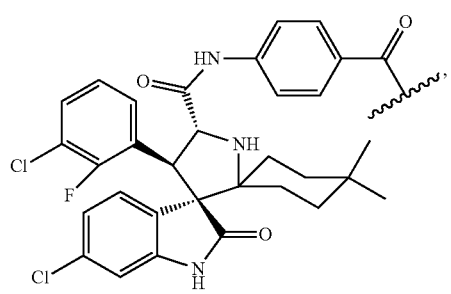

T-3
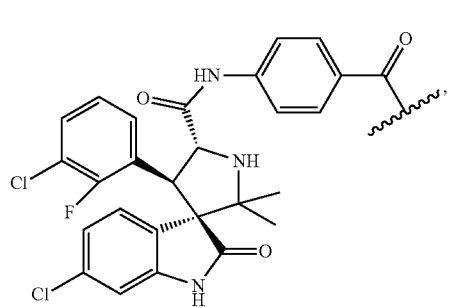

T-4
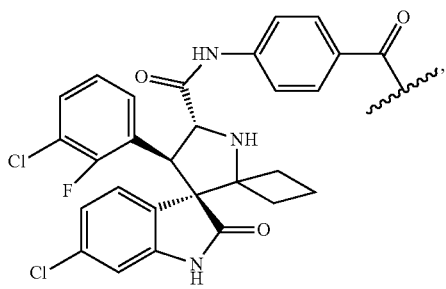

T-5
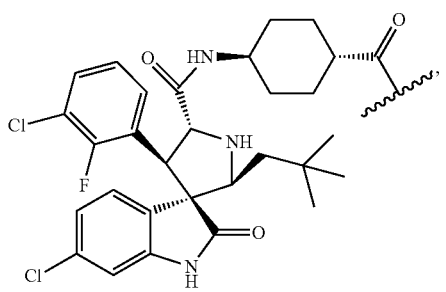

T-6
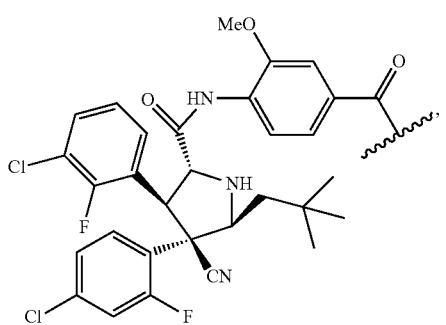

T-7
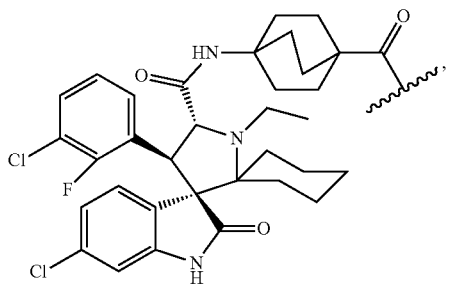

T-8
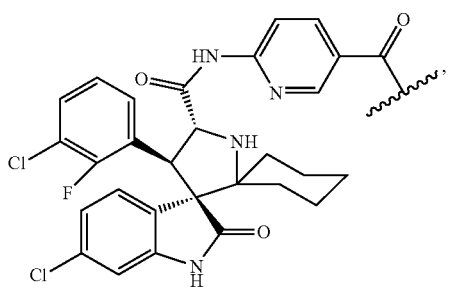

-continued

T-9
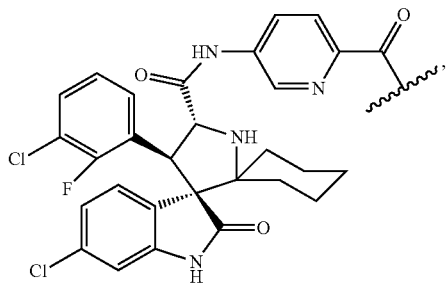

T-10
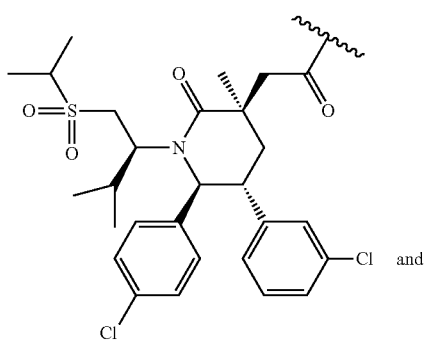 and

T-15
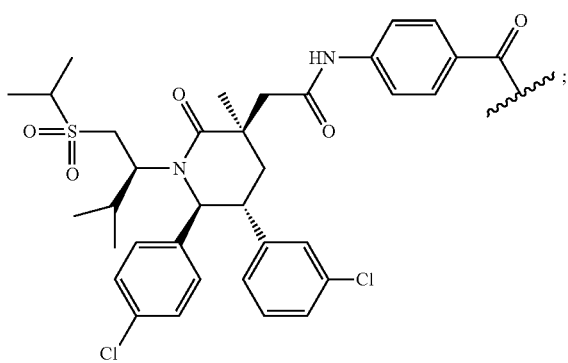

X is selected from the group consisting of —N(R$^{2a}$)—,

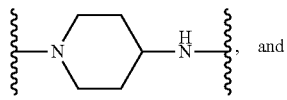 and

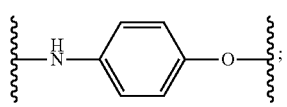;

wherein the —N(H)— of

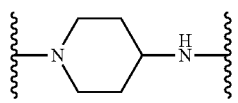

is attached to L and the —O— of

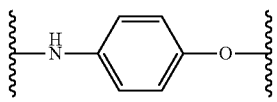

is attached to L;

L is selected from the group consisting of alkylenyl, heteroalkylenyl, and —(CH$_2$)$_m$—W—(CH$_2$)$_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7;

n is 0, 1, 2, 3, 4, 5, 6, 7, or 8;

Y is selected from the group consisting of —C≡C—, —O—, —N(R$^{2c}$)—, —C(═O)N(R$^{2d}$)—, —N(R$^{2e}$)C(═O)CH$_2$O—, and —N(R$^{2e}$)C(═O)CH$_2$N(R$^{2f}$)—; or Y is absent;

wherein the carboxamide nitrogen atom of —N(R$^{2e}$)C(═O)CH$_2$O— and —N(R$^{2e}$)C(═O)CH$_2$N(R$^{2f}$)—, and the carbon atom of —C(═O)N(R$^{2d}$)— is attached to L;

R$^{2a}$, R$^{2b}$, R$^{2c}$, R$^{2d}$, R$^{2e}$, and R$^{2f}$ are each independently selected from the group consisting of hydrogen and C$_{1-4}$ alkyl;

Z is selected from the group consisting of —CH$_2$ and —C(═O)—; and

R$^5$ is selected from the group consisting of hydrogen, methyl, and fluoro, the method comprising:

(1) reacting a compound selected from the group consisting of:

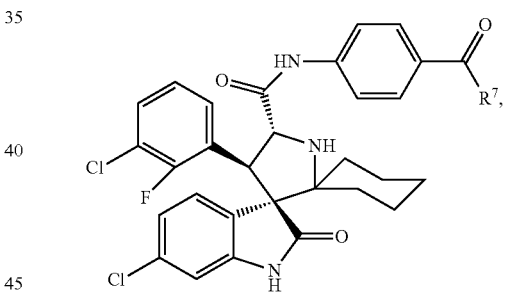

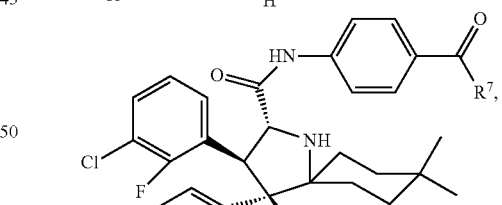

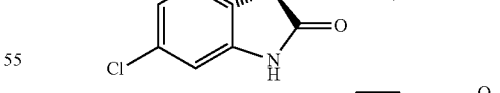

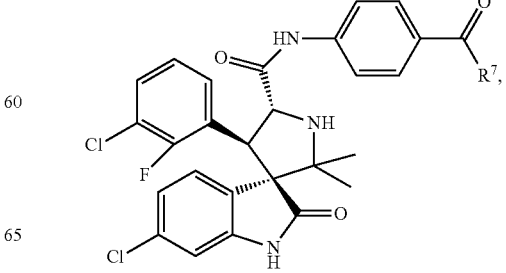

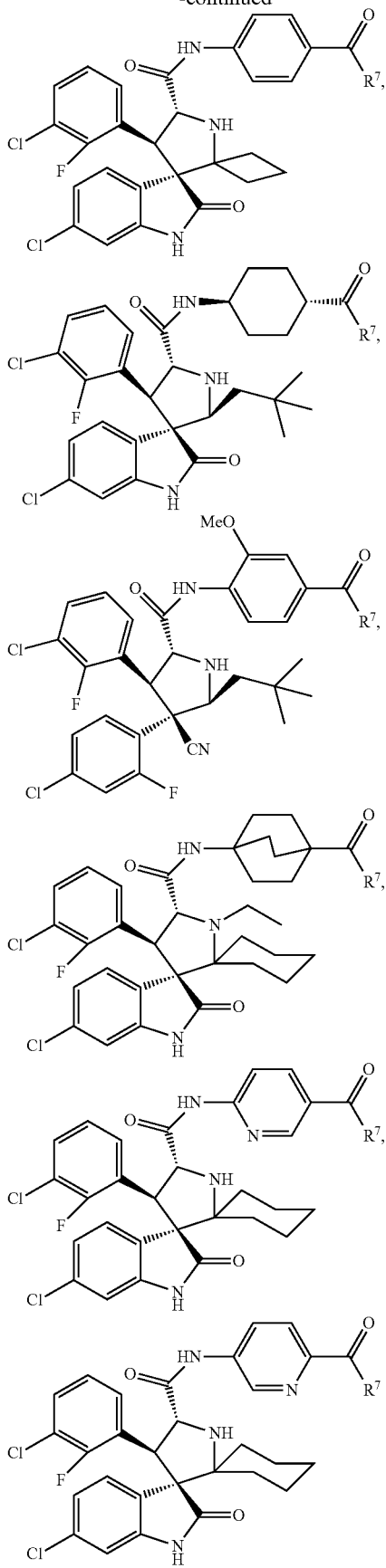

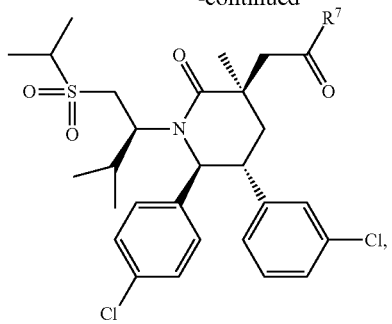

wherein R⁷ is a leaving group, e.g., R⁷ is selected from the group consisting of –Cl and —OH,

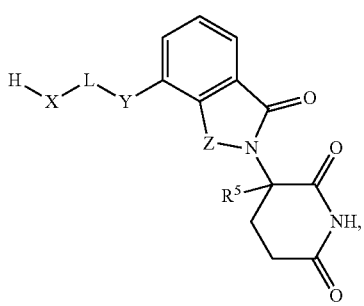

II wherein:

X is selected from the group consisting of —N(R$^{2a}$)—,

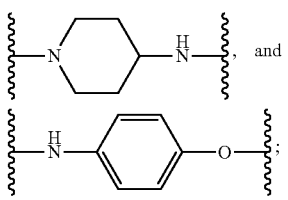
and

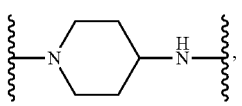

wherein the —N(H)— of

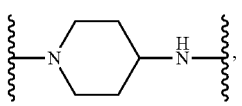

is attached to L and the —O— of

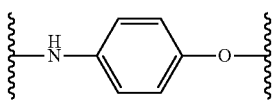

is attached to L;

L is selected from the group consisting of alkylenyl, heteroalkylenyl, and —(CH$_2$)$_m$—W—(CH$_2$)$_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7;
n is 0, 1, 2, 3, 4, 5, 6, 7, or 8;
Y is selected from the group consisting of —C≡C—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or
Y is absent;
wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;
R$^{2a}$, R$^{2b}$, R$^{2c}$, R$^{2d}$, R$^{2e}$, and R$^{2f}$ are each independently selected from the group consisting of hydrogen and C$_{1-4}$ alkyl;
Z is selected from the group consisting of —CH$_2$— and —C(=O)—; and
R$^5$ is selected from the group consisting of hydrogen and fluoro, and
(2) isolating the compound having Formula VII, or a pharmaceutically acceptable salt or solvate thereof.

In another embodiment, the disclosure provides methods of making a compound having Formula VII, or a pharmaceutically acceptable salt or solvate thereof, the method comprising:

(1) reacting a compound having the structure:

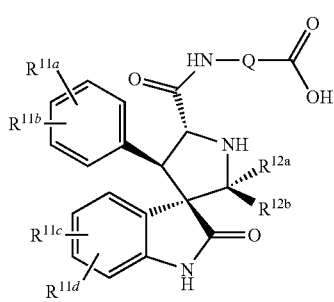

T-16 wherein:
R$^{11a}$, R$^{11b}$, R$^{11c}$, and R$^{11d}$ are independently selected from the group consisting of hydrogen, chloro, and fluoro;
R$^{12a}$ and R$^{12b}$ are independently selected from the group consisting of hydrogen and C$_{1-6}$ alkyl; or
R$^{12a}$ and R$^{12b}$ taken together with the carbon atom to which they are attached form a 4- to 8-membered optionally substituted cycloalkyl; and
Q is selected from the group consisting of substituted phenylenyl, optionally substituted heteroarylenyl, and optionally substituted cycloalkylenyl,
with a compound having Formula II, and
(2) isolating the compound having Formula VII, or a pharmaceutically acceptable salt or solvate thereof.

In another embodiment, the disclosure provides methods of making a compound having Formula VIII:

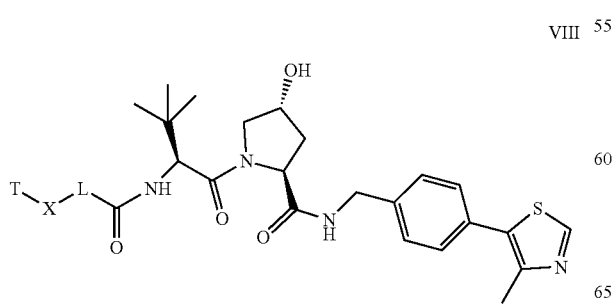

VIII or a pharmaceutically acceptable salt or solvate thereof, wherein:

T is selected from the group consisting of:

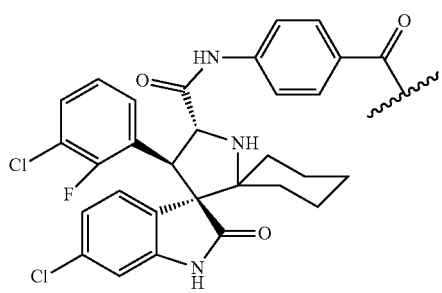

T-1

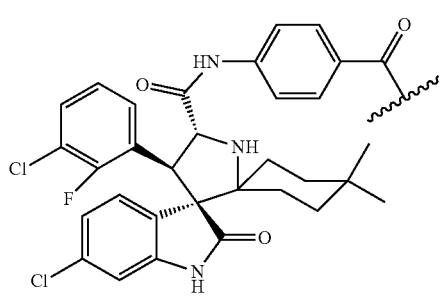

T-2

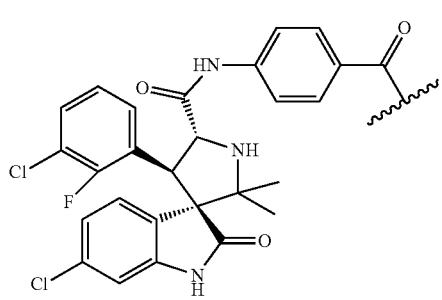

T-3

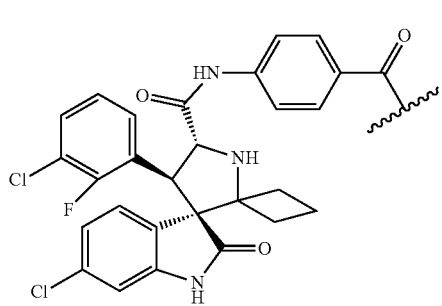

T-4

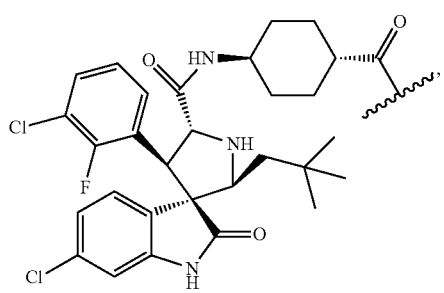

T-5

T-6
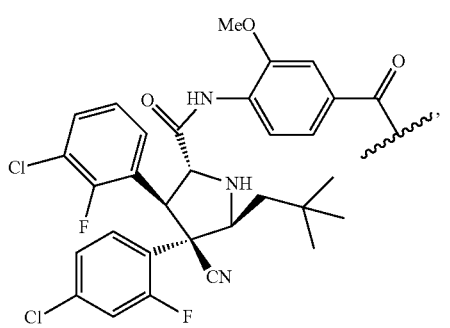

T-7
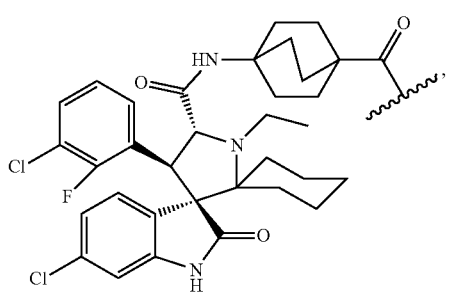

T-8
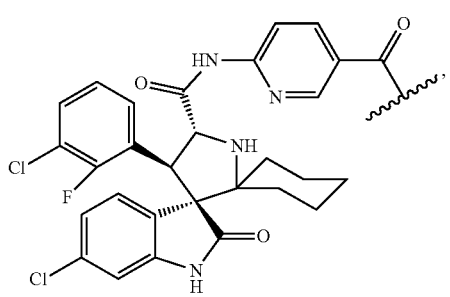

T-9
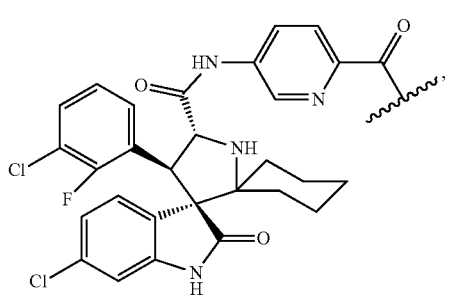

T-10
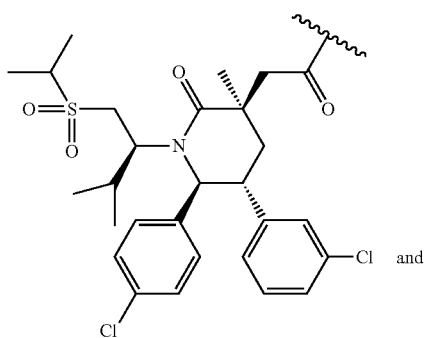
and

T-15
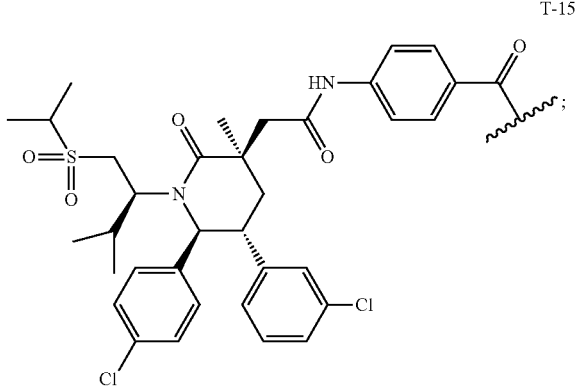 [SMILES: *C(=O)c1ccc(NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1]

X is selected from the group consisting of —N(R$^{2a}$)—,

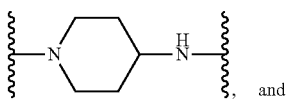, and

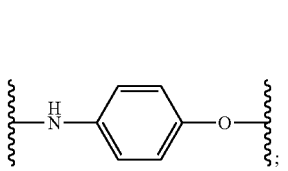;

wherein the —N(H)— of

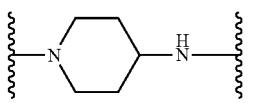 [SMILES: *NC1CCN(*)CC1]

is attached to L and the —O— of

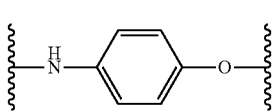

is attached to L;

L is selected from the group consisting of alkylenyl, heteroalkylenyl, and —(CH$_2$)$_m$—W—(CH$_2$)$_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7; and n is 0, 1, 2, 3, 4, 5, 6, 7, or 8; the method comprising:

(1) reacting a compound selected from the group consisting of:

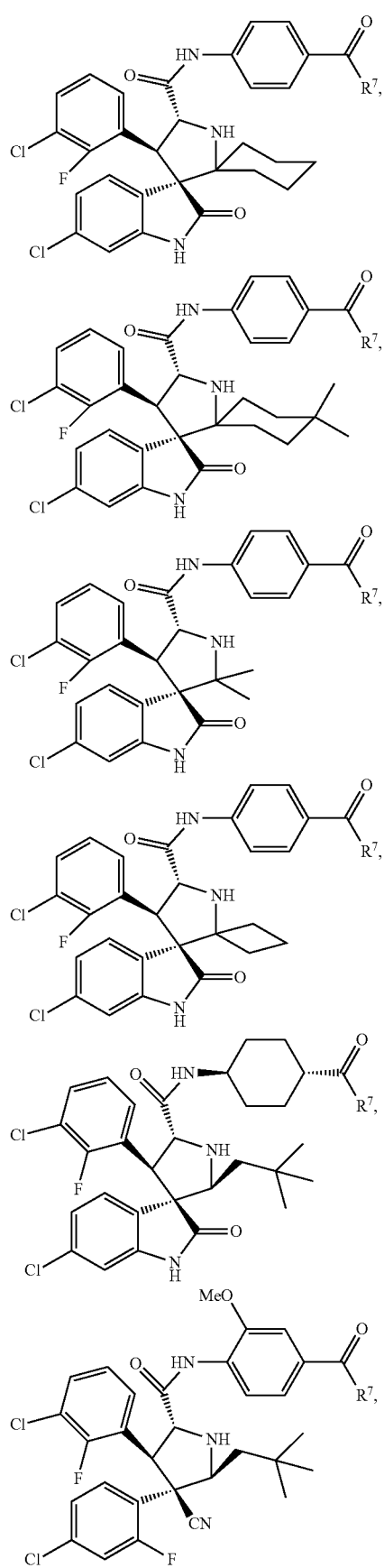
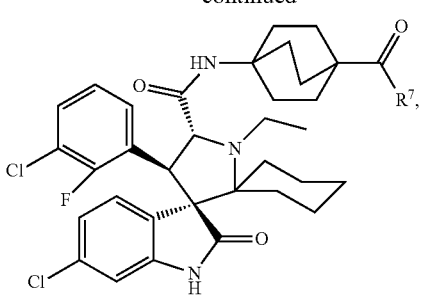
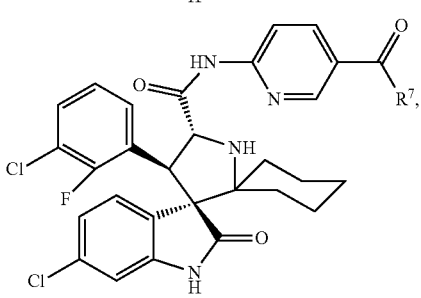
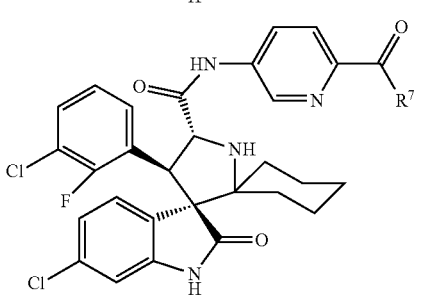
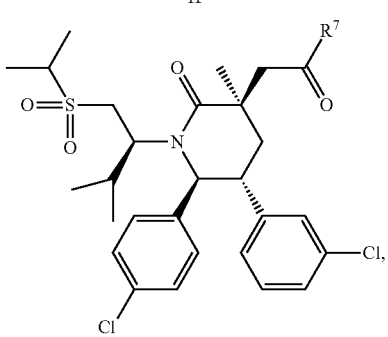
wherein $R^7$ is a leaving group, e.g., $R^7$ is selected from the group consisting of —Cl and —OH,
with a compound having Formula III:
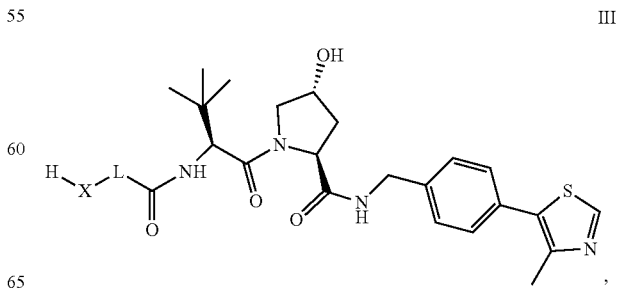
III wherein:

X is selected from the group consisting of —N(R$^{2a}$)—,

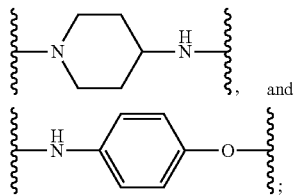, and wherein the —N(H)— of

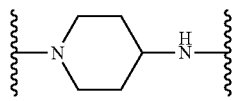

is attached to L and the —O— of

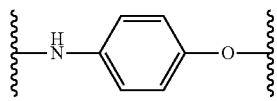

is attached to L;

L is selected from the group consisting of alkylenyl, heteroalkylenyl, and —(CH$_2$)$_m$—W—(CH$_2$)$_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7; and n is 0, 1, 2, 3, 4, 5, 6, 7, or 8, and (2) isolating the compound having Formula VIII, or a pharmaceutically acceptable salt or solvate thereof.

In another embodiment, the disclosure provides methods of making a compound having Formula VIII, or a pharmaceutically acceptable salt or solvate thereof, the method comprising:

(1) reacting a compound having the structure:

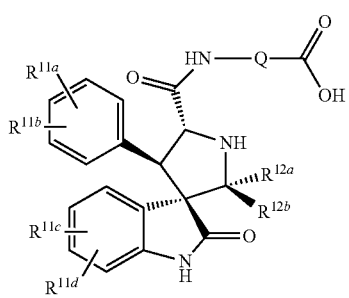

T-16 wherein:

R$^{11a}$, R$^{11b}$, R$^{11c}$, and R$^{11d}$ are independently selected from the group consisting of hydrogen, chloro, and fluoro;

R$^{12a}$ and R$^{12b}$ are independently selected from the group consisting of hydrogen and C$_{1-6}$ alkyl; or R$^{12a}$ and R$^{12b}$ taken together with the carbon atom to which they are attached form a 4- to 8-membered optionally substituted cycloalkyl; and Q is selected from the group consisting of substituted phenylenyl, optionally substituted heteroarylenyl, and optionally substituted cycloalkylenyl, with a compound having Formula III, and (2) isolating the compound having Formula VIII, or a pharmaceutically acceptable salt or solvate thereof.

In another embodiment, the disclosure provides methods of making a compound having Formula XI:

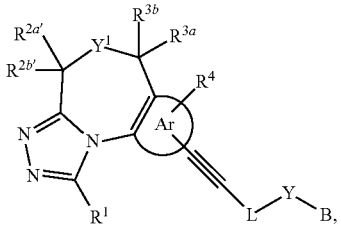

XI or a pharmaceutically acceptable salt or hydrate thereof, wherein:

R$^1$ is selected from the group consisting of hydrogen and optionally substituted C$_{1-4}$ alkyl;

R$^{2a'}$ and R$^{2b'}$ are each independently selected from the group consisting of hydrogen, optionally substituted C$_{1-4}$ alkyl, and (alkoxycarbonyl)alkyl, or R$^{2a'}$ and R$^{2b'}$ together with the carbon atom to which they are attached form a 3- to 6-membered cycloalkyl;

R$^{3a}$ and R$^{3b}$ are each independently selected from the group consisting of hydrogen and optionally substituted C$_{1-4}$ alkyl; or R$^{3a}$ and R$^{3b}$ together with the carbon atom to which they are attached form an optionally substituted 3- to 6-membered cycloalkyl;

R$^4$ is selected from the group consisting of hydrogen, halogen, optionally substituted C$_{1-4}$ alkyl, optionally substituted C$_{2-4}$ alkenyl, optionally substituted C$_{2-4}$ alkynyl, aralkyl, optionally substituted C$_{6-14}$ aryl, optionally substituted C$_{3-12}$ cycloalkyl, optionally substituted 3- to 14-membered heterocyclo, optionally substituted 5- to 14-membered heteroaryl, —NR$^{6a}$R$^{6b}$, —OR$^{7d}$, —SR$^{8a}$, —S(═O)R$^{8b}$, —S(═O)$_2$R$^{8c}$, —C(═O)R$^9$, (heteroaryl)alkyl, and alkoxyalkyl;

R$^{6a}$ and R$^{6b}$ are each independently selected from the group consisting of hydrogen, optionally substituted C$_{1-6}$ alkyl, aralkyl, optionally substituted C$_{6-14}$ aryl, optionally substituted C$_{3-12}$ cycloalkyl, optionally substituted 3- to 14-membered heterocyclo, optionally substituted 5- to 14-membered heteroaryl, alkylcarbonyl, arylcarbonyl, alkoxycarbonyl, alkylsulfonyl, arylsulfonyl, and carboxamido; or R$^{6a}$ and R$^{6b}$ taken together with the nitrogen atom to which they are attached form an optionally substituted 4- to 8-membered heterocyclo;

R$^{7d}$ is selected from the group consisting of hydrogen, optionally substituted C$_{1-4}$ alkyl, aralkyl, optionally substituted C$_{6-14}$ aryl, optionally substituted C$_{3-12}$ cycloalkyl, optionally substituted 3- to 14-membered heterocyclo, optionally substituted 5- to 14-membered heteroaryl, alkylcarbonyl, and carboxamido;

R$^{8a}$ is selected from the group consisting of optionally substituted C$_{1-4}$ alkyl, aralkyl, optionally substituted C$_{6-14}$ aryl, optionally substituted C$_{3-12}$ cycloalkyl, optionally substituted 3- to 14-membered heterocyclo, and optionally substituted 5- to 14-membered heteroaryl;

R$^{8b}$ is selected from the group consisting of optionally substituted C$_{1-4}$ alkyl, aralkyl, optionally substituted C$_{6-14}$ aryl, optionally substituted C$_{3-12}$ cycloalkyl, optionally substituted 3- to 14-membered heterocyclo, and optionally substituted 5- to 14-membered heteroaryl;

$R^{8c}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and amino;

$R^9$ selected from the group consisting of hydrogen, optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, alkoxy, and amino;

$Y^1$ is selected from the group consisting of —O—, —S—, and —$NR^{10}$—;

$R^{10}$ is selected from the group consisting of hydrogen, optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, ($C_{3-6}$ cycloalkyl)$C_{1-4}$ alkyl, aralkyl, (alkoxycarbonyl)alkyl, —C(=O)$R^{11}$, —SO$_2R^{12}$, —C(=O)—$OR^{13}$, and —C(=O)—$NR^{14a}R^{14b}$;

$R^{11}$ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{12}$ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{13}$ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{14a}$ and $R^{14b}$ are each independently selected from the group consisting of hydrogen, optionally substituted $C_{1-6}$ alkyl, optionally substituted $C_{6-14}$ aryl, optionally substituted $C_{3-12}$ cycloalkyl, 3- to 14-membered heterocyclo, optionally substituted 5- to 14-membered heteroaryl, and aralkyl; or $R^{14a}$ and $R^{14b}$ taken together with the nitrogen atom to which they are attached form an optionally substituted 4- to 8-membered heterocyclo;

is a fused thienyl or fused phenyl group, wherein the fused phenyl group is additionally substituted with $R^{15}$;

$R^{15}$ is selected from the group consisting of hydrogen, halogen, $C_{1-4}$ alkyl, and alkoxy;

B is a monovalent radical of a ligand for an E3 ubiquitin ligase protein, e.g., B is:

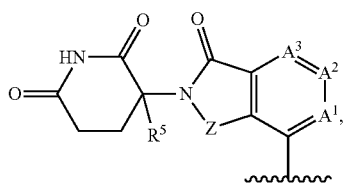

B-1a

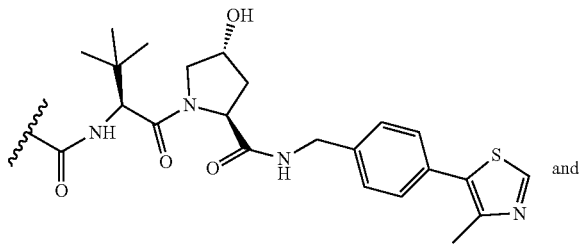

B-2

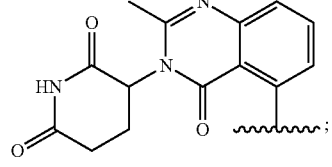

B-3

L is selected from the group consisting of alkylenyl, heteroalkylenyl, -A-(CH$_2$)$_m$—W—(CH$_2$)$_n$— and —(CH$_2$)$_m$—W—(CH$_2$)$_u$—O—(CH$_2$)$_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of —C≡C—, —CH$_2$—, —O—, —N($R^{2c}$)—, —C(=O)N($R^{2d}$)—, —N($R^{2e}$)C(=O)CH$_2$O—, and —N($R^{2e}$)C(=O)CH$_2$N($R^{2f}$)—; or $Y^1$ is absent;

wherein the carboxamide nitrogen atom of —N($R^{2e}$)C(=O)CH$_2$O— and —N($R^{2e}$)C(=O)CH$_2$N($R^{2f}$)—, and the carbon atom of —C(=O)N($R^{2d}$)— is attached to L;

$R^{2c}$, $R^{2d}$, $R^{2e}$, and $R^{2f}$ are each independently selected from the group consisting of hydrogen and $C_{1-4}$ alkyl;

Z is selected from the group consisting of —CH$_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, the method comprising:

(1) reacting, e.g., coupling, a compound having Formula XII:

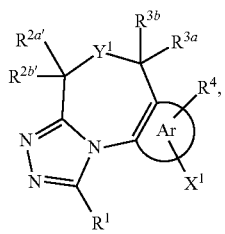

wherein:

X¹ is selected from the group consisting of Br and I;

R¹ is selected from the group consisting of hydrogen and optionally substituted $C_{1-4}$ alkyl;

$R^{2a'}$ and $R^{2b'}$ are each independently selected from the group consisting of hydrogen, optionally substituted $C_{1-4}$ alkyl, and (alkoxycarbonyl)alkyl, or $R^{2a'}$ and $R^{2b'}$ together with the carbon atom to which they are attached form a 3- to 6-membered cycloalkyl;

$R^{3a}$ and $R^{3b}$ are each independently selected from the group consisting of hydrogen and optionally substituted $C_{1-4}$ alkyl; or $R^{3a}$ and $R^{3b}$ together with the carbon atom to which they are attached form an optionally substituted 3- to 6-membered cycloalkyl;

R⁴ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, —NR$^{6a}$R$^{6b}$, —OR⁷, —SR$^{8a}$, —S(=O)R$^{8b}$, —S(=O)₂R$^{8c}$, —C(=O)R⁹, (heteroaryl)alkyl, and alkoxyalkyl;

$R^{6a}$ and $R^{6b}$ are each independently selected from the group consisting of hydrogen, optionally substituted $C_{1-6}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, alkylcarbonyl, arylcarbonyl, alkoxycarbonyl, alkylsulfonyl, arylsulfonyl, and carboxamido; or $R^{6a}$ and $R^{6b}$ taken together with the nitrogen atom to which they are attached form an optionally substituted 4- to 8-membered heterocyclo;

R⁷ is selected from the group consisting of hydrogen, optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, alkylcarbonyl, and carboxamido;

$R^{8a}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

$R^{8b}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

$R^{8c}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and amino;

R⁹ selected from the group consisting of hydrogen, optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, alkoxy, and amino;

Y¹ is selected from the group consisting of —O—, —S—, and —NR¹⁰—;

R¹⁰ is selected from the group consisting of hydrogen, optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, ($C_{3-6}$ cycloalkyl)$C_{1-4}$ alkyl, aralkyl, (alkoxycarbonyl)alkyl, —C(=O)R¹¹, —SO₂R¹², —C(=O)—OR¹³, and —C(=O)—NR$^{14a}$R$^{14b}$;

R¹¹ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

R¹² is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

R¹³ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{14a}$ and $R^{14b}$ are each independently selected from the group consisting of hydrogen, optionally substituted $C_{1-6}$ alkyl, optionally substituted $C_{6-14}$ aryl, optionally substituted $C_{3-12}$ cycloalkyl, 3- to 14-membered heterocyclo, optionally substituted 5- to 14-membered heteroaryl, and aralkyl; or $R^{14a}$ and $R^{14b}$ taken together with the nitrogen atom to which they are attached form an optionally substituted 4- to 8-membered heterocyclo;

is a fused thienyl or fused phenyl group, wherein the fused phenyl group is additionally substituted with R¹⁵; and R¹⁵ is selected from the group consisting of hydrogen, halogen, $C_{1-4}$ alkyl, and alkoxy, with a compound having Formula V:

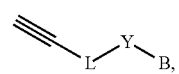

wherein:

B is selected from the group consisting of:

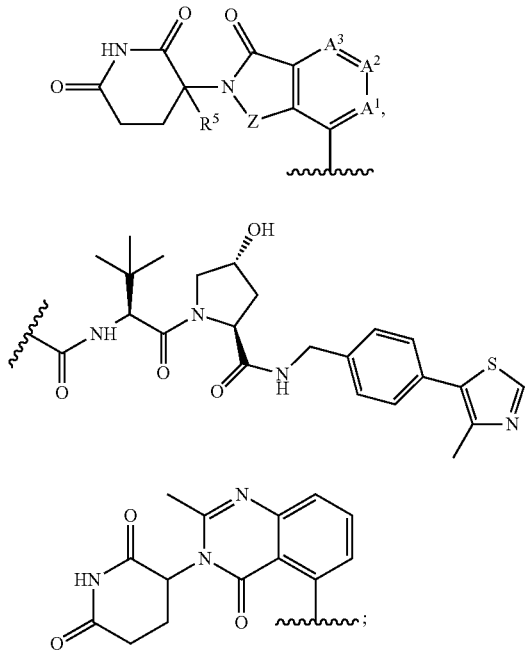

L is selected from the group consisting of alkylenyl, heteroalkylenyl, -A-$(CH_2)_m$—W—$(CH_2)_n$— and —$(CH_2)_m$—W—$(CH_2)$—O—$(CH_2)_v$—; A is selected from the group consisting of 5-membered heteroarylenyl and 6-membered heteroarylenyl; or A is absent:

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;
n is 0, 1, 2, 3, 4, 5, 6, 7, or 8;
u is 0, 1, 2, or 3;
v is 1, 2, 3, or 4;

Y is selected from the group consisting of —C≡C—, —$CH_2$—, —O—, —$N(R^{2c})$—, —C(=O)$N(R^{2d})$—, —$N(R^{2e})$C(=O)$CH_2$O—, and —$N(R^{2e})$C(=O)$CH_2N(R^{2f})$—; or Y is absent;

wherein the carboxamide nitrogen atom of —$N(R^{2e})$C(=O)$CH_2$O— and —$N(R^{2e})$C(=O)$CH_2N(R^{2f})$—, and the carbon atom of —C(=O)$N(R^{2d})$— is attached to L;

$R^{2c}$, $R^{2d}$, $R^{2e}$, and $R^{2f}$ are each independently selected from the group consisting of hydrogen and $C_{1-4}$ alkyl;

Z is selected from the group consisting of —$CH_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, and (2) isolating the compound having Formula XI, or a pharmaceutically acceptable salt or solvate thereof.

In another embodiment, the disclosure provides a method for making a compound represented by Formula XIII:

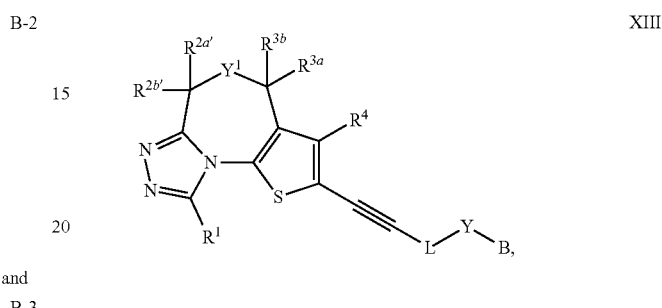

and the pharmaceutically acceptable salts or hydrates thereof, as described above for Formula XI, wherein $R^1$, $R^{2a'}$, $R^{2b'}$, $R^{3a}$, $R^{3b}$, $R^4$, L, Y, $Y^1$, and B are as defined in connection with Formula XI.

In another embodiment, the disclosure provides a method for making a compound represented by Formula XI or Formula XIII, and the pharmaceutically acceptable salts or hydrates thereof, wherein $R^{3a}$ and $R^{3b}$ are hydrogen.

In another embodiment, the disclosure provides a method for making a compound represented by Formula XI or Formula XIII, and the pharmaceutically acceptable salts or hydrates thereof, wherein $R^1$ is $C_{1-4}$ alkyl. In another embodiment, $R^1$ is methyl, or a pharmaceutically acceptable salt or hydrate thereof.

In another embodiment, the disclosure provides a method for making a compound represented by Formula XI or Formula XIII, and the pharmaceutically acceptable salts or hydrates thereof, wherein $R^{2a'}$ and $R^{2b'}$ are each independently selected from the group consisting of hydrogen and $C_{1-4}$ alkyl.

In another embodiment, the disclosure provides a method for making a compound represented by Formula XIV:

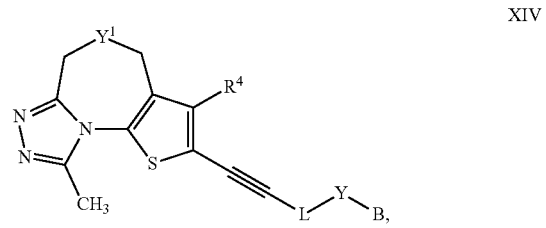

and the pharmaceutically acceptable salts or hydrates thereof, as described above for Formula XI, wherein $R^4$, L, Y, $Y^1$, and B are as defined in connection with Formula XI.

In another embodiment, the disclosure provides a method or making a compound represented by Formula XV:

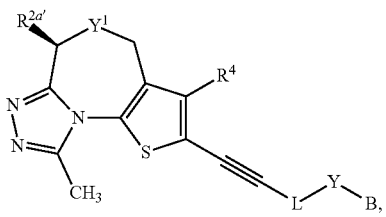

XV and the pharmaceutically acceptable salts or hydrates thereof, as described above for Formula XI, wherein $R^{2a'}$ is $C_{1-4}$ alkyl, and $R^4$, L, Y, Y', and B are as defined in connection with Formula XI.

In another embodiment, the disclosure provides a method for making a compound represented by Formula XVI:

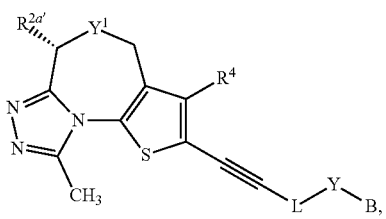

XVI and the pharmaceutically acceptable salts or hydrates thereof, as described above for Formula XI, wherein $R^{2a'}$ is $C_{1-4}$ alkyl, and $R^4$, L, Y, $Y^1$, and B are as defined in connection with Formula XI.

In another embodiment, the disclosure provides a method for making a compound represented by any one of Formulae XI or XIII-XVI, and the pharmaceutically acceptable salts or hydrates thereof, wherein $R^4$ is selected from the group consisting of halogen, $C_{1-4}$ alkyl, optionally $C_{2-4}$ alkenyl, optionally substituted $C_{2-4}$ alkynyl, aralkyl, optionally substituted $C_{6-14}$ aryl, optionally substituted $C_{3-12}$ cycloalkyl, 3- to 14-membered heterocyclo, optionally substituted 5- to 14-membered heteroaryl. In another embodiment, $R^4$ is aralkyl.

In another embodiment, the disclosure provides a method for making a compound represented by any one of Formulae XI or XIII-XVI, and the pharmaceutically acceptable salts or hydrates thereof, $Y^1$ is —O—. In another embodiment, $Y^1$ is —N(H)—.

In another embodiment, the disclosure provides a method for making a compound represented by Formula XVII:

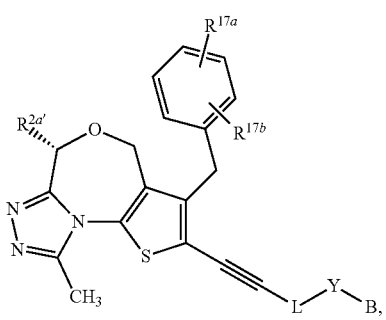

XVII and the pharmaceutically acceptable salts and hydrates thereof, as described above for Formula XI, wherein $R^{2a'}$ is selected from the group consisting of hydrogen and $C_{1-3}$ alkyl; $R^{17a}$ and $R^{17b}$ are each independently selected from the group consisting of hydrogen, $C_{1-4}$ alkyl, haloalkyl, $C_{1-4}$ alkoxy, and halo; and L, Y, and B are as defined in connection with Formula XI.

In another embodiment, the disclosure provides a method for making a compound represented by any one of Formulae XI or XIII-XVII, wherein L is $C_{1-12}$ alkylenyl. In another embodiment, L is selected from the group consisting of —CH$_2$—, —CH$_2$CH$_2$—, —CH$_2$CH$_2$CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, and —CH$_2$(CH$_2$)$_6$CH$_2$—.

In another embodiment, the disclosure provides a method for making a compound represented by any one of Formulae XI or XIII-XVII, wherein, L is 3- to 12-membered heteroalkylenyl. In another embodiment, L is —(CH$_2$)$_o$O—(CH$_2$CH$_2$O)$_p$—(CH$_2$)$_q$—; o is 1, 2, or 3; p is 0, 1, 2, 3, 4, or 5; and q is 1, 2, or 3.

In another embodiment, the disclosure provides methods for making a compound represented by any one of Formulae XI or XIII-XVII, wherein L is selected from the group consisting of: —CH$_2$OCH$_2$CH$_2$—, —CH$_2$CH$_2$OCH$_2$CH$_2$—, —CH$_2$O(CH$_2$CH$_2$O)CH$_2$CH$_2$—, —CH$_2$O(CH$_2$CH$_2$O)$_2$CH$_2$CH$_2$—, —CH$_2$O(CH$_2$CH$_2$O)$_3$CH$_2$CH$_2$—, —CH$_2$CH$_2$O(CH$_2$CH$_2$O)$_6$CH$_2$CH$_2$—, —CH$_2$CH$_2$O(CH$_2$CH$_2$O)$_6$CH$_2$CH$_2$—, —CH$_2$CH$_2$CH$_2$OCH$_2$CH$_2$OCH$_2$CH$_2$—, —CH$_2$CH$_2$CH$_2$O(CH$_2$CH$_2$O)$_2$CH$_2$CH$_2$CH$_2$—, and —CH$_2$CH$_2$CH$_2$O(CH$_2$)$_4$OCH$_2$CH$_2$CH$_2$—.

In another embodiment, the disclosure provides a method for making a compound represented by any one of Formulae XI or XIII-XVII, wherein L is —(CH$_2$)$_m$—W—(CH$_2$)$_n$—. In another embodiment, W is phenylenyl. In another embodiment, W is 5-membered heteroarylenyl. In another embodiment, W is 6-membered heteroarylenyl. In another embodiment, wherein m is 0. In another embodiment, wherein n is 1, 2, 3, 4, or 5.

In another embodiment, the disclosure provides a method for making a compound represented by any one of Formulae XI or XIII-XVII, wherein L is —(CH$_2$)$_m$—W—(CH$_2$)$_u$—O—(CH$_2$)$_v$—. In another embodiment, W is phenylenyl. In another embodiment, W is 5-membered heteroarylenyl. In another embodiment, W is 6-membered heteroarylenyl.

In another embodiment, the disclosure provides a method for making a compound represented by any one of Formulae XI or XIII-XVII, wherein L is selected from the group consisting of:

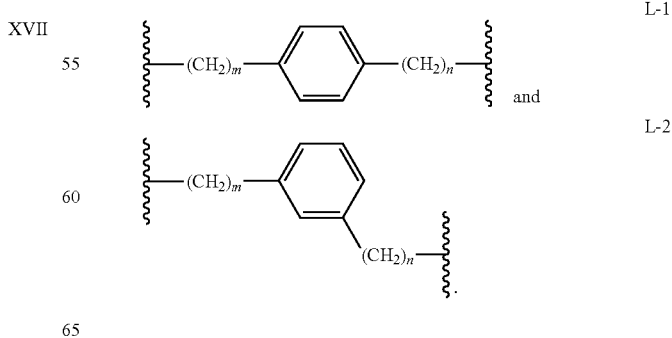

In another embodiment, wherein m is 0. In another embodiment, wherein n is 1, 2, 3, 4, or 5.

In another embodiment, the disclosure provides a method for making a compound represented by any one of Formulae XI or XIII-XVII, wherein L is selected from the group consisting of:

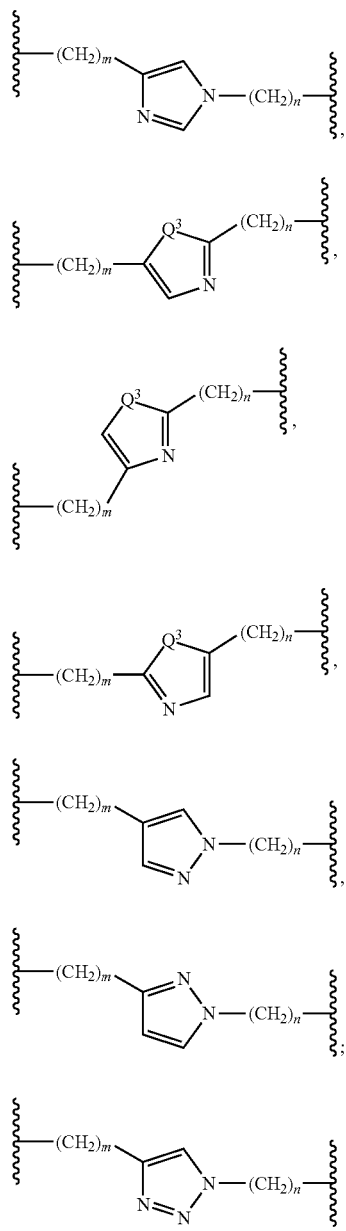

L-3,

L-4,

L-5,

L-6,

L-7,

L-8; and

L-9

$Q^3$ is selected from the group consisting of —O—, —S—, and —N($R^6$)—; and $R^6$ is selected from the group consisting of hydrogen and $C_{1-4}$ alkyl. In another embodiment, wherein m is 0. In another embodiment, wherein n is 1, 2, 3, 4, or 5. In another embodiment, L is L-3. In another embodiment, L is L-4. In another embodiment, L is L-5. In another embodiment, L is L-6. In another embodiment, L is L-7. In another embodiment, L is L-8. In another embodiment, L is L-9.

In another embodiment, the disclosure provides a method for making a compound represented by any one of Formulae XI or XIII-XVII, wherein L is selected

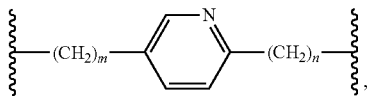

L-10,

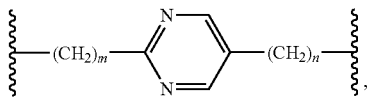

L-11,

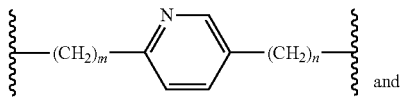

L-12 and

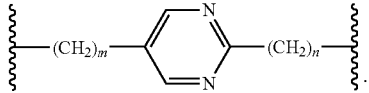

L-13.

In another embodiment, wherein m is 0. In another embodiment, wherein n is 1, 2, 3, 4, or 5. In another embodiment, L is L-10. In another embodiment, L is L-11. In another embodiment, L is L-12. In another embodiment, L is L-13.

In another embodiment, the disclosure provides a method for making a compound represented by Formula XVIII:

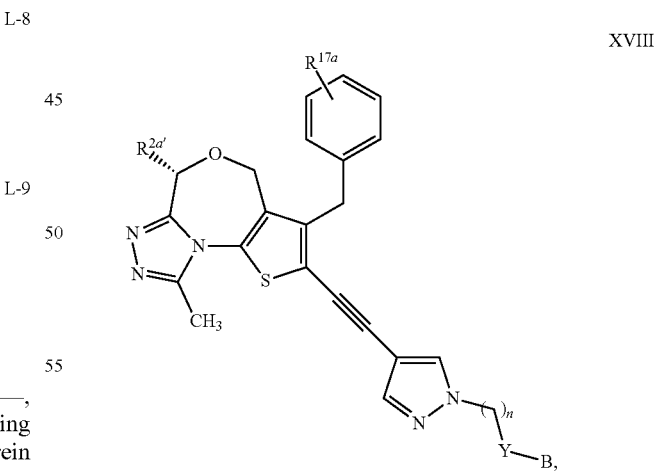

XVIII and the pharmaceutically acceptable salts or solvates thereof, as described above for Formula XI, wherein n is 2, 3, 4, or 5, and $R^{2a'}$, $R^{17a}$, Y, and B are as defined in connection with Formula XVII.

In another embodiment, the disclosure provides a method for making a compound represented by Formula XIX:

XIX

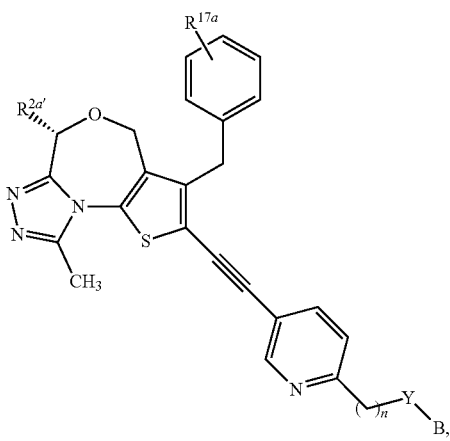

and the pharmaceutically acceptable salts or solvates thereof, as described above for Formula XI, wherein n is 2, 3, 4, or 5, and $R^{2a'}$, $R^{17a}$, Y, and B are as defined in connection with Formula XVII.

In another embodiment, the disclosure provides a method for making a compound represented by Formula XX:

XX

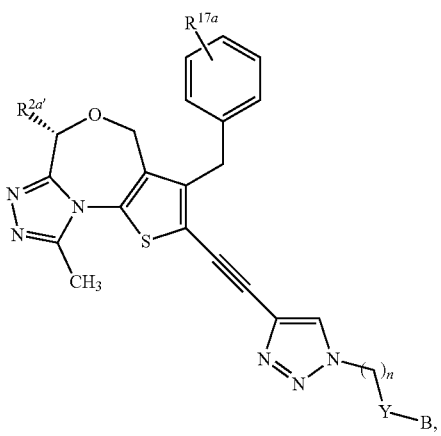

and the pharmaceutically acceptable salts or solvates thereof, as described above for Formula XI, wherein n is 2, 3, 4, or 5, and $R^{2a'}$, $R^{17a}$, Y, and B are as defined in connection with Formula XVII.

In another embodiment, the disclosure provides a method for making a compound represented by Formulae XVIII-XX, and the pharmaceutically acceptable salts or solvates thereof, wherein $R^{2a'}$ is hydrogen. In another embodiment, $R^{2a'}$ is methyl.

In another embodiment, the disclosure provides a method for making a compound represented by Formulae XVIII-XX, and the pharmaceutically acceptable salts or solvates thereof, wherein Y is selected from the group consisting of —C≡C—, —CH₂—, —O—, and —N(H)—. In another embodiment, Y is —C≡C—. In another embodiment, Y is —CH₂—. In another embodiment, Y is —O—. In another embodiment, Y is —N(H)—.

In another embodiment, the disclosure provides a method for making a compound represented by any one of Formulae XI or XIII-XX, wherein B is B-1a. In another embodiment, $A^1$ is —C($R^{16a}$)= and $R^{16a}$ is selected from the group consisting of hydrogen and halo. In another embodiment, $A^2$ is —C($R^{16b}$)= and $R^{16b}$ is selected from the group consisting of hydrogen and halo. In another embodiment, $A^3$ is —C($R^{16c}$)= and $R^{16c}$ is selected from the group consisting of hydrogen and halo. In another embodiment, $A^1$ is —N=, $A^2$ is —C($R^{16b}$)=, and $A^3$ is —C($R^{16c}$)=. In another embodiment, $A^1$ is —C($R^{16a}$)=, $A^2$ is —N=, and $A^3$ is —C($R^{16c}$)=. In another embodiment, $A^1$ is —C($R^{16a}$)=, $A^2$ is —C($R^{16b}$)= and $A^3$ is —N=. In another embodiment, Z is —CH₂—. In another embodiment, Z is —C(=O)—. In another embodiment, $R^5$ is hydrogen. In another embodiment, B-1a is selected from the group consisting of:

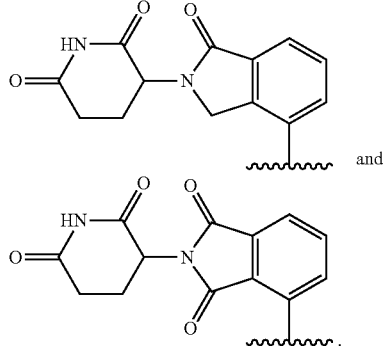

In another embodiment, the disclosure provides a method for making a compound represented by any one of Formulae XI or XIII-XX, and the pharmaceutically acceptable salts or solvates thereof, wherein B is B-2.

In another embodiment, the disclosure provides a method for making a compound represented by any one of Formulae XI or XIII-XX, and the pharmaceutically acceptable salts or solvates thereof, wherein B is B-3.

In another embodiment, the disclosure provides a method of making a compound having Formula XXI:

XXI

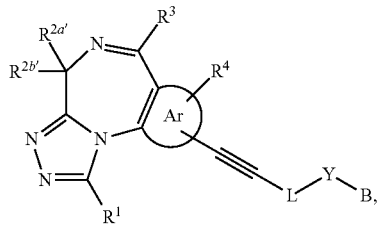

or a pharmaceutically acceptable salt or hydrate thereof, wherein:

$R^1$ is selected from the group consisting of hydrogen and optionally substituted $C_{1-4}$ alkyl;

$R^{2a'}$ and $R^{2b'}$ are each independently selected from the group consisting of hydrogen, optionally substituted $C_{1-4}$ alkyl, and (alkoxycarbonyl)alkyl, or $R^{2a'}$ and $R^{2b'}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl $R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$;

$R^{15}$ is selected from the group consisting of hydrogen, halogen, $C_{1-4}$ alkyl, and alkoxy;

B is a monovalent radical of a ligand for an E3 ubiquitin ligase protein, e.g., B is:

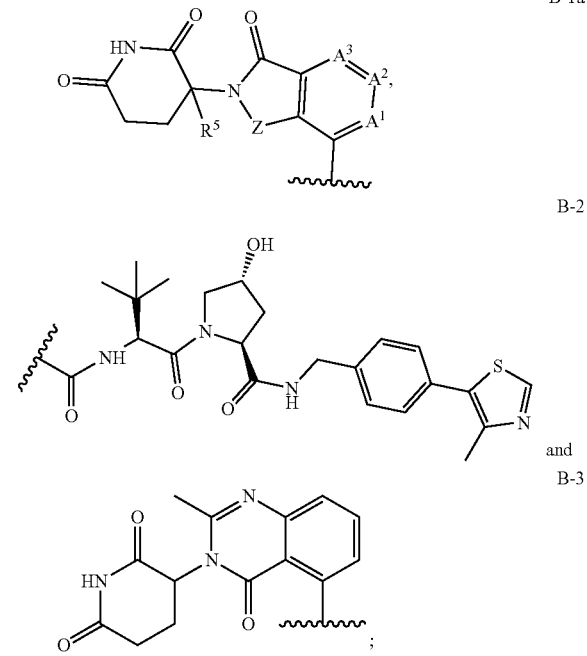

L is selected from the group consisting of alkylenyl, heteroalkylenyl, -A-$(CH_2)_m$—W—$(CH_2)_n$— and —$(CH_2)_m$—W—$(CH_2)_u$—O—$(CH_2)_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

Y is selected from the group consisting of —C≡C—, —$CH_2$—, —O—, —$N(R^{2c})$—, —$C(=O)N(R^{2d})$—, —$N(R^{2e})C(=O)CH_2O$—, and —$N(R^{2e})C(=O)CH_2N(R^{2f})$—; or Y is absent;

wherein the carboxamide nitrogen atom of —$N(R^{2e})C(=O)CH_2O$— and —$N(R^{2e})C(=O)CH_2N(R^{2f})$—, and the carbon atom of —$C(=O)N(R^{2d})$— is attached to L;

$R^{2c}$, $R^{2d}$, $R^{2e}$, and $R^{2f}$ are each independently selected from the group consisting of hydrogen and $C_{1-4}$ alkyl;

Z is selected from the group consisting of —$CH_2$ and —C(=O)—;

$R^5$ is selected from the group consisting of hydrogen, methyl, and fluoro;

$A^1$ is selected from the group consisting of —$C(R^{16a})$= and —N=;

$A^2$ is selected from the group consisting of —$C(R^{16b})$= and —N=;

$A^3$ is selected from the group consisting of —$C(R^{16c})$= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, the method comprising:

(1) reacting a compound having Formula XXII:

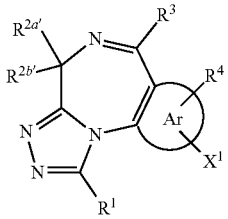

XXII wherein:

$X^1$ is selected from the group consisting of —Br and —I;

$R^1$ is selected from the group consisting of hydrogen and optionally substituted $C_{1-4}$ alkyl;

$R^{2a'}$ and $R^{2b'}$ are each independently selected from the group consisting of hydrogen, optionally substituted $C_{1-4}$ alkyl, and (alkoxycarbonyl)alkyl, or $R^{2a'}$ and $R^{2b'}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl;

$R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$; and $R^{15}$ is selected from the group consisting of hydrogen, halogen, $C_{1-4}$ alkyl, and alkoxy, with a compound having Formula V:

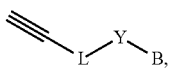

V wherein:

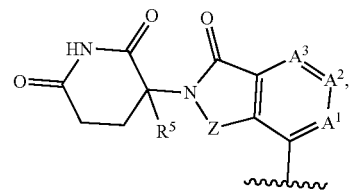

B-1a

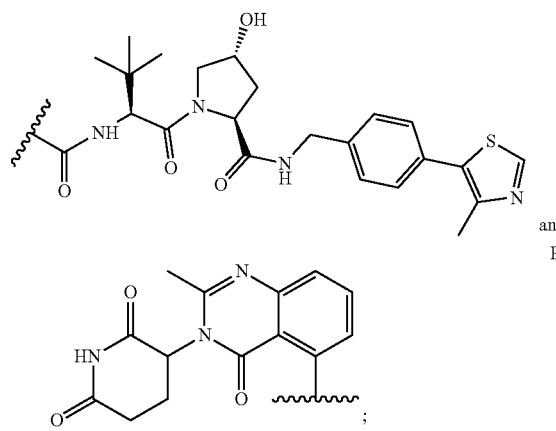

B-2 and

B-3

L is selected from the group consisting of alkylenyl, heteroalkylenyl, -A-(CH$_2$)$_m$—W—(CH$_2$)$_n$— and —(CH$_2$)$_m$—W—(CH$_2$)$_u$—O—(CH$_2$)$_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

Y is selected from the group consisting of —C≡C—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or Y is absent;

wherein the carboxamide nitrogen atom of —N(R$^{2e}$)C (=O)CH$_2$O— and —N(R$^{2e}$)C(=O)CH$_2$N(R$^{2f}$)—, and the carbon atom of —C(=O)N(R$^{2d}$)— is attached to L;

R$^{2c}$, R$^{2d}$, R$^{2e}$, and R$^{2f}$ are each independently selected from the group consisting of hydrogen and C$_{1-4}$ alkyl;

Z is selected from the group consisting of —CH$_2$ and —C(=O)—;

R$^5$ is selected from the group consisting of hydrogen, methyl, and fluoro;

A$^1$ is selected from the group consisting of —C(R$^{16a}$)= and —N=;

A$^2$ is selected from the group consisting of —C(R$^{16b}$)= and —N=;

A$^3$ is selected from the group consisting of —C(R$^{16c}$)= and —N=;

R$^{16a}$ is selected from the group consisting of hydrogen, halo, and C$_{1-4}$ alkyl;

R$^{16b}$ is selected from the group consisting of hydrogen, halo, and C$_{1-4}$ alkyl; and R$^{16c}$ is selected from the group consisting of hydrogen, halo, and C$_{1-4}$ alkyl, and (2) isolating the compound having Formula XXI, or a pharmaceutically acceptable salt or solvate thereof.

In another embodiment, the disclosure provides a method for making a compound represented by Formula XXIII

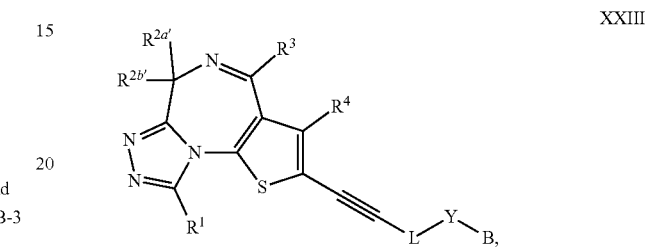

XXIII and the pharmaceutically acceptable salts or hydrates thereof, as described above for Formula XXI, wherein R$^1$, R$^{2a'}$, R$^{2b'}$, R$^3$, R$^4$, L, Y, and B are as defined in connection with Formula XXI.

In another embodiment, the disclosure provides a method for making a compound represented by Formula XXI or Formula XXIII, and the pharmaceutically acceptable salts or hydrates thereof, wherein R$^3$ is optionally substituted phenyl.

In another embodiment, the disclosure provides a method for making a compound represented by Formula XXI or Formula XXIII, and the pharmaceutically acceptable salts or hydrates thereof, wherein R$^1$ is C$_{1-4}$ alkyl. In another embodiment, R$^1$ is methyl.

In another embodiment, the disclosure provides a method for making a compound represented by Formula XXI or Formula XXIII, and the pharmaceutically acceptable salts or hydrates thereof, wherein R$^{2a'}$ and R$^{2b'}$ are each independently selected from the group consisting of hydrogen and C$_{1-4}$ alkyl.

In another embodiment, the disclosure provides a method for making a compound represented by Formula XXIV:

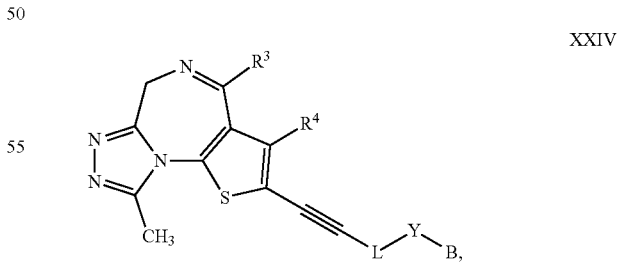

XXIV and the pharmaceutically acceptable salts or hydrates thereof, as described above for Formula XXI, wherein R$^3$, R$^4$, L, Y, and B are as defined in connection with Formula XXI.

In another embodiment, the disclosure provides a method for making a compound represented by Formula XXV:

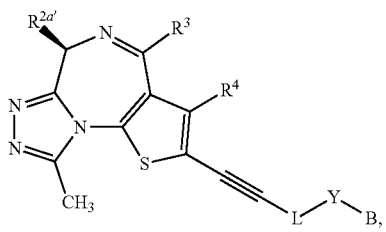

XXV and the pharmaceutically acceptable salts or hydrates thereof, as described above for Formula XXI, wherein $R^{2a'}$ is $C_{1-4}$ alkyl, and $R^3$, $R^4$, L, Y, and B are as defined in connection with Formula XXI.

In another embodiment, the disclosure provides a method for making a compound represented by Formula XXVI:

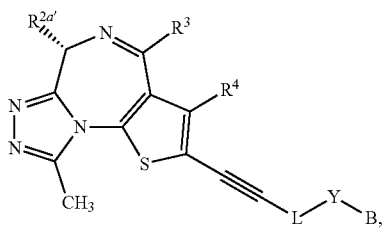

XXVI and the pharmaceutically acceptable salts or hydrates thereof, as described above for Formula XXI, wherein $R^{2a'}$ is $C_{1-4}$ alkyl, and $R^3$, $R^4$, L, Y, and B are as defined in connection with Formula XXI.

In another embodiment, the disclosure provides a method for making a compound represented by any one of Formulae XXI, or XXIII-XXVI, and the pharmaceutically acceptable salts or hydrates thereof, wherein $R^4$ is $C_{1-4}$ alkyl. In another embodiment, $R^4$ is methyl. In another embodiment, $R^4$ is hydrogen.

In another embodiment, the disclosure provides a method for making a compound represented by Formula XXVII:

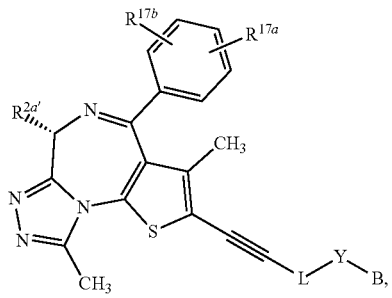

XXVII and the pharmaceutically acceptable salts and hydrates thereof, as described above for Formula XXI, wherein $R^{2a'}$ is selected from the group consisting of hydrogen and $C_{1-3}$ alkyl; $R^{17a}$ and $R^{17b}$ are each independently selected from the group consisting of hydrogen, $C_{1-4}$ alkyl, haloalkyl, $C_{1-4}$ alkoxy, and halo; and L, Y, and B are as defined in connection with Formula XXI. In another embodiment, $R^{17a}$ and $R^{17b}$ are each independently selected from the group consisting of hydrogen and halo.

In another embodiment, the disclosure provides a method for making a compound represented by any one of Formulae XXI or XXIII-XXVII, and the pharmaceutically acceptable salts or solvates thereof, wherein L is $C_{1-12}$ alkylenyl. In another embodiment, L is selected from the group consisting of —$CH_2$—, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, and —$CH_2(CH_2)_6CH_2$—.

In another embodiment, the disclosure provides a method for making a compound represented by any one of Formulae XXI or XXIII-XXVII, and the pharmaceutically acceptable salts or solvates thereof, wherein, L is 3- to 12-membered heteroalkylenyl. In another embodiment, L is —$(CH_2)_oO$—$(CH_2CH_2O)_p$—$(CH_2)_q$—; o is 1, 2, or 3; p is 0, 1, 2, 3, 4, or 5; and q is 1, 2, or 3.

In another embodiment, the disclosure provides a method for making a compound represented by any one of Formulae XXI or XXIII-XXVII, and the pharmaceutically acceptable salts or solvates thereof, wherein L is selected from the group consisting of: —$CH_2OCH_2CH_2$—, —$CH_2CH_2OCH_2CH_2$—, —$CH_2O(CH_2CH_2O)CH_2CH_2$—, —$CH_2O(CH_2CH_2O)_2CH_2CH_2$—, —$CH_2O(CH_2CH_2O)_3CH_2CH_2$—, —$CH_2CH_2O(CH_2CH_2O)_6CH_2CH_2$—, —$CH_2CH_2O(CH_2CH_2O)_6CH_2CH_2$—, —$CH_2CH_2CH_2OCH_2CH_2OCH_2CH_2$—, —$CH_2CH_2CH_2O(CH_2CH_2O)_2CH_2CH_2CH_2$—, and —$CH_2CH_2CH_2O(CH_2)_4OCH_2CH_2CH_2$—.

In another embodiment, the disclosure provides a method for making a compound represented by any one of Formulae XXI or XXIII-XXVII, and the pharmaceutically acceptable salts or solvates thereof, wherein L is —$(CH_2)_m$—W—$(CH_2)_n$—. In another embodiment, W is phenylenyl. In another embodiment, W is 5-membered heteroarylenyl. In another embodiment, W is 6-membered heteroarylenyl. In another embodiment, wherein m is 0. In another embodiment, wherein n is 1, 2, 3, 4, or 5.

In another embodiment, the disclosure provides a method for making a compound represented by any one of Formulae XXI or XXIII-XXVII, and the pharmaceutically acceptable salts or solvates thereof, wherein L is —$(CH_2)_m$—W—$(CH_2)_u$—O—$(CH_2)_v$—. In another embodiment, W is phenylenyl. In another embodiment, W is 5-membered heteroarylenyl. In another embodiment, W is 6-membered heteroarylenyl.

In another embodiment, the disclosure provides a method for making a compound represented by any one of Formulae XXI or XXIII-XXVII, and the pharmaceutically acceptable salts or solvates thereof, wherein L is selected from the group consisting of:

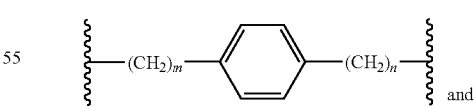

L-1 and

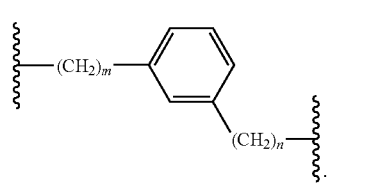

L-2

In another embodiment, m is 0. In another embodiment, n is 1, 2, 3, 4, or 5.

In another embodiment, the disclosure provides a method for making a compound represented by any one of Formulae XXI or XXIII-XXVII, and the pharmaceutically acceptable salts or solvates thereof, wherein L is selected from the group consisting of:

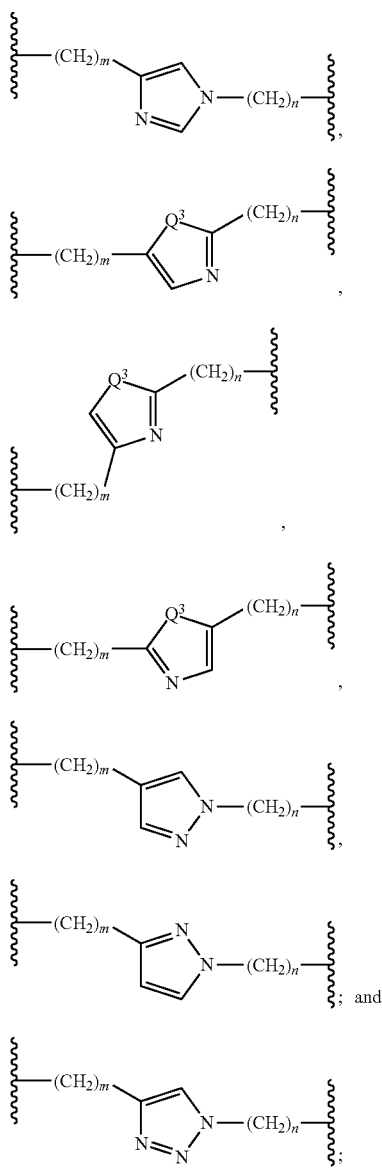

$Q^3$ is selected from the group consisting of —O—, —S—, and —N($R^6$)—; and $R^6$ is selected from the group consisting of hydrogen and $C_{1-4}$ alkyl. In another embodiment, m is 0. In another embodiment, n is 1, 2, 3, 4, or 5. In another embodiment, n is 2, 3, or 4. In another embodiment, L is L-3. In another embodiment, L is L-4. In another embodiment, L is L-5. In another embodiment, L is L-6. In another embodiment, L is L-7. In another embodiment, L is L-8. In another embodiment, L is L-9.

In another embodiment, the disclosure provides a method for making a compound represented by any one of Formulae XXI or XXIII-XXVII, and the pharmaceutically acceptable salts or solvates thereof, wherein L is selected from the group consisting of:

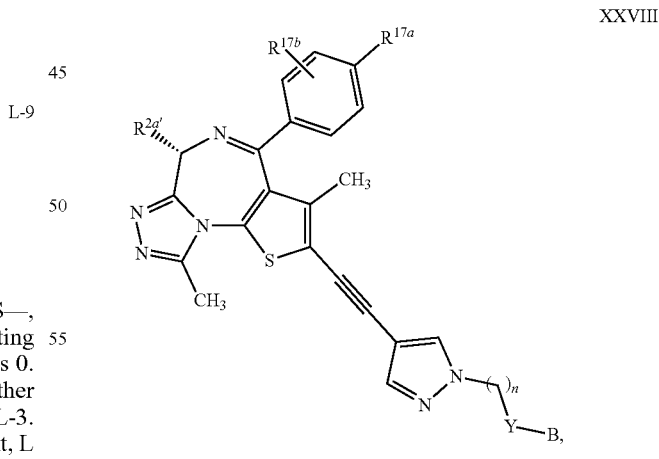

In another embodiment, m is 0. In another embodiment, n is 1, 2, 3, 4, or 5. In another embodiment, n is 2, 3, or 4. In another embodiment, L is L-10. In another embodiment, L is L-11. In another embodiment, L is L-12. In another embodiment, L is L-13.

In another embodiment, the disclosure provides a method for making a compound represented by any one of Formulae XXI or XXIII-XXVII, and the pharmaceutically acceptable salts or solvates thereof, wherein L is —(CH$_2$)$_m$—W—(CH$_2$)$_u$—O—(CH$_2$)$_v$—; W is selected from the group consisting of 5-membered heteroarylenyl and optionally substituted 6-membered heteroarylenyl; m is 0, 1, 2, 3, 4, 5, 6, or 7; u is 0; and v is 1, 2, 3, or 4. In another embodiment, m is 0.

In another embodiment, the disclosure provides a method for making a compound represented by Formula XXVIII:

XXVIII and the pharmaceutically acceptable salts or solvates thereof, as described above for Formula XXI, wherein n is 2, 3, 4, or 5, and $R^{2a}$, $R^{17a}$, $R^{17b}$, Y, B, and n are as defined in connection with Formula XXVII.

In another embodiment, the disclosure provides a method for making a compound represented by Formula XXIX:

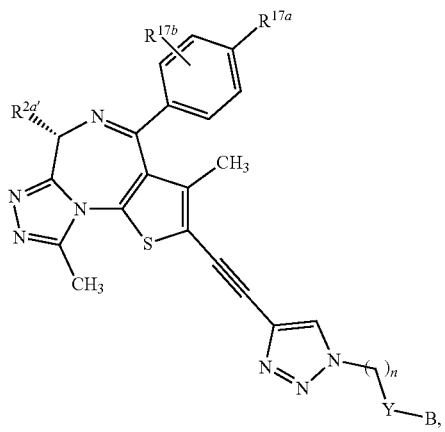

XXIX and the pharmaceutically acceptable salts or solvates thereof, as described above for Formula XXI, wherein n is 2, 3, 4, or 5, and $R^{2a}$, $R^{17a}$, $R^{17b}$, Y, B, and n are as defined in connection with Formula XXVII.

In another embodiment, the disclosure provides a method for making a compound represented by Formula XXX:

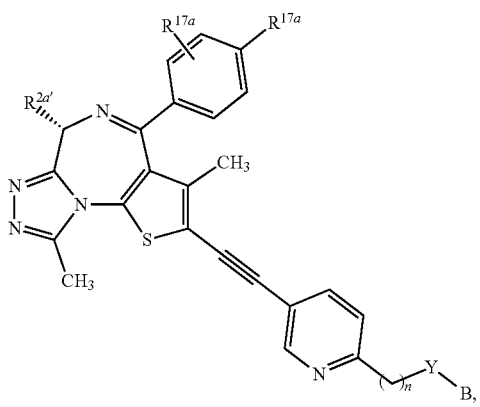

XXX and the pharmaceutically acceptable salts or solvates thereof, as described above for Formula XXI, wherein n is 2, 3, 4, or 5, and $R^{2a'}$, $R^{17a}$, $R^{17b}$, Y, B, and n are as defined in connection with Formula XXVII.

In another embodiment, the disclosure provides a method for making a compound represented by any one of Formulae XXVIII-XXX, and the pharmaceutically acceptable salts or solvates thereof, wherein $R^{2a'}$ is hydrogen. In another embodiment, $R^{2a'}$ is methyl.

In another embodiment, the disclosure provides a method for making a compound represented by any one of Formulae XXVIII-XXX, and the pharmaceutically acceptable salts or solvates thereof, wherein Y is selected from the group consisting of —C≡C—, —CH$_2$—, —O—, and —N(H)—. In another embodiment, Y is —C≡C—. In another embodiment, Y is —CH$_2$—. In another embodiment, Y is —O—. In another embodiment, Y is —N(H)—.

In another embodiment, the disclosure provides a method for making a compound represented by any one of Formulae XXI or XXIII-XXX, and the pharmaceutically acceptable salts or solvates thereof, wherein B is B-1a. In another embodiment, $A^1$ is —C($R^{16a}$)= and $R^{16a}$ is selected from the group consisting of hydrogen and halo. In another embodiment, $A^2$ is —C($R^{16b}$)= and $R^{16b}$ is selected from the group consisting of hydrogen and halo. In another embodiment, $A^3$ is —C($R^{16c}$)= and $R^{16c}$ is selected from the group consisting of hydrogen and halo. In another embodiment, $A^1$ is —N=, $A^2$ is —C($R^{16b}$)=, and $A^3$ is —C($R^{16c}$)=. In another embodiment, $A^1$ is —C($R^{16a}$)=, $A^2$ is —N=, and $A^3$ is —C($R^{16c}$)=. In another embodiment, $A^1$ is —C($R^{16a}$)=, $A^2$ is —C($R^{16b}$)= and $A^3$ is —N=. In another embodiment, Z is —CH$_2$—. In another embodiment, Z is —C(=O)—. In another embodiment, $R^5$ is hydrogen. In another embodiment, B-1a is selected from the group consisting of:

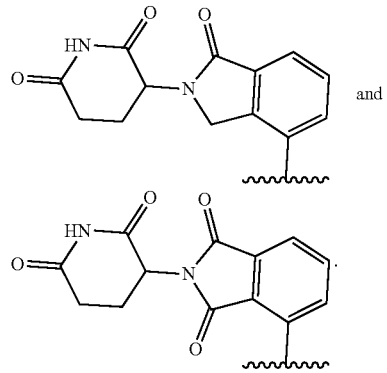

and

In another embodiment, the disclosure provides a method for making a compound represented by any one of Formulae XXI or XXIII-XXX, and the pharmaceutically acceptable salts or solvates thereof, wherein B is B-2.

In another embodiment, the disclosure provides a method for making a compound represented by any one of Formulae XXI or XXIII-XXX, and the pharmaceutically acceptable salts or solvates thereof, wherein B is B-3.

In another embodiment, the disclosure provides methods of making a compound having Formula XXXI:

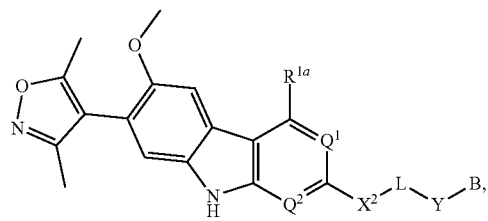

XXXI and the pharmaceutically acceptable salts and solvates thereof, wherein:
B is selected from the group consisting of:

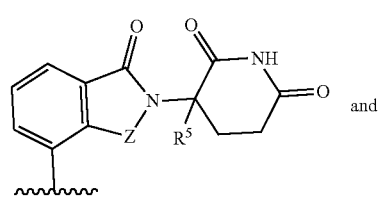

B-1 and

-continued

B-2

[Chemical structure B-2: pyrrolidine-based structure with OH, NH, thiazole group]

R$^{1a}$ is selected from the group consisting of optionally substituted aryl, optionally substituted heteroaryl, and —N(H)R$^{3c}$;
Q$^1$ is =CH— and Q$^2$ is —N=; or
Q$^1$ is =N— and Q$^2$ is —CH=; or
Q$^1$ is =N— and Q$^2$ is —N=;
R$^{3c}$ is selected from the group consisting of optionally substituted aryl and optionally substituted heteroaryl;
X$^2$ is —C(=O)N(H)—, wherein the nitrogen atom of —C(=O)N(H)— is attached to L,
L is selected from the group consisting of alkylenyl, heteroalkylenyl, and —(CH$_2$)$_m$—W—(CH$_2$)$_n$—;
W is selected from the group consisting of optionally substituted phenylenyl, optionally substituted 5-membered heteroarylenyl, and optionally substituted 6-membered heteroarylenyl;
m is 0, 1, 2, 3, 4, 5, 6, or 7;
n is 0, 1, 2, 3, 4, 5, 6, 7, or 8;
Y is selected from the group consisting of —C≡C—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or
Y is absent;
wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;
R$^{2c}$, R$^{2d}$, R$^{2e}$, and R$^{2f}$ are each independently selected from the group consisting of hydrogen and C$_{1-4}$ alkyl;
Z is selected from the group consisting of —CH$_2$— and —C(=O)—; and
R$^5$ is selected from the group consisting of hydrogen and fluoro,
with the proviso that Y is absent when B is B-2,
the method comprising:
(1) reacting, e.g., condensing, a compound having Formula XXXII:

XXXII

[Chemical structure XXXII: isoxazole-substituted indole/pyran structure with R$^{1a}$, Q$^1$, Q$^2$, R$^{7a}$]

wherein:
R$^{1a}$ is selected from the group consisting of optionally substituted aryl, optionally substituted heteroaryl, and —N(H)R$^3$;

Q$^1$ is =CH— and Q$^2$ is —N=; or
Q$^1$ is =N— and Q$^2$ is —CH=; or
Q$^1$ is =N— and Q$^2$ is —N=;
R$^{3c}$ is selected from the group consisting of optionally substituted aryl and optionally substituted heteroaryl;
R$^{7a}$ is a leaving group, e.g., R$^{7a}$ is selected from the group consisting of chloro and —OR$^{7b}$; and
R$^{7b}$ is hydrogen,
with a compound having Formula VI:

VI $$H_2N-L-Y-B,$$

wherein:
B is selected from the group consisting of:

B-1

[Chemical structure B-1: isoindolinone-piperidinedione structure with Z, R$^5$]

and

B-2

[Chemical structure B-2: pyrrolidine-based structure with OH, NH, thiazole group]

L is selected from the group consisting of alkylenyl, heteroalkylenyl, and —(CH$_2$)$_m$—W—(CH$_2$)$_n$—;
W is selected from the group consisting of optionally substituted phenylenyl, optionally substituted 5-membered heteroarylenyl, and optionally substituted 6-membered heteroarylenyl;
m is 0, 1, 2, 3, 4, 5, 6, or 7;
n is 0, 1, 2, 3, 4, 5, 6, 7, or 8;
Y is selected from the group consisting of —C≡C—, —CH$_2$—, —O—, —N(R$^{2c}$)—, —C(=O)N(R$^{2d}$)—, —N(R$^{2e}$)C(=O)CH$_2$O—, and —N(R$^{2e}$)C(=O)CH$_2$N(R$^{2f}$)—; or
Y is absent;
wherein the carboxamide nitrogen atom of —N(R$^{2e}$)C(=O)CH$_2$O— and —N(R$^{2e}$)C(=O)CH$_2$N(R$^{2f}$)—, and the carbon atom of —C(=O)N(R$^{2d}$)— is attached to L;
R$^{2c}$, R$^{2d}$, R$^{2e}$, and R$^{2f}$ are each independently selected from the group consisting of hydrogen and C$_{1-4}$ alkyl;
Z is selected from the group consisting of —CH$_2$— and —C(=O)—; and
R$^5$ is selected from the group consisting of hydrogen and fluoro,
with the proviso that Y is absent when B is B-2,
in a suitable organic solvent, e.g., DMF, THF, etc, and
(2) isolating the compound having Formula XXXI, and the pharmaceutically acceptable salts and solvates thereof.
Salts, hydrates, and solvates of the Compounds of the Disclosure can also be used in the methods disclosed herein.

The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry,* 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure and the heterobifunctional target protein degraders prepared from Compounds of the Disclosure, including pharmaceutically acceptable salts. As used herein, the pharmaceutical "pharmaceutically acceptable salt" refers to salts or zwitterionic forms of Compounds of the Disclosure and the heterobifunctional target protein degraders prepared from Compounds of the Disclosure. Salts of Compounds of the Disclosure and the heterobifunctional target protein degraders prepared from Compounds of the Disclosure can be prepared during the final isolation and purification of the compounds or separately by reacting the compound with an acid having a suitable cation. The pharmaceutically acceptable salts of Compounds of the Disclosure and the heterobifunctional target protein degraders prepared from Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure and the heterobifunctional target protein degraders prepared from Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure and the heterobifunctional target protein degraders prepared from Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides heterobifunctional target protein degraders for the treatment of a variety of diseases and conditions wherein degradation of the target proteins has a beneficial effect. Heterobifunctional target protein degraders typically have a binding affinity ($IC_{50}$) to the target protein of interest of less than 100 µM, e.g., less than 50 µM, less than 25 µM, and less than 5 µM, less than about 1 µM, less than about 0.5 µM, or less than about 0.1 µM. In one embodiment, the present disclosure relates to a method of treating an individual suffering from a disease or condition wherein degradation of a target protein provides a benefit comprising administering a therapeutically effective amount of a heterobifunctional target protein degrader to an individual in need thereof.

A "monovalent radical of a target protein inhibitor" is derived from the removal of a hydrogen or other suitable atom, e.g., Br, I, or group, e.g., —OH, from a parent protein inhibitor, e.g., an oncogenic protein inhibitor such as BET bromodomain inhibitor or a MDM2 inhibitor. The removal of a hydrogen atom or other suitable atom or group facilitates the linkage of the target protein inhibitor to an E3 ubiquitin ligase protein ligand to give a heterobifunctional compound having Formula IX, as defined above. In one embodiment, a hydrogen atom is removed from any suitable —$NH_2$ group of the target protein inhibitor. In another embodiment, a hydrogen atom is removed from any suitable —OH group of the target protein inhibitor. In another embodiment, a hydrogen atom is removed from any suitable —N(H)— group of the target protein inhibitor. In another embodiment, a hydrogen atom is removed from any suitable —CH₃, —CH₂—, —CH═, or —C≡CH group of the target protein inhibitor. In another embodiment, the hydrogen atom is removed from any suitable —OH group of the target protein inhibitor. In another embodiment, a Br or I atom is removed from any suitable aryl or heteroaryl group of the target protein inhibitor.

The term "target protein inhibitor" or "parent target protein inhibitor" and the like refers to a compound that disrupts, interferes with, or inhibits protein activity.

The term "oncogenic protein inhibitor" or "parent oncogenic protein inhibitor" and the like refers to a compound that disrupts, interferes with, or inhibits oncogenic protein activity.

"Oncogenic proteins" are proteins encoded by oncogenes (dysregulated or activated genes).

An "oncogene" is any gene that is a causative factor in the initiation of cancerous growth, e.g., a gene that has a potential to cause cancer. For example, transcription factors, kinases, and growth factors are oncogenic proteins because they are generically involved in signaling systems leading to cell growth, survival, differentiation, and programmed cell death (apoptosis). Other oncogenic proteins include MDM2 and BET bromodomain proteins.

A "monovalent radical of a ligand for an E3 ubiquitin ligase protein" is derived from the removal of a hydrogen or other suitable atom, e.g., Br, I, or group, e.g., —OH, from a parent E3 ubiquitin ligase protein ligand. The removal of a hydrogen atom or other suitable atom or group facilitates the linkage of the parent E3 ubiquitin ligase protein ligand to a target protein inhibitor to give a heterobifunctional compound having Formula IX, as defined above. In one embodiment, a hydrogen atom is removed from any suitable —NH₂ group of the parent E3 ubiquitin ligase protein ligand. In another embodiment, a hydrogen atom is removed from any suitable —OH group of the parent E3 ubiquitin ligase protein ligand. In another embodiment, a hydrogen atom is removed from any suitable —N(H)— group of the parent E3 ubiquitin ligase protein ligand. In another embodiment, a hydrogen atom is removed from any suitable —CH₃, —CH₂—, —CH═ group of the parent E3 ubiquitin ligase protein ligand. In another embodiment, the hydrogen atom is removed from any suitable —OH group of the the parent E3 ubiquitin ligase protein ligand. In another embodiment, a Br or I atom is removed from any suitable aryl or heteroaryl group of the parent E3 ubiquitin ligase protein ligand. Exemplary non-limiting monovalent radicals of E3 ubiquitin ligase protein ligands include:

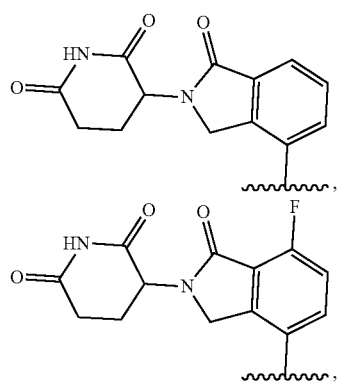

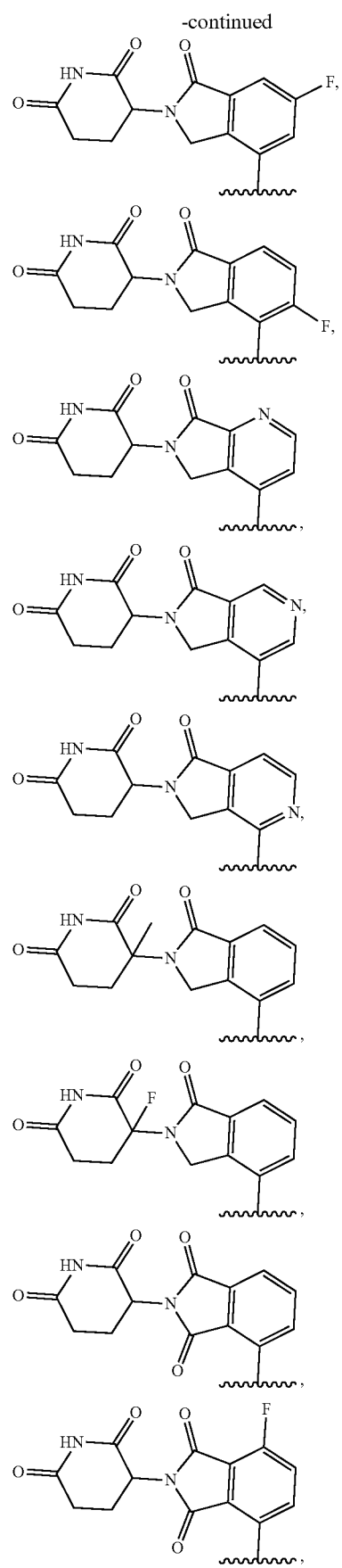

-continued

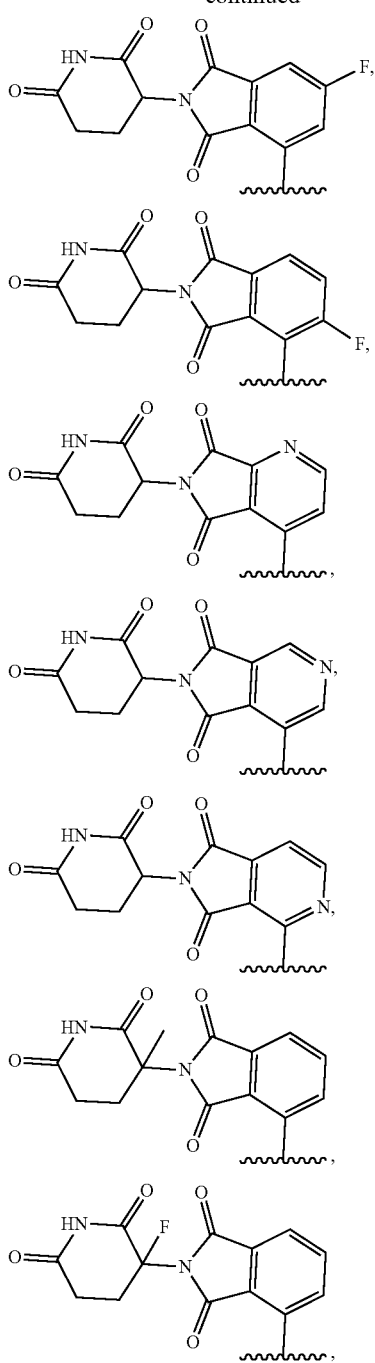

-continued

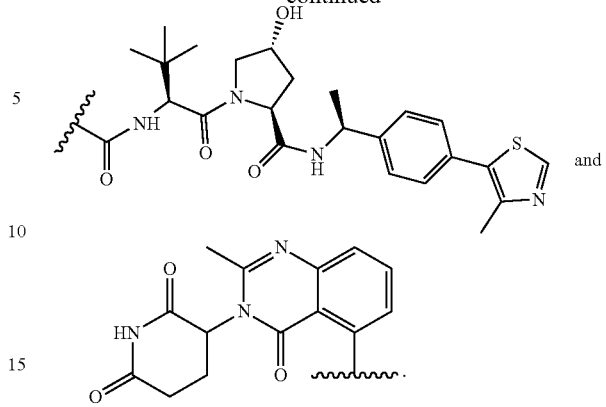

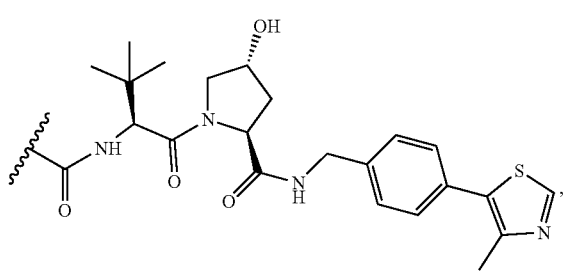

A "ligand for an E3 ubiquitin ligase protein" or "parent ligand for an E3 ubiquitin ligase protein" or "E3 ubiquitin ligase protein ligand" refers to a compound that binds, e.g., inhibits, an E3 ubiquitin ligase protein, including the von Hippel-Lindau protein (VHL). Ligands for E3 ubiquitin ligase proteins are known to those of ordinary skill in the art. Exemplary non-limiting ligands for an E3 ubiquitin ligase protein include phthalimide-based drugs such as thalidomide.

A "monovalent radical of a MDM2 inhibitor" is derived from the removal of a hydrogen or other suitable atom, e.g., Br, I, or group, e.g., —OH, from a parent MDM2 inhibitor. The removal of a hydrogen atom or other suitable atom or group facilitates the linkage of the MDM2 inhibitor to an E3 ubiquitin ligase protein ligand to give a heterobifunctional compound having Formula IX, as defined above. In one embodiment, a hydrogen atom is removed from any suitable —NH$_2$ group of the parent MDM2 inhibitor. In another embodiment, a hydrogen atom is removed from any suitable —OH group of the parent MDM2 inhibitor. In another embodiment, a hydrogen atom is removed from any suitable —N(H)— group of the parent MDM2 inhibitor. In another embodiment, a hydrogen atom is removed from any suitable —CH$_3$, —CH$_2$—, —CH=, or —C≡CH group of the parent MDM2 inhibitor. In another embodiment, the hydrogen atom is removed from any suitable —OH group of the parent MDM2 inhibitor. In another embodiment, the —OH group is removed from any suitable —C(=O)OH group of the parent MDM2 inhibitor. In another embodiment, a Br or I atom is removed from any suitable aryl or heteroaryl group of the parent MDM2 inhibitor.

A "MDM2 inhibitor" or "parent MDM2 inhibitor" refers to a compound that disrupts the p53-MDM2 interaction and/or interferes with MDM2 activity. MDM2 inhibitors are known to those of ordinary skill in the art. See, e.g., Shangary. et al., *Annual Review Of Pharmacology and Toxicology* 49: 223-241 (2009); and Weber, *Expert Opinion On Therapeutic Patents* 20: 179-191 (2010).

In one embodiment, the MDM2 inhibitor is a spiro-oxindole compound. As used herein, the term "spiro-oxindole MDM2 inhibitor" refers, for example, to a compound disclosed and/or claimed in U.S. Pat. No. 7,759,383; 7,737,174; 8,518,984; 8,680,132; or 8,629,141.

In another embodiment, the MDM2 inhibitor is a cis-imidazoline compound As used herein, the term "cis-imidazoline MDM2 inhibitor" refers, for example, to a compound disclosed and/or claimed in U.S. Pat. No. 6,617,346; 6,734,302; 7,132,421; 7,425,638; or 7,579,368; or U.S. Patent Application Publication No. 2005/0288287 or U.S. 2009/

0143364. A cis-imidazoline MDM2 inhibitor is commonly referred to as a "nutlin." In a particular embodiment, the cis-imidazoline is Nutlin-1, Nutlin-2, or Nutlin-3 (Chart 3; see Vassilev, L. T. et al., *Science* 303:844-848 (2004)).

Chart 3: Nutlin MDM2 Inhibitors

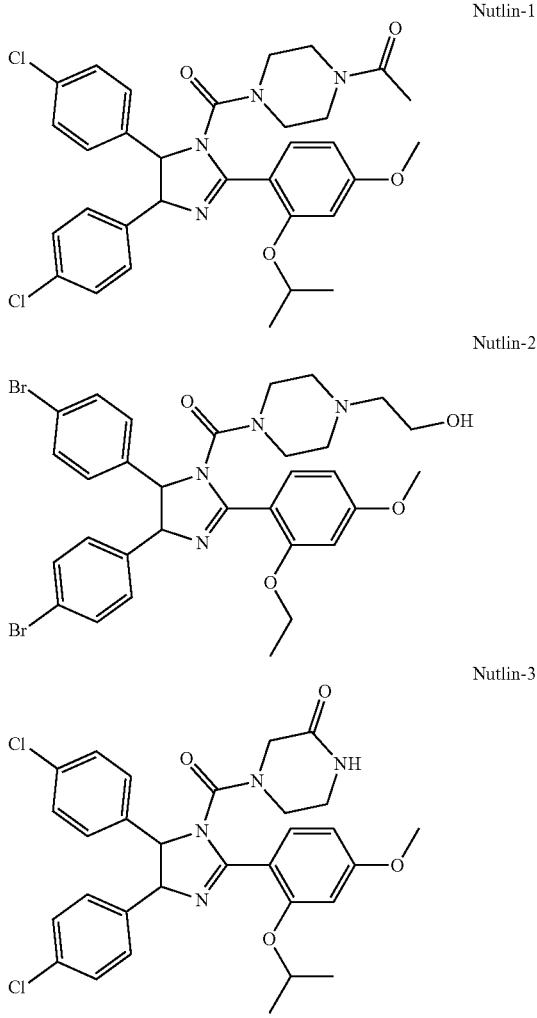

In another particular embodiment, the MDM2 inhibitor is any one of the inhibitors disclosed and/or claimed in U.S. Pat. No. 6,734,302. For example, the MDM2 inhibitor is a compound of Formula III-A:

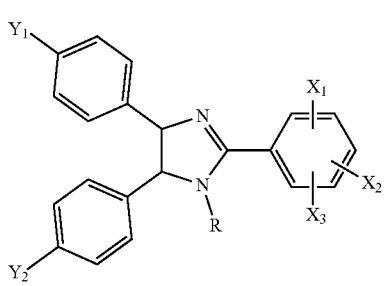

III-A or pharmaceutically acceptable salts or esters thereof, wherein:

R is —C=OR$^1$;

wherein R$^1$ is selected from $C_1$-$C_4$ alkyl, —C=CHCOOH, —NHCH$_2$CH$_2$R$^2$, —N(CH$_2$CH$_2$OH)CH$_2$CH$_2$OH, —N(CH$_3$)CH$_2$CH$_2$NHCH$_3$, —N(CH$_3$)CH$_2$CH$_2$N(CH$_3$)CH$_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, —C=O—R$^5$, —OH, lower alkyl substituted with hydroxy, lower alkyl substituted with —NH$_2$, N-lower alkyl, —SO$_2$CH$_3$, =O, —CH$_2$C=OCH$_3$, and 5- and 6-membered saturated rings containing at least one hetero atom selected from S, N and O;

wherein R$^5$ is selected from H, lower alkyl, —NH$_2$, —N-lower alkyl, lower alkyl substituted with hydroxy, and lower alkyl substituted with NH$_2$;

wherein R$^2$ is selected from —N(CH$_3$)CH$_3$, —NHCH$_2$CH$_2$NH$_2$, —NH$_2$, morpholinyl and piperazinyl;

$X_1$, $X_2$ and $X_3$ are independently selected from —OH, $C_1$-$C_2$ alkyl, $C_1$-$C_5$ alkoxy, —Cl, —Br, —F, —CH$_2$OCH$_3$, and —CH$_2$OCH$_2$CH$_3$;

or one of $X_1$, $X_2$ or $X_3$ is H and the other two are independently selected from hydroxy, lower alkyl, lower alkoxy, —Cl, —Br, —F, —CF$_3$, —CH$_2$OCH$_3$, —CH$_2$OCH$_2$CH$_3$, —OCH$_2$CH$_2$R$^3$, —OCH$_2$CF$_3$, and —OR$^4$;

or one of $X_1$, $X_2$ or $X_3$ is H and the other two taken together with the two carbon atoms and the bonds between them from the benzene ring to which they are substituted form a 5- or 6-membered saturated ring that contains at least one hetero atom selected from S, N, and O, wherein R$^3$ is selected from —F, —OCH$_3$, —N(CH$_3$)CH$_3$, unsaturated 5- and 6-membered rings containing at least one hetero atom wherein the hetero atom is selected from S, N and O;

wherein R$^4$ is a 3- to 5-membered saturated ring; and $Y_1$ and $Y_2$ are each independently selected from —Cl, —Br, —NO$_2$, —C≡N, and —C≡CH.

In another embodiment, the MDM2 inhibitor is a substituted piperidine compound. As used herein, the term "substituted piperidine MDM2 inhibitor" refers, for example, to a compound disclosed and/or claimed in U.S. Pat. No. 7,060,713 or 7,553,833.

In another embodiment, the MDM2 inhibitor is a spiroindolinone compound. As used herein, the term "spiroindolinone MDM2 inhibitor" refers, for example, to a compound disclosed and/or claimed in U.S. Pat. No. 6,916,833; 7,495,007; or 7,638,548.

In another embodiment, the MDM2 inhibitor is an oxindole compound. As used herein, the term "oxindole MDM2 inhibitor" refers, for example, to a compound disclosed and/or claimed in U.S. Pat. No. 7,576,082.

In another embodiment, the MDM2 inhibitor is a diphenyl-dihydro-imidazopyridinone compound. As used herein, the term "diphenyl-dihydro-imidazopyridinone MDM2 inhibitor" refers, for example, to a compound disclosed and/or claimed in U.S. Pat. No. 7,625,895.

In another embodiment, the MDM2 inhibitor is an imidazothiazole compound. As used herein, the term "imidazothiazole MDM2 inhibitor" refers, for example, to a compound disclosed and/or claimed in U.S. 2009/0312310.

In another embodiment, the MDM2 inhibitor is a deazaflavin compound. As used herein, the term "deazaflavin MDM2 inhibitor" refers, for example, to a compound disclosed and/or claimed in U.S. Patent Application Publication No. 2006/0211718 or 2010/0048593.

In another embodiment, the MDM2 inhibitor is a benzodiazapine compound. As used herein, the term "benzodiazapine MDM2 inhibitor" refers, for example, to a compound disclosed and/or claimed in U.S. 2005/0227932.

In another embodiment, the MDM2 inhibitor is a isoindolin-1-one compound. As used herein, the term "isoindolin-1-one MDM2 inhibitor" refers, for example, to a compound disclosed and/or claimed in U.S. 2008/0261917.

In another embodiment, the MDM2 inhibitor is a boronic acid. As used herein, the term "boronic acid MDM2 inhibitor" refers, for example, to a compound disclosed and/or claimed in U.S. Patent Application Publication No. 2009/0227542 or 2008/0171723.

In another embodiment, the MDM2 inhibitor is a peptide or polypeptide. As used herein, the term "peptidic MDM2 inhibitor" refers for example, to a compound disclosed and/or claimed in U.S. Pat. No. 7,083,983; U.S. 2006/0211757 A1; U.S. 2005/0137137; U.S. 2002/0132977; U.S. 2009/0030181; or WO 2008/106507.

In another embodiment, the MDM2 inhibitor is a compound disclosed and/or claimed in any of Shangary, S, et al., *Proc. Natl. Acad. Sci. USA.* 105:3933-3938 (2008); Vassilev, L. T., *Trends Mol. Med.* 13:23-31 (2007); Vassilev, L. T. et al., *Science* 303:844-848 (2004); Ding, K. et al., *J. Med. Chem.* 49:3432-3435 2006; Shangary, S. et al., *Clin. Cancer Res.* 14:5318-5324 (2008); Chene, P., *Molecular Cancer Research* 2:20-28 (2004); Pazgier et al., *Proc. Natl. Acad. Sci. USA.* 106:4665-4670 (2009); U.S. 2008/0280769; U.S. 008/0039472; U.S. 2009/0149493; or U.S. 2004/0171035.

In another embodiment, the MDM2 inhibitor is a compound disclosed and/or claimed in any of WO 2009/151069 A1; WO 2009/037343 A1 (U.S. application Ser. No. 12/678, 680); WO 2008/125487 A1 (U.S. Pat. No. 7,625,895); WO 2008/119741 A2 (U.S. application Ser. No. 12/593,721); and WO 2009/156735 A2.

In another particular embodiment, the MDM2 inhibitor is any one of the inhibitors disclosed and/or claimed in WO 2009/156735 A2. For example, the MDM2 inhibitor is a compound of Formulae IV-F or V-F:

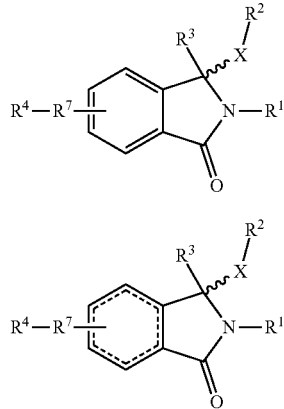

wherein in both Formulae IV-F and V-F:
X is selected from O, N or S;
R¹ is selected from hydrogen, substituted or unsubstituted alkyl, substituted or unsubstituted hydroxyalkyl, substituted or unsubstituted alkylamine, substituted or unsubstituted aryl, substituted or unsubstituted heteroaryl, substituted or unsubstituted aralkyl, and substituted or unsubstituted heteroaralkyl;

R² is selected from hydrogen, substituted or unsubstituted alkenyl, substituted or unsubstituted alkynyl, substituted or unsubstituted branched hydroxyalkyl, substituted or unsubstituted cycloalkyl having 6 ring carbon atoms or greater, substituted or unsubstituted cycloalkenyl, hydroxyalkylaralkyl, hydroxyalkylhetero aralkyl, and a carboxylic acid-containing group;

R³ is selected from hydrogen, substituted or unsubstituted alkyl, substituted or unsubstituted hydroxyalkyl, substituted or unsubstituted alkylamine, substituted or unsubstituted alkoxy, substituted or unsubstituted aryl, substituted or unsubstituted heteroaryl, substituted or unsubstituted aralkyl, and substituted or unsubstituted heteroaralkyl; and R⁴-R⁷ represents groups R⁴, R⁵, R⁶ and R⁷ which are independently selected from hydrogen, halo, hydroxy, substituted or unsubstituted alkyl, substituted or unsubstituted hydroxyalkyl, substituted or unsubstituted alkenyl, substituted or unsubstituted alkynyl, substituted or unsubstituted heteroaryl, substituted or unsubstituted heteroaralkyl, substituted or unsubstituted alkylamine, substituted or unsubstituted alkoxy, trifluoromethyl, amino, nitro, carboxyl, carbonylmethylsulfone, trifluoromethylsulfone, cyano and substituted or unsubstituted sulfonamide;

wherein R² is substituted or unsubstituted branched hydroxyalkyl, X is O or S; and wherein R² is hydrogen, at least one of R⁴-R⁷ is not hydrogen and R³ is not a benzimidazole derivative or a benzimidazoline derivative; and wherein, in the Formula V, the 6-membered ring may have 0, 1, or 2 C=C double bonds.

In a particular embodiment, the MDM2 inhibitor is any one of the inhibitors disclosed and/or claimed in WO 2009/1511069 A1. For example, the MDM2 inhibitor is a compound of Formula VI-G:

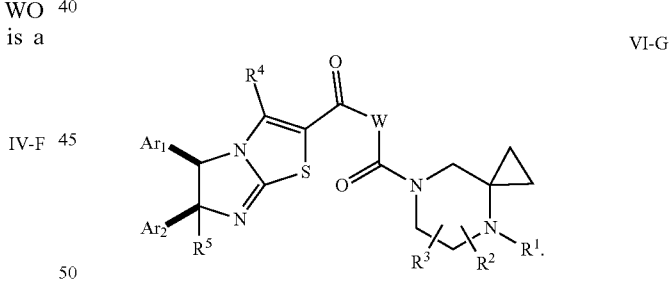

Possible examples of substituent groups include where:
Ar₁ and Ar₂ are each independently selected from the group consisting of optionally substituted aryl and optionally substituted heteroaryl;
R¹ is selected from the group consisting of hydrogen, optionally substituted alkyl, and —COR¹ᵃ;
R¹ᵃ is selected from the group consisting of hydrogen, optionally substituted alkyl, optionally substituted cycloalkyl, and optionally substituted aryl;
R² and R³ are each independently selected from the group consisting of hydrogen and optionally substituted alkyl; or
R² and R³ taken together form a 3- to 6-membered optionally substituted cycloalkyl or heterocyclo;
R⁴ and R⁵ are each independently selected from the group consisting of hydrogen, optionally substituted alkyl, optionally substituted cycloalkyl, and optionally substituted aryl;

W is selected from the group consisting of:

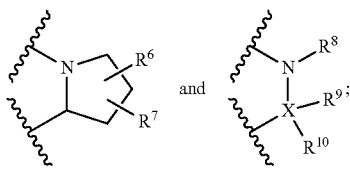

wherein:
$R^6$ and $R^7$ are each independently selected from the group consisting of hydrogen, hydroxy and optionally substituted alkyl; or $R^6$ and $R^7$ taken together form a 3- to 6-membered optionally substituted cycloalkyl or an oxo, i.e., C=O;

$R^8$ is selected from the group consisting of hydrogen or optionally substituted alkyl;

$R^9$ and $R^{10}$ are each independently selected from the group consisting of hydrogen or optionally substituted alkyl; or $R^9$ and $R^{10}$ taken together form a 3- to 6-membered optionally substituted cycloalkyl or heterocyclo; and X is a carbon atom.

In a particular embodiment, MDM2 inhibitor is a compound of Formula VI-G wherein possible examples of substituent groups include where:

$Ar_1$ and $Ar_2$ are each independently selected from the group consisting of optionally substituted phenyl and optionally substituted pyridyl;

$R^1$ is selected from the group consisting of hydrogen, optionally substituted $C_1$-$C_6$ alkyl, and —COR$^a$;

$R^{1a}$ is selected from the group consisting of hydrogen and optionally substituted $C_1$-$C_6$ alkyl;

$R^2$ and $R^3$ are each independently selected from the group consisting of hydrogen and optionally substituted $C_1$-$C_6$ alkyl; or $R^2$ and $R^3$ taken together form a 3- to 6-membered optionally substituted cycloalkyl;

$R^4$ and $R^5$ are each independently selected from the group consisting of hydrogen and optionally substituted $C_1$-$C_6$ alkyl;

W is:

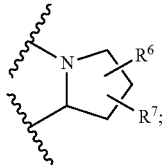

wherein:
$R^6$ and $R^7$ are each independently selected from the group consisting of hydrogen and optionally substituted $C_1$-$C_6$ alkyl; or $R^6$ and $R^7$ taken together form a 3- to 6-membered optionally substituted cycloalkyl or an oxo.

A "monovalent radical of a BET bromodomain protein inhibitor" is derived from the removal of a hydrogen or other suitable atom, e.g., Br, I, or group, e.g., —OH, from a parent BET bromodomain inhibitor. The removal of a hydrogen atom or other suitable atom or group facilitates the linkage of the BET bromodomain inhibitor to an E3 ubiquitin ligase protein ligand to give a heterobifunctional compound having Formula IX, as defined above. In one embodiment, a hydrogen atom is removed from any suitable —NH$_2$ group of the parent BET bromodomain inhibitor. In another embodiment, a hydrogen atom is removed from any suitable —OH group of the parent BET bromodomain inhibitor. In another embodiment, a hydrogen atom is removed from any suitable —N(H)— group of the parent BET bromodomain inhibitor. In another embodiment, a hydrogen atom is removed from any suitable —CH$_3$, —CH$_2$—, —CH=, or —C≡CH group of the parent BET bromodomain inhibitor. In another embodiment, the hydrogen atom is removed from any suitable —OH group of the parent BET bromodomain inhibitor. In another embodiment, the —OH group is removed from any suitable —C(=O)OH group of the parent BET bromodomain inhibitor. In another embodiment, a Br or I atom is removed from any suitable aryl or heteroaryl group of the parent BET bromodomain inhibitor.

A "BET bromodomain inhibitor" or "parent BET bromodomain inhibitor" refers to a compound that interferes with, e.g., inhibits, BET bromodomain activity. BET bromodomain inhibitors are known to those of ordinary skill in the art. For example, BET bromodomain protein inhibitors are disclosed in the following U.S. patents: U.S. Pat. Nos. 8,044,042, 8,476,260, 8,114,995, 8,557,984, and 8,580,957; the following U.S. patent application publications: US 20120059002, US 20120208800, US 2012202799, US 2012252781, US 20130252331, US 20140011862, US 20130184264, US 2013079335, US 20140011862, US 20140005169, US 20130331382, US 20130281450, US 20130281399, US 20120157428, US 20100286127, US 20140256706, and US 2015/0246923; and the following international applications: WO 1998011111, WO 2006129623, WO 2008092231, WO 2009084693, WO 2009158404, WO 2010123975, WO 2011054843, WO 2011054844, WO 2011054845, WO 2011054846, WO 2011054848, WO 2011143651, WO 2011143660, WO 2011143669, WO 2011161031, WO 2012075383, WO 2012116170, WO 2012151512, WO 2012174487, WO 2013024104, WO 2013027168, WO 2013030150, WO 2013033268, WO 2013097601, and WO 2014164596. BET bromodomain inhibitors are also disclosed in Delmore et al., *Cell* 146:904-917 (2011) and Seal et al., *Bioorg. Med. Chem. Lett.* 22:2968-2972 (2012).

The term "leaving group" or "LG" refers to an atom or group of atoms that becomes detached from an atom or group of atoms in what is considered to be the residual or main part of the molecule in a specified reaction. Non-limiting exemplary leaving groups include —Cl, —I, —Br, —OTf, —OMs, and —OTs.

The terms "condensing" or "reacting" and the like refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. Reacting can take place in the presence or absence of solvent.

The term "about," as used herein, includes the recited number ±10%. Thus, "about 10" means 9 to 11.

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-20}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "heteroalkyl" as used by itself or part of another group refers to unsubstituted straight- or branched-chain aliphatic hydrocarbons containing from three to thirty chain atoms, i.e., 3- to 30-membered heteroalkyl, or the number of chain atoms designated, wherein at least one —CH$_2$— is replaced with at least one —O—, —N(H)—, or —S—. The —O—, N(H)—, or —S— can independently be placed at any interior position of the aliphatic hydrocarbon chain so long as each —O—, N(H)—, or —S— group is separated by at least two —CH$_2$— groups. In one embodiment, one —CH$_2$— group is replaced with one —O— group. In another embodiment, two —CH$_2$— groups are replaced with two —O— groups. In another embodiment, three —CH$_2$— groups are replaced with three —O— groups. In another embodiment, four —CH$_2$— groups are replaced with four —O— groups. Non-limiting exemplary heteroalkyl groups include:
—CH$_2$OCH$_3$;
—CH$_2$OCH$_2$CH$_2$CH$_3$;
—CH$_2$CH$_2$CH$_2$OCH$_3$;
—CH$_2$OCH$_2$CH$_2$OCH$_3$; and
—CH$_2$OCH$_2$CH$_2$OCH$_2$CH$_2$OCH$_3$.

In the present disclosure, the term "alkylenyl" as used herein by itself or part of another group refers to a divalent form of an alkyl group. In one embodiment, the alkylenyl is a divalent form of a $C_{1-12}$ alkyl. In one embodiment, the alkylenyl is a divalent form of a $C_{1-10}$ alkyl. In one embodiment, the alkylenyl is a divalent form of a $C_{1-8}$ alkyl. In one embodiment, the alkylenyl is a divalent form of a $C_{1-6}$ alkyl. In another embodiment, the alkylenyl is a divalent form of a $C_{1-4}$ alkyl. Non-limiting exemplary alkylenyl groups include:
—CH$_2$—,
—CH$_2$CH$_2$—,
—CH$_2$CH$_2$CH$_2$—,
—CH$_2$(CH$_2$)$_2$CH$_2$—,
—CH(CH$_2$)$_3$CH$_2$—,
—CH$_2$(CH$_2$)$_4$CH$_2$—,
—CH$_2$(CH$_2$)$_5$CH$_2$—,
—CH$_2$CH(CH$_3$)CH$_2$—, and
—CH$_2$C(CH$_3$)$_2$CH$_2$—.

In the present disclosure, the term "heteroalkylenyl" as used herein by itself or part of another group refers to a divalent form of a heteroalkyl group. In one embodiment, the heteroalkylenyl is a divalent form of a 3- to 12-membered heteroalkyl. In another embodiment, the heteroalkylenyl is a divalent form of a 3- to 10-membered heteroalkyl. In another embodiment, the heteroalkylenyl is a divalent form of a 3- to 8-membered heteroalkyl. In another embodiment, the heteroalkylenyl is a divalent form of a 3- to 6-membered heteroalkyl. In another embodiment, the heteroalkylenyl is a divalent form of a 3- to 4-membered heteroalkyl. In another embodiment, the heteroalkylenyl is a radical of the formula: —(CH$_2$)$_o$O—(CH$_2$CH$_2$O)$_p$—(CH$_2$)$_q$—, wherein o is 2 or 3; p is 0, 1, 2, 3, 4, 5, 6, or 7; and q is 2 or 3. In another embodiment, the heteroalkylenyl is a radical of the formula: —(CH$_2$)$_r$O—(CH$_2$)$_s$—O(CH$_2$)$_t$—, wherein r is 2, 3, or 4; s is 3, 4, or 5; and t is 2 or 3. Non-limiting exemplary heteroalkylenyl groups include:
—CH$_2$OCH$_2$—; —CH$_2$CH$_2$OCH$_2$CH$_2$—;
—CH$_2$OCH$_2$CH$_2$CH$_2$—; —CH$_2$CH$_2$OCH$_2$CH$_2$CH$_2$—;
—CH$_2$CH$_2$OCH$_2$CH$_2$OCH$_2$CH$_2$—; and
—CH$_2$CH$_2$OCH$_2$CH$_2$OCH$_2$CH$_2$O—.

In the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$SO$_2$CH$_3$CH$_2$CH$_2$CO$_2$H, —CH$_2$CH$_2$SO$_2$CH$_3$, —CH$_2$CH$_2$COPh, and —CH$_2$C$_6$H$_{11}$.

In the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

In the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

In the present disclosure, the term "cycloalkylenyl" as used herein by itself or part of another group refers to a divalent form of an optionally substituted cycloalkyl group. Non-limiting examples of a 5 cycloalkylenyl include:

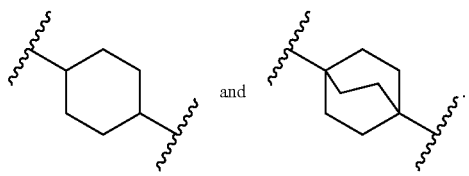 [SMILES: *C1CCC(*)CC1 ; *C12CCC(*)(CC1)CC2]

In the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

In the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

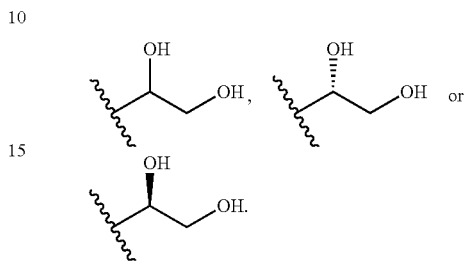

In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

In the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

In the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

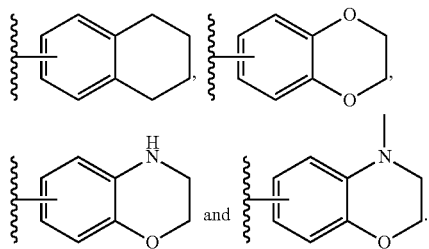

In the present disclosure, the term "phenylenyl" as used herein by itself or part of another group refers to a divalent form of an optionally substituted phenyl group. Non-limiting examples include:

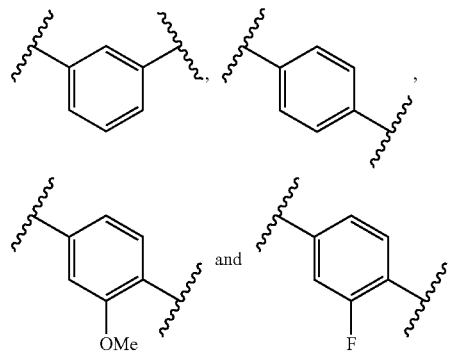

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is PhCH$_2$O—.

In the present disclosure, the term "heteroaryl" or "heteroaromatic" refers to monocyclic and bicyclic aromatic ring systems having 5 to 14 ring atoms (i.e., $C_5$-$C_{14}$ heteroaryl), wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. In one embodiment, the optionally substituted heteroaryl has one substituent. Any available carbon or nitrogen atom can be substituted. Non-limiting exemplary optionally substituted 5-membered heteroaryl groups include, but are not limited to:

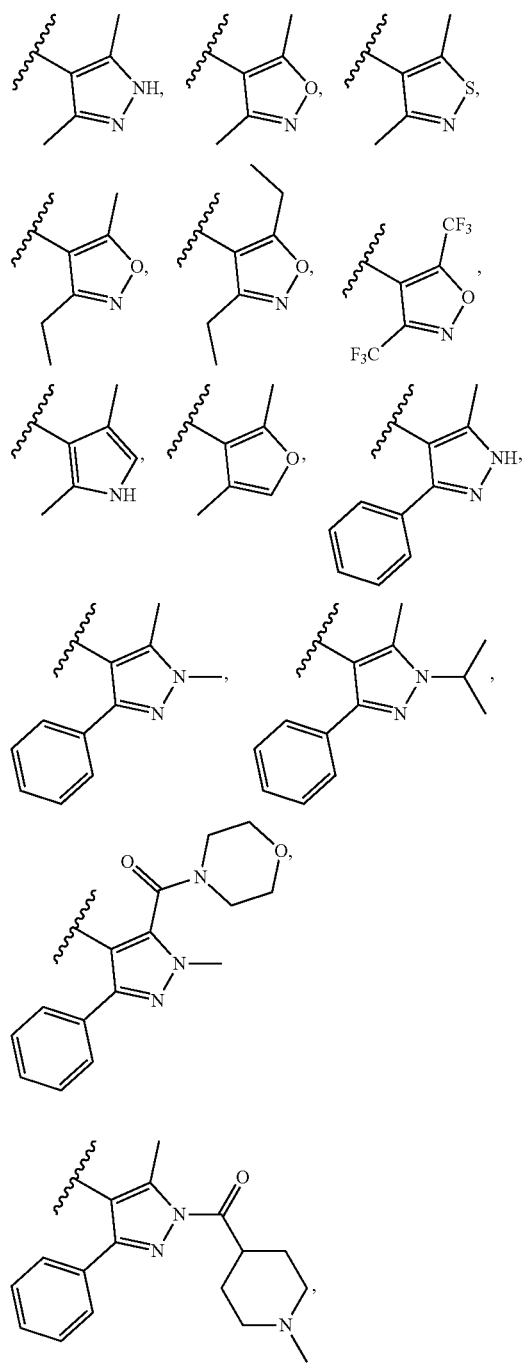

-continued

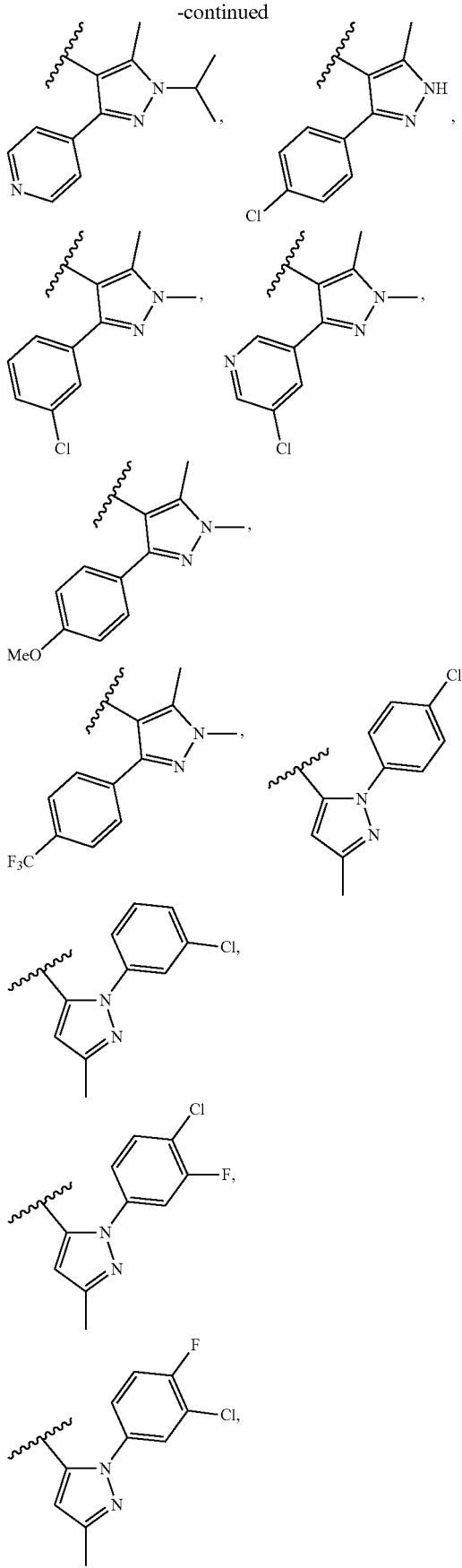

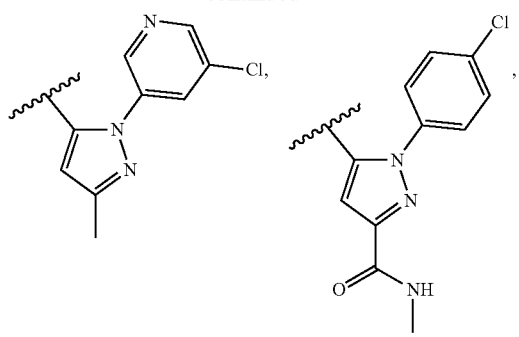
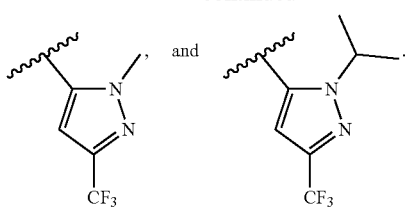
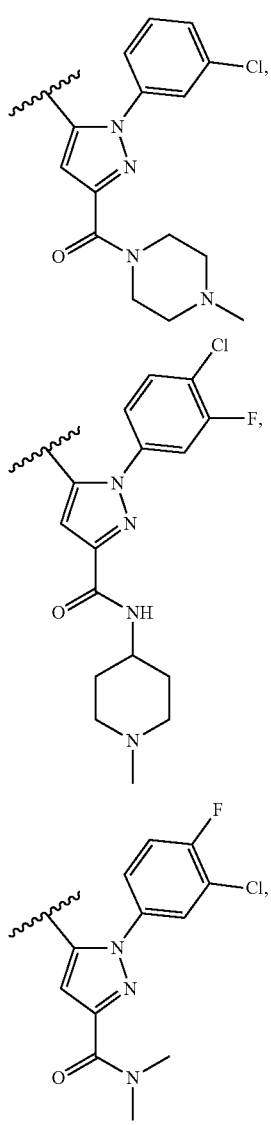
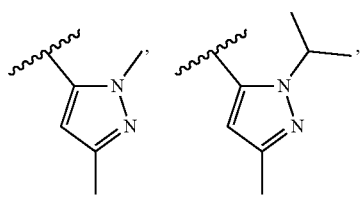

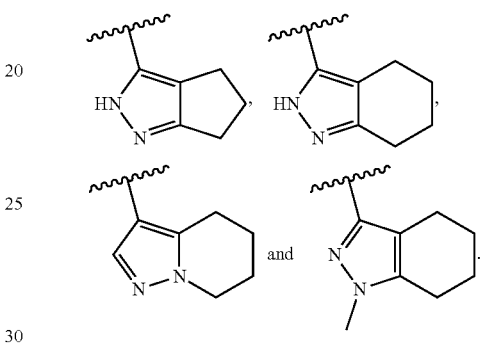

The term optionally substituted heteroaryl is also meant to include groups having fused optionally substituted cycloalkyl and fused optionally substituted heterocyclo rings. Non-limiting examples include:

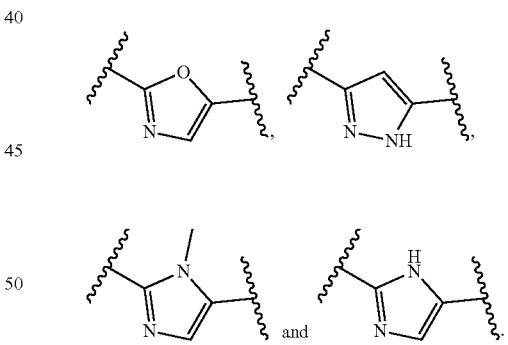

In the present disclosure, the term "heteroarylenyl" as used herein by itself or part of another group refers to a divalent form of an optionally substituted heteroaryl group. In one embodiment, the heteroarylenyl is a 5-membered heteroarylenyl. Non-limiting examples of a 5-membered heteroarylenyl include:

In one embodiment, the heteroarylenyl is a 6-membered heteroarylenyl. Non-limiting examples of a 6-membered heteroarylenyl include:

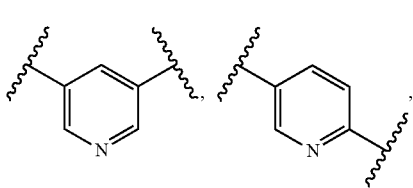

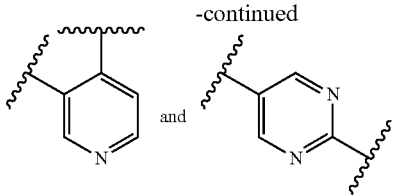
and

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

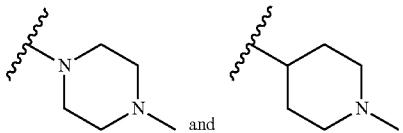
and

In the present disclosure, the term "amino" as used by itself or as part of another group refers to —NR$^{10a}$R$^{10b}$, wherein R$^{10a}$ and R$^{10b}$ are each independently hydrogen, alkyl, hydroxyalkyl, optionally substituted cycloalkyl, optionally substituted aryl, optionally substituted heterocyclo, or optionally substituted heteroaryl, or R$^{10a}$ and R$^{10b}$ are taken together to form a 3- to 8-membered optionally substituted heterocyclo. Non-limiting exemplary amino groups include —NH$_2$ and —N(H)(CH$_3$).

In the present disclosure, the term "(amino)alkyl" as used by itself or as part of another group refers to an alkyl group substituted with an amino group. Non-limiting exemplary amino alkyl groups include —CH$_2$CH$_2$NH$_2$, and —CH$_2$CH$_2$N(H)CH$_3$, —CH$_2$CH$_2$N(CH$_3$)$_2$, and —CH$_2$N(H) cyclopropyl.

In the present disclosure, the term "carboxamido" as used by itself or as part of another group refers to a radical of formula —C(=O)NR$^{9a}$R$^{9b}$, wherein R$^{9a}$ and R$^{9b}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{9a}$ and R$^{9b}$ taken together with the nitrogen to which they are attached form a 3- to 8-membered optionally substituted heterocyclo group. In one embodiment, R$^{9a}$ and R$^{9b}$ are each independently hydrogen or optionally substituted alkyl. In one embodiment, R$^{9a}$ and R$^{9b}$ are taken together to taken together with the nitrogen to which they are attached form a 3- to 8-membered optionally substituted heterocyclo group. Non-limiting exemplary carboxamido groups include, but are not limited to, —CONH$_2$, —CON(H)CH$_3$, —CON(CH$_3$)$_2$, —CON(H)Ph,

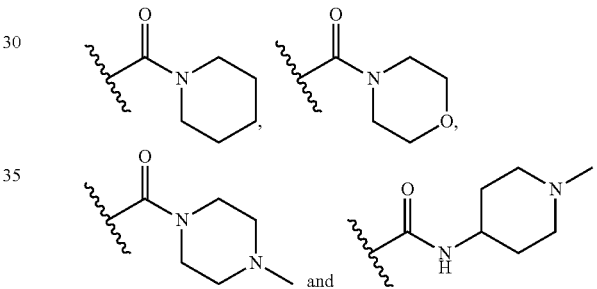
and

In the present disclosure, the term "sulfonamido" as used by itself or as part of another group refers to a radical of the formula —SO$_2$NR$^{8a}$R$^{8b}$, wherein R$^{8a}$ and R$^{8b}$ are each independently hydrogen, optionally substituted alkyl, or optionally substituted aryl, or R$^{8a}$ and R$^{8b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

In the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

In the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

In the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the terms "(heterocyclo)alkyl" as used by itself or part of another group refers to an alkyl group substituted with an optionally substituted heterocyclo group. In one embodiment, the (heterocyclo)alkyl is a C$_{1-4}$ alkyl substituted with one optionally substituted heterocyclo group. Non-limiting exemplary (heterocyclo)alkyl groups include:

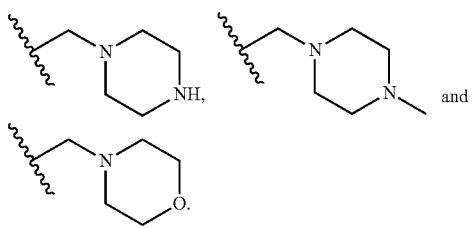

The present disclosure encompasses any of the Compounds of the Disclosure being isotopically-labelled, i.e., radiolabeled, by having one or more atoms replaced by an atom having a different atomic mass or mass number. Examples of isotopes that can be incorporated into Compounds of the Disclosure include isotopes of hydrogen, carbon, nitrogen, sulfur, oxygen, fluorine, and chlorine, such as $^2$H (or deuterium (D)), $^3$H, $^{11}$C, $^{13}$C, $^{14}$C, $^{15}$N, $^{18}$O, $^{17}$O, $^{35}$S, $^{18}$F, and $^{36}$Cl, e.g., $^2$H, $^3$H, and $^{13}$C. In one embodiment, a portion of the atoms at a position within a Compound of the Disclosure are replaced, i.e., the Compound of the Disclosure is enriched at a position with an atom having a different atomic mass or mass number. In one embodiment, at least about 1% of the atoms are replaced with an atom having a different atomic mass or mass number. In another embodiment, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% of the atoms are replaced with an atom having a different atomic mass or mass number. For example, when B of Formula I, is B-1a, B-1b, B-1c, or B-1d, and R$^5$ is hydrogen, the hydrogen at R$^5$ may be replaced entirely or partially with deuterium, e.g., at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the hydrogen atoms at R$^5$ are deuterium atoms. Isotopically-labeled Compounds of the Disclosure can be prepared by methods known in the art.

General Synthesis of Compounds

Compounds of the Disclosure are prepared using methods known to those skilled in the art in view of this disclosure, or by the illustrative methods shown in the General Schemes below. Suitable protecting can be employed in the synthesis, if needed. See Wuts, P. G. M.; Greene, T. W., "Greene's Protective Groups in Organic Synthesis", 4th Ed., J. Wiley & Sons, N Y, 2007.

Heterobifunctional protein degraders of the disclosure are prepared using methods known to those skilled in the art in view of this disclosure, or by the illustrative methods shown in General Scheme 1, below.

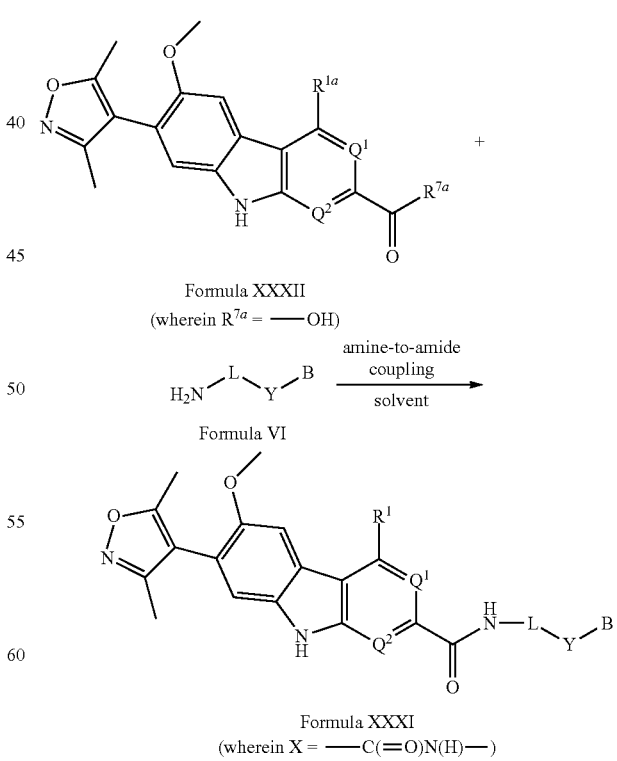

In General Scheme 1, a compound having Formula XXXII, wherein R$^{7a}$ is —OH, is reacted with a compound having Formula VI in an organic solvent to give a compound having Formula XXXI, wherein X is —C(=O)N(H)—. Compounds having Formula XXXII may be prepared as described in US 2014/0256706 and US 2015/0246923. Compounds having Formula VI may be prepared using methods known in the art and/or as illustrated in the Examples below. Suitable amine-to-amide coupling reagents and conditions e.g., HATU/base, HBTU/base, or EDCI/HOBt/base, are well known in the art. See Montalbetti and Falque, Tetrahedron 61:10827-10852 (2005).

EXAMPLES

Example 1

Synthesis of (3'R,4'S,5'R)-6"-chloro-4'-(3-chloro-2-fluorophenyl)-N-(4-((4-(2-((2-(2,6-dioxopiperidin-3-yl)-1,3-dioxoisoindolin-4-yl)oxy)acetamido)butyl)carbamoyl)phenyl)-2"-oxodispiro[cyclohexane-1,2'-pyrrolidine-3',3"-indoline]-5'-carboxamide Step 1: Synthesis of S1

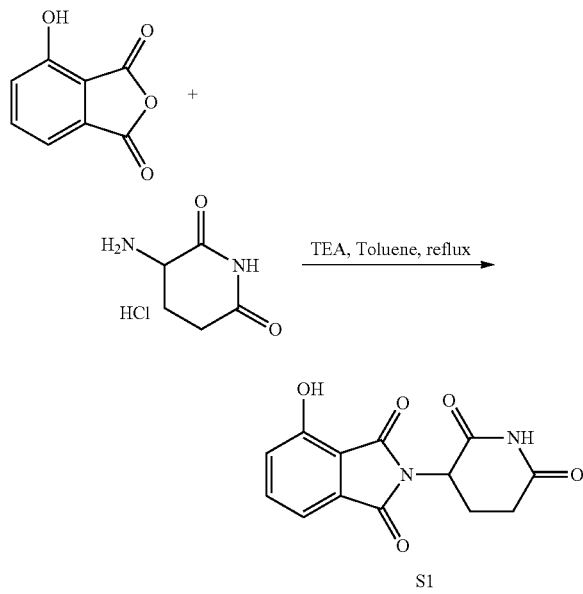

To a round-bottom flask, 3-hydroxyphthalic anhydride (1 g, 6.09 mmol) and 3-aminoperidine-2,6-dione hydrochloride (1.0 g, 6.09 mmol) were mixed in 50 mL of toluene. Triethyl amine (0.93 mL, 6.7 mmol) was added. The resulting reaction mixture was heated to reflux for 12 h with Dean-Stark Trap equipment. After cooling to ambient temperature, evaporation of most of the solvent to give a crude product, which was purified by flash column chromatography with DCM:EA to get the desired product as a slightly yellow solid S1 (1.5 g, 90% yield). $^1$H NMR (400 MHz, DMSO-d$^6$) δ (ppm) 11.16 (s, 1H), 11.08 (s, 1H), 7.65 (t, J=7.6 Hz, 1H), 7.32 (d, J=7.2 Hz, 1H), 7.25 (d, J=8.4 Hz, 1H), 5.07 (dd, J=12.8 Hz, J=5.2 Hz, 1H), 2.93-2.84 (m, 1H), 2.61-2.46 (m, 1H), 2.05-2.01 (m, 1H).

Step 1: Synthesis of S2

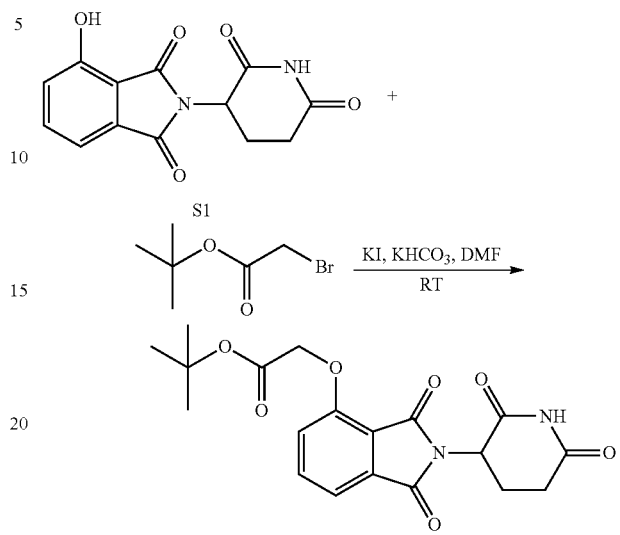

To a round-bottom flask, S1 (1.5 g, 5.5 mmol) was dissolved in 10 mL of DMF. To the stirred solution, KI (91 mg, 0.55 mmol) and KHCO$_3$ (826 mg, 8.25 mmol) were added. Then tert-butyl bromoacetate (0.98 mL, 6.6 mmol) was dropwised. The resulting mixture was stirred at room temperature for 12 h. After normal workup with EtOAc and saturated brine, the combined organic layer was dried over Na$_2$SO$_4$. After filtration and evaporation, the residue was purified by flash column chromatography with DCM:EA to get the desired product S2 as a white solid (1.7 g, 80% yield). $^1$H NMR (400 MHz, DMSO-d$^6$) δ (ppm) 11.13 (s, 1H), 7.80 (t, J=8.0 Hz, 1H), 7.48 (d, J=7.2 Hz, 1H), 7.38 (d, J=8.4 Hz, 1H), 5.13 (dd, J=12.8 Hz, J=5.2 Hz, 1H), 4.97 (s, 2H), 2.97-2.85 (m, 1H), 2.65-2.52 (m, 2H), 2.14-2.03 (m, 1H), 1.43 (s, 9H); $^{13}$C NMR (100 MHz, DMSO-d$^6$) δ (ppm) 173.2, 170.3, 167.5, 167.2, 165.6, 155.5, 137.2, 133.7, 120.4, 116.9, 116.3, 66.0, 60.2, 49.3, 31.4, 28.1, 22.5.

Step 3: Synthesis of S3

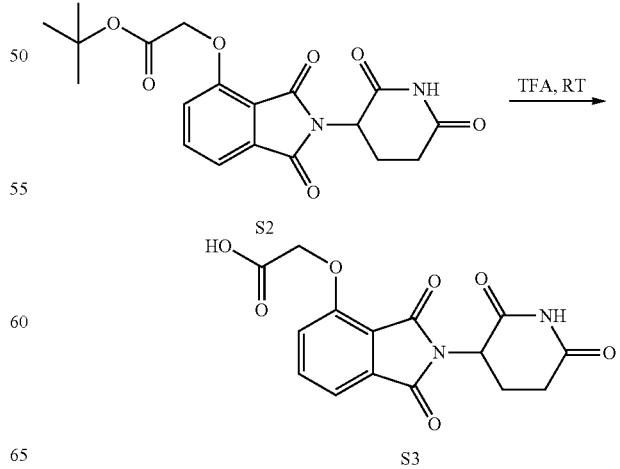

To a round-bottom flask, S2 (1.7 g, 4.4 mmol) was dissolved in 8.0 mL of TFA. The reaction mixture was stirred at room temperature for 2 h. After evaporation of the solvent, the residue was used in the following steps without further purification. ESI-MS calculated for $C_{15}H_{13}N_2O_7$ [M+H]$^+$=333.07, obtained: 333.17. $^1$H NMR (400 MHz, DMSO-d$^6$) δ (ppm) 13.16 (s, 1H), 11.11 (s, 1H), 7.80 (t, J=8.0 Hz, 1H), 7.48 (d, J=7.2 Hz, 1H), 7.40 (d, J=8.8 Hz, 1H), 5.11 (dd, J=12.8 Hz, J=5.2 Hz, 1H), 4.99 (s, 2H), 2.95-2.86 (m, 1H), 2.63-2.48 (m, 2H), 2.08-2.03 (m, 1H).

Step 4: Synthesis of S4

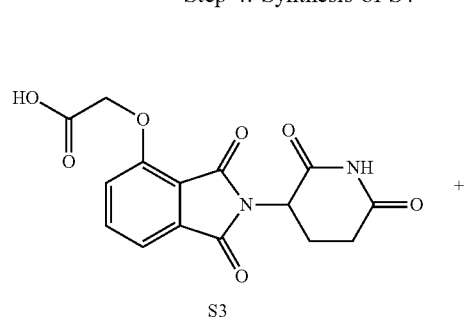

S3

+

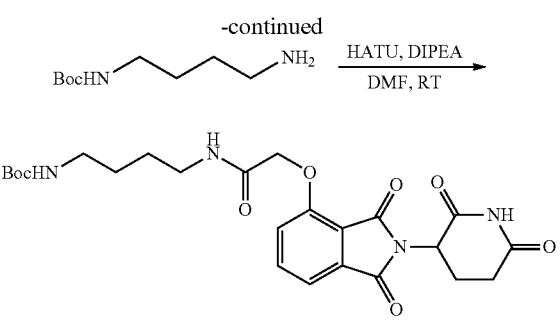

S4

To a round-bottom flask, S3 (99.7 mg, 0.3 mmol) was dissolved in 2 mL of anhydrous DMF. N-Boc-1,4-butanediamine (68 mg, 0.36 mmol), HATU (137 mg, 0.36 mmol) and DIPEA (157 μL, 0.9 mmol) were added sequentially. The reaction mixture was stirred at room temperature for 2 h, and then purified by HPLC to get the desired compound S4 as a slightly yellow solid (128 mg, 85% yield).

Step 5: Synthesis of S5

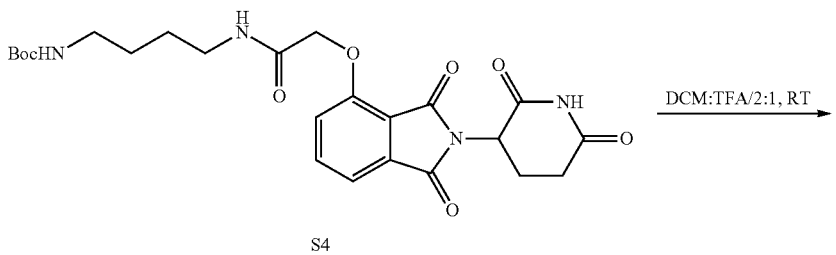

S4

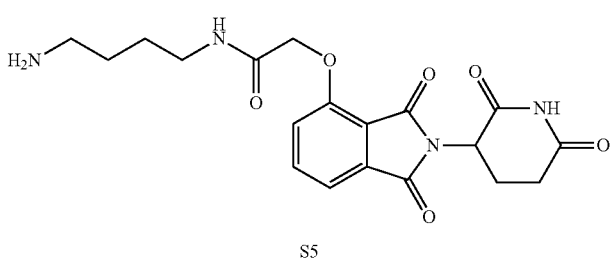

S5

To a round-bottom flask, S4 (15.1 mg, 0.03 mmol) was dissolved in 3 mL of DCM and TFA (2:1). After stirring for 1 h, the solvent was evaporated to give the crude product S5, which was used in the next step without further purification. ESI-MS calculated for $C_{19}H_{23}N_4O_6$ $[M+H]^+$=403.16, obtained: 403.17.

Step 6: Synthesis of (3'R,4'S,5'R)-6"-chloro-4'-(3-chloro-2-fluorophenyl)-N-(4-((4-(2-((2-(2,6-dioxopiperidin-3-yl)-1,3-dioxoisoindolin-4-yl)oxy)acetamido)butyl)carbamoyl)phenyl)-2"-oxodispiro[cyclohexane-1,2'-pyrrolidine-3',3"-indoline]-5'-carboxamide HATU (13.3 mg, 0.035 mmol) and N,N-diisopropylethylamine (0.026 mL, 0.15 mmol) were added to a solution of Cpd. A (20 mg, 0.029 mmol) in 0.5 mL DMF and stirred. After 10 minutes, S5 (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in $H_2O$, frozen and lyophilized to give Compound A (TFA salt) as a white powder.

LC-MS(ESI) m/z $(M+H)^+$: 966.28, 5.13 min; calcd: 966.28; >98% purity. $^1$H NMR (400 MHz, MeOD) δ 7.80-

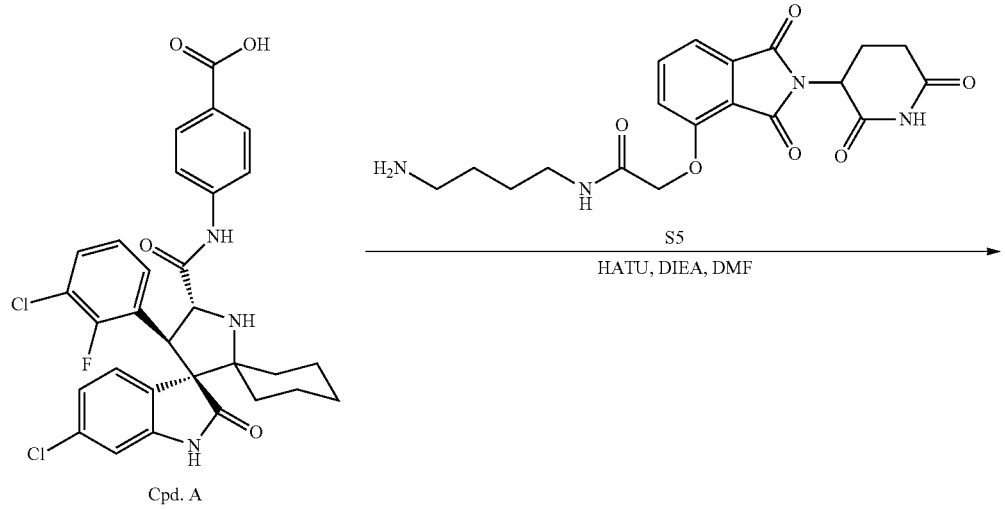

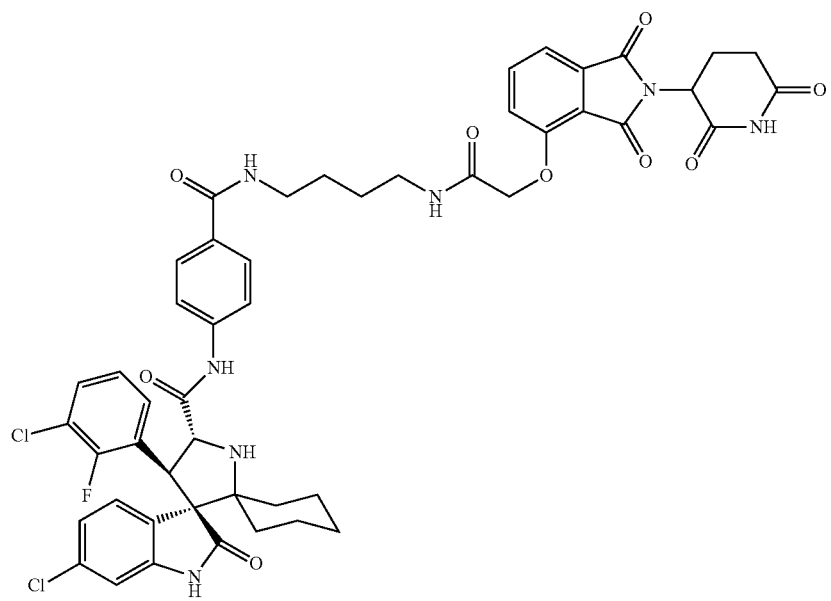

7.68 (m, 4H), 7.62-7.56 (m, 2H), 7.54 (dd, J=8.3, 2.5 Hz, 1H), 7.48 (dd, J=7.2, 1.4 Hz, 1H), 7.43-7.32 (m, 2H), 7.18 (t, J=8.1 Hz, 1H), 7.11 (dd, J=8.2, 1.9 Hz, 1H), 6.79 (d, J=1.9 Hz, 1H), 5.31 (d, J=10.8 Hz, 1H), 5.08 (dd, J=12.6, 5.2 Hz, 1H), 4.97 (d, J=10.8 Hz, 1H), 4.75 (s, 2H), 3.36 (dd, J=4.6, 3.0 Hz, 4H), 2.92-2.64 (m, 4H), 2.25-2.13 (m, 1H), 2.13-2.04 (m, 1H), 2.04-1.84 (m, 3H), 1.78 (d, J=11.5 Hz, 2H), 1.72-1.48 (m, 5H), 1.31-1.16 (m, 2H).

Example 2

Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide Step 1: Synthesis of S7

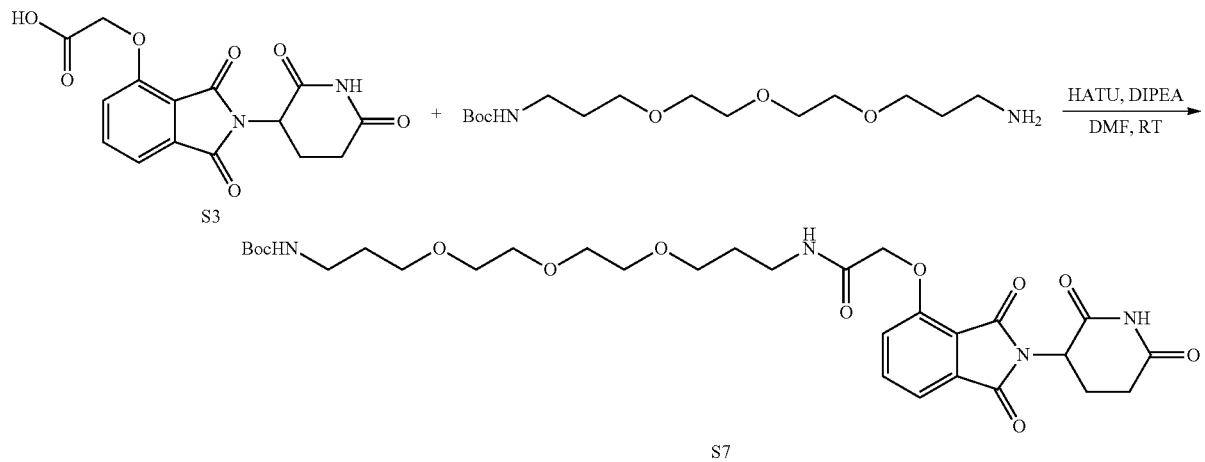

To a round-bottom flask, S3 (99.7 mg, 0.3 mmol) was dissolved in 2 mL of anhydrous DMF. tert-butyl (3-(2-(2-(3-aminopropoxy)ethoxy)ethoxy)propyl)carbamate (68 mg, 0.36 mmol), HATU (137 mg, 0.36 mmol) and DIPEA (157 μL, 0.9 mmol) were added sequentially. The reaction mixture was stirred at room temperature for 2 h, and then purified by HPLC to get the desired compound S7 as a slightly yellow solid (128 mg, 85% yield).

Step 2: Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide

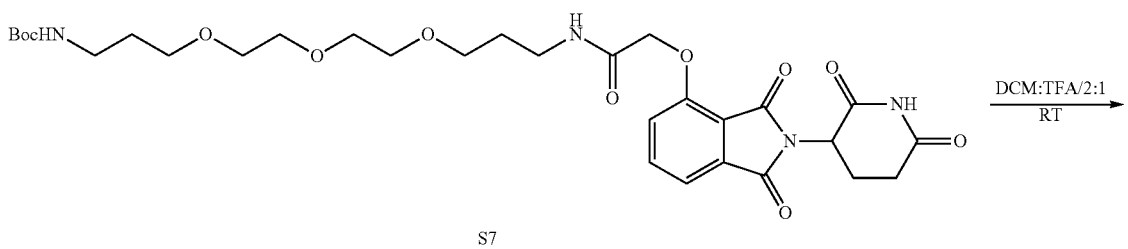

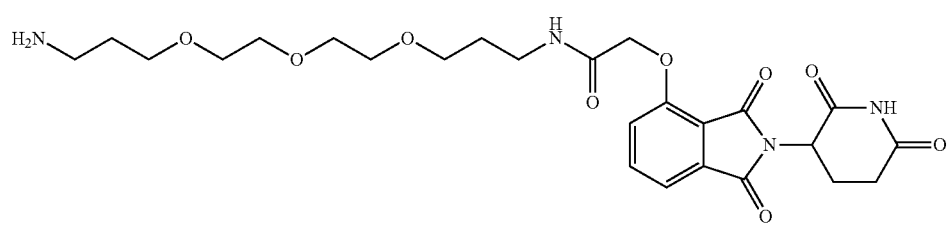

To a round-bottom flask, S7 (15 mg) was dissolved in 3 mL of DCM and TFA (2:1). After stirring for 1 h, the solvent was evaporated to give the crude product N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide. [M+H]⁺=535.24, obtained: 535.14.

Example 3

Synthesis of N-(3-(2-(2-(3-aminopropoxy)ethoxy)ethoxy)propyl)-2-((2-(2,6-dioxopiperidin-3-yl)-1,3-dioxoisoindolin-4-yl)amino)acetamide Step 1: Synthesis of S16

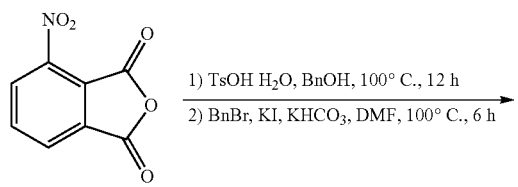

To a round-bottom flask, 3-nitrophthalic anhydride (5.79 g, 30 mmol) and p-toluenesulfonic acid monohydrate (571 mg, 3 mmol) were mixed in 20 mL of benzyl alcohol. The mixture was heat to 100° C. to stir overnight. After cooling to room temperature, benzyl bromide (7.1 mL, 45 mmol), KI (498 mg, 3 mmol), KHCO₃ (9.0 g, 90 mmol) and DMF (25 mL) were added. The mixture was heated to 100° C. for 6 h. After the reaction was cooled to room temperature, the solvent was evaporated as much as possible and was poured into larger amount of water. The solution was extracted with ethyl acetate. The combined organic layer was washed with brine and dried over anhydrous Na₂SO₄. After filtration and evaporation, the crude residue was purified by flash column chromatography with hexane/ethyl acetate to give S16 as a slightly yellow solid (9.4 g, 80% yield).

Step 2: Synthesis of S17

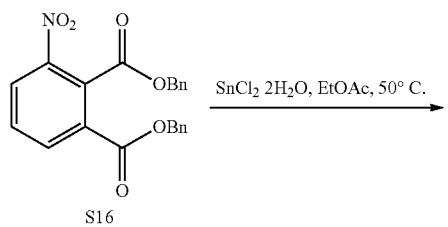

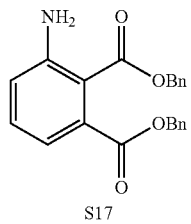

To a round-bottom flask, compound S16 (9.4 g, 24 mmol) was dissolved in 100 mL of ethyl acetate. Then Tin (II) chloride dehydrate (11.3 g, 50 mmol) was added portionwisely to the reaction mixture. The resulting reaction mixture was heated to 50° C. to stir overnight. Aqueous NaOH and NaHCO₃ solution were added to the reaction mixture to quench the reaction. The reaction mixture was filtered through celite and washed with ethyl acetate. The filtrate was extracted with ethyl acetate and brine. The combined organic layer was dried over anhydrous Na₂SO₄. After filtration and evaporation, the crude residue was purified by flash column chromatography with hexane/ethyl acetate to give compound S17 as a slightly yellow solid (7.8 g, 90% yield).

Step 3: Synthesis of S18

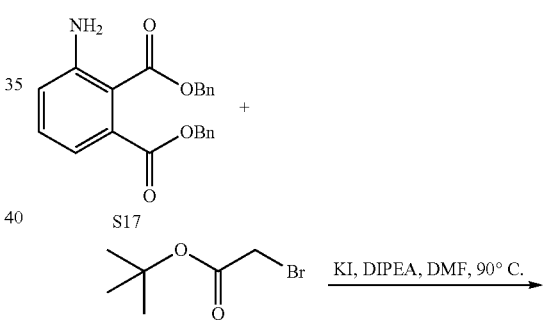

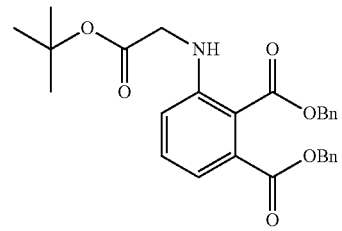

To a round-bottom flask, compound S17 (2.0 g, 5.54 mmol) and KI (100 mg, 0.56 mmol) were added to 10 mL of anhydrous DMF. Tert-butyl bromoacetate (2.4 mL, 16.6 mmol) and DIPEA (4.8 mL, 27.7 mmol) were added to the reaction mixture. The reaction mixture was heated to 90° C. to stir overnight. After cooling to room temperature, most of the solvent was evaporated and the residue was purified by column chromatography with hexane/ethyl acetate to give compound S18 as a slightly yellow solid (1.05 g, 40% yield).

Step 4: Synthesis of S19

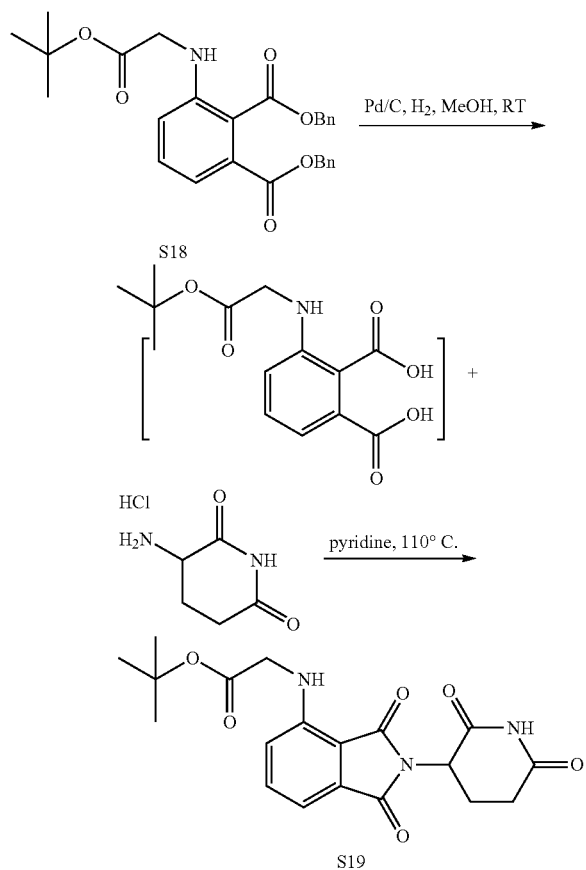

To a round-bottom flask, compound S18 (1.0 g, 2.1 mmol) was dissolved in 20 mL of methanol. 100 mg of Pd/C (10 wt %) was added. The reaction mixture was stirred at room temperature under 1 atm H₂ atmosphere. Once the starting material disappeared by TLC, the mixture was filtrated through celite and washed with methanol. After evaporation of the solvent, 3-aminopiperidine-2,6-dione hydrochloride (380 mg, 2.31 mmol) and 20 mL of pyridine were added. The reaction mixture was heated to 110° C. to stir overnight. After cooling to room temperature, the solvent was evaporated as much as possible and the residue was poured into water. After extraction with ethyl acetate for three times, the combined organic layer was washed with brine and dried over anhydrous $Na_2SO_4$. After filtration and evaporation, the crude residue was purified by flash column chromatography with DCM/ethyl acetate to give compound S19 as a yellow solid (325 mg, 40% yield).

Step 5: Synthesis of S20

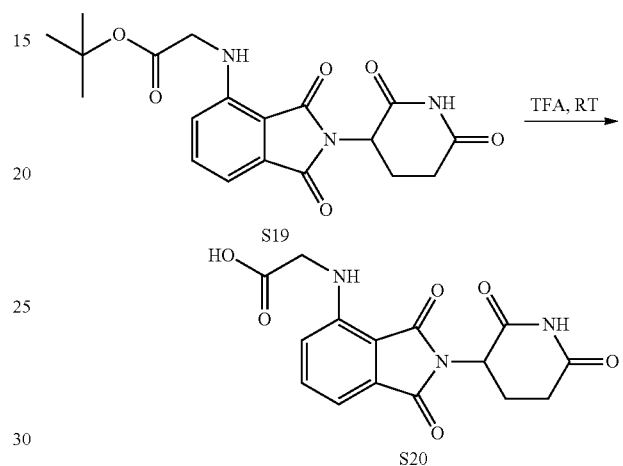

To a round-bottom flask, S19 (1.7 g) was dissolved in 8.0 mL of TFA. The reaction mixture was stirred at room temperature for 2 h. After evaporation of the solvent, the residue was used in the following steps without further purification. $^1$H NMR (400 MHz, DMSO-$d^6$) δ (ppm) 12.91 (s, 1H), 11.10 (s, 1H), 7.59 (t, J=8.0 Hz, 1H), 7.08 (d, J=6.80 Hz, 1H), 6.99 (d, J=8.4 Hz, 1H), 6.86 (t, J=5.6 Hz, 1H), 5.08 (dd, J=13.2 Hz, J=5.6 Hz, 1H), 4.12 (d, J=5.2 Hz, 2H), 2.94-2.85 (m, 1H), 2.63-2.49 (m, 2H), 2.09-2.07 (m, 1H); $^{13}$C NMR (100 MHz, DMSO-$d^6$) δ (ppm) 173.3, 171.9, 170.5, 169.3, 167.8, 146.3, 136.6, 132.5, 118.2, 111.5, 110.1, 60.2, 49.1, 31.5, 22.6.

Step 6: Synthesis of S21

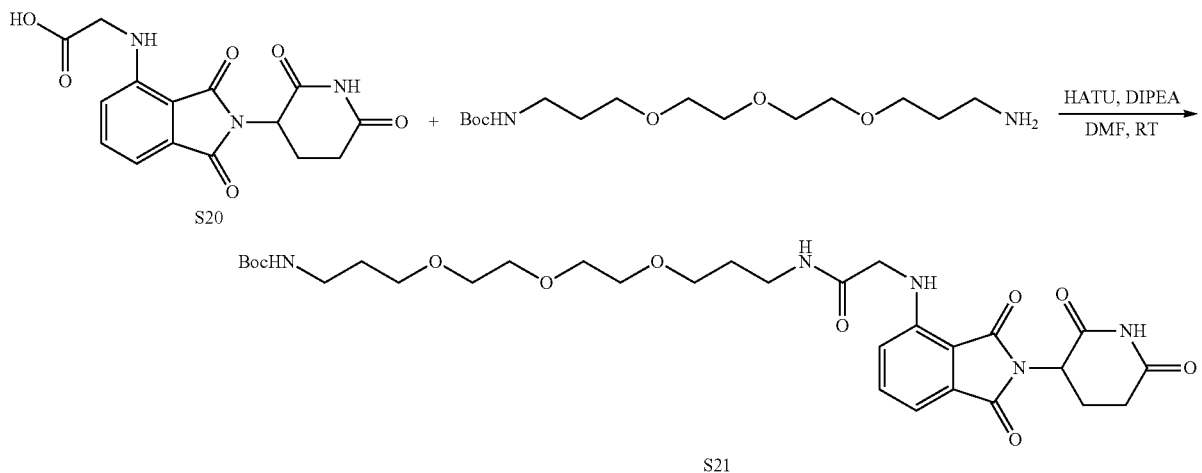

Following the procedure for S4 synthesis, compound S21 was synthesized with S20 (99.7 mg, 0.3 mmol), amine (115 mg, 0.36 mmol), HATU (137 mg, 0.36 mmol) and DIPEA (157 μL, 0.9 mmol). ESI-MS calculated for $C_{30}H_{43}N_5NaO_{10}$ [M+Na]$^+$=656.29, obtained: 656.26.

Step 7: Synthesis of N-(3-(2-(2-(3-aminopropoxy) ethoxy)ethoxy)propyl)-2-((2-(2,6-dioxopiperidin-3-yl)-1,3-dioxoisoindolin-4-yl)amino)acetamide

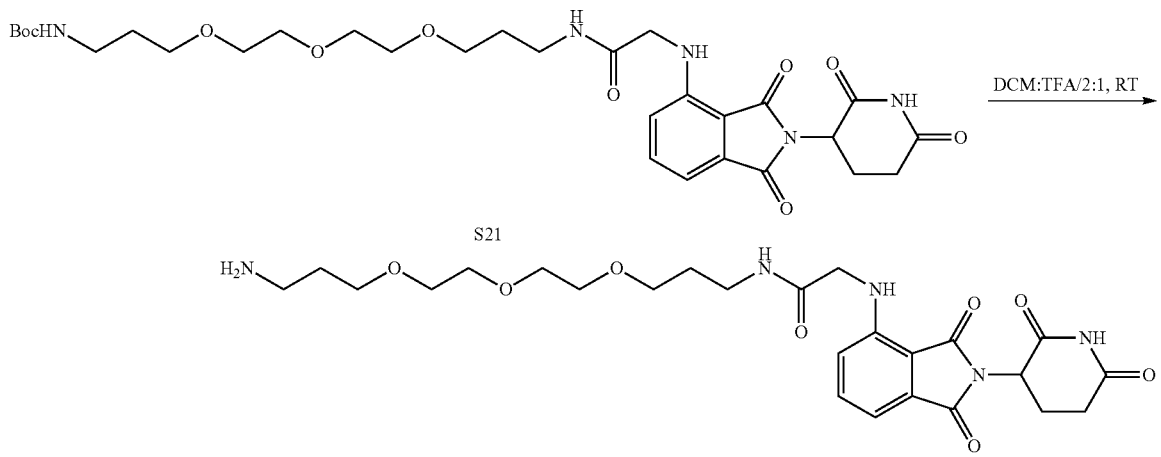

To a round-bottom flask, S21 (15.1 mg) was dissolved in 3 mL of DCM and TFA (2:1). After stirring for 1 h, the solvent was evaporated to give crude product N-(3-(2-(2-(3-aminopropoxy)ethoxy)ethoxy)propyl)-2-((2-(2,6-dioxopiperidin-3-yl)-1,3-dioxoisoindolin-4-yl)amino)acetamide, which was used in the next step without further purification.

Example 4

Synthesis of 4-((3-(2-(2-(3-aminopropoxy)ethoxy) ethoxy)propyl)amino)-2-(2,6-dioxopiperidin-3-yl) isoindoline-1,3-dione Step 1: Synthesis of S13

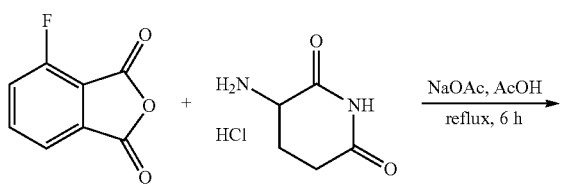

-continued

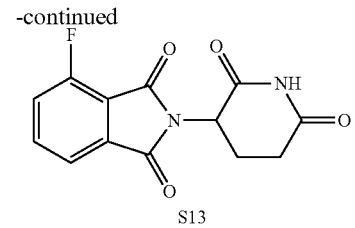

To a round-bottom flask, 3-fluorophthalic anhydride (6.64 g, 40 mmol), 3-aminopiperidine-2,6-dione hydrochloride (6.58 g, 40 mmol) and sodium acetate (3.94 g, 48 mmol) were mixed in 120 mL of acetic acid. The resulting reaction mixture was heated to reflux at 140° C. for 12 h. After cooling to room temperature, most of acetic acid was evaporated and the residue was purified by flash column chromatography with DCM/MeOH to get S13 as a slightly yellow solid (9.7 g, 88% yield). ESI-MS calculated for $C_{13}H_{10}FN_2O_4$[M+H]$^+$=277.06, obtained: 277.02. $^1$H NMR (400 MHz, DMSO-d$^6$) δ (ppm) 11.15 (s, 1H), 7.98-7.93 (m, 1H), 7.80-7.72 (m, 2H), 5.17 (dd, J=13.2 Hz, J=5.2 Hz, 1H), 2.95-2.86 (m, 1H), 2.64-2.47 (m, 2H), 2.10-2.06 (m, 1H);

Step 2: Synthesis of S14

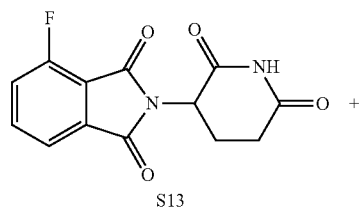

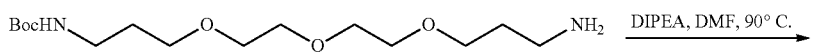

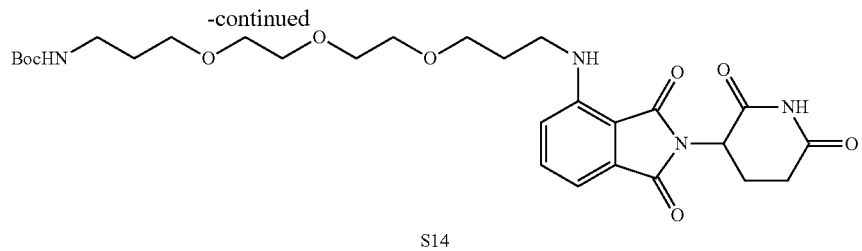

S14

To a round-bottom flask, S13 (276 mg, 1.0 mmol) was dissolved in 3.0 mL of anhydrous DMF. Amine (320 mg, 1.0 mmol) and DIPEA (259 mg, 2.0 mmol) were added. The reaction mixture was stirred at 90° C. for 12 h. The mixture was cooled to room temperature, poured into water and extracted with ethyl acetate for two times. The combined organic layer was washed with brine, dried over anhydrous $Na_2SO_4$. After filtration and evaporation, the crude residue was purified by HPLC with $H_2O$/MeCN to give compound S14 as colorless oil (172 mg, 30% yield). ESI-MS calculated for $C_{28}H_{41}N_4O_9$ $[M+H]^+$=577.2; Observed: 577.3.

Step 3: Synthesis of 4-((3-(2-(2-(3-aminopropoxy)ethoxy)ethoxy)propyl)amino)-2-(2,6-dioxopiperidin-3-yl)isoindoline-1,3-dione

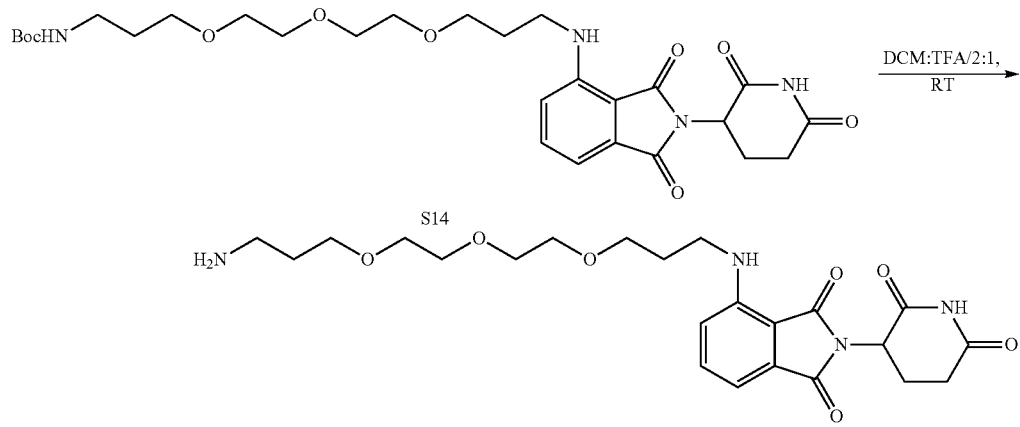

To a round-bottom flask, S14 (15 mg) was dissolved in 3 mL of DCM and TFA (2:1). After stirring for 1 h, the solvent was evaporated to give crude product 4-((3-(2-(2-(3-aminopropoxy)ethoxy)propyl)amino)-2-(2,6-dioxopiperidin-3-yl)isoindoline-1,3-dione.

Example 5

Synthesis of 4-(2-(2-(2-(2-aminoethoxy)ethoxy)ethoxy)ethoxy)-2-(2,6-dioxopiperidin-3-yl)isoindoline-1,3-dione Step 1: Synthesis of S9

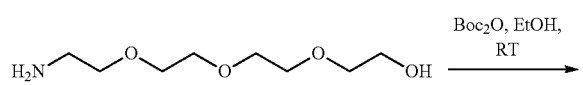

S9

To a round-bottom flask, 2-(2-(2-(2-aminoethoxy)ethoxy)ethoxy)ethanol (2.9 g, 15 mmol) was diluted in 10 mL of ethanol. Di-tert-butyl dicarbonate (3.6 g, 16.5 mmol) was dissolved in 10 mL of ethanol and the solution was dropwised within a period of 10 min. The resulting reaction mixture was stirred at room temperature for 2 h. After evaporation of the solvent, the residue was purified by column chromatography with DCM/MeOH to obtain S9 as colorless oil (3.69 g, 80% yield). $^1$H NMR (400 MHz, $CDCl_3$) δ (ppm) 5.49 (s, 1H), 3.46-3.25 (m, 14H), 3.02 (s, 2H), 1.18 (s, 9H); ESI-MS calculated for $C_{13}H_{27}NNaO_6$ $[M+Na]^+$=316.17, obtained: 316.18.

Step 2: Synthesis of S10

To a round-bottom flask, S9 (3.69 g, 12 mmol) was diluted in 100 mL of DCM. After cooling to 0° C., 4-toluenesulfonyl chloride (2.75 g, 14.4 mmol) and triethyl amine (2.51 mL, 18 mmol) were added sequentially. The resulting reaction mixture was stirred at 0° C. for 30 min and then room temperature for 2 h. After workup with DCM and saturated NaHCO$_3$ solution, the combined organic layer was dried over anhydrous Na$_2$SO$_4$. After filtration and evaporation, the residue was purified by column chromatography with hexane:ethyl acetate to give S10 as colorless oil (4.98 g, 90% yield). $^1$H NMR (400 MHz, CDCl$_3$) δ (ppm) 7.76 (d, J=8.4 Hz, 2H), 7.31 (d, J=8.4 Hz, 2H), 4.12 (m, 2H), 3.67-3.47 (m, 12H), 3.25-3.23 (m, 2H), 2.40 (s, 3H), 1.39 (s, 9H); ESI-MS calculated for C$_{20}$H$_{33}$NNaO$_8$S [M+Na]$^+$= 470.18, obtained: 470.20.

Step 3: Synthesis of S11

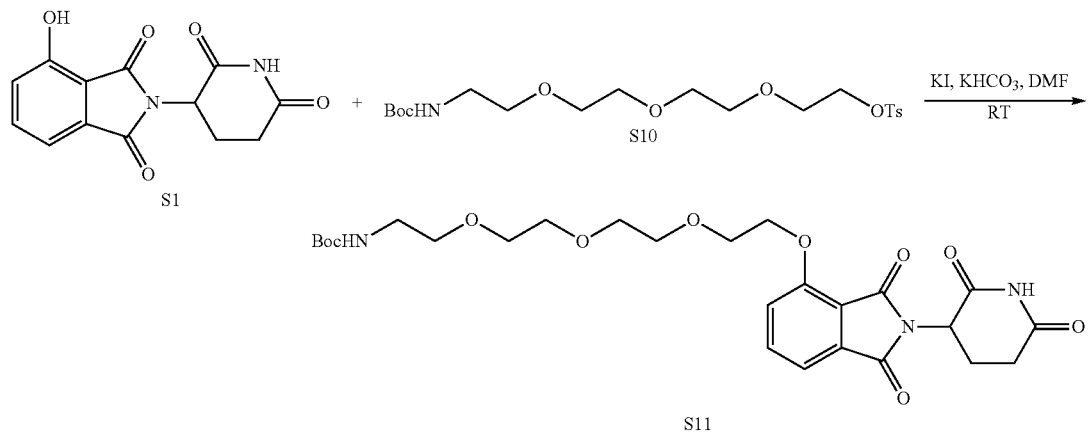

To a round-bottom flask, S1 (274 mg, 1.0 mmol) and S10 (492 mg, 1.1 mmol) were mixed in 5.0 mL of anhydrous DMF. KI (17 mg, 0.1 mmol) and KHCO$_3$ (150 mg, 1.5 mmol) were added sequentially. The reaction mixture was stirred at room temperature for 12 h. After evaporation of most of the solvent, the residue was purified by column chromatography with DCM/MeOH to get S11 as colorless oil (453 mg, 82% yield). ESI-MS calculated for C$_{25}$H$_{36}$N$_3$O$_{10}$Na [M+Na]$^+$=572.22, obtained: 572.13.

Step 4: Synthesis of 4-(2-(2-(2-(2-aminoethoxy)ethoxy)ethoxy)ethoxy)-2-(2,6-dioxopiperidin-3-yl)isoindoline-1,3-dione

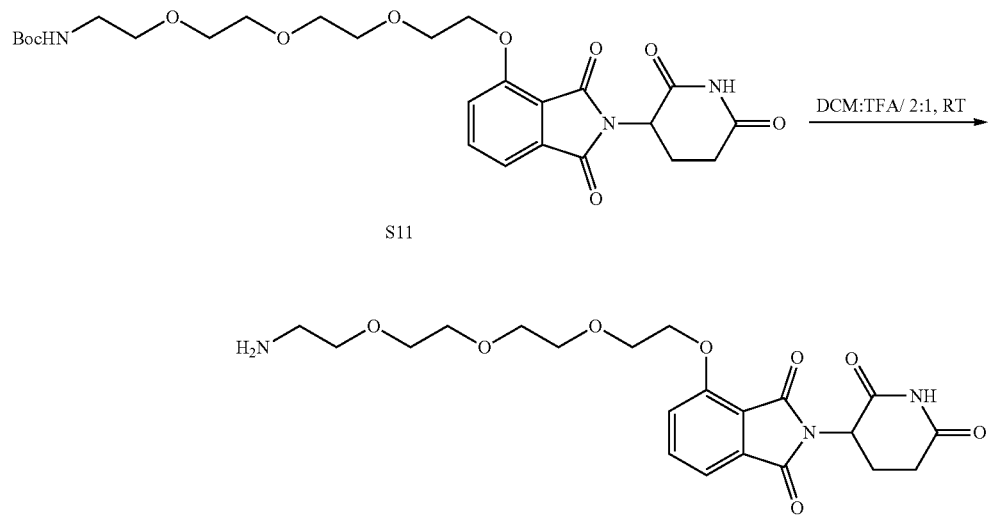

231

To a round-bottom flask, S11 (15 mg) was dissolved in 3 mL of DCM and TFA (2:1). After stirring for 1 h, the solvent was evaporated to give crude product 4-(2-(2-(2-(2-aminoethoxy)ethoxy)ethoxy)-2-(2,6-dioxopiperidin-3-yl)isoindoline-1,3-dione. ESI-MS calculated for $C_{21}H_{28}N_3O_8$ $[M+Na]^+$=450.19, obtained: 450.20.

Example 6

Synthesis of 3-(4-(5-aminopentyl)-1-oxoisoindolin-2-yl)piperidine-2,6-dione

Step 1: Synthesis of S23

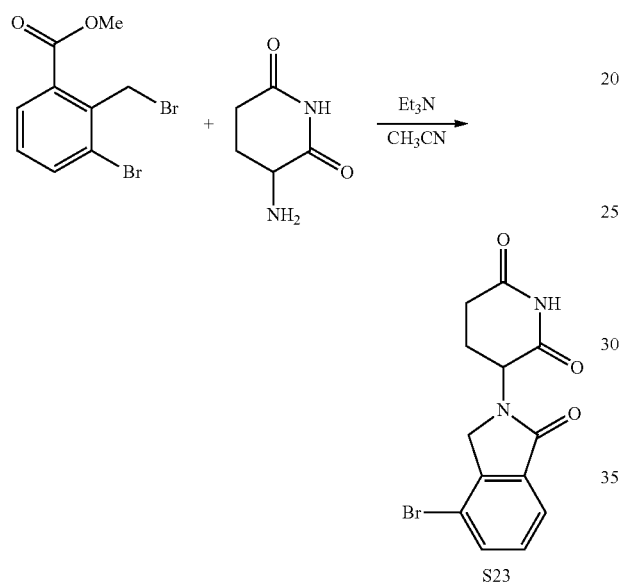

To a round-bottom flask, methyl 3-bromo-2-(bromomethyl)benzoate (50 mg) and Et$_3$N (60 mg) were added to a solution of 3-aminopiperidine-2,6-dione (30 mg) in CH$_3$CN (5 mL). The mixture was stirred for 10 hours at 60° C. and purified by flash column chromatography to yield S23 in 30 mg. ESI-MS calculated for $C_{13}H_{12}BrN_2O_3$ $[M+H]^+$=323.0; Observed: 323.2.

Step 2: Synthesis of S24

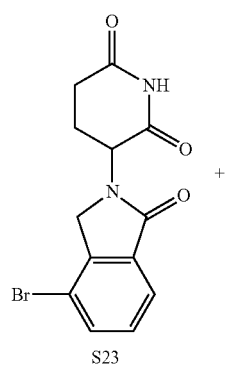

232

-continued

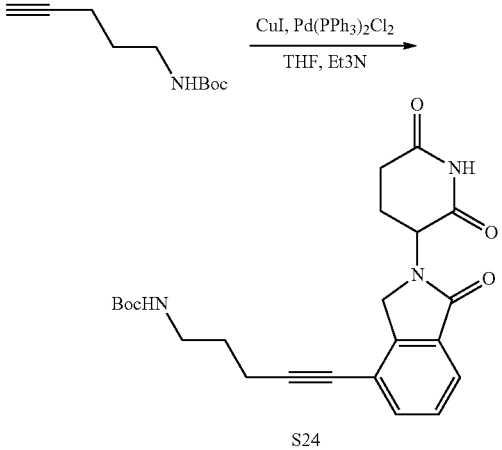

To a round-bottom flask, S23 (50 mg) and tert-butyl pent-4-yn-1-ylcarbamate (50 mg) were added to a solution of CuI (6.3 mg) and Pd(PPh$_3$)$_2$Cl$_2$ (11 mg) in THF (5 mL) and Et$_3$N (2 mL). The mixture was stirred for 10 hours at 70° C. under Ar and purified directly by flash column chromatography to yield S24 in 20 mg. ESI-MS calculated for $C_{23}H_{28}N_3O_5$ $[M+H]^+$=426.2; Observed: 426.4.

Step 3: Synthesis of 3-(4-(5-aminopentyl)-1-oxoisoindolin-2-yl)piperidine-2,6-dione

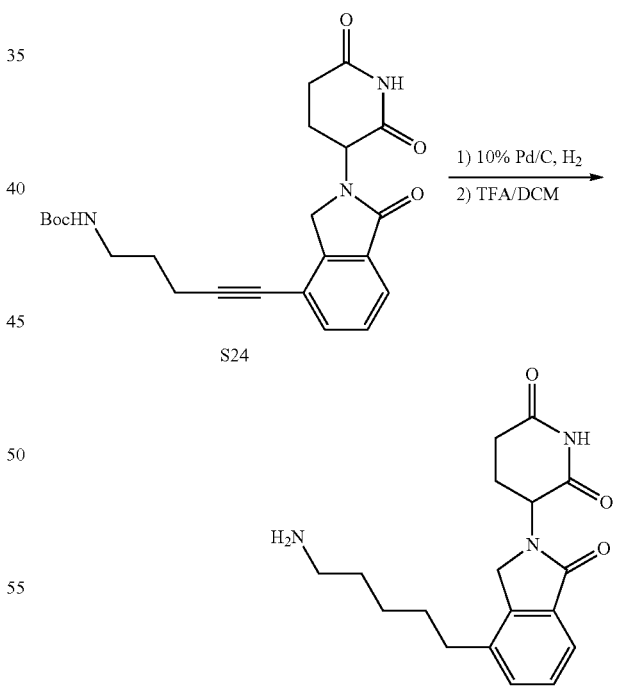

S24 (30 mg) was dissolved in MeOH (10 mL). 5 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give the crude which was dissolved in 3 mL of DCM and TFA (2:1). After stirring for 1 h, the solvent was evaporated to give crude product 3-(4-(5-aminopentyl)-1-oxoisoindolin-2-yl)piperidine-2,6-dione. ESI-MS calculated for $C_{18}H_{24}N_3O_3$ [M+H]$^+$=330.1; Observed: 330.4.

Example 7

Synthesis of 4-((4-aminobutyl)amino)-2-(2,6-dioxopiperidin-3-yl)isoindoline-1,3-dione

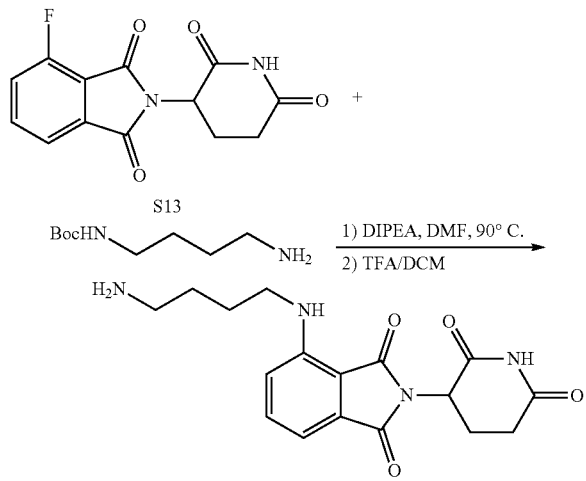

To a round-bottom flask, S13 (276 mg, 1.0 mmol) was dissolved in 3.0 mL of anhydrous DMF. tert-butyl (4-aminobutyl)carbamate (320 mg) and DIPEA (259 mg, 2.0 mmol) were added. The reaction mixture was stirred at 90° C. for 12 h. The mixture was cooled to room temperature, poured into water and extracted with ethyl acetate for two times. The combined organic layer was washed with brine, dried over anhydrous $Na_2SO_4$. After filtration and evaporation, the crude residue was dissolved in 3 mL of DCM and TFA (2:1). After stirring for 1 h, the solvent was evaporated to give the crude which was purified by HPLC with $H_2O$/MeCN to give compound 4-((4-aminobutyl)amino)-2-(2,6-dioxopiperidin-3-yl)isoindoline-1,3-dione as colorless oil (100 mg). ESI-MS calculated for $C_{17}H_{21}N_4O_4$ [M+H]$^+$=345.1; Observed: 345.4.

Example 8

Synthesis of 4-((2-(2-(2-aminoethoxy)ethoxy)ethyl)amino)-2-(2,6-dioxopiperidin-3-yl)isoindoline-1,3-dione

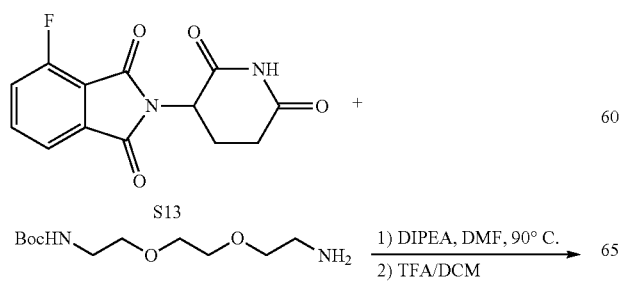

-continued

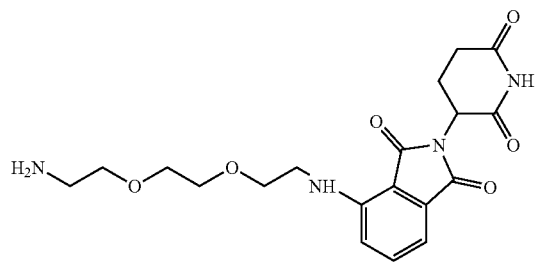

To a round-bottom flask, S13 (276 mg, 1.0 mmol) was dissolved in 3.0 mL of anhydrous DMF. tert-butyl (2-(2-(2-aminoethoxy)ethoxy)ethyl)carbamate (320 mg) and DIPEA (259 mg, 2.0 mmol) were added. The reaction mixture was stirred at 90° C. for 12 h. The mixture was cooled to room temperature, poured into water and extracted with ethyl acetate for two times. The combined organic layer was washed with brine, dried over anhydrous $Na_2SO_4$. After filtration and evaporation, the crude residue was dissolved in 3 mL of DCM and TFA (2:1). After stirring for 1 h, the solvent was evaporated to give the crude which was purified by HPLC with $H_2O$/MeCN to give 4-((2-(2-(2-aminoethoxy)ethoxy)ethyl)amino)-2-(2,6-dioxopiperidin-3-yl)isoindoline-1,3-dione as colorless oil (130 mg). ESI-MS calculated for $C_{19}H_{25}N_4O_6$ [M+H]$^+$=405.1; Observed: 405.4.

Example 9

Synthesis of 3-(4-(3-(2-aminoethoxy)propyl)-1-oxoisoindolin-2-yl)piperidine-2,6-dione Step 1: Synthesis of S28

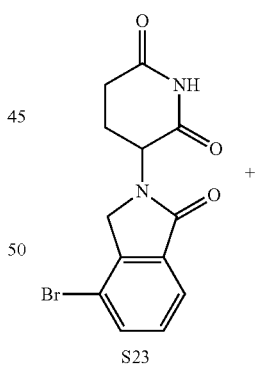

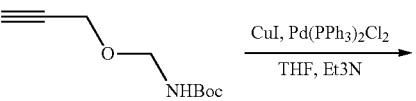

235

-continued

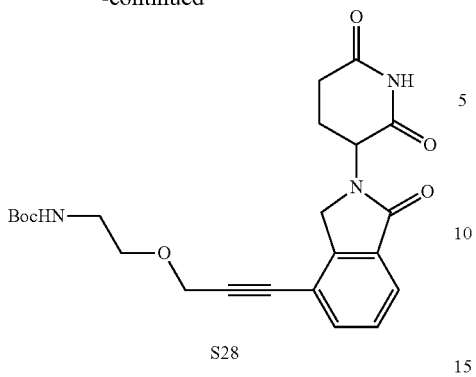

S28

To a round-bottom flask, S23 (50 mg) and tert-butyl (2-(prop-2-yn-1-yloxy)ethyl)carbamate (60 mg) were added to a solution of CuI (6.3 mg) and Pd(PPh$_3$)$_2$Cl$_2$ (11 mg) in THF (5 mL) and Et$_3$N (2 mL). The mixture was stirred for 10 hours at 70° C. under Ar and purified directly by flash column chromatography to yield 22 mg of S28. ESI-MS calculated for C$_{23}$H$_{28}$N$_3$O$_6$ [M+H]$^+$=442.1; Observed: 442.3.

Step 2: Synthesis of 3-(4-(3-(2-aminoethoxy)propyl)-1-oxoisoindolin-2-yl)piperidine-2,6-dione

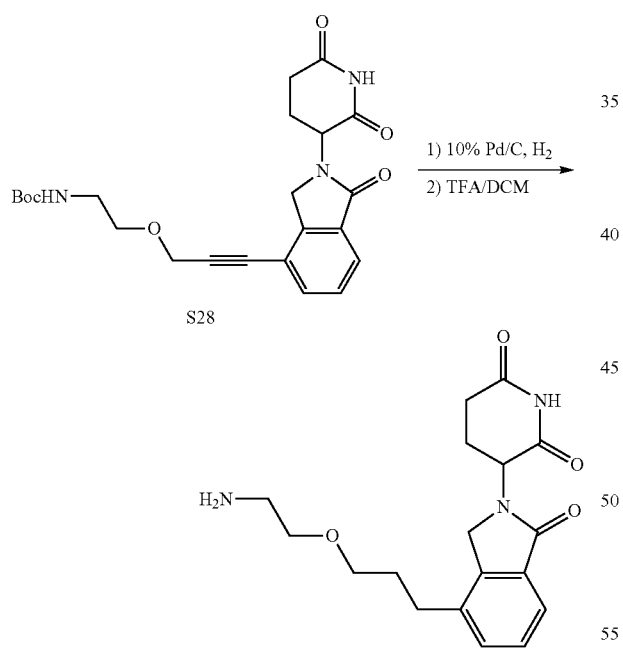

S28 (30 mg) was dissolved in MeOH (10 mL). 5 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give the crude which was dissolved in 3 mL of DCM and TFA (2:1). After stirring for 1 h, the solvent was evaporated to give 3-(4-(3-(2-aminoethoxy)propyl)-1-oxoisoindolin-2-yl)piperidine-2,6-dione. ESI-MS calculated for C$_{18}$H$_{24}$N$_3$O$_4$ [M+H]$^+$=346.1; Observed: 346.3.

236

Example 10

Synthesis of 4-(5-aminopentyl)-2-(2,6-dioxopiperidin-3-yl)isoindoline-1,3-dione

Step 1: Synthesis of S30

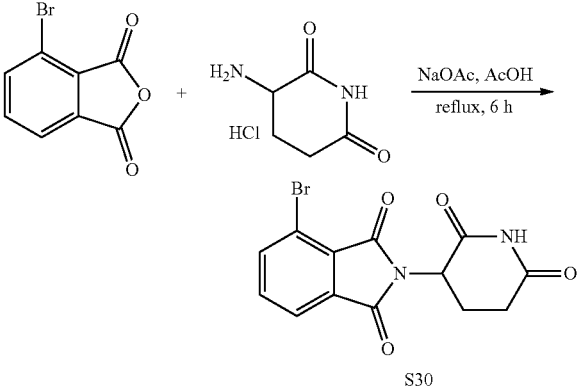

S30

To a round-bottom flask, 3-bromophthalic anhydride (6.64 g), 3-aminopiperidine-2,6-dione hydrochloride (6.58 g, 40 mmol) and sodium acetate (3.94 g, 48 mmol) were mixed in 120 mL of acetic acid. The resulting reaction mixture was heated to reflux at 140° C. for 12 h. After cooling to room temperature, most of acetic acid was evaporated and the residue was purified by flash column chromatography with DCM/MeOH to get S130 as a solid (7 g). ESI-MS calculated for C$_{13}$H$_{10}$BrN$_2$O$_4$[M+H]$^+$=336.9, obtained: 336.9.

Step 2: Synthesis of S31

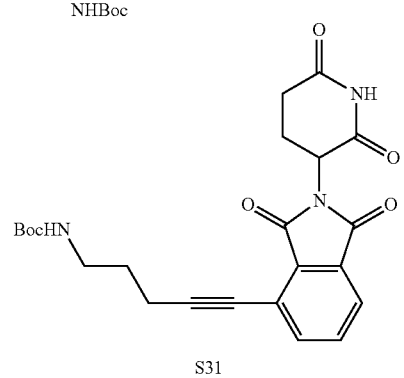

To a round-bottom flask, S30 (50 mg) and tert-butyl pent-4-yn-1-ylcarbamate (50 mg) were added to a solution of CuI (6.3 mg) and Pd(PPh₃)₂Cl₂ (11 mg) in THF (5 mL) and Et₃N (2 mL). The mixture was stirred for 10 hours at 70° C. under Ar and purified directly by flash column chromatography to yield 14 mg of S31. ESI-MS calculated for $C_{23}H_{26}N_3O_6$ [M+H]⁺=440.1; Observed: 440.3.

Step 3: Synthesis of 4-(5-aminopentyl)-2-(2,6-dioxopiperidin-3-yl)isoindoline-1,3-dione

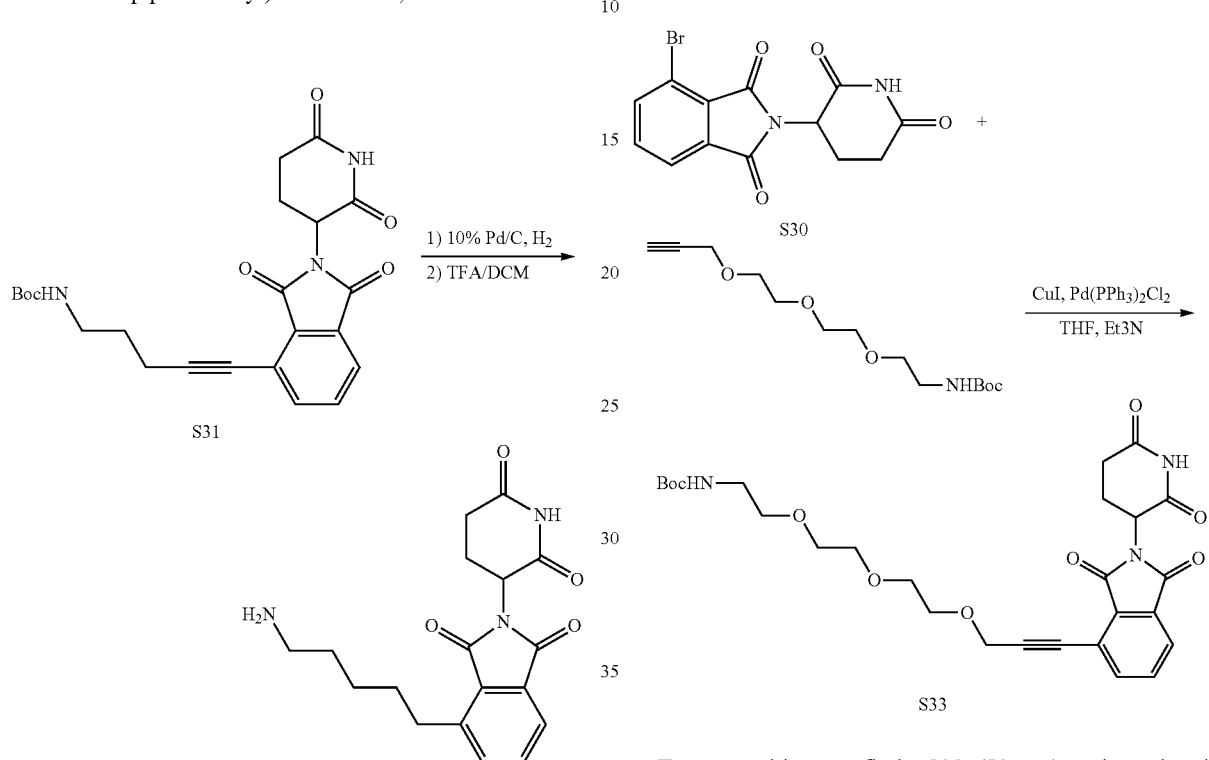

S31 (30 mg) was dissolved in MeOH (10 mL). 5 mg 10% Pd/C was added. the reaction mixture was degassed 2 times, each time replacing the vacuum with hydrogen, then stirred at room temperature under H₂ overnight. The mixture was filtered and concentrated on a rotary evaporator to give the crude which was dissolved in 3 mL of DCM and TFA (2:1). After stirring for 1 h, the solvent was evaporated to give 4-(5-aminopentyl)-2-(2,6-dioxopiperidin-3-yl)isoindoline-1,3-dione. ESI-MS calculated for $C_{18}H_{22}N_3O_4$ [M+H]⁺= 344.1; Observed: 344.4.

Example 11

Synthesis of 4-(3-(2-(2-(2-aminoethoxy)ethoxy)ethoxy)propyl)-2-(2,6-dioxopiperidin-3-yl)isoindoline-1,3-dione Step 1: Synthesis of S33

To a round-bottom flask, S30 (50 mg) and tert-butyl (2-(2-(2-(prop-2-yn-1-yloxy)ethoxy)ethoxy)ethyl)carbamate (60 mg) were added to a solution of CuI (6.3 mg) and Pd(PPh₃)₂Cl₂ (11 mg) in THF (5 mL) and Et₃N (2 mL). The mixture was stirred for 10 hours at 70° C. under Ar and purified directly by flash column chromatography to yield S33 in 18 mg. ESI-MS calculated for $C_{27}H_{34}N_3O_9$ [M+H]⁺= 544.2; Observed: 544.4.

Step 2: Synthesis of 4-(3-(2-(2-(2-aminoethoxy)ethoxy)ethoxy)propyl)-2-(2,6-dioxopiperidin-3-yl)isoindoline-1,3-dione

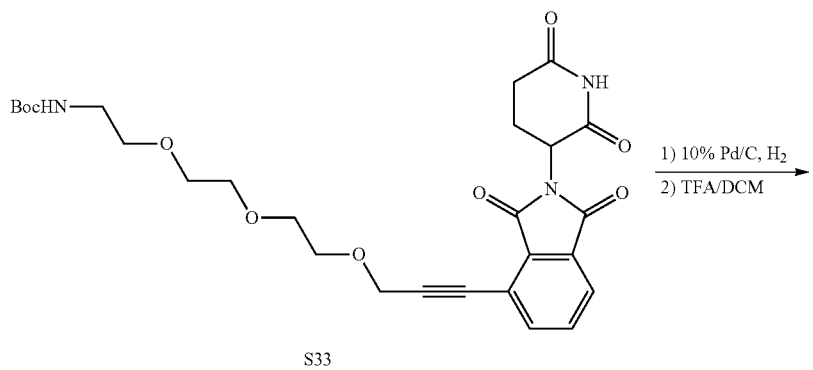

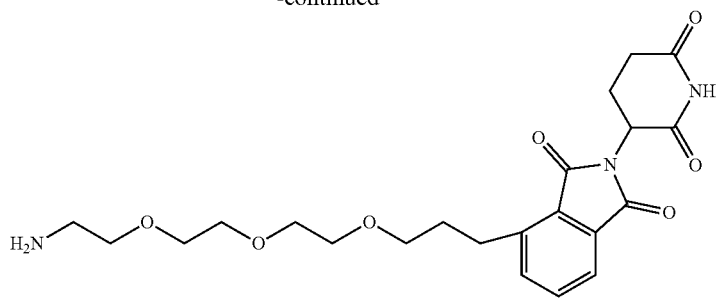

S33 (30 mg) was dissolved in MeOH (10 mL) and 5 mg 10% Pd/C was added. The reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product 4-(3-(2-(2-(2-aminoethoxy)ethoxy)ethoxy)propyl)-2-(2,6-dioxopiperidin-3-yl)isoindoline-1,3-dione. ESI-MS calculated for $C_{22}H_{30}N_3O_7$ $[M+H]^+=448.2$; Observed: 448.3.

Example 12

Synthesis of 4-(3-(2-aminoethoxy)propyl)-2-(2,6-dioxopiperidin-3-yl)isoindoline-1,3-dione Step 1: Synthesis of S35

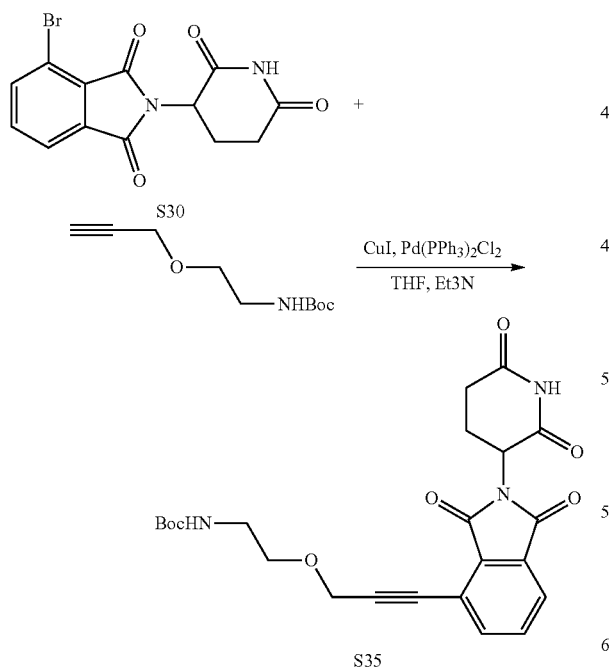

To a round-bottom flask, S30 (50 mg) and tert-butyl (2-(prop-2-yn-1-yloxy)ethyl)carbamate (60 mg) were added to a solution of CuI (6.3 mg) and $Pd(PPh_3)_2Cl_2$ (11 mg) in THF (5 mL) and $Et_3N$ (2 mL). The mixture was stirred for 10 hours at 70° C. under Ar and purified directly by flash column chromatography to yield 19 mg of S35. ESI-MS calculated for $C_{23}H_{26}N_3O_7$ $[M+H]^+=456.1$; Observed: 456.3.

Step 2: Synthesis of 4-(3-(2-aminoethoxy)propyl)-2-(2,6-dioxopiperidin-3-yl)isoindoline-1,3-dione

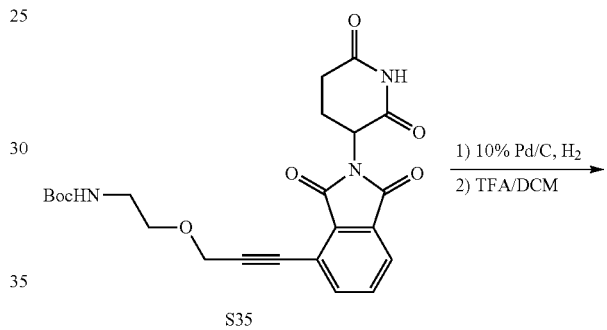

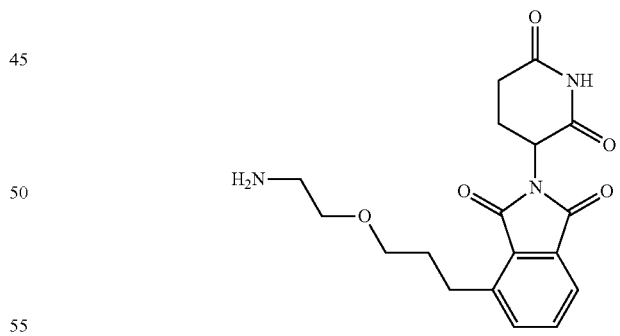

S35 (30 mg) was dissolved in MeOH (10 mL). 5 mg 10% Pd/C was added. the reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product 4-(3-(2-aminoethoxy)propyl)-2-(2,6-dioxopiperidin-3-yl)isoindoline-1,3-dione. ESI-MS calculated for $C_{18}H_{22}N_3O_5$ $[M+H]^+=360.1$; Observed: 360.2.

Example 13

Synthesis of 3-(2-(2-aminoethoxy)ethoxy)-N-(2-(2,6-dioxopiperidin-3-yl)-1-oxoisoindolin-4-yl)propanamide

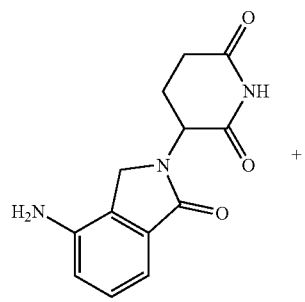

To a round-bottom flask, N,N-diisopropylethylamine (50 mg) were added to a solution of 3-(4-amino-1-oxoisoindolin-2-yl)piperidine-2,6-dione (20 mg), HATU (30 mg), and 2,2-dimethyl-4-oxo-3,8,11-trioxa-5-azatetradecan-14-oic acid (50 mg) in DMF (1 mL) at room temperature. The mixture was stirred for 30 min and the solvent was evaporated as much as possible and the residue was poured into water. After extraction with ethyl acetate for three times, the combined organic layer was washed with brine and dried over anhydrous $Na_2SO_4$. After filtration and evaporation, the crude residue was dissolved in 3 mL of DCM and TFA (2:1). After stirring for 1 h, the solvent was evaporated to give the crude product which was purified by flash column chromatography to yield 3-(2-(2-aminoethoxy)ethoxy)-N-(2-(2,6-dioxopiperidin-3-yl)-1-oxoisoindolin-4-yl)propanamide. ESI-MS calculated for $C_{20}H_{27}N_4O_6[M+H]^+$=419.1; Observed: 419.2.

Example 14

Synthesis of 3-(2-(2-(2-aminoethoxy)ethoxy)ethoxy)-N-(2-(2,6-dioxopiperidin-3-yl)-1-oxoisoindolin-4-yl)propanamide

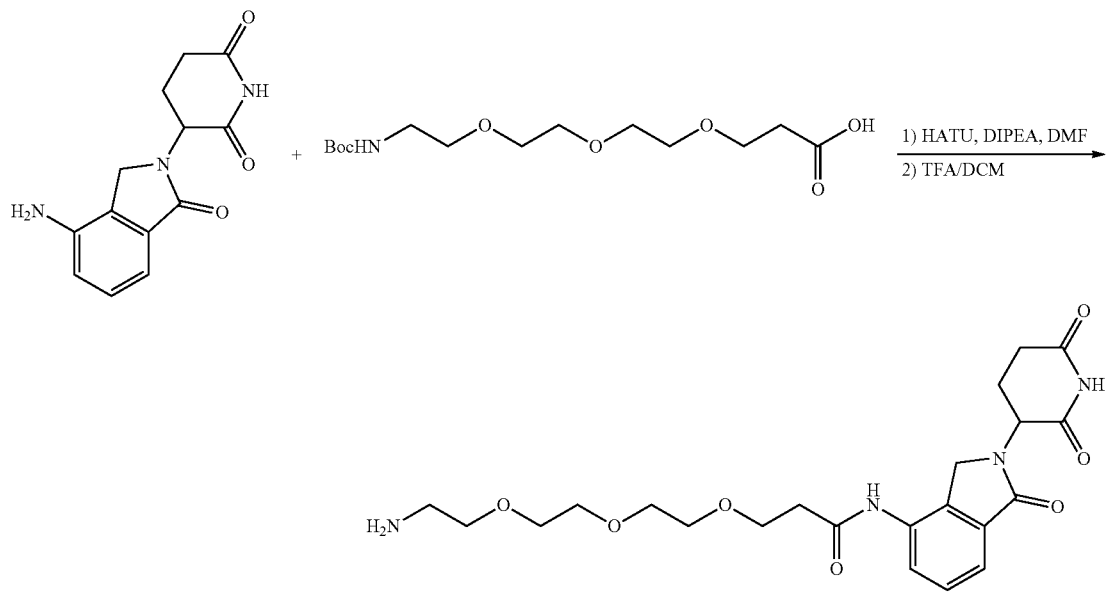

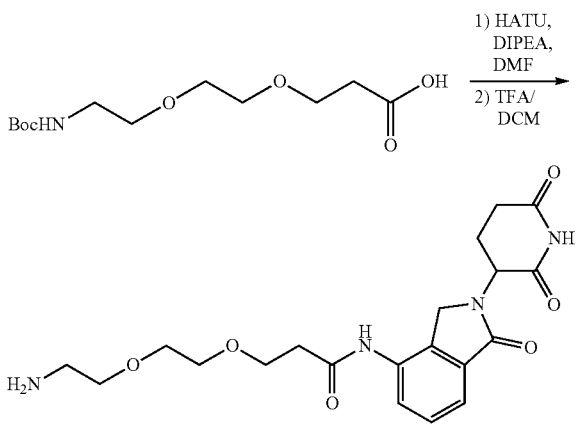

To a round-bottom flask, N,N-diisopropylethylamine (50 mg) were added to a solution of 3-(4-amino-1-oxoisoindolin-2-yl)piperidine-2,6-dione (20 mg), HATU (30 mg), and 2,2-dimethyl-4-oxo-3,8,11,14-tetraoxa-5-azaheptadecan-17-oic acid (50 mg) in DMF (1 mL) at room temperature. The mixture was stirred for 30 min and the solvent was evaporated as much as possible and the residue was poured into water. After extraction with ethyl acetate for three times, the combined organic layer was washed with brine and dried over anhydrous $Na_2SO_4$. After filtration and evaporation, the crude residue was dissolved in 3 mL of DCM and TFA (2:1). After stirring for 1 h, the solvent was evaporated to give the crude product which was purified by flash column chromatography to yield 3-(2-(2-(2-aminoethoxy)ethoxy)ethoxy)-N-(2-(2,6-dioxopiperidin-3-yl)-1-oxoisoindolin-4-yl)propanamide. ESI-MS calculated for $C_{22}H_{31}N_4O_7[M+H]^+$=463.2; Observed: 463.4.

Example 15

Synthesis of 3-(4-((4-aminobutyl)amino)-1-oxoisoindolin-2-yl)piperidine-2,6-dione

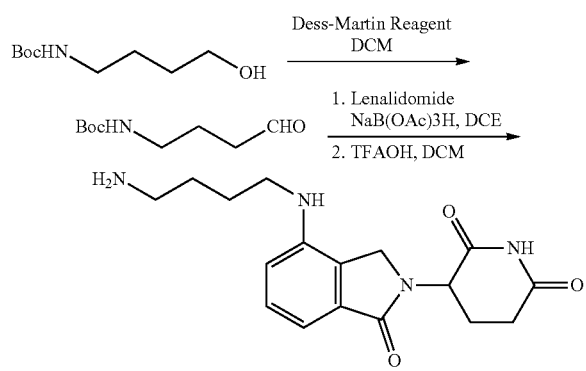

Step 1: Synthesis of tert-butyl (4-oxobutyl)carbamate

To solution of tert-butyl 4-hydroxybutyl)carbamate (380 mg, 2 mmol) in 15 ml of DCM was added Dess-Martin periodinane reagent (1.7 g, 4 mmol). After stirring at room temperature for 1 h the reaction mixture was filtered by celite. The filtrate was then washed with brine, dried over Na₂SO₄, filtered, and the solvent evaporated in vacuo. The residue was purified by chromatography over silica gel, to yield tert-butyl (4-oxobutyl)carbamate as colorless oil.

Step 2: Synthesis of 3-(4-((4-aminobutyl)amino)-1-oxoisoindolin-2-yl)piperidine-2,6-dione To tert-butyl (4-oxobutyl)carbamate (190 mg, 1 mmol) in 1,2-dichloroethane (15 mL) was added Lenalidomide (285 mg, 1.1 mmol), and the resulting solution was stirred at room temperature for 30 min. The solution was treated with Na(OAc)₃BH (0.42 g, 2 mmol), and the resulting suspension was stirred overnight. The solvent was diluted with DCM and washed with sat. NaHCO₃, brine, dried (Na₂SO₄), filtered, and concentrated. Then residue was diluted in 10 mL DCM then 2 mL trifluoroacetic acid was added to the reaction and stirred for 30 min. The solvent was removed by vacuo and the residue was purified by reverse phase chromatography over C18 column to yield 3-(4-((4-aminobutyl)amino)-1-oxoisoindolin-2-yl)piperidine-2,6-dione as colorless oil.

Example 16

Synthesis of 5-amino-N-(2-(2,6-dioxopiperidin-3-yl)-1-oxoisoindolin-4-yl)pentanamide

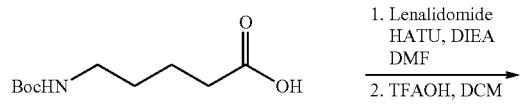

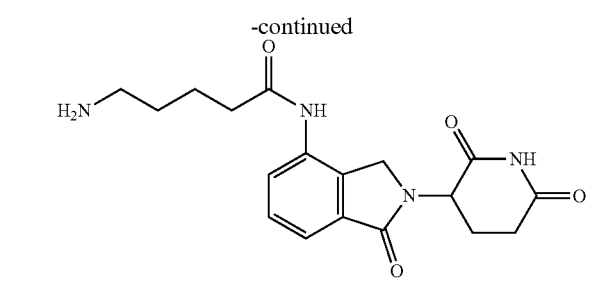

HATU (380 mg, 1 mmol) and N,N-diisopropylethylamine (0.44 mL, 2.5 mmol) were added to a solution of Boc-5-aminopentanoic acid (110 mg, 0.5 mmol) in 3 mL DMF and stirred. After 10 minutes, Lenalidomide (200 mg, 0.75 mmol) was added to the reaction. After 30 minutes, the solvent was removed and the crude was dissolved in 10 mL DCM and 2 mL trifluoroacetic acid. The reaction was stirred for 30 min and then the solvent was removed by vacuo. The residue was purified by reverse phase chromatography over C18 column to yield 5-amino-N-(2-(2,6-dioxopiperidin-3-yl)-1-oxoisoindolin-4-yl)pentanamide as colorless oil.

Example 17

Synthesis of 3-(4-(5-aminopentyl)-1-oxoisoindolin-2-yl)piperidine-2,6-dione

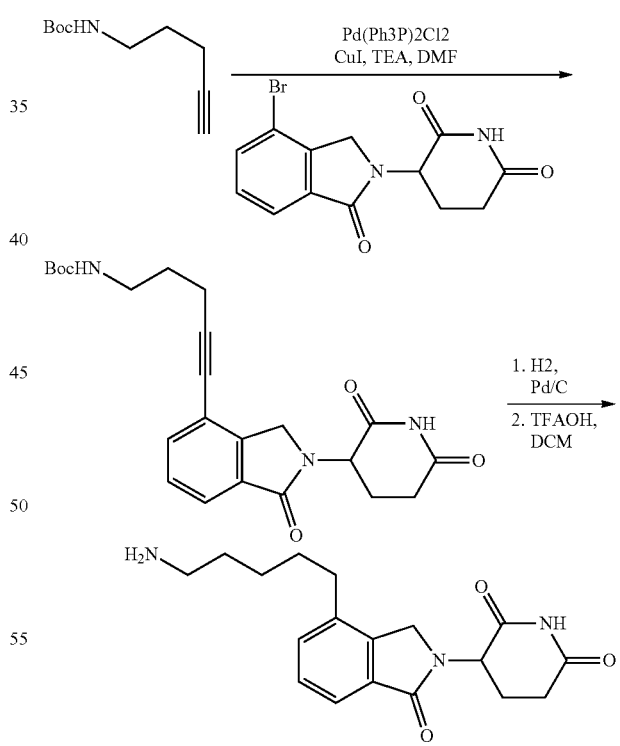

Step 1: Synthesis of tert-butyl (5-(2-(2,6-dioxopiperidin-3-yl)-1-oxoisoindolin-4-yl)pent-4-yn-1-yl)carbamate To a solution of tert-butyl pent-4-yn-1-ylcarbamate (236 mg, 1.29 mmol) and 3-(4-bromo-1-oxoisoindolin-2-yl)piperidine-2,6-dione (400 mg, 1.29 mmol) in triethylamine (3 mL) and DMF (3 mL), CuI (50 mg, 0.25 mmol) and the Pd(Ph$_3$P)$_2$Cl$_2$ (90 mg, 0.13 mmol) were added. The mixture was stirred at 80° C. under N$_2$-atmosphere overnight. The reaction mixture was poured into a saturated aqueous solution of NH$_4$Cl and after separation of the organic layer the aqueous layer was extracted with Ethyl Acetate. The combined organic layers were washed with brine, dried over Na$_2$SO$_4$ and concentrated in vacuo. The crude product was purified by flash chromatography to afford tert-butyl (5-(2-(2,6-dioxopiperidin-3-yl)-1-oxoisoindolin-4-yl)pent-4-yn-1-yl)carbamate as white solid.

Step 2: Synthesis of 3-(4-(5-aminopentyl)-1-oxoisoindolin-2-yl)piperidine-2,6-dione To a solution of tert-butyl (5-(2-(2,6-dioxopiperidin-3-yl)-1-oxoisoindolin-4-yl)pent-4-yn-1-yl)carbamate (210 mg, 0.5 mmol) in EtOH (5 mL) was added Pd/C (20 mg). The reaction was stirred under H$_2$-atmosphere for 2 hr. Then the mixture was filtered by celite and the solvent was removed by vacuo. The residue was dissolved in 10 mL DCM and 2 mL trifluoroacetic acid. The reaction was stirred for 30 min and then the solvent was removed by vacuo. The residue was purified by reverse phase chromatography over C18 column to 3-(4-(5-aminopentyl)-1-oxoisoindolin-2-yl)piperidine-2,6-dione as colorless oil.

Example 18

Synthesis of 2-(2,6-dioxopiperidin-3-yl)-4-((2-(prop-2-yn-1-yloxy)ethyl)amino)isoindoline-1,3-dione

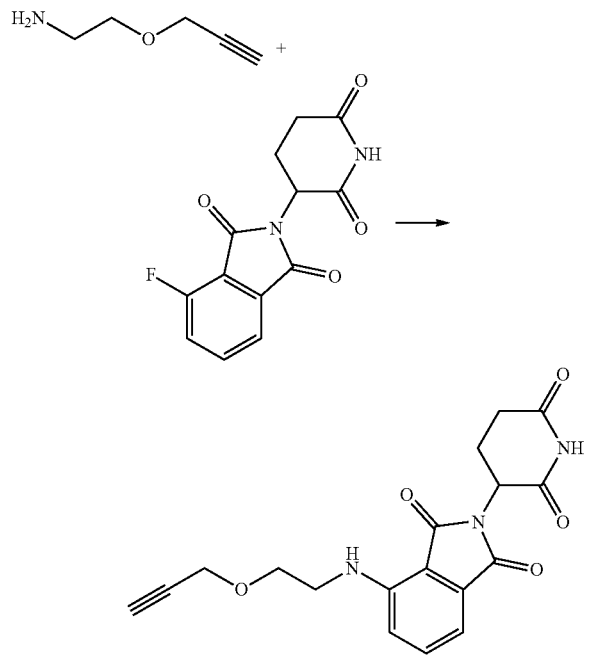

Step 1:
To a solution of 2-(prop-2-yn-1-yloxy)ethan-1-amine (99 mg, 1 mmol) and 2-(2,6-dioxopiperidin-3-yl)-4-fluoroisoindoline-1,3-dione (276 mg, 1 mmol) in DMF (1 mL) was added DIPEA (0.35 mL, 2 mmol). The reaction mixture was heated at 90° C. for 12 hours. The reaction mixture was cooled and treated with EtOAc and brine. The organic layer was separated, dried, and evaporated. The residue was subject to HPLC purification to afford 2-(2,6-dioxopiperidin-3-yl)-4-((2-(prop-2-yn-1-yloxy)ethyl) amino)isoindoline-1,3-dione (25 mg, 7% yield). $^1$H NMR (400 MHz, CDCl$_3$) δ 8.01 (s, 1H), 7.53 (t, J=7.8 Hz, 1H), 7.14 (d, J=7.1 Hz, 1H), 6.96 (d, J=8.6 Hz, 1H), 4.94 (dd, J=11.2, 5.3 Hz, 1H), 4.24 (s, 2H), 3.80 (t, J=4.9 Hz, 2H), 3.53 (t, J=5.0 Hz, 2H), 2.88 (dd, J=25.7, 11.5 Hz, 1H), 2.77 (ddd, J=16.3, 13.2, 3.6 Hz, 2H), 2.49 (s, 1H), 2.23-2.05 (m, 1H). ESI-MS: (M+H) 356.07.

Example 19

Synthesis of 2-(2,6-dioxopiperidin-3-yl)-4-(2-(2-(prop-2-yn-1-yloxy)ethoxy)ethoxy) isoindoline-1,3-dione

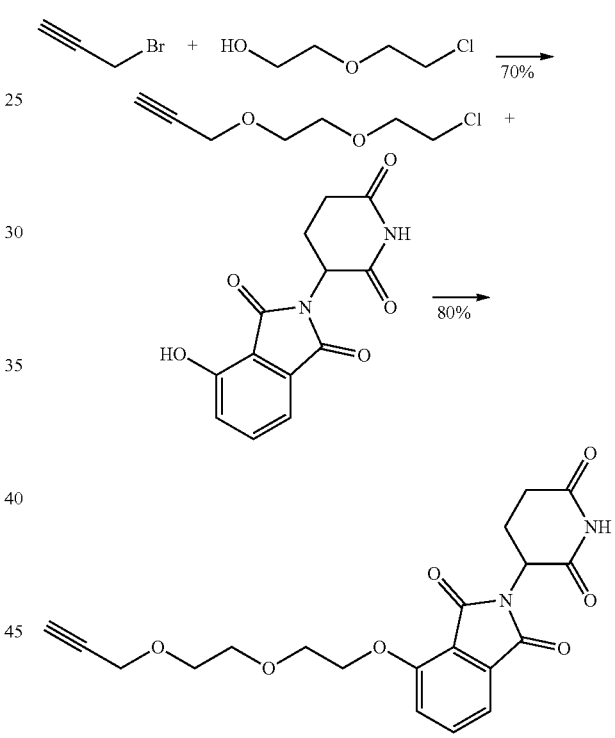

Step 1:
Chloropoly(ethyoxy)ethanol (2.49 g, 20 mmol) was added dropwise to a suspension of NaH (60% in mineral oil, 1.6 g, 40 mmol) in THF (50 mL) at −20° C. under N2. After cooled to −78° C., propargyl bromide solution (3.6 mL, 20 mmol) was added dropwise and the mixture was refluxed for 2 h. The THF solvent was evaporated and the residue was taken up in DCM, washed with water. The organic layer was separated, dried, and evaporated. The residue was purified by chromatography (dichloramethane) to afford 3-(2-(2-chloroethoxy)ethoxy)prop-1-yne in 70% yield.
Step 2:
To a solution of 3-(2-(2-chloroethoxy)ethoxy)prop-1-yne (81 mg, 0.5 mmol), 2-(2,6-dioxopiperidin-3-yl)-4-hydroxy-isoindoline-1,3-dione (70 mg, 0.25 mmol) in DMF (2 mL) was added KHCO$_3$ (50 mg) and KI (10 mg). The reaction mixture was stirred at 70° C. for 12 hour prior to being taken up in ethyl acetate and water. The organic layer was separated, dried, and evaporated. The residue was purified by chromatography (DCM:EtOAc 2:1) to afford 2-(2,6-dioxopiperidin-3-yl)-4-(2-(2-(prop-2-yn-1-yloxy)ethoxy) ethoxy) isoindoline-1,3-dione (80 mg, 80%). $^1$H NMR (400 MHz, CDCl$_3$) δ 7.69 (dd, J=8.4, 7.4, Hz, 1H), 7.48 (d, J=7.3 Hz, 1H), 7.32-7.27 (m, 1H), 5.00-4.96 (m, 1H), 4.43-4.32 (m, 2H), 4.22 (s, 2H), 3.99-3.90 (m, 2H), 3.85-3.80 (m, 2H), 3.74-3.70 (m, 2H), 2.99-2.71 (m, 3H), 2.52 (s, 1H), 2.14-2.10 (m, 1H). ESI-MS: 401.10.

Example 20

Synthesis of 2-(2,6-dioxopiperidin-3-yl)-4-((4-(4-ethynyl-1H-pyrazol-1-yl)butyl)amino) isoindoline-1,3-dione

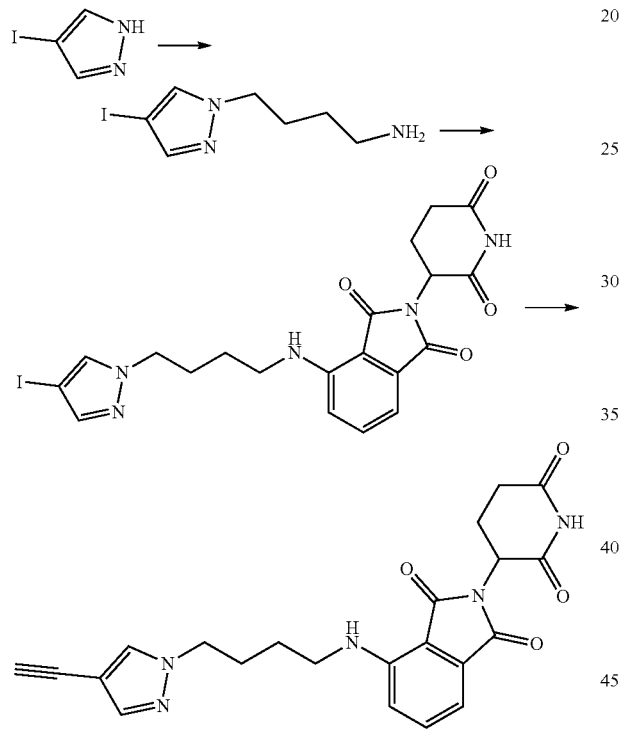

Step 1:

To a solution of 4-iodo-1H-pyrazole (2.4 g, 12 mmol) and triethylamine (1.85 mL, 13 mmol) in DCM (20 mL) at 0° C. was added MsCl (1 mL, 12.6 mmol). The reaction mixture was allowed to warm to r.t. and stirred for another 1 hour. The reaction mixture was quenched with saturated NH4Cl solution, extracted with DCM. The organic layer was separated, washed with brine, dried, and evaporated. The residue was dissolved in CH$_3$CN (70 mL) and tert-butyl (4-hydroxybutyl)carbamate (1.89 g, 10 mmol) and Cs$_2$CO$_3$ (3.9 g, 12 mmol) was added. The reaction mixture was heated to reflux for 12 h. After the reaction was cooled, the mixture was filtered and the filtrate was evaporated. The residue was taken up in EtOAc and water. The organic layer was separated, washed with brine, dried, and evaporated. The residue was purified by chromatography (EtOAc/Hexanes: 1:2) to afford crude tert-butyl (4-(4-iodo-1H-pyrazol-1-yl) butyl)carbamate (2.3 g, 53%), which was treated with DCM (5 mL) and TFA (5 mL). The reaction mixture was stirred for 12 hours. All the volatiles were removed under vacuum and the residue was subject to HPLC purification to afford the 4-(4-iodo-1H-pyrazol-1-yl)butan-1-amine.

Step 2:

To a solution of TFA salt of 4-(4-iodo-1H-pyrazol-1-yl)butan-1-amine (378 mg, 1 mmol) and 2-(2,6-dioxopiperidin-3-yl)-4-fluoroisoindoline-1,3-dione (276 mg, 1 mmol) in DMF (1 mL) was added DIPEA (0.52 mL, 3 mmol). The reaction mixture was heated at 90° C. for 12 hours. The reaction mixture was cooled and treated with EtOAc and brine. The organic layer was separated, dried, and evaporated. The residue was subject to HPLC purification to afford 2-(2,6-dioxopiperidin-3-yl)-4-((4-(4-iodo-1H-pyrazol-1-yl) butyl)amino)isoindoline-1,3-dione (122 mg, 23% yield).

Step 3:

To a Schlenk tube was added CuI (5.3 mg), Pd(Ph$_3$P)$_2$Cl$_2$ (20 mg), 2-(2,6-dioxopiperidin-3-yl)-4-((4-(4-iodo-1H-pyrazol-1-yl)butyl)amino)isoindoline-1,3-dione (100 mg, 0.2 mmol), and ethynyltrimethylsilane (39.2 mg, 0.4 mmol), THF (4 mL) and Et$_3$N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford 2-(2,6-dioxopiperidin-3-yl)-4-((4-(4-ethynyl-1H-pyrazol-1-yl)butyl)amino) isoindoline-1,3-dione (50 mg, 60% yield). ESI-MS: 420.13.

Example 21

Synthesis of 3-(4-((4-(4-ethynyl-1H-pyrazol-1-yl) butyl)amino)-1-oxoisoindolin-2-yl)piperidine-2,6-dione

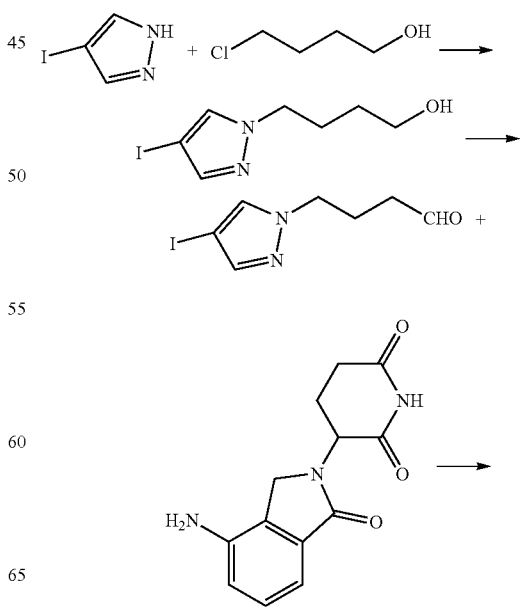

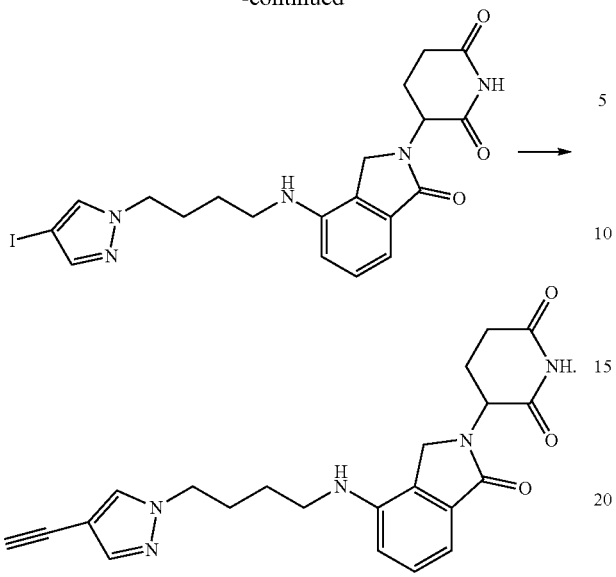

Step 1:

To a solution of 4-iodo-1H-pyrazole (3.88 g, 20 mmol) in $CH_3CN$ (140 mL) was added 4-chlorobutan-1-ol (3.3 g, 1.3 eq), $Cs_2CO_3$ (16.4 g, 60 mmol), and NaI (600 mg). The reaction mixture was heated at 50° C. for 12 hour. The reaction mixture was filtered and the filtrate was evaporated. The residue was purified by chromatography (EtOAc/Hexanes: 1:1 to EtOAc) to afford 4-(4-iodo-1H-pyrazol-1-yl)butan-1-ol (4 g, 75%).

Step 2:

To a solution of 4-(4-iodo-1H-pyrazol-1-yl)butan-1-ol (4 g, 15 mmol) in DMSO (24 mL) and $Et_3N$ (16 mL) was added $SO_3$-pyridine complex (7.1 g, 45 mmol). The reaction mixture was stirred for 3 h prior to being quenched with water. The reaction mixture was extracted with EtOAc. The organic layer was separated, washed with brine, dried, and evaporated. The residue was purified by chromatography (EtOAc/Hexanes: 1:2 to EtOAc) to afford 4-(4-iodo-1H-pyrazol-1-yl)butanal (2.8 g, 73%). $^1$H NMR (400 MHz, $CDCl_3$) δ 9.76 (s, 1H), 7.52 (s, 1H), 7.44 (s, 1H), 4.20 (t, J=6.7 Hz, 2H), 2.48 (t, J=6.9 Hz, 2H), 2.18-2.10 (m, 2H).

Step 3:

To a solution of 4-(4-iodo-1H-pyrazol-1-yl)butanal (526 mg, 2 mmol) and lenalidomide (520 mg, 2 mmol) in DCE (20 mL) was added acetic acid (0.06 mL). The reaction was stirred for 20 minutes prior to the addition of $NaHB(OAc)_3$ (848 mg). The reaction mixture was stirred for 12 h prior to being quenched with water. The reaction mixture was extracted with DCM. The organic layer was separated, washed with brine, dried, and evaporated. The residue was purified by HPLC to afford 3-(4-((4-(4-iodo-1H-pyrazol-1-yl)butyl)amino)-1-oxoisoindolin-2-yl)piperidine-2,6-dione (420 mg, 38%). $^1$H NMR (400 MHz, MeOD) δ 7.73-7.70 (m, 1H), 7.50-7.45 (m, 1H), 7.32-7.25 (m, 1H), 7.10-7.05 (m, 1H), 6.80-6.75 (m, 1H), 5.16-5.06 (m, 1H), 4.28-4.20 (m, 2H), 4.22-4.12 (m, 2H), 3.24-3.20 (m, 2H), 2.84-2.80 (m, 2H), 2.48-2.40 (m, 1H), 2.20-2.15 (m, 1H), 1.99-1.89 (m, 2H), 1.63-1.58 (m, 2H). ESI-MS: 508.95.

Step 4:

To a Schlenk tube was added CuI (9.5 mg), $Pd(Ph_3P)_2Cl_2$ (35 mg), 3-(4-((4-(4-iodo-1H-pyrazol-1-yl)butyl)amino)-1-oxoisoindolin-2-yl)piperidine-2,6-dione (267 mg, 0.5 mmol), and ethynyltrimethylsilane (98 mg, 1 mmol), THF (4 mL) and $Et_3N$ (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product (215 mg, 90%), which was dissolved in THF and a solution of TBAF in THF (1M, 0.45 mL) was added. After 5 minutes, the reaction mixture was evaporated and the residue was purified by chromatography (EtOAc) to afford crude product, which was further purified by HPLC to afford 3-(4-((4-(4-ethynyl-1H-pyrazol-1-yl)butyl)amino)-1-oxoisoindolin-2-yl)piperidine-2,6-dione (100 mg, 55% yield). ESI-MS: 406.24.

Example 22

Synthesis of 3-(4-((4-(4-ethynyl-1H-imidazol-1-yl)butyl)amino)-1-oxoisoindolin-2-yl)piperidine-2,6-dione

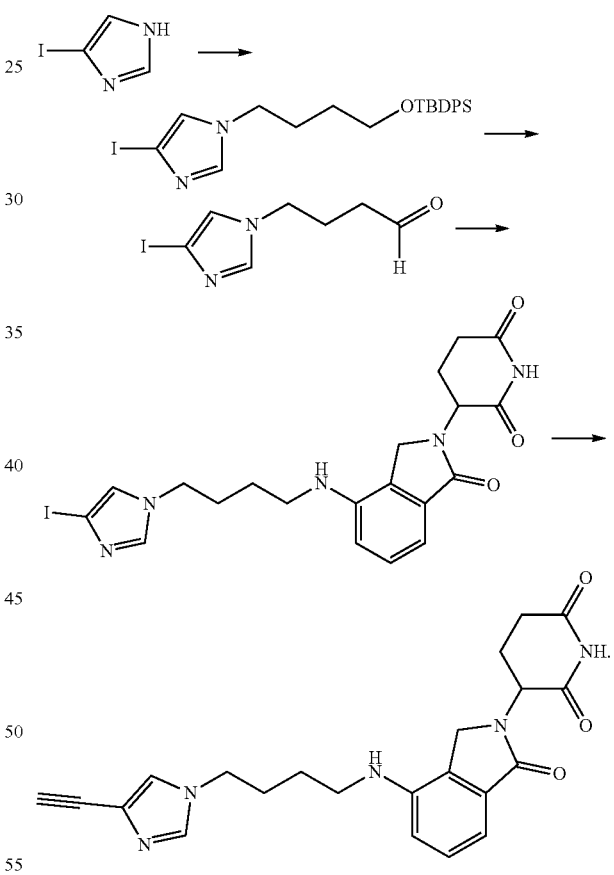

Step 1:

To a suspension of 4-iodo-1H-imidazole (3.88 g, 20 mmol) in THF (140 mL) was added NaH (960 mg, 24 mmol, 1.2 eq) portionwise at 0° C. under $N_2$. The mixture was stirred for 20 minutes at 0° C. prior to the addition of (4-bromobutoxy)(tert-butyl)diphenylsilane (3.5 g, 9 mmol). The reaction mixture was allowed to warm to r.t. and stirred for 1 h. The reaction mixture was heated at reflux for 4 hours. The reaction mixture was quenched with water and extracted with EtOAc. The residue was purified by chromatography (EtOAc/Hexanes: 1:1 to EtOAc) to afford 1-(4-

((tert-butyldiphenylsilyl)oxy)butyl)-4-iodo-1H-imidazole (1 g, 22%). $^1$H NMR (400 MHz, CDCl$_3$) δ 7.70-7.62 (m, 4H), 7.51-7.38 (m, 6H), 7.33 (s, 1H), 6.97 (s, 1H), 3.92 (t, J=6.9 Hz, 2H), 3.70 (t, J=5.5 Hz, 2H), 1.94-1.83 (m, 2H), 1.57-1.50 (m, 2H), 1.07 (s, 9H).

Step 2:

To a solution of 1-(4-((tert-butyldiphenylsilyl)oxy)butyl)-4-iodo-1H-imidazole (1 g, 2 mmol) in THF (8 mL) was added a solution of TBAF in THF (1M, 2 mL) was added. After 1 hour, the reaction mixture was evaporated and the residue was purified by chromatography (EtOAc) to afford 4-(4-iodo-1H-imidazol-1-yl)butan-1-ol (80 mg), which was dissolved in DMSO (2 mL) and Et$_3$N (1 mL). SO$_3$-pyridine complex (96 mg, 0.6 mmol) was then added. The reaction mixture was stirred for 1 h prior to being quenched with water. The reaction mixture was extracted with EtOAc. The organic layer was separated, washed with brine, dried, and evaporated. The residue was purified by chromatography (EtOAc/Hexanes: 1:2 to EtOAc) to afford 4-(4-iodo-1H-imidazol-1-yl)butanal. $^1$H NMR (400 MHz, CDCl$_3$) δ 9.80 (s, 1H), 7.37 (s, 1H), 7.02 (s, 1H), 4.01 (t, J=7.0 Hz, 2H), 2.50 (t, J=6.9 Hz, 2H), 2.25-2.01 (m, 2H).

Step 3:

To a solution of 4-(4-iodo-1H-imidazol-1-yl)butanal (240 mg, 0.9 mmol) and lenalidomide (235 mg, 0.9 mmol) in DCE (10 mL) was added acetic acid (0.06 mL). The reaction was stirred for 20 minutes prior to the addition of NaHB(OAc)$_3$ (381 mg). The reaction mixture was stirred for 12 h prior to being quenched with water. The reaction mixture was extracted with DCM. The organic layer was separated, washed with brine, dried, and evaporated. The residue was purified by HPLC to afford 3-(4-((4-(4-iodo-1H-imidazol-1-yl)butyl)amino)-1-oxoisoindolin-2-yl)piperidine-2,6-dione (320 mg, 70%). H NMR (400 MHz, MeOD) δ 8.85 (s, 1H), 7.74 (s, 1H), 7.35 (t, J=7.6 Hz, 1H), 7.12 (d, J=7.6 Hz, 1H), 6.84 (d, J=8.0 Hz, 1H), 5.18 (dd, J=13.2, 5.1 Hz, 1H), 4.28-4.20 (m, 4H), 3.39-3.30 (m, 2H), 2.99-2.87 (m, 1H), 2.81-2.71 (m, 1H), 2.57-2.40 (m, 1H), 2.21-2.15 (m, 1H), 2.09-1.93 (m, 3H), 1.75-1.62 (m, 2H). ESI-MS: 508.03.

Step 4:

To a Schlenk tube was added CuI (5.7 mg), Pd(Ph$_3$P)$_2$Cl$_2$ (21 mg), 3-(4-((4-(4-iodo-1H-imidazol-1-yl)butyl)amino)-1-oxoisoindolin-2-yl)piperidine-2,6-dione (150 mg, 0.3 mmol), and ethynyltriisopropylsilane (109 mg, 0.6 mmol), THF (4 mL) and Et$_3$N (1 mL). The reaction mixture was heated at 60° C. for 12 hours. The reaction mixture was cooled and treated with EtOAc and brine. The organic layer was separated, dried, and evaporated. The residue was purified by chromatography (DCM:MeOH 9:1) to afford crude product (100 mg, 0.18 mmol), which was dissolved in THF and a solution of TBAF in THF (1M, 0.2 mL) was added. After 5 minutes, the reaction mixture was evaporated and the residue was purified by HPLC to afford 3-(4-((4-(4-ethynyl-1H-imidazol-1-yl)butyl)amino)-1-oxoisoindolin-2-yl)piperidine-2,6-dione (55 mg). ESI-MS: 406.12.

Example 23

Synthesis of 3-(4-(5-(5-ethynyl-1-methyl-1H-imidazol-2-yl)pent-1-yn-1-yl)-1-oxoisoindolin-2-yl)piperidine-2,6-dione

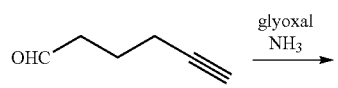

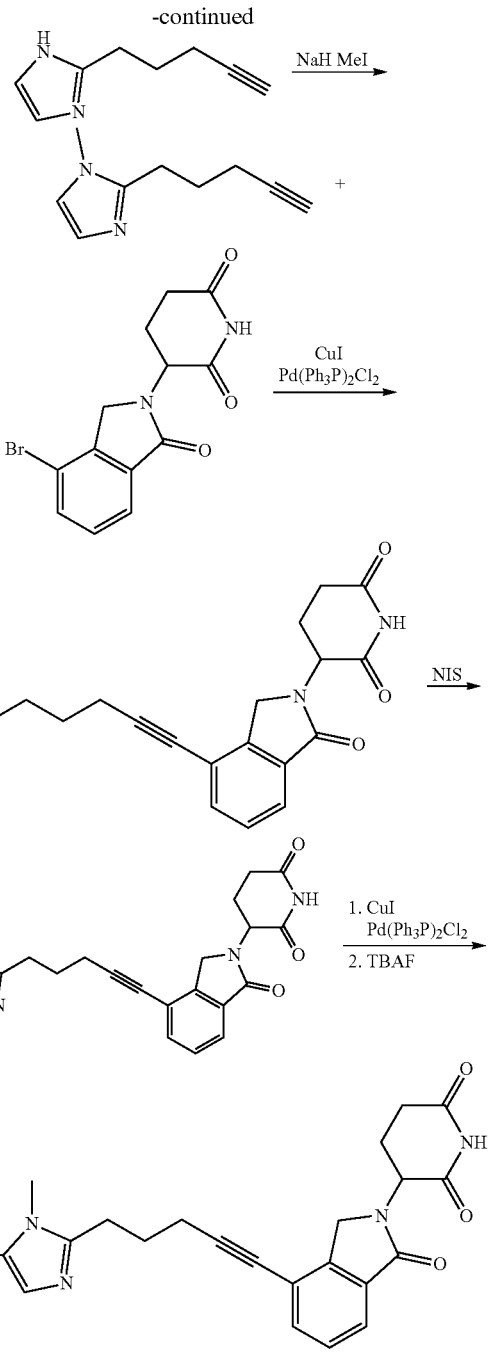

Step 1:

Hex-5-ynal (2 g, 15 mmol) was carefully dissolved in a solution of ammonia in methanol (7M, 21.4 mL) at 0° C. To this mixture was added glyoxal (10.87 g, 40% wt solution in water) dropwise. The reaction mixture was allowed to warm to r.t. and stirred for 12 h. The reaction mixture was concentrated, extracted with EtOAc. The organic layer was filtered to remove the insoluble. The residue was purified by chromatography (DCM/MeOH: 9:1) to afford 2-(pent-4-yn-1-yl)-1H-imidazole (1 g, 50%). H NMR (400 MHz, CDCl$_3$) δ 9.10 (s, 1H), 6.99 (s, 2H), 2.91-2.85 (m, 2H), 2.28-2.20 (m, 2H), 2.04-2.00 (m, J=10.8 Hz, 4H).

Step 2:

To a solution of 2-(pent-4-yn-1-yl)-1H-imidazole (1.4 g, 10 mmol) in THF (100 mL) was added NaH (600 mg, 15 mmol) portionwise at 0° C. under N₂. The mixture was stirred for 20 minutes at 0° C. prior to the addition of MeI (0.62 mL, 10 mmol). The reaction mixture was allowed to warm to r.t. and stirred for 12 h. The reaction mixture was quenched with water and extracted with EtOAc. The residue was purified by chromatography (EtOAc/Hexanes: 1:1 to EtOAc) to afford 1-methyl-2-(pent-4-yn-1-yl)-1H-imidazole (1.4 g, 95%). ¹H NMR (400 MHz, CDCl₃) δ 6.92 (s, 1H), 6.78 (s, 1H), 3.59 (s, 3H), 2.88-2.71 (m, 2H), 2.31-2.11 (m, 2H), 2.14-1.91 (m, 3H).

Step 3:

To a Schlenk tube was added CuI (5 mg), Pd(Ph₃P)₂Cl₂ (17 mg), 1-methyl-2-(pent-4-yn-1-yl)-1H-imidazole (71 mg, 0.5 mmol), and 3-(4-bromo-1-oxoisoindolin-2-yl)piperidine-2,6-dione (80 mg, 0.25 mmol), DMF (1 mL) and Et₃N (0.5 mL). The reaction mixture was heated at 60-70° C. for 12 hours. The reaction mixture was cooled and treated with EtOAc and brine. The organic layer was separated, dried, and evaporated. The residue was purified by HPLC to afford 3-(4-(5-(1-methyl-1H-imidazol-2-yl)pent-1-yn-1-yl)-1-oxoisoindolin-2-yl)piperidine-2,6-dione (70 mg, 32% yield). ESI-MS: 724.13.

Step 4:

To a solution of 3-(4-(5-(1-methyl-1H-imidazol-2-yl)pent-1-yn-1-yl)-1-oxoisoindolin-2-yl)piperidine-2,6-dione (96 mg, 0.25 mmol) in acetic acid (2 mL) was added NIS (56 mg). The reaction was stirred for 1 h prior to being concentrated. The residue was purified by HPLC to afford 3-(4-(5-(5-iodo-1-methyl-1H-imidazol-2-yl)pent-1-yn-1-yl)-1-oxoisoindolin-2-yl)piperidine-2,6-dione (36 mg, 27%). ESI-MS: 517.12.

Step 5:

To a Schlenk tube was added CuI (1 mg), Pd(Ph₃P)₂Cl₂ (3.5 mg), 3-(4-(5-(5-iodo-1-methyl-1H-imidazol-2-yl)pent-1-yn-1-yl)-1-oxoisoindolin-2-yl)piperidine-2,6-dione (36 mg, 0.069 mmol), and ethynyltrimethylsilane (20 mg), THF (2 mL) and Et₃N (0.5 mL). The reaction mixture was heated at 50° C. for 12 hours. The reaction mixture was cooled and treated with EtOAc and brine. The organic layer was separated, dried, and evaporated. The residue was purified by chromatography (DCM:MeOH 9:1) to afford crude product, which was dissolved in THF and a solution of TBAF in THF (1M, 0.1 mL) was added. After 5 minutes, the reaction mixture was evaporated and the residue was purified by HPLC to afford 3-(4-(5-(5-ethynyl-1-methyl-1H-imidazol-2-yl)pent-1-yn-1-yl)-1-oxoisoindolin-2-yl)piperidine-2,6-dione (20 mg, 70%). ESI-MS: 406.12.

Example 24

Synthesis of 3-(4-(5-(4-ethynyl-1H-pyrazol-1-yl)pent-1-yn-1-yl)-1-oxoisoindolin-2-yl)piperidine-2,6-dione

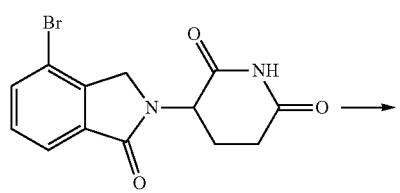 →

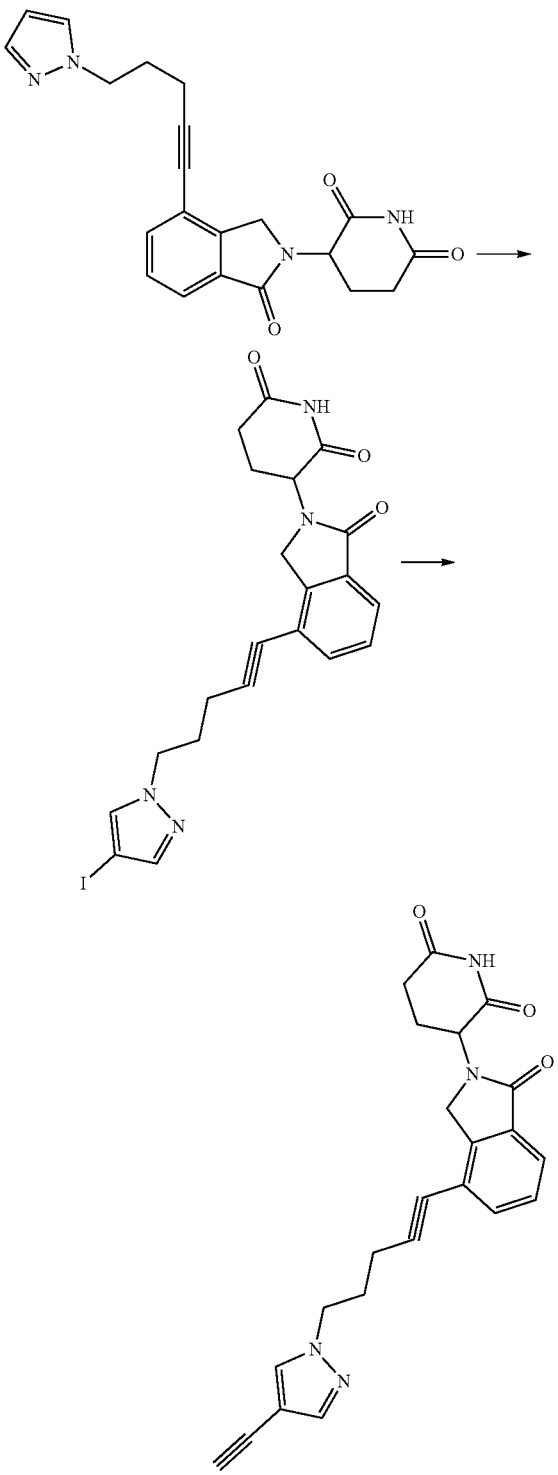

Step 1:

To a Schlenk tube was added CuI (5.3 mg), Pd(Ph₃P)₂Cl₂ (20 mg), 3-(4-bromo-1-oxoisoindolin-2-yl)piperidine-2,6-dione (100 mg, 0.31 mmol), and 1-(pent-4-yn-1-yl)-1H-pyrazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford the desired product (82 mg, 70% yield). ESI-MS: 377.15.

Step 2:

3-(4-(5-(1H-pyrazol-1-yl)pent-1-yn-1-yl)-1-oxoisoindolin-2-yl)piperidine-2,6-dione (94 mg, 0.25 mmol) in acetic acid (2 mL) was added NIS (56 mg). The reaction was stirred for 6 h prior to being concentrated. The residue was purified by HPLC to afford 3-(4-(5-(4-iodo-1H-pyrazol-1-yl)pent-1-yn-1-yl)-1-oxoisoindolin-2-yl)piperidine-2,6-dione (113 mg, 90%). ESI-MS: 503.19.

Step 3:

To a Schlenk tube was added CuI (5.3 mg), Pd(Ph$_3$P)$_2$Cl$_2$ (20 mg), 3-(4-(5-(4-iodo-1H-pyrazol-1-yl)pent-1-yn-1-yl)-1-oxoisoindolin-2-yl)piperidine-2,6-dione (100 mg, 0.2 mmol), and ethynyltrimethylsilane (39.2 mg, 0.4 mmol), THF (4 mL) and Et$_3$N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford 3-(4-(5-(4-ethynyl-1H-pyrazol-1-yl)pent-1-yn-1-yl)-1-oxoisoindolin-2-yl)piperidine-2,6-dione (40 mg, 50% yield). ESI-MS: 401.11.

Example 25

Synthesis of 3-(4-(5-(4-ethynyl-1H-pyrazol-1-yl)pentyl)-1-oxoisoindolin-2-yl)piperidine-2,6-dione

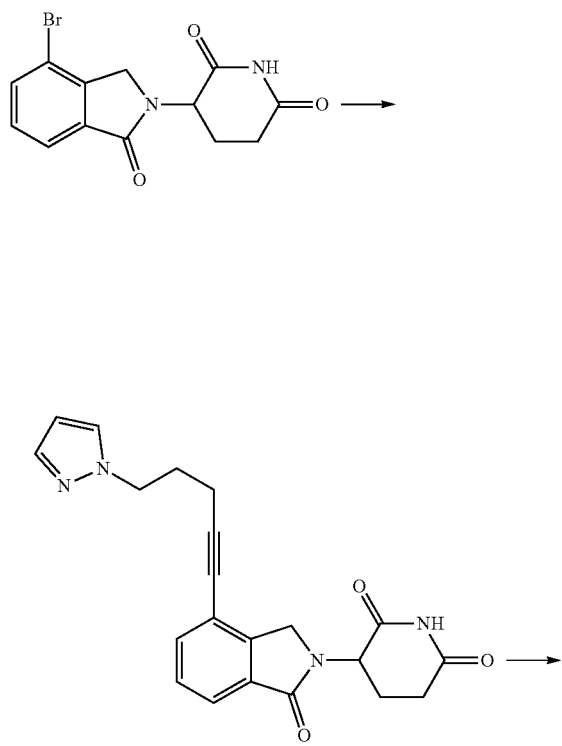

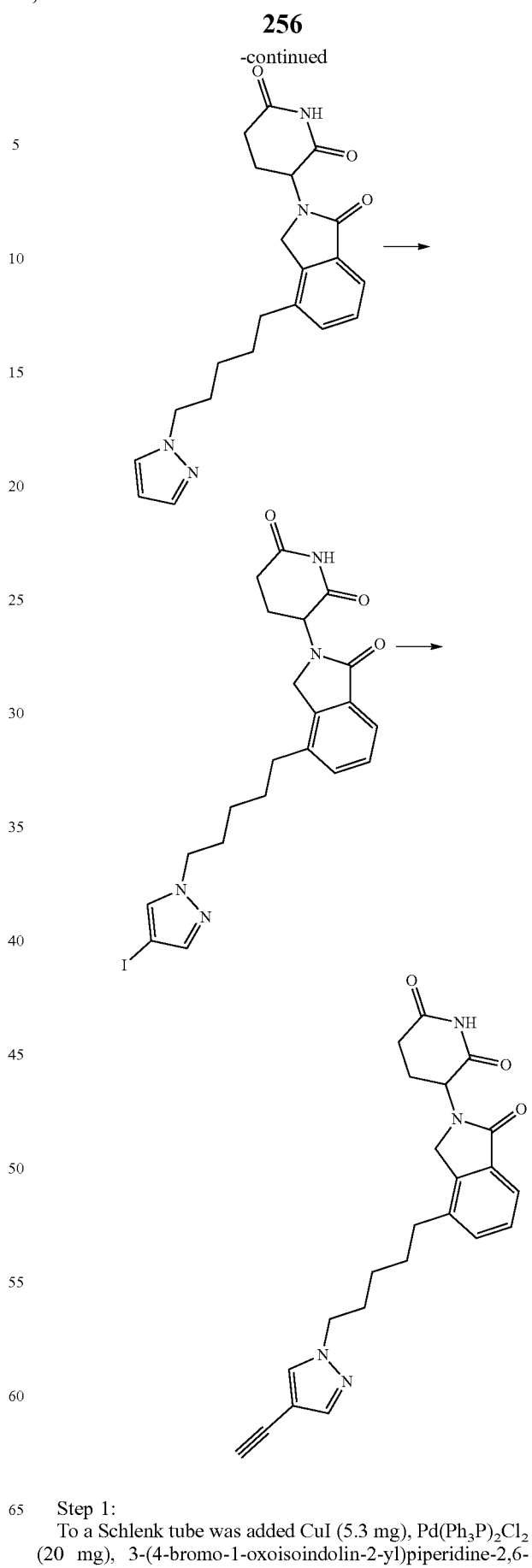

Step 1:
To a Schlenk tube was added CuI (5.3 mg), Pd(Ph$_3$P)$_2$Cl$_2$ (20 mg), 3-(4-bromo-1-oxoisoindolin-2-yl)piperidine-2,6- dione (100 mg, 0.31 mmol), and 1-(pent-4-yn-1-yl)-H-pyrazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford the desired product (82 mg, 70% yield). ESI-MS: 377.15.

Step 2:
To a solution of the product from step 1 (100 mg, 0.266 mmol) in MeOH (2 mL) was added 10% Pd/C. The reaction was stirred under H₂ balloon for 4 h prior to being filtered. The organic solvent was removed to afford 3-(4-(5-(1H-pyrazol-1-yl)pentyl)-1-oxoisoindolin-2-yl)piperidine-2,6-dione (97 mg, 95%).

Step 3:
3-(4-(5-(1H-pyrazol-1-yl)pentyl)-1-oxoisoindolin-2-yl) piperidine-2,6-dione (100 mg, 0.26 mmol) in acetic acid (2 mL) was added NIS (56 mg). The reaction was stirred for 6 h prior to being concentrated. The residue was purified by HPLC to afford 3-(4-(5-(4-iodo-1H-pyrazol-1-yl)pentyl)-1-oxoisoindolin-2-yl)piperidine-2,6-dione (118 mg, 90%). ESI-MS: 507.19.

Step 4:
To a Schlenk tube was added CuI (5.3 mg), Pd(Ph₃P)₂Cl₂ (20 mg), 3-(4-(5-(4-iodo-1H-pyrazol-1-yl)pentyl)-1-oxoisoindolin-2-yl)piperidine-2,6-dione (101 mg, 0.2 mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford 3-(4-(5-(4-ethynyl-1H-pyrazol-1-yl) pentyl)-1-oxoisoindolin-2-yl)piperidine-2,6-dione (44 mg, 55% yield). ESI-MS: 405.19.

Example 26

Synthesis of 3-(4-(5-(4-ethynyl-1H-imidazol-1-yl) pent-1-yn-1-yl)-1-oxoisoindolin-2-yl)piperidine-2,6-dione

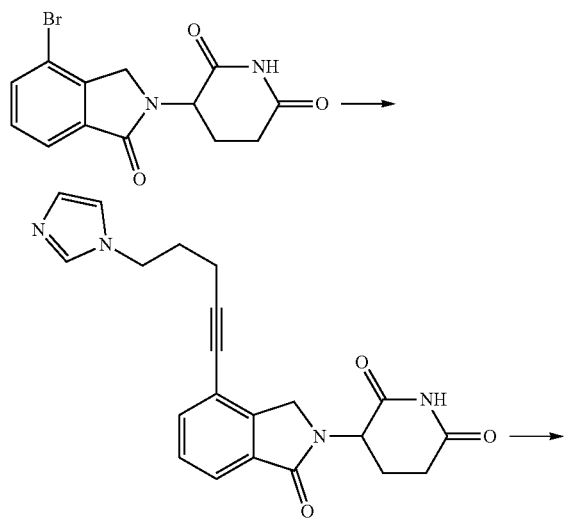

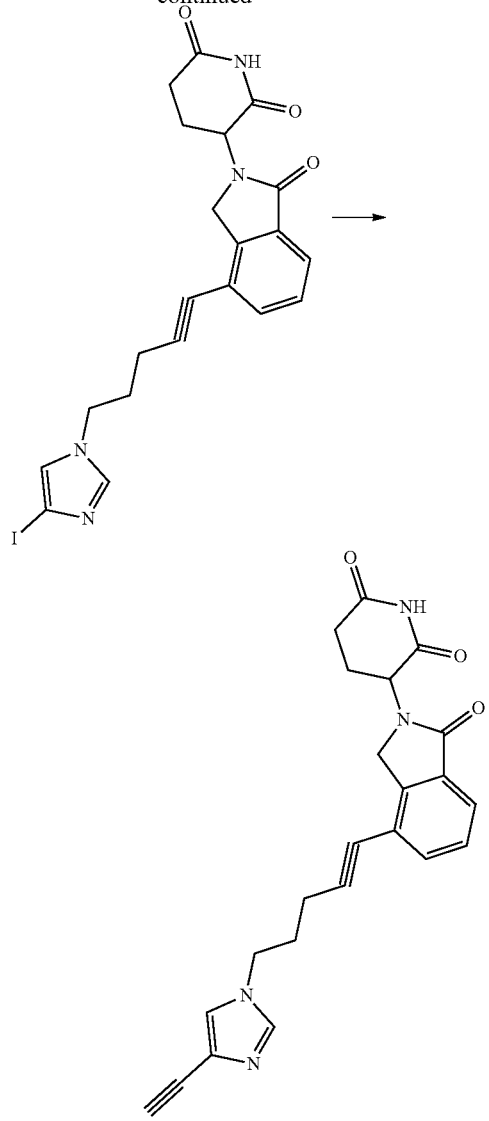

Step 1:
To a Schlenk tube was added CuI (5.3 mg), Pd(Ph₃P)₂Cl₂ (20 mg), 3-(4-bromo-1-oxoisoindolin-2-yl)piperidine-2,6-dione (100 mg, 0.31 mmol), and 1-(pent-4-yn-1-yl)-1H-imidazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford 3-(4-(5-(1H-imidazol-1-yl)pent-1-yn-1-yl)-1-oxoisoindolin-2-yl)piperidine-2,6-dione (42 mg, 36% yield). ESI-MS: 377.22.

Step 2:
3-(4-(5-(1H-imidazol-1-yl)pent-1-yn-1-yl)-1-oxoisoindolin-2-yl)piperidine-2,6-dione (100 mg, 0.26 mmol) in acetic acid (2 mL) was added NIS (56 mg). The reaction was stirred for 1 h prior to being concentrated. The residue was purified by HPLC to afford 3-(4-(5-(4-iodo-1H-imidazol-1-yl)pent-1-yn-1-yl)-1-oxoisoindolin-2-yl)piperidine-2,6-dione (39 mg, 30%). ESI-MS: 503.11.

Step 3:
To a Schlenk tube was added CuI (5.3 mg), Pd(Ph₃P)₂Cl₂ (20 mg), 3-(4-(5-(4-iodo-1H-imidazol-1-yl)pent-1-yn-1-yl)-

1-oxoisoindolin-2-yl)piperidine-2,6-dione (101 mg, 0.2 mmol), and ethynyltrimethylsilane (39.2 mg, 0.4 mmol), THF (4 mL) and Et$_3$N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford 3-(4-(5-(4-ethynyl-1H-imidazol-1-yl)pent-1-yn-1-yl)-1-oxoisoindolin-2-yl)piperidine-2,6-dione (50 mg, 63% yield). ESI-MS: 401.17.

Example 27

Synthesis of 3-(4-(5-(4-ethynyl-1H-1,2,3-triazol-1-yl)pent-1-yn-1-yl)-1-oxoisoindolin-2-yl)piperidine-2,6-dione

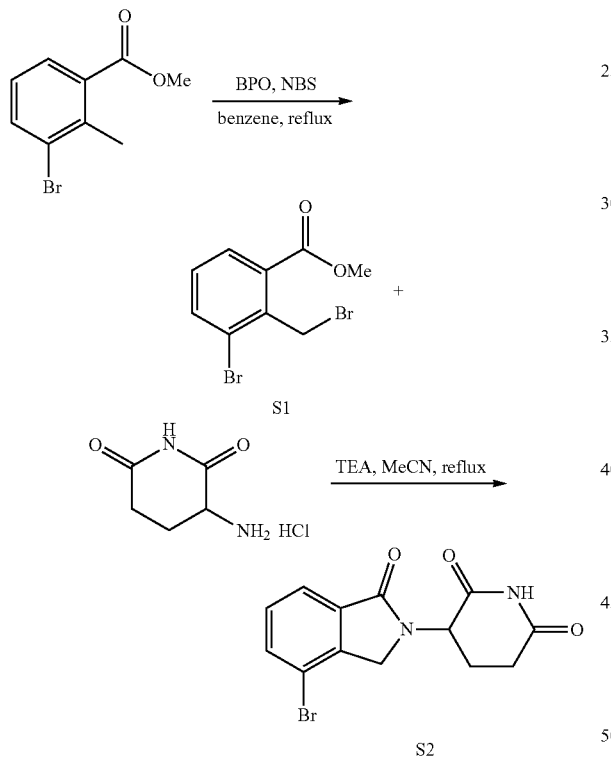

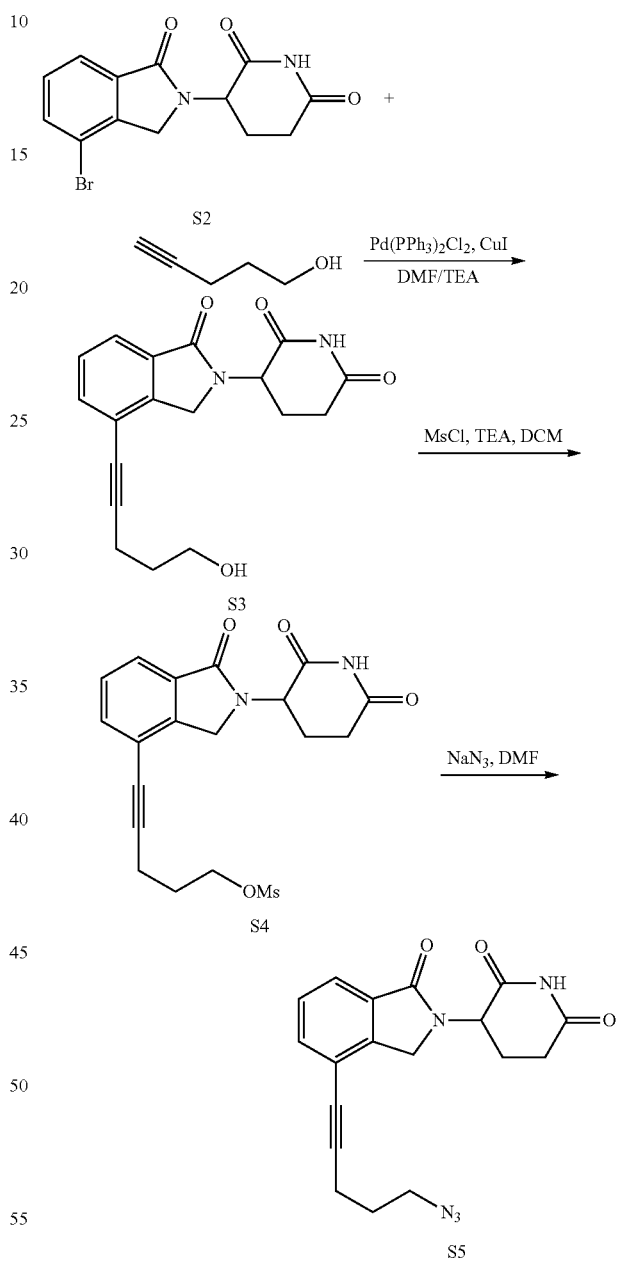

To a round-bottomed flask, methyl 3-bromo-2-methylbenzoate (18.3 g, 80 mmol, 1.0 eq), N-bromosuccinimide (17.1 g, 96 mmol, 1.2 eq) and benzoyl peroxide (1.9 g, 8.0 mmol, 0.1 eq) were mixed in 150 mL of benzene. The reaction mixture was stirred at 80° C. for 12 h. After cooling to room temperature, the reaction mixture was evaporated to remove most of the solvent. The resulting residue was purified by flash column chromatography with hexane/ethyl acetate to give the desired product S1 as colorless oil (23.4 g, 95% yield).

To a round-bottomed flask, compound S1 (23.4 g, 76 mmol, 1.0 eq) and 3-aminopiperidine-2,6-dione hydrochloride (13.8 g, 83.6 mmol, 1.1 eq) were mixed in 150 mL of acetonitrile. The resulting reaction mixture was stirred at 85° C. for 12 h. After cooling to room temperature, the reaction mixture was poured into 200 mL of cooled water. The resulting mixture was filtrated and the solid was washed with water and ethyl acetate sequentially. After drying, a slightly purple solid was obtained, which was used directly in the following reactions without further purification (19.6 g, 80% yield). UPLC-MS calculated for C$_{13}$H$_{12}$BrN$_2$O$_3$ [M+1]$^+$: 323.00, found 322.96.

To a round-bottomed flask, compound S2 (2.59 g, 8.0 mmol, 1.0 eq), 4-pentyn-1-ol (1.01 g, 12.0 mmol, 1.5 eq), Pd(PPh$_3$)$_2$Cl$_2$ (421 mg, 0.6 mmol, 0.075 eq) and CuI (228 mg, 1.2 mmol, 0.15 eq) were mixed in 24 mL of DMF. The reaction mixture was sealed and filled with nitrogen. 10 mL of triethylamine was added and the reaction mixture was heated to 80° C. to stir for 8 h. After cooling to room temperature, the reaction mixture was evaporated to remove most of the solvent to give the dark residue, which was purified by flash column chromatography with DCM/MeOH to afford the final compound S3 as a white solid (2.08 g, 80% yield). UPLC-MS calculated for $C_{18}H_{19}N_2O_4$ [M+1]$^+$: 327.13, found 327.15.

To a round-bottomed flask, compound S3 (1.04 g, 3.2 mmol, 1.0 eq) was suspended in 100 mL of dichloromethane. Mesyl chloride (495 μL, 6.4 mmol, 2.0 eq) was added dropwise to the upper solution at 0° C. Then triethylamine (1.33 mL, 9.6 mmol, 3.0 eq) was added. The suspended solution turned clear within 1 min. The reaction mixture was stirred at room temperature for 1 h. Then the solvent was evaporated to give crude product S4, which was used in the next step reaction without further purification. UPLC-MS calculated for $C_{19}H_{21}N_2O_6S$ [M+1]$^+$: 405.11, found 405.14.

Crude S4 was dissolved in 15 mL of DMF. Then sodium azide (416 mg, 6.4 mmol, 2.0 eq) was added and the solution was stirred at 60° C. for 1 h. After cooling to room temperature, the reaction mixture was diluted with water and purified by HPLC with MeCN/H$_2$O (0.1% TFA) as the eluent to afford the desired compound S5 as a white solid (690 mg, 61% yield). UPLC-MS calculated for $C_{18}H_{18}N_5O_3$ [M+1]$^+$: 352.14, found 352.15.

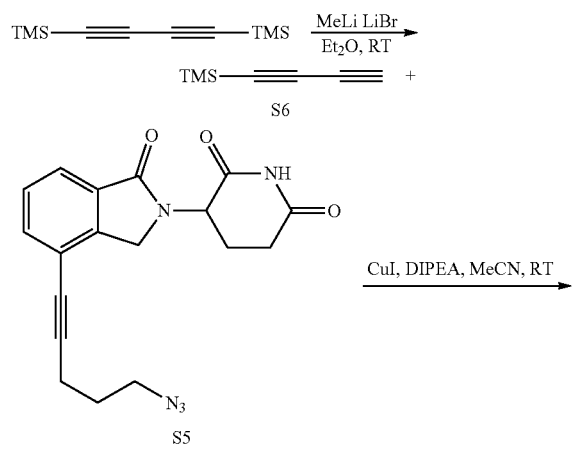

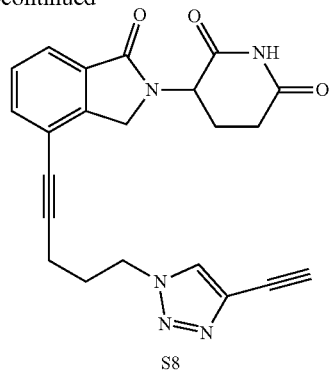

To a solution of 1,4-bis(trimethylsiliyl)-buta-1,3-diyne (1.0 g, 5.14 mmol) in 15 mL of dry ethyl ether, MeLi LiBr (1.5 M in ether, 6.68 mmol, 4.45 mL) was added and the reaction mixture was stirred at room temperature for 12 h. The reaction was quenched with saturated NH$_4$Cl (aq) at 0° C. and the product was extracted with ethyl ether. The combined organic layer was dried over anhydrous Na$_2$SO$_4$. After filtration, the solution was carefully evaporated in vacuum to give the crude S6 as slightly dark oil, which was diluted in 5 mL of t-BuOH and stored below 0° C.

To a solution of azide S5 (690 mg, 1.97 mmol, 1.0 eq), S6 (0.5 M in t-BuOH, 4.7 mL, 2.36 mmol, 1.2 eq) in 30 mL of acetonitrile was added CuI (74 mg, 0.39 mmol, 0.2 eq) and DIPEA (1.7 mL, 9.83 mmol, 5.0 eq). The reaction mixture was stirred at room temperature for 12 h. After evaporation to remove the solvent, the crude residue was purified by reverse flash column with MeCN/H$_2$O (0.1% TFA) to give the product S7 as a white solid (338 mg, 36% yield). UPLC-MS calculated for $C_{25}H_{28}N_5O_3Si$ [M+1]$^+$: 474.20, found 474.23.

To suspended solution of S7 (338 mg, 0.71 mmol, 1.0 eq) in 10 mL of acetonitrile was added TBAF (1.0 M in THF, 1.42 mL, 1.42 mmol, 2.0 eq). The solution turned clear within 1 min. After 1 h, the reaction mixture was diluted with water and purified by HPLC with MeCN/H$_2$O (0.1% TFA) to afford the desired product S8 as a white solid (270 mg, 95% yield). UPLC-MS calculated for $C_{22}H_{20}N_5O_3$ [M+1]$^+$: 402.16, found 402.21.

Example 28

Synthesis of 3-(4-(5-(4-ethynyl-1H-1,2,3-triazol-1-yl)pentyl)-1-oxoisoindolin-2-yl)piperidine-2,6-dione

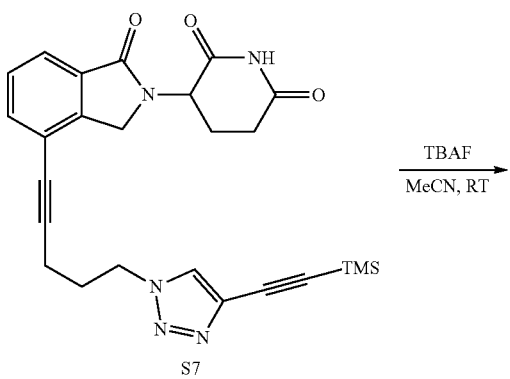

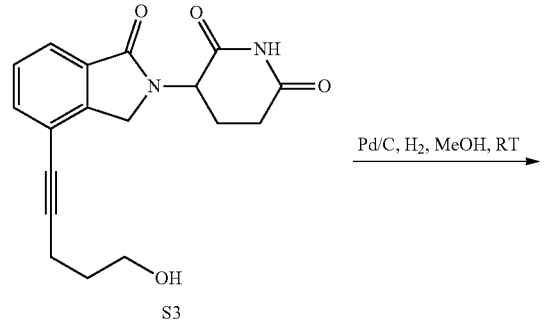

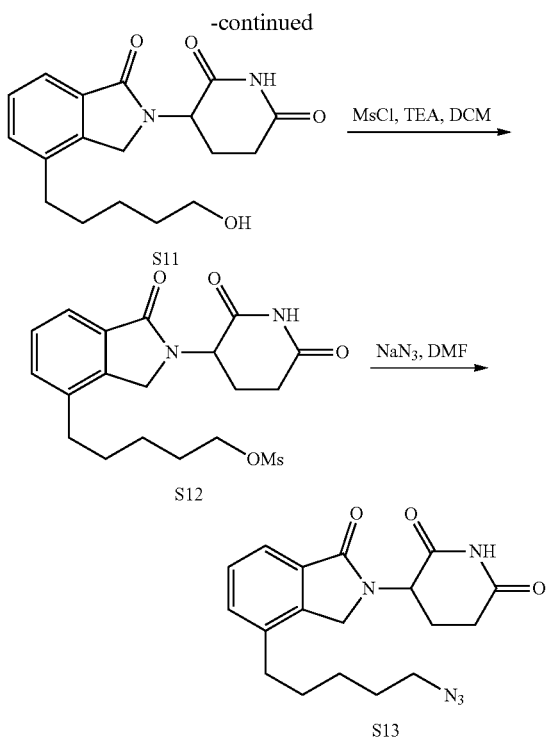

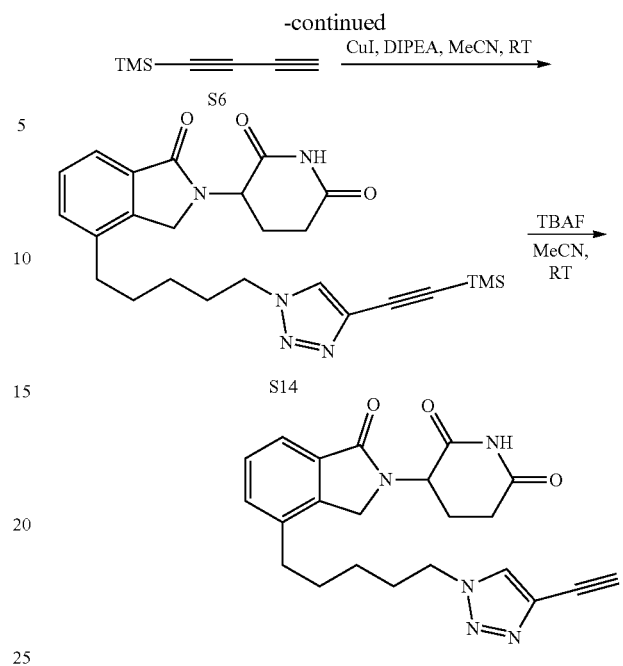

To a suspended solution of S3 (684 mg) in 100 mL of MeOH under nitrogen atmosphere was added 70 mg of Pd/C (10 wt %). Hydrogen was filled/evacuated into the flask three times. The solution was stirred at room temperature under 1 atm hydrogen atmosphere for 12 h. After consumption of the starting material, the solvent was evaporated and the residue was purified by flash column chromatography with DCM/MeOH to afford the desired product S11 as a white solid (693 mg, 90% yield). UPLC-MS calculated for $C_{18}H_{23}N_2O_4$ [M+1]$^+$: 331.17, found 331.13.

To a suspended solution of S11 (693 mg, 2.1 mmol, 1.0 eq) in 30 mL of DCM was added mesyl chloride (325 μL, 4.2 mmol, 2.0 eq) at 0° C. Then trimethylamine (0.88 mL, 6.3 mmol, 3.0 eq) was added dropwise. The solution turned clear within 1 min. After 1 h, the solvent was evaporated to give crude compound S12, which was used in the next step reaction without further purification.

The above obtained crude compound S12 was dissolved in 10 mL of DMF, and sodium azide (275 mg, 4.2 mmol, 2.0 eq) was added. Then the reaction mixture was stirred at 60° C. for 5 h. After cooling to room temperature, the reaction was diluted in water and purified by HPLC with MeCN/H$_2$O (0.1% TFA) to afford the compound S13 as a white solid (682 mg, 91% yield). UPLC-MS calculated for $C_{18}H_{22}N_5O_3$ [M+1]$^+$: 356.17, found 356.29.

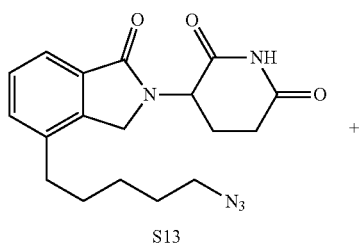

Following the procedure for the synthesis of S7, S13 (682 mg, 1.92 mmol, 1.0 eq) was used in the reaction. Finally compound S14 was obtained as a white solid (704 mg, 76% yield). UPLC-MS calculated for $C_{25}H_{32}N_5O_3Si$ [M+1]$^+$: 478.23, found 478.24.

Following the procedure for the synthesis of S8, compound S14 (704 mg, 1.47 mmol, 1.0 eq) was used in the reaction. Finally compound S15 was obtained as a white solid (565 mg, 95% yield). UPLC-MS calculated for $C_{22}H_{124}N_5O_3$ [M+1]$^+$: 406.19, found 406.26.

Example 29

Synthesis of 3-(4-((4-(4-ethynyl-1H-1,2,3-triazol-1-yl)butyl)amino)-1-oxoisoindolin-2-yl)piperidine-2,6-dione

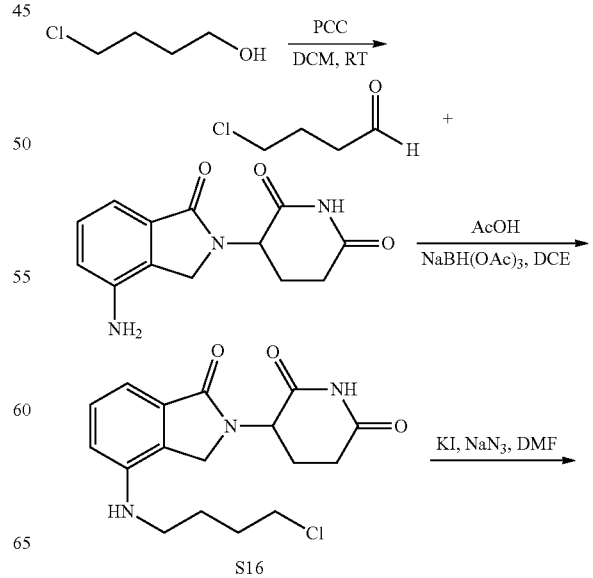

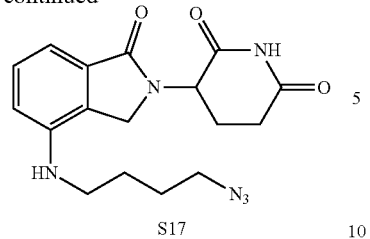

S17

To a solution of PCC (7.29 g, 33.8 mmol, 1.2 eq) in 30 mL of DCM was added dropwise a solution of 4-chloro-1-butanol (3.06 g, 28.2 mmol, 1.0 eq) in 10 mL of DCM. The solution was stirred at room temperature for 1 h. Then the solution was filtered through celite and washed with ethyl ether. The combined organic layer was evaporated and the concentrated residue was purified by flash column chromatography with DCM to afford the desired product as colorless oil.

To a solution of lenalidomide (950 mg, 3.66 mmol, 1.0 eq) and 4-chloro-1-butanal (429 mg, 4.03 mmol, 1.1 eq) in 30 mL of DCE was added acetic acid (0.2 mL, 3.66 mmol, 1.0 eq) and sodium triacetoxyborohydride (1.55 g, 7.32 mmol, 2.0 eq). The suspended solution was stirred at room temperature for 12 h. The reaction mixture was quenched with brine and the product was extracted with DCM. The combined organic layer was dried over anhydrous $Na_2SO_4$ and the solvent was evaporated to give the crude product, which was purified by flash column chromatography with DCM/MeOH to afford the desired product S16 as a white solid (128 mg, 10% yield). UPLC-MS calculated for $C_{17}H_{21}ClN_3O_3$ $[M+1]^+$: 350.13, found 350.11.

To a solution of S16 (128 mg, 0.366 mmol, 1.0 eq) in 3 mL of DMF was added potassium iodide (6.1 mg, 0.037 mmol, 0.1 eq) and sodium azide (47.6 mg, 0.732 mmol, 2.0 eq). The solution was heat to 60° C. to stir for 2 h. After cooling to room temperature, the solution was diluted in water and purified by HPLC with $MeCN/H_2O$ (0.1% TFA) to afford the compound S17 as a white solid (117 mg, 90% yield). UPLC-MS calculated for $C_{17}H_{21}N_6O_3$ $[M+1]^+$: 357.17, found 350.20.

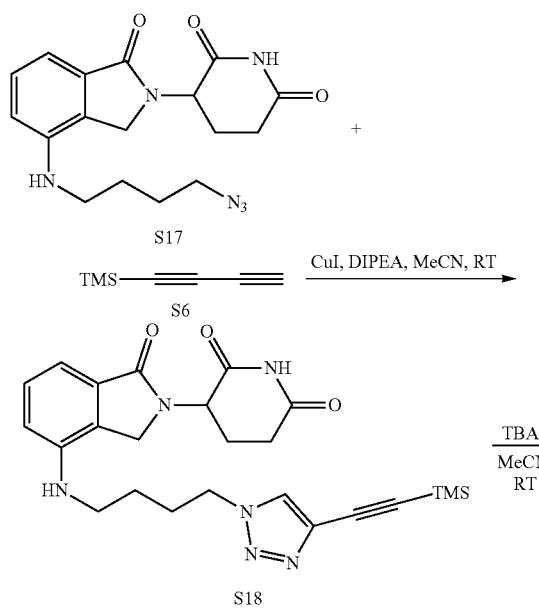

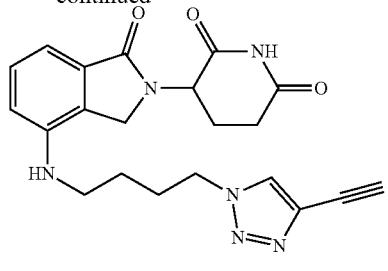

S19

Following the procedure for the synthesis of S7, the reaction was conducted with S17 (117 mg, 0.33 mmol, 1.0 eq). The compound S18 was obtained as a white solid (71 mg, 45% yield). UPLC-MS calculated for $C_{24}H_{31}N_6O_3Si$ $[M+1]^+$: 479.22, found 478.97.

Following the procedure for the synthesis of S8, the reaction was conducted with S18 (71 mg, 0.15 mmol, 1.0 eq). The compound S19 was obtained as a white solid (57 mg, 95% yield). UPLC-MS calculated for $C_{21}H_{23}N_6O_3$ $[M+1]^+$: 407.18, found 406.93.

Example 30

Synthesis of 3-(4-((4-(6-ethynylpyridin-3-yl)butyl)amino)-1-oxoisoindolin-2-yl)piperidine-2,6-dione

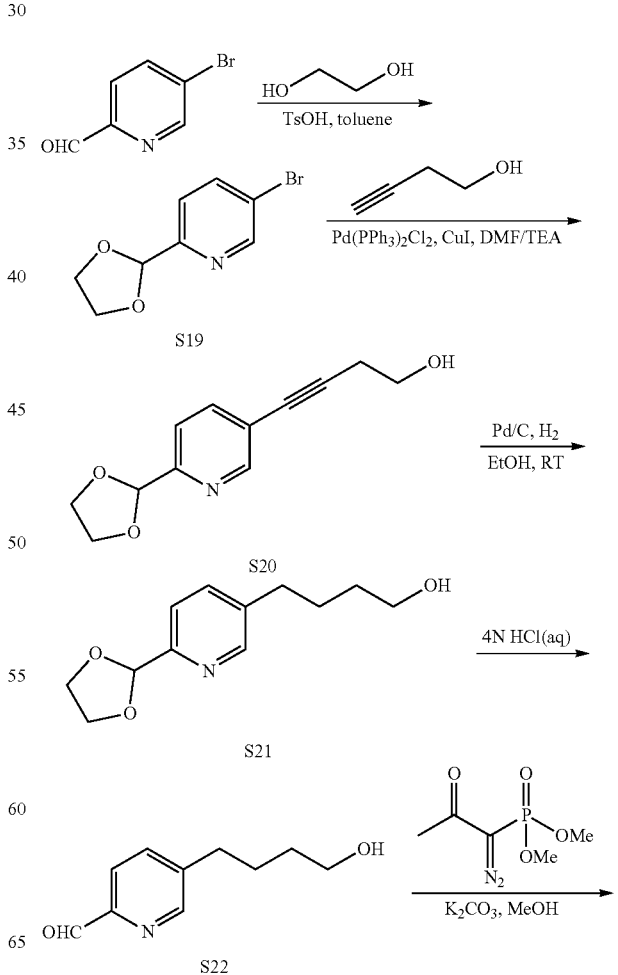

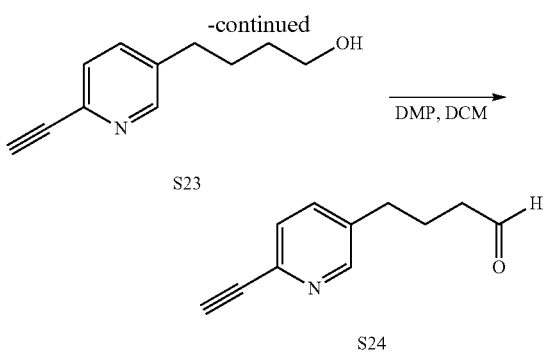

To a solution of 5-bromopyridine-2-aldehyde (13.24 g, 71.2 mmol, 1.0 eq) in 200 ml of toluene was added TsOH monohydrate (677 mg, 3.56 mmol, 0.05 eq) and ethyl-eneglycol (8.0 mL, 142.4 mmol, 2.0 eq). The solution was heated to reflux with a Dean-Stark trap for 12 h. After cooling to room temperature, the solvent was evaporated and the residue was purified by flash column chromatography with DCM/MeOH to afford the compound S19 as colorless oil (14.74 g, 90% yield).

To a round-bottomed flask, compound S19 (5.95 g, 25.9 mmol, 1.0 eq), 4-butyn-1-ol (2.36 g, 33.6 mmol, 1.3 eq), Pd(PPh$_3$)$_2$Cl$_2$ (909 mg, 1.295 mmol, 0.05 eq) and CuI (494 mg, 2.59 mmol, 0.1 eq) were mixed in 24 mL of DMF. The reaction mixture was sealed and filled with Nitrogen. 24 mL of triethylamine was added and the reaction mixture was heated to 80° C. to stir for 5 h. After cooling to room temperature, most of the solvent was evaporated and the residue was diluted in DCM and brine. The combined organic layer was dried and purified by flash column chromatography with DCM/MeOH to afford the final compound S20 as colorless oil (4.54 g. 80% yield). UPLC-MS calculated for C$_{12}$H$_{14}$NO$_3$ [M+1]$^+$: 220.10, found 220.09.

To the solution of S20 (4.54 g) in 100 mL of EtOH under nitrogen atmosphere was added 500 mg of Pd/C (10 wt %). Hydrogen was filled into the flask with three times. The solution was stirred at room temperature under 1 atm hydrogen atmosphere for 12 h. After consumption of the starting material, the solvent was evaporated and the residue was purified by flash column chromatography with DCM/MeOH to afford the desired product S21 as colorless oil (3.93 g, 85% yield). UPLC-MS calculated for C$_{12}$H$_{18}$NO$_3$ [M+1]$^+$: 224.13, found 224.14.

To the solution of S21 (1.84 g, 8.25 mmol, 1.0 eq) in 30 mL of THF was added 30 mL of 4N HCl (aq). The solution was heated to reflux for 6 h. After cooling to room temperature, the solvent was evaporated and diluted in ethyl acetate and saturated NaHCO$_3$ aqueous solution. After extraction several times, the combined organic layer was dried and the concentrated residue was purified by flash column chromatography with DCM/MeOH to afford the compound S22 as colorless oil (3.0 g, 95% yield). UPLC-MS calculated for C$_{10}$H$_{14}$NO$_2$ [M+1]$^+$: 180.10, found 180.05.

To the solution of dimethyl (1-diazo-2-oxopropyl)phosphonate (25.14 mmol, 1.5 eq) and K$_2$CO$_3$ (2.0 eq) in 80 mL of methanol was added dropwise a solution of S22 (3.0 g, 16.76 mmol, 1.0 eq) in 20 mL of methanol. The resulting solution was stirred at room temperature for 2 h. The solvent was evaporated and the residue was diluted in ethyl acetate and brine. The combined organic layer was dried over anhydrous Na$_2$SO$_4$. After filtration and evaporation, the crude product was purified by flash column chromatography to afford the desired compound S23 as colorless oil (2.1 g, 72% yield). UPLC-MS calculated for C$_{10}$H$_{14}$NO [M+1]$^+$: 176.11, found 176.01.

To a solution of S23 (1.1 g, 6 mmol, 1.0 eq) in 100 mL of DCM was added Dess-Martin Periodinane (4.6 g, 10.8 mmol, 1.8 eq). The reaction was stirred at room temperature for 2 h. 10 mL of water and 20 mL of saturated Na$_2$S$_2$O$_8$ aqueous solution was added. After being stirred for 10 min, the reaction solution was filtered through celite and washed with DCM. After extraction for 3 times, the combined organic layer was dried over anhydrous Na$_2$SO$_4$. After filtration and evaporation, the crude product was purified by flash column chromatography to afford the desired compound S24 as colorless oil (680 mg, 65% yield). UPLC-MS calculated for C$_{11}$H$_{12}$NO [M+1]$^+$: 174.09, found 174.08.

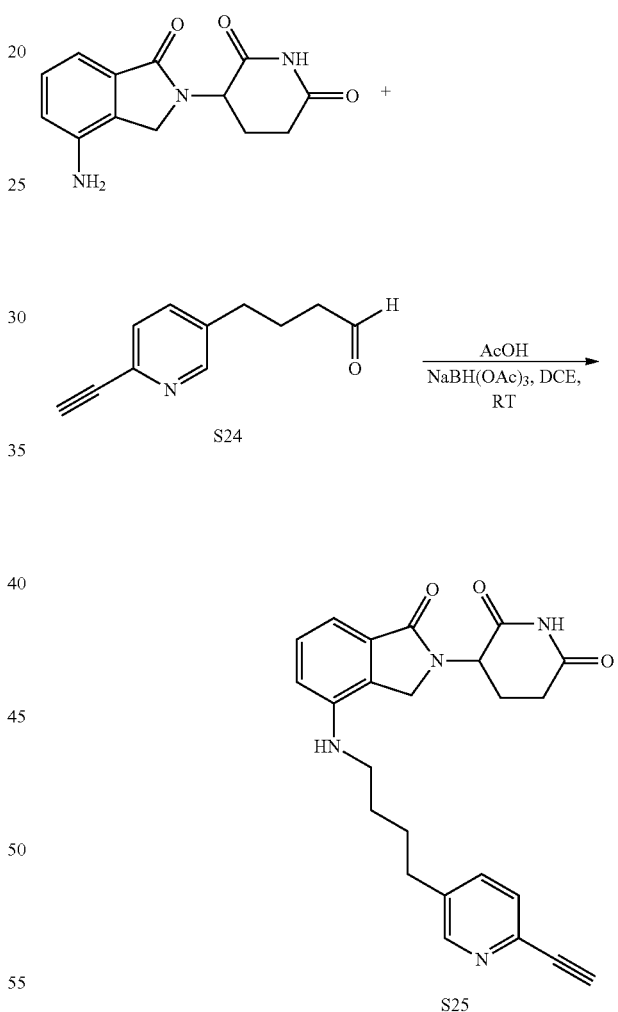

To a solution of lenalidomide (1.01 g, 3.9 mmol, 1.0 eq) and compound S24 (680 mg, 3.9 mmol, 1.0 eq) in 50 mL of DCE was added acetic acid (0.23 mL, 3.9 mmol, 1.0 eq) and sodium triacetoxyborohydride (1.66 g, 3.9 mmol, 2.0 eq). The suspended solution was stirred at room temperature for 12 h. DCM and saturated NaHCO$_3$ aqueous solution was added. After extraction, the combined organic layer was dried 974 mg, 60% yield). UPLC-MS calculated for C$_{24}$H$_{25}$N$_4$O$_3$ [M+1]$^+$: 417.19, found 416.98.

Example 31

Synthesis of 2-(2,6-dioxopiperidin-3-yl)-4-(4-(6-ethynylpyridin-3-yl)butoxy)isoindoline-1,3-dione

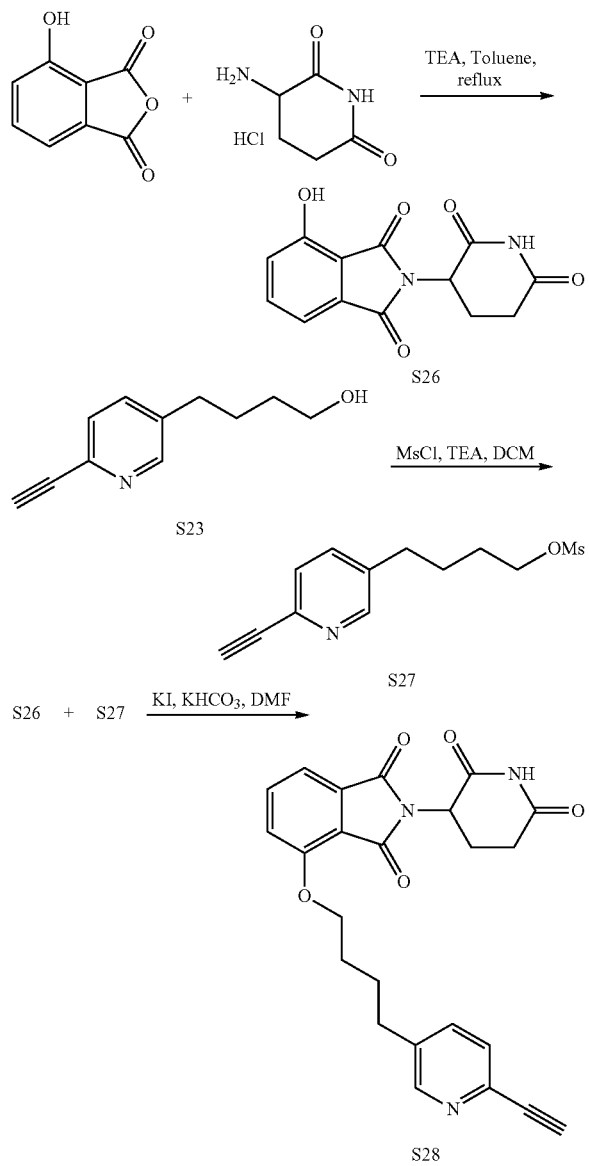

To a round-bottom flask, 3-hydroxyphthalic anhydride (1 g, 6.09 mmol) and 3-aminoperidine-2,6-dione hydrochloride (1.0 g, 6.09 mmol) were mixed in 50 mL of toluene. Triethyl amine (0.93 mL, 6.7 mmol) was added. The resulting reaction mixture was heated to reflux for 12 h with Dean-Stark trap equipment. After cooling to ambient temperature, evaporation of most of the solvent to give a crude product, which was purified by flash column chromatography with DCM:ethyl acetate to get the desired product as a slightly yellow solid S26 (1.5 g, 90% yield). $^1$H NMR (400 MHz, DMSO-d$^6$) δ (ppm) 11.16 (s, 1H), 11.08 (s, 1H), 7.65 (t, J=7.6 Hz, 1H), 7.32 (d, J=7.2 Hz, 1H), 7.25 (d, J=8.4 Hz, 1H), 5.07 (dd, J=12.8 Hz, J=5.2 Hz, 1H), 2.93-2.84 (m, 1H), 2.61-2.46 (m, 1H), 2.05-2.01 (m, 1H).

To a solution of compound S23 (210 mg, 1.2 mmol, 1.0 eq) in 10 mL of DCM at 0° C. was added mesyl chloride (0.14 mL, 1.8 mmol, 1.5 eq) and triethyl amine (0.34 mL, 2.4 mmol, 2.0 eq) sequentially. The resulting solution was stirred at room temperature for 1 h. After evaporation of the solvent, the residue was purified by flash column chromatography with DCM/MeOH to afford the compound S27 as colorless oil (224 mg, 74% yield). UPLC-MS calculated for $C_{12}H_{16}NO_3S$ [M+1]$^+$: 254.09, found 253.92.

To a solution of compound S27 (224 mg, 0.89 mmol, 1.0 eq) and S26 (243 mg, 0.89 mmol, 1.0 eq) in 4 mL of DMF was added KI (15 mg, 0.09 mmol, 0.1 eq) and KHCO$_3$ (178 mg, 1.78 mmol, 2.0 eq). The resulting solution was stirred at room temperature for 5 h. After cooling to room temperature, the solution was diluted in water and purified by HPLC with MeCN/H$_2$O (0.1% TFA) to afford the compound S28 as a white solid (290 mg, 75% yield). UPLC-MS calculated for $C_{24}H_{22}N_3O_5$ [M+1]$^+$: 432.16, found 431.92.

Example 32

Synthesis of 3-(4-(4-((6-ethynylpyridin-3-yl)oxy)butyl)-1-oxoisoindolin-2-yl)piperidine-2,6-dione

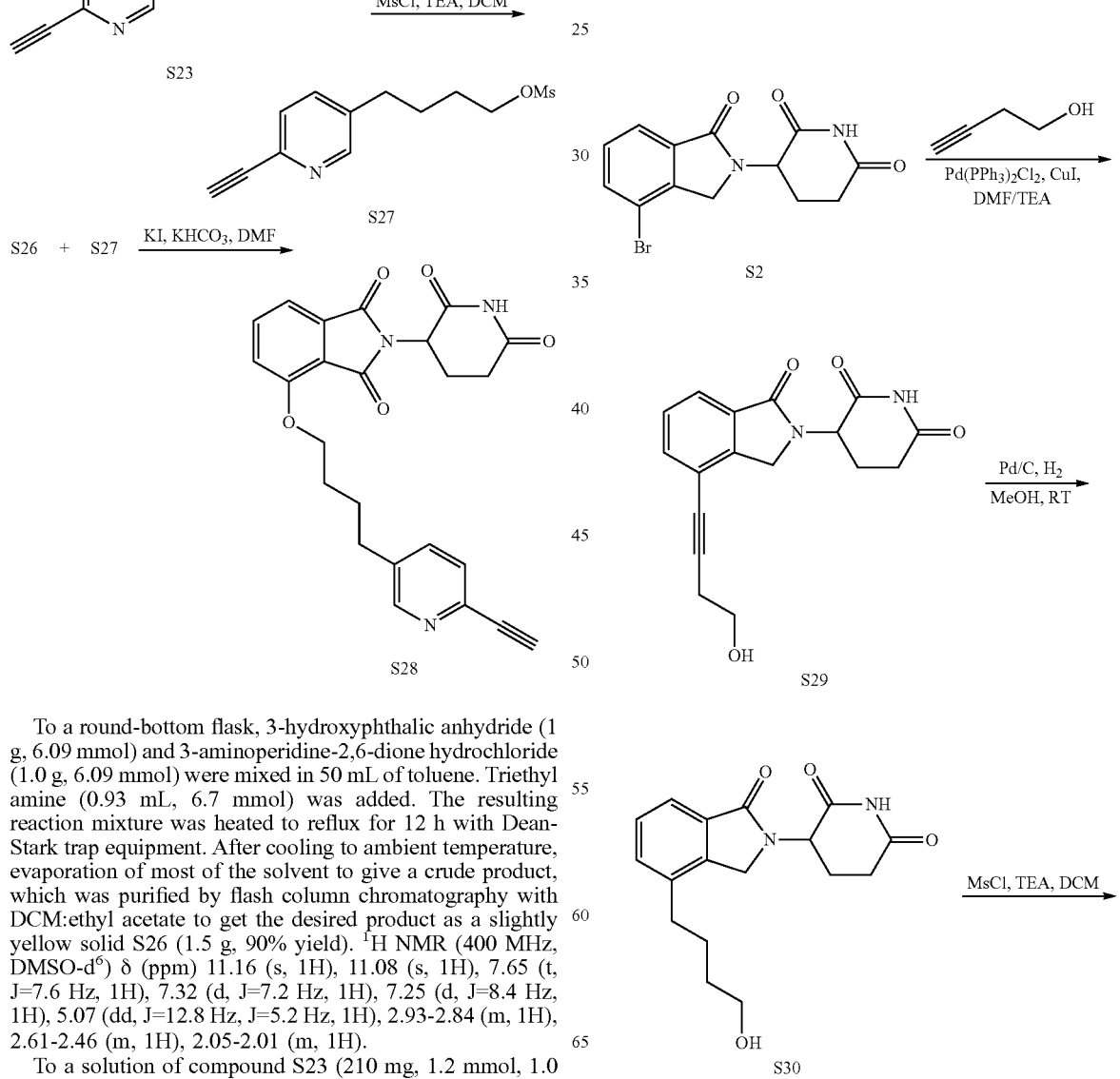

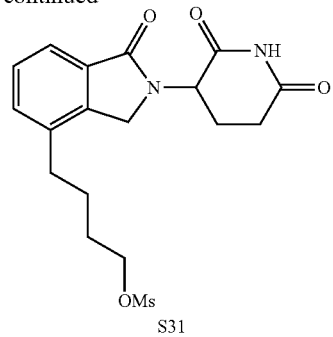

Following the procedure for the synthesis of compound S3, the reaction was conducted with S2 (1.29 g, 4.0 mmol, 1.0 eq). Finally, compound S29 was obtained as a slightly yellow solid (1.12 g, 90% yield). UPLC-MS calculated for $C_{17}H_{17}N_2O_4$ [M+1]$^+$: 313.12, found 313.13.

Following the procedure for the synthesis of compound S11, the reaction was conducted with S29 (157 mg, 0.50 mmol, 1.0 eq). Finally, compound S30 was obtained as a white solid (148 mg, 94% yield). UPLC-MS calculated for $C_{17}H_{21}N_2O_4$ [M+1]$^+$ 317.15, found 317.15.

Following the procedure for the synthesis of compound S4, the reaction was conducted with S30 (148 mg, 0.468 mmol, 1.0 eq). Finally, compound S31 was obtained as a white solid (175 mg, 95% yield). UPLC-MS calculated for $C_{18}H_{23}N_2O_6S$ [M+1]$^+$: 395.13, found 395.17.

To a solution of 2-bromo-5-hydroxypyridine (1.04 g, 6.0 mmol, 1.0 eq) and trimethylsilylacetylene (1.7 mL, 12.0 mmol, 2.0 eq) in 30 mL of anhydrous THF were added Pd(PPh$_3$)$_2$Cl$_2$ (420 mg, 0.6 mmol, 0.1 eq) and CuI (228 mg, 1.2 mmol, 0.2 eq) under nitrogen atmosphere. Then 8 mL of triethylamine was injected. The reaction flask was sealed and the reaction solution was stirred at 60° C. for 5 h. After cooling to room temperature, the solvent was evaporated and the residue was purified by flash column chromatography with DCM/MeOH to afford the compound S32 as colorless oil (803 mg, 70% yield). UPLC-MS calculated for $C_{10}H_{14}NOSi$ [M+1]$^+$: 192.08, found 191.98.

Following the procedure for the synthesis of compound S8, the reaction was conducted with S32 (803 mg, 4.2 mmol, 1.0 eq). Finally, the compound S33 was obtained as a white solid (400 mg, 80% yield). UPLC-MS calculated for $C_7H_6NO$ [M+1]$^+$: 120.04, found 119.93.

To a solution of compound S31 (175 mg, 0.44 mmol, 1.0 eq) and S33 (79 mg, 0.66 mmol, 1.5 eq) in 5.0 mL of DMF were added KI (7.3 mg, 0.044 mmol, 0.1 eq) and KHCO$_3$ (88 mg, 0.88 mmol, 2.0 eq) sequentially. The resulted solution was stirred at 70° C. for 6 h. After cooling to room temperature, the reaction mixture was diluted in water and ethyl acetate. After extraction for 3 times, the combined organic layer was dried over Na$_2$SO$_4$. The concentrated residue was purified by reverse flash column chromatography with MeCN/H$_2$O (0.1% TFA) to afford the compound S34 as a white solid (156 mg, 85% yield). UPLC-MS calculated for $C_{24}H_{24}N_3O_4$ [M+1]$^+$: 418.18, found 418.20.

Example 33

Synthesis of 3-(4-(5-(4-ethynyl-1H-pyrazol-1-yl) pent-1-yn-1-yl)-1-oxoisoindolin-2-yl)piperidine-2,6-dione

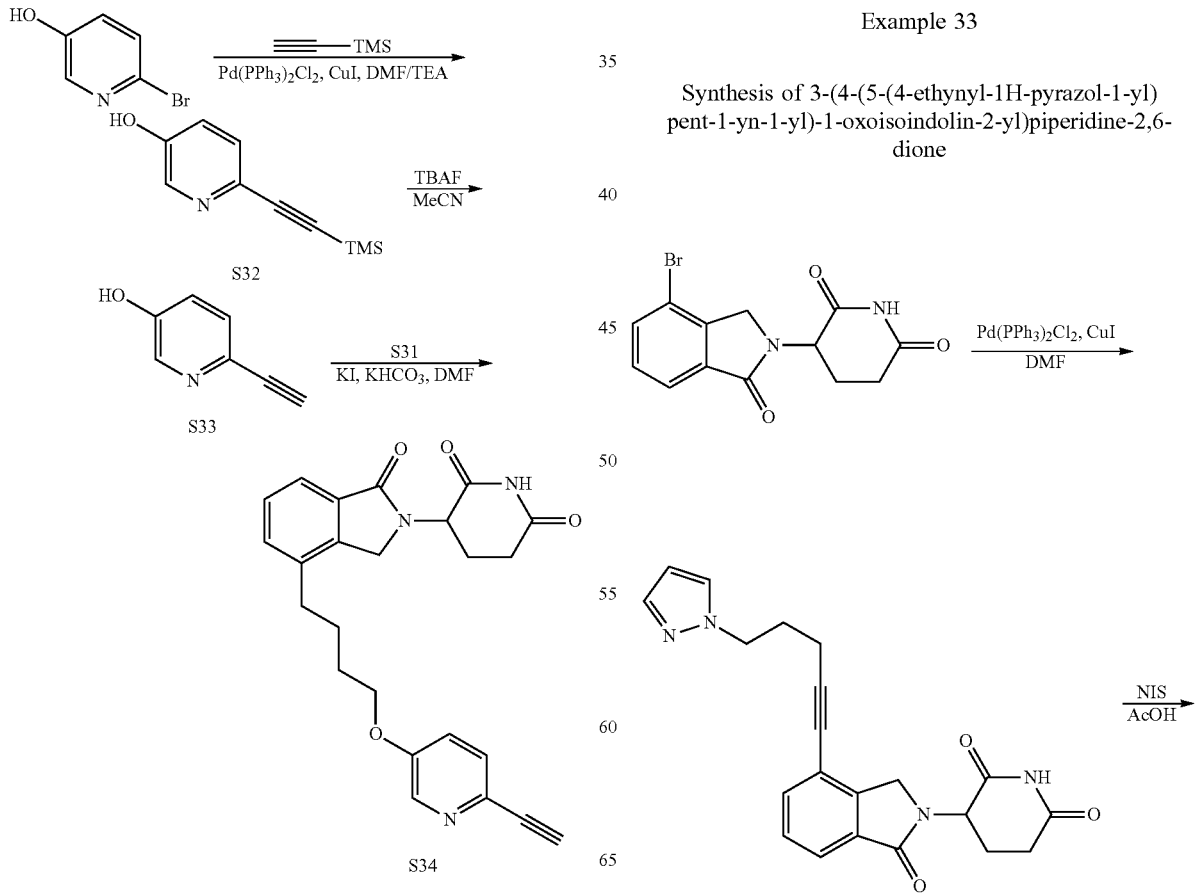

-continued

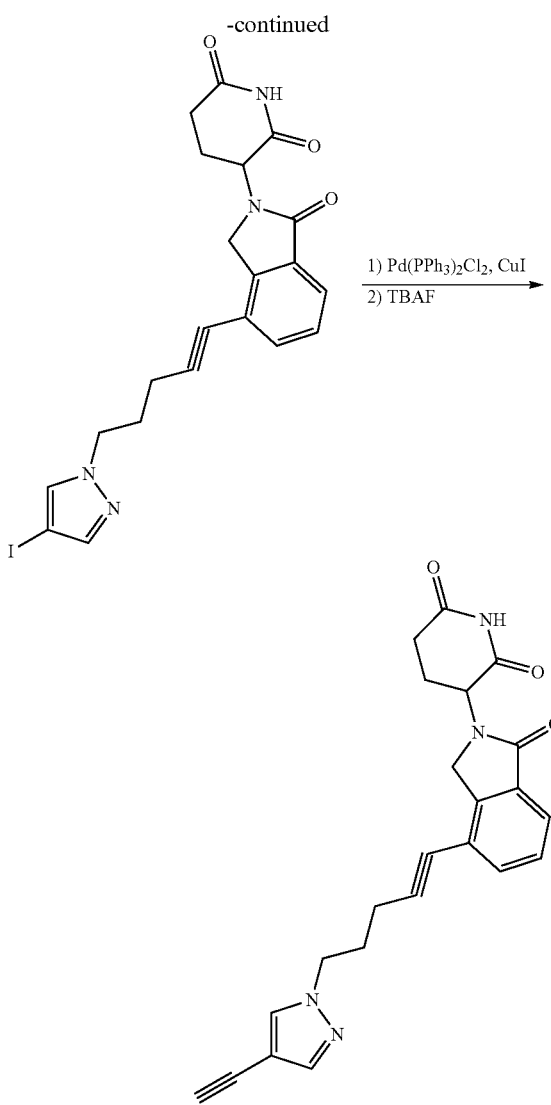

1) Pd(PPh₃)₂Cl₂, CuI
2) TBAF mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford 3-(4-(5-(4-ethynyl-1H-pyrazol-1-yl)pent-1-yn-1-yl)-1-oxoisoindolin-2-yl)piperidine-2,6-dione (50 mg, 63% yield). ESI-MS: 401.17.

Example 34

Synthesis of 2-(2,6-dioxopiperidin-3-yl)-4-((4-(4-ethynyl-1H-pyrazol-1-yl)butyl)amino)isoindoline-1,3-dione

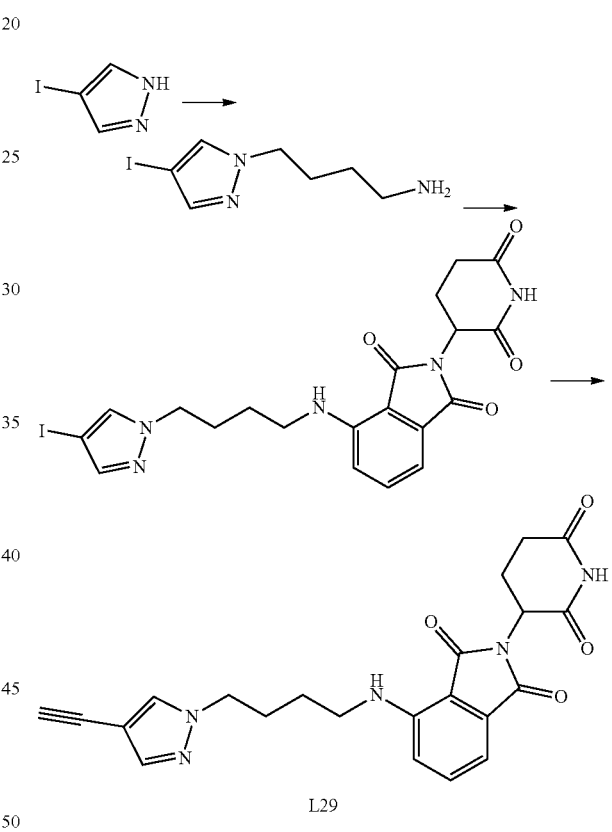

L29

Step 1:
To a Schlenk tube was added CuI (5.3 mg), Pd(Ph₃P)₂Cl₂ (20 mg), 3-(4-bromo-1-oxoisoindolin-2-yl)piperidine-2,6-dione (100 mg, 0.31 mmol), and 1-(pent-4-yn-1-yl)-1H-imidazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford 3-(4-(5-(1H-imidazol-1-yl)pent-1-yn-1-yl)-1-oxoisoindolin-2-yl)piperidine-2,6-dione (42 mg, 36% yield). ESI-MS: 377.22.

Step 2:
3-(4-(5-(1H-imidazol-1-yl)pent-1-yn-1-yl)-1-oxoisoindolin-2-yl)piperidine-2,6-dione (100 mg, 0.26 mmol) in acetic acid (2 mL) was added NIS (56 mg). The reaction was stirred for 1 h prior to being concentrated. The residue was purified by HPLC to afford 3-(4-(5-(4-iodo-1H-imidazol-1-yl)pent-1-yn-1-yl)-1-oxoisoindolin-2-yl)piperidine-2,6-dione (39 mg, 30%). ESI-MS: 503.11.

Step 3:
To a Schlenk tube was added CuI (5.3 mg), Pd(Ph₃P)₂Cl₂ (20 mg), 3-(4-(5-(4-iodo-1H-imidazol-1-yl)pent-1-yn-1-yl)-1-oxoisoindolin-2-yl)piperidine-2,6-dione (101 mg, 0.2

Step 1:
To a solution of 4-iodo-1H-pyrazole (2.4 g, 12 mmol) and triethylamine (1.85 mL, 13 mmol) in DCM (20 mL) at 0° C. was added MsCl (1 mL, 12.6 mmol). The reaction mixture was allowed to warm to r.t. and stirred for another 1 hour. The reaction mixture was quenched with saturated NH₄Cl solution, extracted with DCM. The organic layer was separated, washed with brine, dried, and evaporated. The residue was dissolved in CH₃CN (70 mL) and tert-butyl (4-hydroxybutyl)carbamate (1.89 g, 10 mmol) and Cs₂CO₃ (3.9 g, 12 mmol) was added. The reaction mixture was heated to reflux for 12 h. After the reaction was cooled, the mixture was filtered and the filtrate was evaporated. The residue was taken up in EtOAc and water. The organic layer was separated, washed with brine, dried, and evaporated. The residue was purified by chromatography (EtOAc/Hexanes:

1:2) to afford crude tert-butyl (4-(4-iodo-1H-pyrazol-1-yl)butyl)carbamate (2.3 g, 53%), which was treated with DCM (5 mL) and TFA (5 mL). The reaction mixture was stirred for 12 hours. All the volatiles were removed under vacuum and the residue was subjected to HPLC purification to afford 4-(4-iodo-1H-pyrazol-1-yl)butan-1-amine.

Step 2:

To a solution of TFA salt of 4-(4-iodo-1H-pyrazol-1-yl)butan-1-amine (378 mg, 1 mmol) and 2-(2,6-dioxopiperidin-3-yl)-4-fluoroisoindoline-1,3-dione (276 mg, 1 mmol) in DMF (1 mL) was added DIPEA (0.52 mL, 3 mmol). The reaction mixture was heated at 90° C. for 12 hours. The reaction mixture was cooled and treated with EtOAc and brine. The organic layer was separated, dried, and evaporated. The residue was subject to HPLC purification to afford 2-(2,6-dioxopiperidin-3-yl)-4-((4-(4-iodo-1H-pyrazol-1-yl)butyl)amino)isoindoline-1,3-dione (122 mg, 23% yield).

Step 3:

To a Schlenk tube was added CuI (5.3 mg), Pd(Ph₃P)₂Cl₂ (20 mg), 2-(2,6-dioxopiperidin-3-yl)-4-((4-(4-iodo-1H-pyrazol-1-yl)butyl)amino)isoindoline-1,3-dione (100 mg, 0.2 mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford compound L29 (50 mg, 60% yield). ESI-MS: 420.13.

Example 35

Synthesis of 3-(4-(5-(4-ethynyl-1H-pyrazol-1-yl)pentyl)-1-oxoisoindolin-2-yl)piperidine-2,6-dione

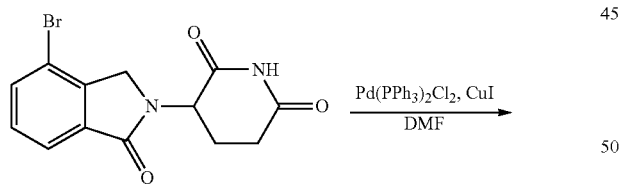

Step 1:

To a Schlenk tube was added CuI (5.3 mg), Pd(Ph₃P)₂Cl₂ (20 mg), 3-(4-bromo-1-oxoisoindolin-2-yl)piperidine-2,6- dione (100 mg, 0.31 mmol), and 1-(pent-4-yn-1-yl)-1H-pyrazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford the desired product (82 mg, 70% yield). ESI-MS: 377.15.

Step 2:
To a solution of the product from step 1 (100 mg, 0.266 mmol) in MeOH (2 mL) was added 10% Pd/C. The reaction was stirred under H₂ balloon for 4 h prior to being filtered. The organic solvent was removed to afford 3-(4-(5-(1H-pyrazol-1-yl)pentyl)-1-oxoisoindolin-2-yl)piperidine-2,6-dione (97 mg, 95%).

Step 3:
3-(4-(5-(1H-pyrazol-1-yl)pentyl)-1-oxoisoindolin-2-yl)piperidine-2,6-dione (100 mg, 0.26 mmol) in acetic acid (2 mL) was added NIS (56 mg). The reaction was stirred for 6 h prior to being concentrated. The residue was purified by HPLC to afford 3-(4-(5-(4-iodo-1H-pyrazol-1-yl)pentyl)-1-oxoisoindolin-2-yl)piperidine-2,6-dione (118 mg, 90%). ESI-MS: 507.19.

Step 4:
To a Schlenk tube was added CuI (5.3 mg), Pd(Ph₃P)₂Cl₂ (20 mg), 3-(4-(5-(4-iodo-1H-pyrazol-1-yl)pentyl)-1-oxoisoindolin-2-yl)piperidine-2,6-dione (101 mg, 0.2 mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford compound L41 (44 mg, 55% yield). ESI-MS: 405.19.

Example 36

Synthesis of 2-(2,6-dioxopiperidin-3-yl)-4-(4-(4-ethynyl-1H-pyrazol-1-yl)butoxy)isoindoline-1,3-dione Step 1:
To a suspension of 4-ethynyl-1H-pyrazole (920 mg, 10 mmol) and 4-chlorobutan-1-ol (216 mg, 20 mmol) in acetonitrile (25 mL) was added K₂CO₃ (4.1 g, 30 mmol, 3 eq) and KI (166 mg, 1 mmol, 0.1 eq). The mixture was stirred for 6 hours at 85° C. under N₂ protection. The reaction mixture was quenched with water and extracted with EtOAc. The residue was purified by chromatography (DCM:MeOH 10:1) to afford to afford 1.3 g of 4-(4-ethynyl-1H-pyrazol-1-yl)butan-1-ol with 80% yield. ESI-MS m/z 165.02 [M+H]⁺.

Step 2:
To a suspended solution of 4-(4-ethynyl-1H-pyrazol-1-yl)butan-1-ol (328 mg, 2 mmol, 1.0 eq) in 30 mL of DCM was added mesyl chloride (310 μL, 4 mmol, 2.0 eq) at 0° C. Then trimethylamine (0.77 mL, 6 mmol, 3.0 eq) was added dropwise. The solution turned clear within 1 min. After 1 h, the solvent was evaporated to give crude 4-(4-ethynyl-1H-pyrazol-1-yl)butyl methanesulfonate, which was used in the next step reaction without further purification.

Step 3:
To a solution of 2-(2,6-dioxopiperidin-3-yl)-4-hydroxy-isoindoline-1,3-dione (137 mg, 0.5 mmol), 4-(4-ethynyl-1H-pyrazol-1-yl)butyl methanesulfonate (61 mg, 0.25 mmol) in DMF (2 mL) was added KHCO₃ (50 mg) and KI (10 mg). The reaction mixture was stirred at 70° C. for 12 hour prior to being taken up in ethyl acetate and water. The organic layer was separated, dried, and evaporated. The residue was purified by HPLC to afford 2-(2,6-dioxopiperidin-3-yl)-4-(4-(4-ethynyl-1H-pyrazol-1-yl)butoxy)isoindoline-1,3-dione (80 mg, 60%).

Example 37

Synthesis of (3'R,4'S,5'R)-6"-chloro-4'-(3-chloro-2-fluorophenyl)-N-(4-((4-((2-(2,6-dioxopiperidin-3-yl)-1-oxoisoindolin-4-yl)amino)butyl)carbamoyl)phenyl)-2"-oxodispiro[cyclohexane-1,2'-pyrrolidine-3',3"-indoline]-5'-carboxamide

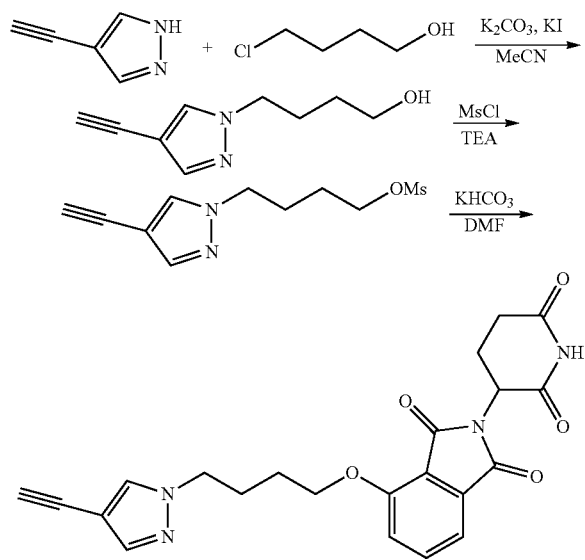

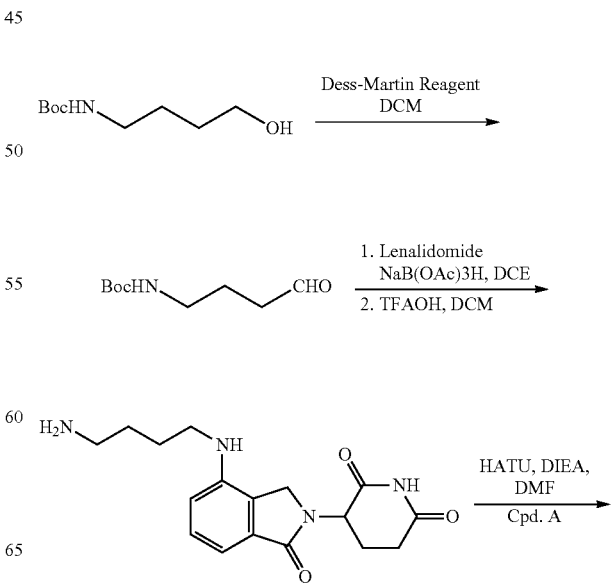

-continued

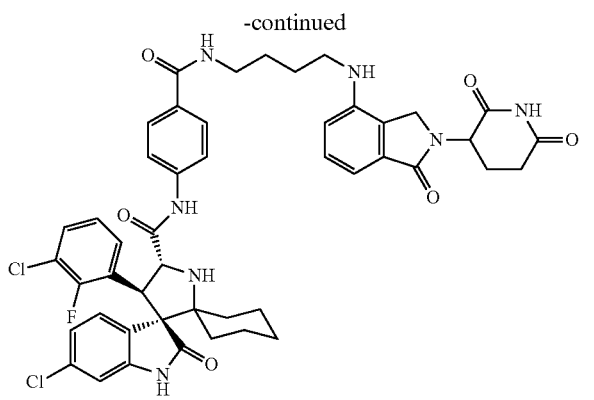

Step 1: Synthesis of tert-butyl (4-oxobutyl)carbamate

To solution of tert-butyl 4-hydroxybutyl)carbamate (380 mg, 2 mmol) in 15 ml of DCM was added Dess-Martin periodinane reagent (1.7 g, 4 mmol). After stirring at room temperature for 1 h the reaction mixture was filtered by celite. The filtrate was then washed with brine, dried over $Na_2SO_4$, filtered, and the solvent evaporated in vacuo. The residue was purified by chromatography over silica gel, to yield tert-butyl (4-oxobutyl)carbamate as colorless oil.

Step 2: Synthesis of 3-(4-((4-aminobutyl)amino)-1-oxoisoindolin-2-yl)piperidine-2,6-dione To tert-butyl (4-oxobutyl)carbamate (190 mg, 1 mmol) in 1,2-dichloroethane (15 mL) was added Lenalidomide (285 mg, 1.1 mmol), and the resulting solution was stirred at room temperature for 30 min. The solution was treated with $Na(OAc)_3BH$ (0.42 g, 2 mmol), and the resulting suspension was stirred overnight. The solvent was diluted with DCM and washed with sat. $NaHCO_3$, brine, dried ($Na_2SO_4$), filtered, and concentrated. Then residue was diluted in 10 mL DCM then 2 mL trifluoroacetic acid was added to the reaction and stirred for 30 min. The solvent was removed by vacuo and the residue was purified by reverse phase chromatography over C18 column to yield 3-(4-((4-aminobutyl)amino)-1-oxoisoindolin-2-yl)piperidine-2,6-dione as colorless oil.

Step 3: Synthesis of (3'R,4'S,5'R)-6"-chloro-4'-(3-chloro-2-fluorophenyl)-N-(4-((4-((2-(2,6-dioxopiperidin-3-yl)-1-oxoisoindolin-4-yl)amino)butyl)carbamoyl)phenyl)-2"-oxodispiro[cyclohexane-1,2'-pyrrolidine-3',3"-indoline]-5'-carboxamide HATU (13.3 mg, 1.2 eq.) and N,N-Diisopropylethylamine (0.026 mL, 0.15 mmol) were added to a solution of Cpd. A (20 mg, 0.029 mmol) in 0.5 mL DMF and stirred. After 10 minutes, 3-(4-((4-aminobutyl)amino)-1-oxoisoindolin-2-yl)piperidine-2,6-dione (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in $H_2O$, frozen and lyophilized to give title compound (TFA salt) as a white powder. LC-MS(ESI) m/z (M+H)⁺: 894.25, 4.96 min; calcd: 894.29; >98% purity.

Example 38

Synthesis of (3'R,4'S,5'R)-6"-chloro-4'-(3-chloro-2-fluorophenyl)-N-(4-((5-((2-(2,6-dioxopiperidin-3-yl)-1-oxoisoindolin-4-yl)amino)-5-oxopentyl)carbamoyl)phenyl)-2"-oxodispiro[cyclohexane-1,2'-pyrrolidine-3',3"-indoline]-5'-carboxamide

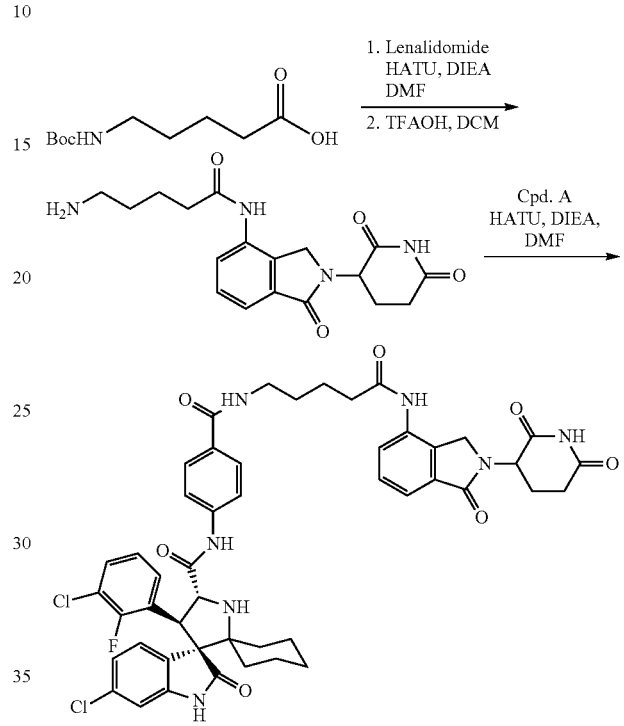

Step 1: Synthesis of 5-amino-N-(2-(2,6-dioxopiperidin-3-yl)-1-oxoisoindolin-4-yl)pentanamide HATU (380 mg, 1 mmol) and N,N-diisopropylethylamine (0.44 mL, 2.5 mmol) were added to a solution of Boc-5-aminopentanoic acid (110 mg, 0.5 mmol) in 3 mL DMF and stirred. After 10 minutes, Lenalidomide (200 mg, 0.75 mmol) was added to the reaction. After 30 minutes, the solvent was removed and the crude was dissolved in 10 mL DCM and 2 mL trifluoroacetic acid. The reaction was stirred for 30 min and then the solvent was removed by vacuo. The residue was purified by reverse phase chromatography over C18 column to yield 5-amino-N-(2-(2,6-dioxopiperidin-3-yl)-1-oxoisoindolin-4-yl)pentanamide as colorless oil.

Reaction 2: Synthesis of (3'R,4'S,5'R)-6"-chloro-4'-(3-chloro-2-fluorophenyl)-N-(4-((5-((2-(2,6-dioxopiperidin-3-yl)-1-oxoisoindolin-4-yl)amino)-5-oxopentyl)carbamoyl)phenyl)-2"-oxodispiro[cyclohexane-1,2'-pyrrolidine-3',3"-indoline]-5'-carboxamide HATU (13.3 mg, 1.2 eq.) and N,N-diisopropylethylamine (0.026 mL, 0.15 mmol) were added to a solution of Cpd. A (20 mg, 0.029 mmol) in 0.5 mL DMF and stirred. After 10 minutes, 5-amino-N-(2-(2,6-dioxopiperidin-3-yl)-1-oxoisoindolin-4-yl)pentanamide (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in H$_2$O, frozen and lyophilized to give the title compound (TFA salt) as a white powder.

LC-MS(ESI) m/z (M+H)$^+$: 922.26, 5.39 min; calcd: 922.29; >98% purity. $^1$H NMR (400 MHz, MeOD) δ 7.77 (d, J=8.2 Hz, 2H), 7.74-7.67 (m, 2H), 7.63-7.57 (m, 3H), 7.54 (dd, J=8.2, 2.4 Hz, 1H), 7.47 (t, J=7.7 Hz, 1H), 7.39-7.31 (m, 1H), 7.17 (t, J=8.1 Hz, 1H), 7.11 (dd, J=8.2, 1.9 Hz, 1H), 6.79 (d, J=1.9 Hz, 1H), 5.38 (d, J=10.9 Hz, 1H), 5.12 (dd, J=13.3, 5.1 Hz, 1H), 4.98 (d, J=10.9 Hz, 1H), 4.45 (d, J=2.1 Hz, 2H), 3.40 (t, J=6.7 Hz, 2H), 3.02-2.79 (m, 2H), 2.78-2.66 (m, 1H), 2.57-2.30 (m, 3H), 2.21 (d, J=14.0 Hz, 1H), 2.17-2.07 (m, 1H), 2.06-1.88 (m, 3H), 1.81-1.63 (m, 6H), 1.60-1.46 (m, 1H), 1.24 (td, J=13.8, 3.9 Hz, 2H).

Example 38

Synthesis of (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pentyl)carbamoyl)phenyl)-2"-oxodispiro[cyclohexane-1,2'-pyrrolidine-3',3"-indoline]-5'-carboxamide

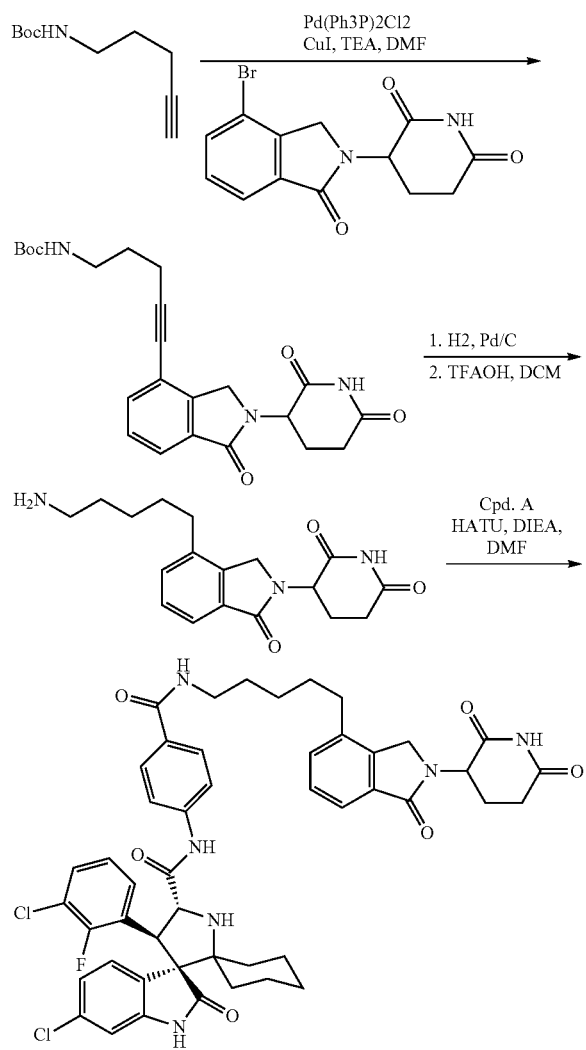

Step 1: Synthesis of tert-butyl (5-(2-(2,6-dioxopiperidin-3-yl)-1-oxoisoindolin-4-yl)pent-4-yn-1-yl)carbamate To a solution of tert-butyl pent-4-yn-1-ylcarbamate (236 mg, 1.29 mmol) and 3-(4-bromo-1-oxoisoindolin-2-yl)piperidine-2,6-dione (400 mg, 1.29 mmol) in triethylamine (3 mL) and DMF (3 mL), CuI (50 mg, 0.25 mmol) and the Pd(Ph$_3$P)$_2$Cl$_2$ (90 mg, 0.13 mmol) were added. The mixture was stirred at 80° C. under N$_2$-atmosphere overnight. The reaction mixture was poured into a saturated aqueous solution of NH4Cl and after separation of the organic layer the aqueous layer was extracted with Ethyl Acetate. The combined organic layers were washed with brine, dried over Na$_2$SO$_4$ and concentrated in vacuo. The crude product was purified by flash chromatography to afford tert-butyl (5-(2-(2,6-dioxopiperidin-3-yl)-1-oxoisoindolin-4-yl)pent-4-yn-1-yl)carbamate as white solid.

Step 2: Synthesis of 3-(4-(5-aminopentyl)-1-oxoisoindolin-2-yl)piperidine-2,6-dione To a solution of tert-butyl (5-(2-(2,6-dioxopiperidin-3-yl)-1-oxoisoindolin-4-yl)pent-4-yn-1-yl)carbamate (210 mg, 0.5 mmol) in EtOH (5 mL) was added Pd/C (20 mg). The reaction was stirred under H$_2$-atmosphere for 2 hr. Then the mixture was filtered by celite and the solvent was removed by vacuo. The residue was dissolved in 10 mL DCM and 2 mL trifluoroacetic acid. The reaction was stirred for 30 min and then the solvent was removed by vacuo. The residue was purified by reverse phase chromatography over C18 column to 3-(4-(5-aminopentyl)-1-oxoisoindolin-2-yl)piperidine-2,6-dione as colorless oil.

Step 3: Synthesis of (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pentyl)carbamoyl)phenyl)-2"-oxodispiro[cyclohexane-1,2'-pyrrolidine-3',3"-indoline]-5'-carboxamide HATU (13.3 mg, 1.2 eq.) and N,N-diisopropylethylamine (0.026 mL, 0.15 mmol) were added to a solution of Cpd. A (20 mg, 0.029 mmol) in 0.5 mL DMF and stirred. After 10 minutes, 3-(4-(5-aminopentyl)-1-oxoisoindolin-2-yl)piperidine-2,6-dione (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in H$_2$O, frozen and lyophilized to give the title compound (TFA salt) as a white powder.

LC-MS(ESI) m/z (M+H)$^+$: 893.19, 6.12 min; calcd (M+H)$^+$: 893.30; >98% purity. $^1$H NMR (400 MHz, MeOD) δ 7.78-7.66 (m, 3H), 7.66-7.56 (m, 3H), 7.53 (dd, J=8.2, 2.5 Hz, 1H), 7.47-7.38 (m, 2H), 7.38-7.32 (m, 1H), 7.17 (t, J=8.1 Hz, 1H), 7.11 (dd, J=8.2, 2.0 Hz, 1H), 6.79 (d, J=1.9 Hz, 1H), 5.29 (d, J=10.7 Hz, 1H), 5.14 (dd, J=13.3, 5.2 Hz, 1H), 4.97 (d, J=10.8 Hz, 1H), 4.46 (dd, J=5.7, 2.5 Hz, 2H), 3.41-3.33 (m, 2H), 2.96-2.64 (m, 5H), 2.50 (qdd, J=13.3, 4.6, 2.5 Hz, 1H), 2.22-2.09 (m, 2H), 2.02-1.84 (m, 3H), 1.79-1.48 (m, 7H), 1.48-1.35 (m, 2H), 1.22 (td, J=13.7, 4.0 Hz, 2H).

Example 40

Synthesis of 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione

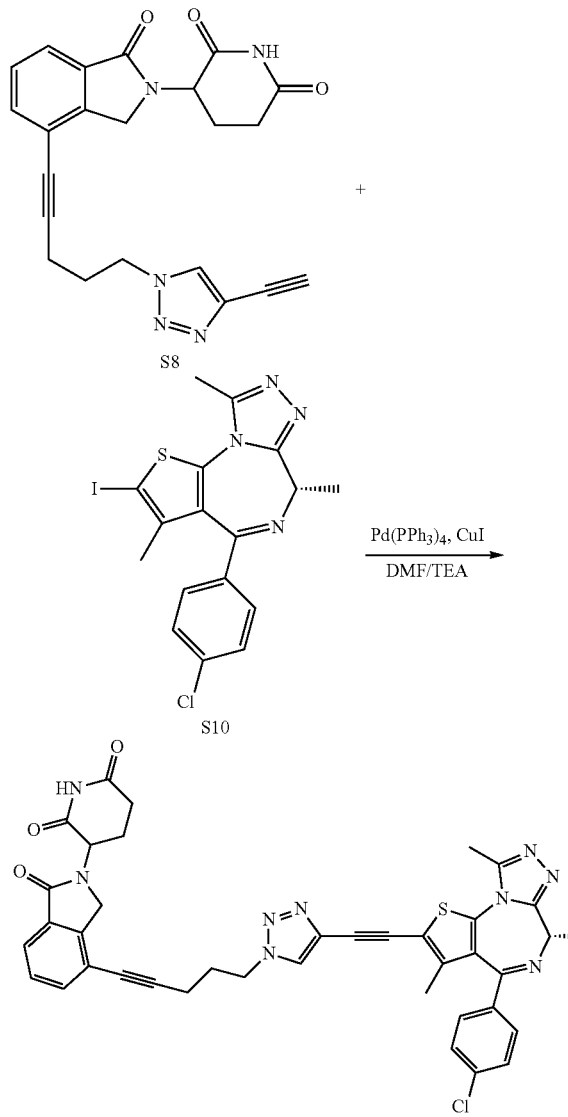

To a solution of S10 (14.1 mg, 0.03 mmol, 1.0 eq), S8 (18.1 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione as a white solid (16 mg, 70% yield). $^1$H NMR (400 MHz, CD$_3$OD) δ (ppm) 8.35 (s, 1H), 7.71 (d, J=7.2 Hz, 1H), 7.59 (d, J=7.6 Hz, 1H), 7.52-7.44 (m, 5H), 5.15 (dd, J=13.2 Hz, J=5.2 Hz, 1H), 4.65 (t, J=7.2 Hz, 2H), 4.53 (d, J=17.6 Hz, 1H), 4.46 (d, J=17.6 Hz, 1H), 4.39 (q, J=6.7 Hz, 1H), 2.95-2.86 (m, 1H), 2.81-2.75 (m, 1H), 2.75 (s, 3H), 2.58 (t, J=6.8 Hz, 2H), 2.57-2.50 (m, 1H), 2.30-2.21 (m, 2H), 2.20-2.17 (m, 1H), 2.01 (d, J=6.8 Hz, 3H), 1.86 (s, 3H); UPLC-MS calculated for C$_{39}$H$_{33}$ClN$_9$O$_3$S [M+1]$^+$: 742.21, found 742.17.

Example 41

Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione

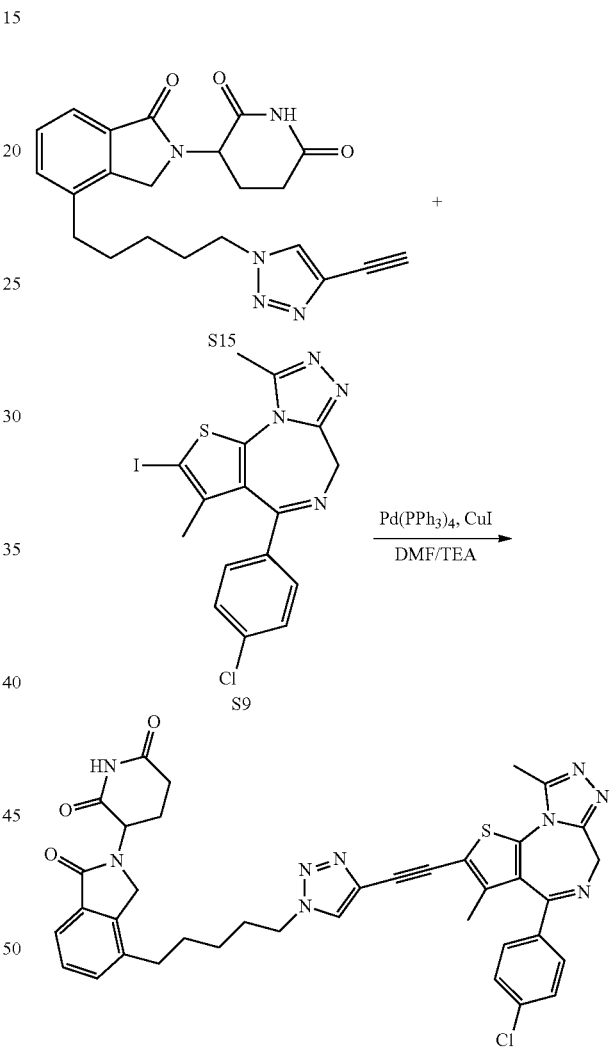

To a solution of S9 (14.1 mg, 0.03 mmol, 1.0 eq), S15 (18.2 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione as a white solid (14 mg, 63% yield). $^1$H NMR (400 MHz, CD$_3$OD) δ (ppm) 8.26 (s, 1H), 7.65-7.63 (m, 1H), 7.53 (d, J=8.4 Hz, 2H), 7.48-7.44

(m, 4H), 5.36 (d, J=13.2 Hz, 1H), 5.16 (dd, J=13.6 Hz, J=5.2 Hz, 1H), 4.52-4.42 (m, 4H), 4.35 (d, J=13.2 Hz, 1H), 2.96-2.87 (m, 1H), 2.82-2.80 (m, 1H), 2.76 (s, 3H), 2.71 (t, J=7.6 Hz, 2H), 2.59-2.48 (m, 1H), 2.23-2.17 (m, 1H), 1.99-1.96 (m, 2H), 1.92 (s, 3H), 1.76-1.68 (m, 2H), 1.40-1.30 (m, 2H); UPLC-MS calculated for $C_{38}H_{35}ClN_9O_3S$ [M+1]$^+$: 732.23, found 732.17.

Example 42

Synthesis of 4-((3-cyclopropyl-1-ethyl-1H-pyrazol-5-yl)amino)-7-(3,5-dimethylisoxazol-4-yl)-N-(2-(2-(2-(3-((2-(2,6-dioxopiperidin-3-yl)-1-oxoisoindolin-4-yl)amino)-3-oxopropoxy)ethoxy)ethoxy)ethyl)-6-methoxy-9H-pyrimido[4,5-b]indole-2-carboxamide To a round-bottom flask, N,N-diisopropylethylamine (50 mg) were added to a solution of 4-((3-cyclopropyl-1-ethyl-1H-pyrazol-5-yl)amino)-7-(3,5-dimethylisoxazol-4-yl)-6-methoxy-9H-pyrimido[4,5-b]indole-2-carboxylic acid (20 mg), HATU (20 mg), and 3-(2-(2-(2-aminoethoxy)ethoxy)ethoxy)-N-(2-(2,6-dioxopiperidin-3-yl)-1-oxoisoindolin-4-yl)propanamide (50 mg) in DMF (1 mL) at room temperature. The mixture was stirred for 30 min and purified by HPLC to yield 17 mg of 4-((3-cyclopropyl-1-ethyl-1H-pyrazol-5-yl)amino)-7-(3,5-dimethylisoxazol-4-yl)-N-(2-(2-(2-(3-((2-(2,6-dioxopiperidin-3-yl)-1-oxoisoindolin-4-yl)amino)-3-oxopropoxy)ethoxy) ethoxy)ethyl)-6-methoxy-9H-pyrimido[4,5-b]indole-2-carboxamide as a TFA salt. ESI-MS calculated for $C_{47}H_{54}N_{11}O_{10}$ [M+H]$^+$=932.4; Observed: 932.5.

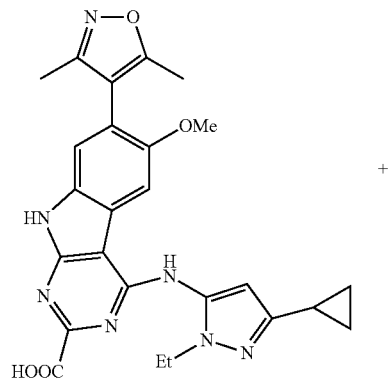

+

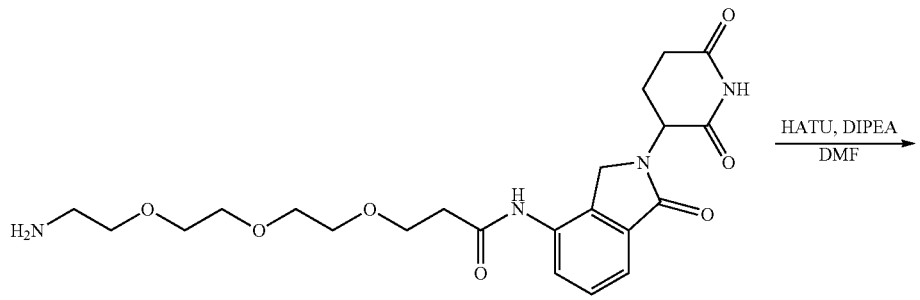

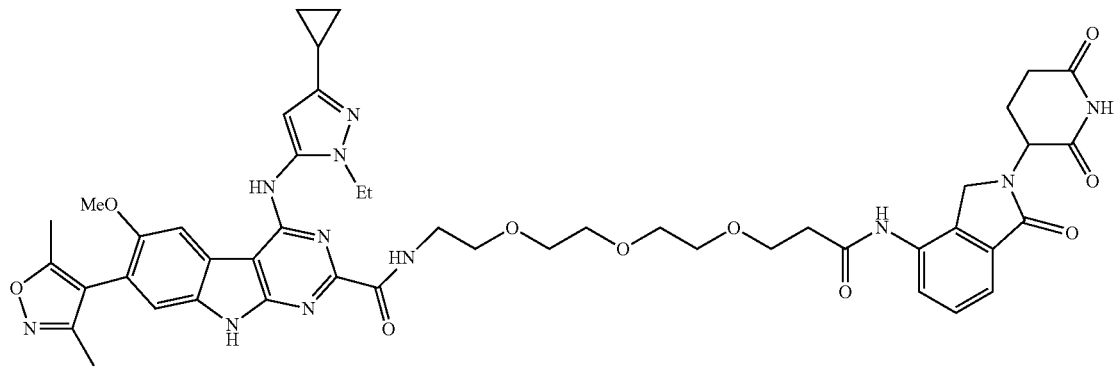

Example 43

Synthesis of 4-((2-(4-(((S)-3-benzyl-6,9-dimethyl-4H,6H-thieno[2,3-e][1,2,4]triazolo[3,4-c][1,4]oxazepin-2-yl)ethynyl)-1H-pyrazol-1-yl)ethyl)amino)-2-(2,6-dioxopiperidin-3-yl)isoindoline-1,3-dione

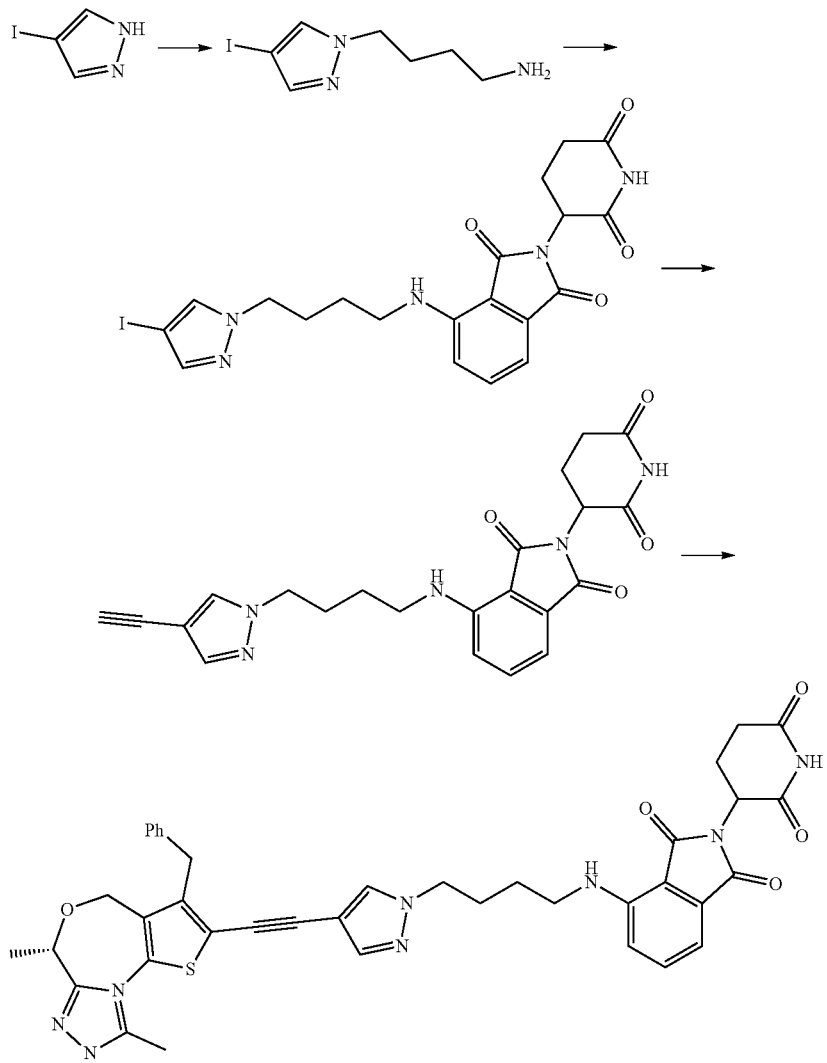

Step 1:

To a solution of 4-iodo-1H-pyrazole (2.4 g, 12 mmol) and triethylamine (1.85 mL, 13 mmol) in DCM (20 mL) at 0° C. was added MsCl (1 mL, 12.6 mmol). The reaction mixture was allowed to warm to r.t. and stirred for another 1 hour. The reaction mixture was quenched with saturated NH4Cl solution, extracted with DCM. The organic layer was separated, washed with brine, dried, and evaporated. The residue was dissolved in CH$_3$CN (70 mL) and tert-butyl (4-hydroxybutyl)carbamate (1.89 g, 10 mmol) and Cs$_2$CO$_3$ (3.9 g, 12 mmol) was added. The reaction mixture was heated to reflux for 12 h. After the reaction was cooled, the mixture was filtered and the filtrate was evaporated. The residue was taken up in EtOAc and water. The organic layer was separated, washed with brine, dried, and evaporated. The residue was purified by chromatography (EtOAc/Hexanes:

1:2) to afford crude tert-butyl (4-(4-iodo-1H-pyrazol-1-yl)butyl)carbamate (2.3 g, 53%), which was treated with DCM (5 mL) and TFA (5 mL). The reaction mixture was stirred for 12 hours. All the volatiles were removed under vacuum and the residue was subject to HPLC purification to afford the 4-(4-iodo-1H-pyrazol-1-yl)butan-1-amine.

Step 2:

To a solution of TFA salt of 4-(4-iodo-1H-pyrazol-1-yl)butan-1-amine (378 mg, 1 mmol) and 2-(2,6-dioxopiperidin-3-yl)-4-fluoroisoindoline-1,3-dione (276 mg, 1 mmol) in DMF (1 mL) was added DIPEA (0.52 mL, 3 mmol). The reaction mixture was heated at 90° C. for 12 hours. The reaction mixture was cooled and treated with EtOAc and brine. The organic layer was separated, dried, and evaporated. The residue was subject to HPLC purification to afford 2-(2,6-dioxopiperidin-3-yl)-4-((4-(4-iodo-1H-pyrazol-1-yl)butyl)amino)isoindoline-1,3-dione (122 mg, 23% yield).

Step 3:

To a Schlenk tube was added CuI (5.3 mg), Pd(Ph$_3$P)$_2$Cl$_2$ (20 mg), 2-(2,6-dioxopiperidin-3-yl)-4-((4-(4-iodo-1H-pyrazol-1-yl)butyl)amino)isoindoline-1,3-dione (100 mg, 0.2 mmol), and ethynyltrimethylsilane (39.2 mg, 0.4 mmol), THF (4 mL) and Et$_3$N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford 2-(2,6-dioxopiperidin-3-yl)-4-((4-(4-ethynyl-1H-pyrazol-1-yl)butyl)amino)isoindoline-1,3-dione (50 mg, 60% yield). ESI-MS: 420.13.

Step 4:
To a Schlenk tube was added CuI (3.8 mg), Pd(Ph$_3$P)$_2$Cl$_2$ (7 mg), (S)-3-benzyl-2-bromo-6,9-dimethyl-4H,6H-thieno[2,3-e][1,2,4]triazolo[3,4-c][1,4]oxazepine (20 mg, 0.05 mmol), and 2-(2,6-dioxopiperidin-3-yl)-4-((4-(4-ethynyl-1H-pyrazol-1-yl)butyl)amino)isoindoline-1,3-dione (42 mg, 0.1 mmol), THF (2 mL) and Et$_3$N (0.5 mL). The reaction mixture was heated at 70° C. for 12 hours. The reaction mixture was cooled and treated with EtOAc and brine. The organic layer was separated, dried, and evaporated. The residue was subjected to HPLC purification to afford the title compound (14 mg, 38% yield). $^1$H NMR (400 MHz, MeOD) δ 7.95 (s, 1H), 7.67 (s, 1H), 7.53 (t, J=7.2 Hz, 1H), 7.31 (t, J=7.7 Hz, 2H), 7.23-7.18 (m, 3H), 7.02-6.98 (m, 2H), 5.05 (dd, J=12.3, 5.2 Hz, 1H), 4.82 (d, J=15.6 Hz, 1H), 4.66-4.61 (m, 1H), 4.60 (d, J=15.6 Hz, 1H), 4.23 (t, J=6.7 Hz, 2H), 4.14 (d, J=15.7 Hz, 1H), 4.04 (d, J=15.4 Hz, 1H), 3.38-3.33 (m, 2H), 2.93-2.60 (m, 6H), 2.14-2.09 (m, 1H), 2.06-1.91 (m, 2H), 1.64-1.59 (m, 5H). ESI-MS: 729.20.

It is to be understood that the foregoing embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. A compound having Formula I:

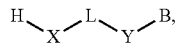
I and the salts thereof,
wherein:
X is selected from the group consisting of —N(R$^{2a}$)—, —OC(=O)—,

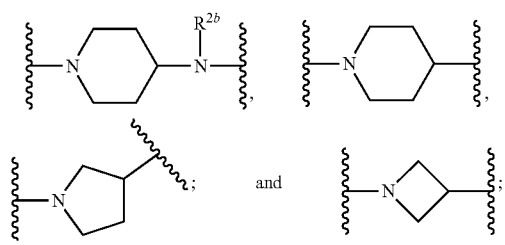

wherein the —N(R$^{2b}$)— of

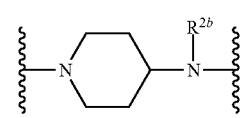

is attached to L; the —C(=O)— of —OC(=O)— is attached to L;
and the carbon atom of

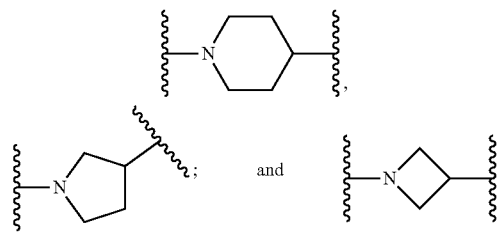

is attached to L;
L is alkylenyl;
Y is —C≡C—;
R$^{2a}$ and R$^{2b}$ are each independently selected from the group consisting of hydrogen and C$_{1-4}$ alkyl;
B is:

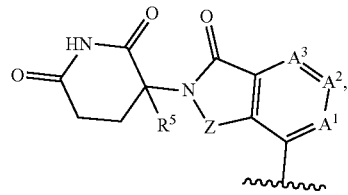
B-1a

A$^1$ is —C(R$^{16a}$)=;
A$^2$ is —C(R$^{16b}$)=;
A$^3$ is —C(R$^{16c}$)=;
Z is selected from the group consisting of —CH$_2$ and —C(=O)—;
R$^5$ is selected from the group consisting of hydrogen, methyl, and fluoro;
R$^{16a}$ is selected from the group consisting of hydrogen, halo, and C$_{1-4}$ alkyl;
R$^{16b}$ is selected from the group consisting of hydrogen, halo, and C$_{1-4}$ alkyl and
R$^{16c}$ is selected from the group consisting of hydrogen, halo, and C$_{1-4}$ alkyl.

2. The compound of claim 1, and the salts thereof, wherein:

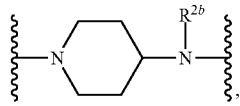

X is selected from the group consisting of —N(R$^{2a}$)—, and wherein the —N(R$^{2b}$)— of

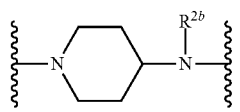

is attached to L.

3. The compound of claim 1, or a pharmaceutically acceptable salt thereof, having Formula II:

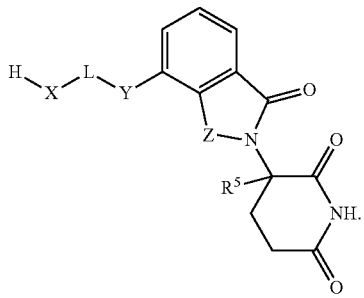

4. The compound of claim 3, or a pharmaceutically acceptable salt thereof, wherein L is $C_{1-12}$ alkylenyl.

5. The compound of claim 1, or a pharmaceutically acceptable salt thereof, selected from the group consisting of:

3-(4-(3-aminoprop-1-yn-1-yl)-1-oxoisoindolin-2-yl)piperidine-2,6-dione;

3-(4-(5-aminopent-1-yn-1-yl)-1-oxoisoindolin-2-yl)piperidine-2,6-dione;

3-(4-(4-aminobut-1-yn-1-yl)-1-oxoisoindolin-2-yl)piperidine-2,6-dione;

3-(1-oxo-4-(piperidin-4-ylethynyl)isoindolin-2-yl)piperidine-2,6-dione; and 3-(4-(5-aminopent-1-yn-1-yl)-7-fluoro-1-oxoisoindolin-2-yl)piperidine-2,6-dione.

6. The compound of claim 1, wherein X is —OC(═O)—.

7. The compound of claim 1, wherein X is —N(H)—.

8. The compound of claim 1, wherein X is selected from the group consisting of

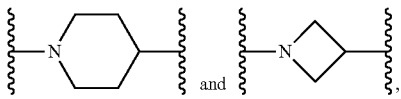 [SMILES: *C1CCN(*)CC1 ; *C1CN(*)C1]

wherein the carbon atom of

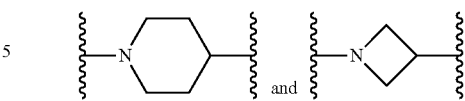

is attached to L.

9. The compound of claim 1, wherein L is $C_{1-12}$ alkylenyl.

10. The compound of claim 1, wherein L is selected from the group consisting of —CH$_2$—, —CH$_2$CH$_2$—, —CH$_2$CH$_2$CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, and —CH$_2$(CH$_2$)$_6$CH$_2$—.

11. The compound of claim 1, wherein $R^{16a}$ is selected from the group consisting of hydrogen and halo.

12. The compound of claim 1, wherein $R^{16b}$ is selected from the group consisting of hydrogen and halo.

13. The compound of claim 1, wherein $R^{16c}$ is selected from the group consisting of hydrogen and halo.

14. The compound of claim 1, wherein Z is —CH$_2$—.

15. The compound of claim 1, wherein Z is —C(═O)—.

16. The compound of claim 1, wherein $R^5$ is hydrogen.

17. The compound of claim 1, wherein B is:

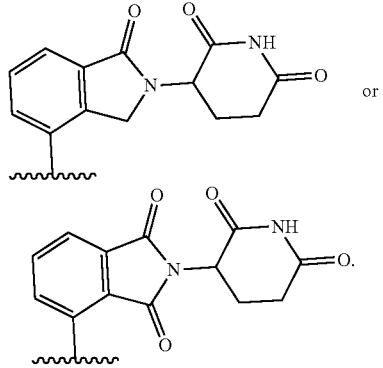

18. The compound of claim 3, wherein $R^5$ is hydrogen.

19. The compound of claim 3, wherein Z is —CH$_2$—.

20. The compound of claim 3, wherein Z is —C(═O)—.

* * * * *

UNITED STATES PATENT AND TRADEMARK OFFICE
CERTIFICATE OF CORRECTION

PATENT NO. : 10,759,808 B2  
APPLICATION NO. : 16/091544  
DATED : September 1, 2020  
INVENTOR(S) : Shaomeng Wang et al.

Page 1 of 2

It is certified that error appears in the above-identified patent and that said Letters Patent is hereby corrected as shown below:

In the Claims

At Column 289, Line 55, Claim 1: "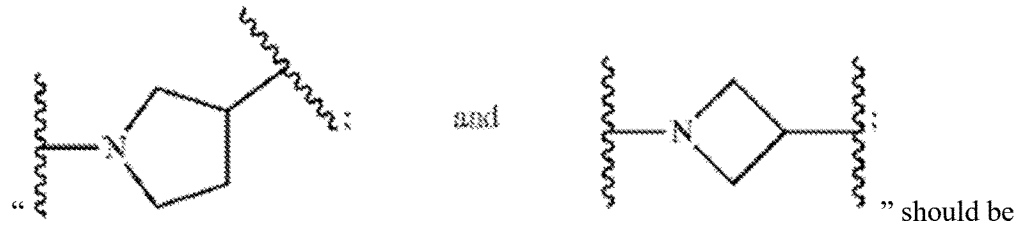 " should be

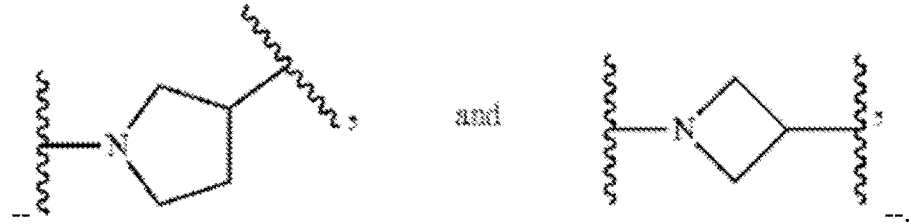 --.

At Column 290, Line 6, Claim 1: "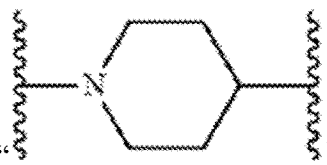 " should be

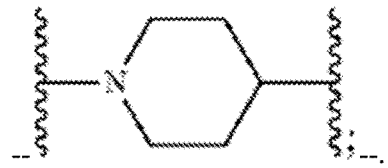 --.

Signed and Sealed this  
Twenty-second Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,759,808 B2

At Column 290, Lines 23-32, Claim 1: " 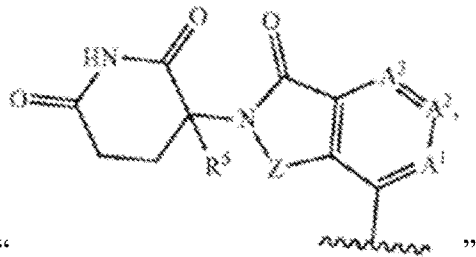 "

should be -- 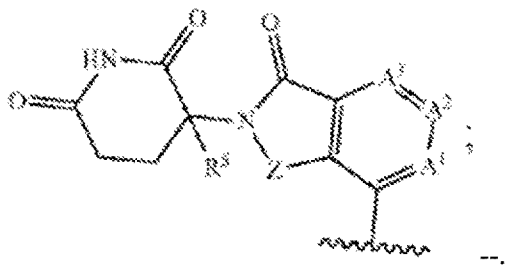 --.

At Column 290, Line 43, Claim 1: "alkyl and" should be -- alkyl; and --.

At Column 290, Lines 47-54, Claim 2: " 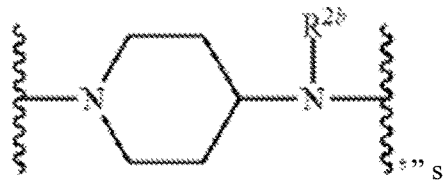 " should be
-- wherein: --.

At Column 290, Line 57, Claim 2: "and" should be -- and 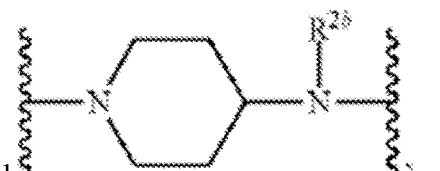 --.

At Column 291, Line 37, Claim 8: "consisting of" should be -- consisting of: --.